United States Patent
Busser et al.

(10) Patent No.: US 12,391,933 B2
(45) Date of Patent: Aug. 19, 2025

(54) TARGETED GENE INSERTION FOR IMPROVED IMMUNE CELLS THERAPY

(71) Applicant: CELLECTIS, Paris (FR)

(72) Inventors: Brian Busser, New York, NY (US);
Philippe Duchateau, Draveil (FR);
Alexandre Juillerat, New York, NY (US); Laurent Poirot, Paris (FR);
Julien Valton, New York, NY (US)

(73) Assignee: CELLECTIS, Paris (FR)

( * ) Notice: Subject to any disclaimer, the term of this patent is extended or adjusted under 35 U.S.C. 154(b) by 0 days.

(21) Appl. No.: 18/540,309

(22) Filed: Dec. 14, 2023

(65) Prior Publication Data

US 2024/0141293 A1    May 2, 2024

Related U.S. Application Data

(62) Division of application No. 16/340,222, filed as application No. PCT/EP2017/076798 on Oct. 19, 2017, now Pat. No. 11,873,511.

(60) Provisional application No. 62/410,187, filed on Oct. 19, 2016.

(30) Foreign Application Priority Data

Oct. 27, 2016   (DK) .............................. PA201670840

(51) Int. Cl.
| | | |
|---|---|---|
| *C12N 5/0783* | (2010.01) | |
| *A61K 35/17* | (2025.01) | |
| *A61K 40/11* | (2025.01) | |
| *A61K 40/30* | (2025.01) | |
| *A61K 40/31* | (2025.01) | |
| *A61K 40/36* | (2025.01) | |
| *A61K 40/42* | (2025.01) | |
| *C12N 5/078* | (2010.01) | |
| *C12N 9/22* | (2006.01) | |
| *C12N 15/90* | (2006.01) | |

(52) U.S. Cl.
CPC .............. *C12N 9/22* (2013.01); *A61K 40/11* (2025.01); *A61K 40/30* (2025.01); *A61K 40/31* (2025.01); *A61K 40/36* (2025.01); *A61K 40/4203* (2025.01); *A61K 40/4212* (2025.01); *C12N 5/0634* (2013.01); *C12N 5/0636* (2013.01); *C12N 5/0638* (2013.01); *C12N 15/907* (2013.01); *A61K 2239/48* (2023.05); *C12N 2510/00* (2013.01); *C12N 2750/14143* (2013.01); *C12N 2830/008* (2013.01)

(58) Field of Classification Search
CPC ...... C12N 9/22; C12N 5/0634; C12N 5/0636; C12N 5/0638; C12N 15/907; C12N 2510/00; C12N 2750/14143; C12N 2830/008; A61K 39/4611; A61K 39/4631; A61K 39/4636; A61K 39/4637; A61K 39/464403; A61K 39/464413; A61K 2239/48; C07K 14/7051; C07K 2319/03
See application file for complete search history.

(56) References Cited

U.S. PATENT DOCUMENTS

| | | |
|---|---|---|
| 10,166,255 B2 | 1/2019 | Moriarity et al. |
| 2013/0315884 A1 | 11/2013 | Galetto et al. |
| 2016/0272999 A1 | 9/2016 | Duchateau et al. |
| 2016/0361359 A1 | 12/2016 | Valton et al. |
| 2017/0065636 A1 | 3/2017 | Moriarity et al. |

FOREIGN PATENT DOCUMENTS

| | | | | |
|---|---|---|---|---|
| WO | WO-2014191128 A1 | * | 12/2014 | ............. A61K 35/17 |
| WO | 2015075195 A1 | | 5/2015 | |
| WO | 2016124765 A1 | | 8/2016 | |
| WO | WO-2017023803 A1 | * | 2/2017 | ............. A61K 35/00 |

OTHER PUBLICATIONS

Fesnak, A.D., June, C.H. and Levine, B.L., 2016. Engineered T cells: the promise and challenges of cancer immunotherapy. Nature reviews cancer, 16(9), pp. 566-581. (Year: 2016).*

Pegram, H.J., Lee, J.C., Hayman, E.G., Imperato, G.H., Tedder, T.F., Sadelain, M. and Brentjens, R.J., 2012. Tumor-targeted T cells modified to secrete IL-12 eradicate systemic tumors without need for prior conditioning. Blood, The Journal of the American Society of Hematology, 119(18), pp. 4133-4141. (Year: 2012).*

Austin, J.W., Lu, P., Majumder, P., Ahmed, R. and Boss, J.M., 2014. STAT3, STAT4, NFATc1, and CTCF regulate PD-1 through multiple novel regulatory regions in murine T cells. The Journal of Immunology, 192(10), pp. 4876-4886. (Year: 2014).*

(Continued)

*Primary Examiner* — Christopher M Babic
*Assistant Examiner* — Masudur Rahman
(74) *Attorney, Agent, or Firm* — ARRIGO, LEE, GUTTMAN & MOUTA-BELLUM LLP

(57) ABSTRACT

The invention pertains to the field of adaptive cell immunotherapy. It provides with the genetic insertion of exogenous coding sequence(s) that help the immune cells to direct their immune response against infected or malignant cells. These exogenous coding sequences are more particularly inserted under the transcriptional control of endogenous gene promoters that are sensitive to immune cells activation. Such method allows the production of safer immune primary cells of higher therapeutic potential.

15 Claims, 16 Drawing Sheets

Figure 1:
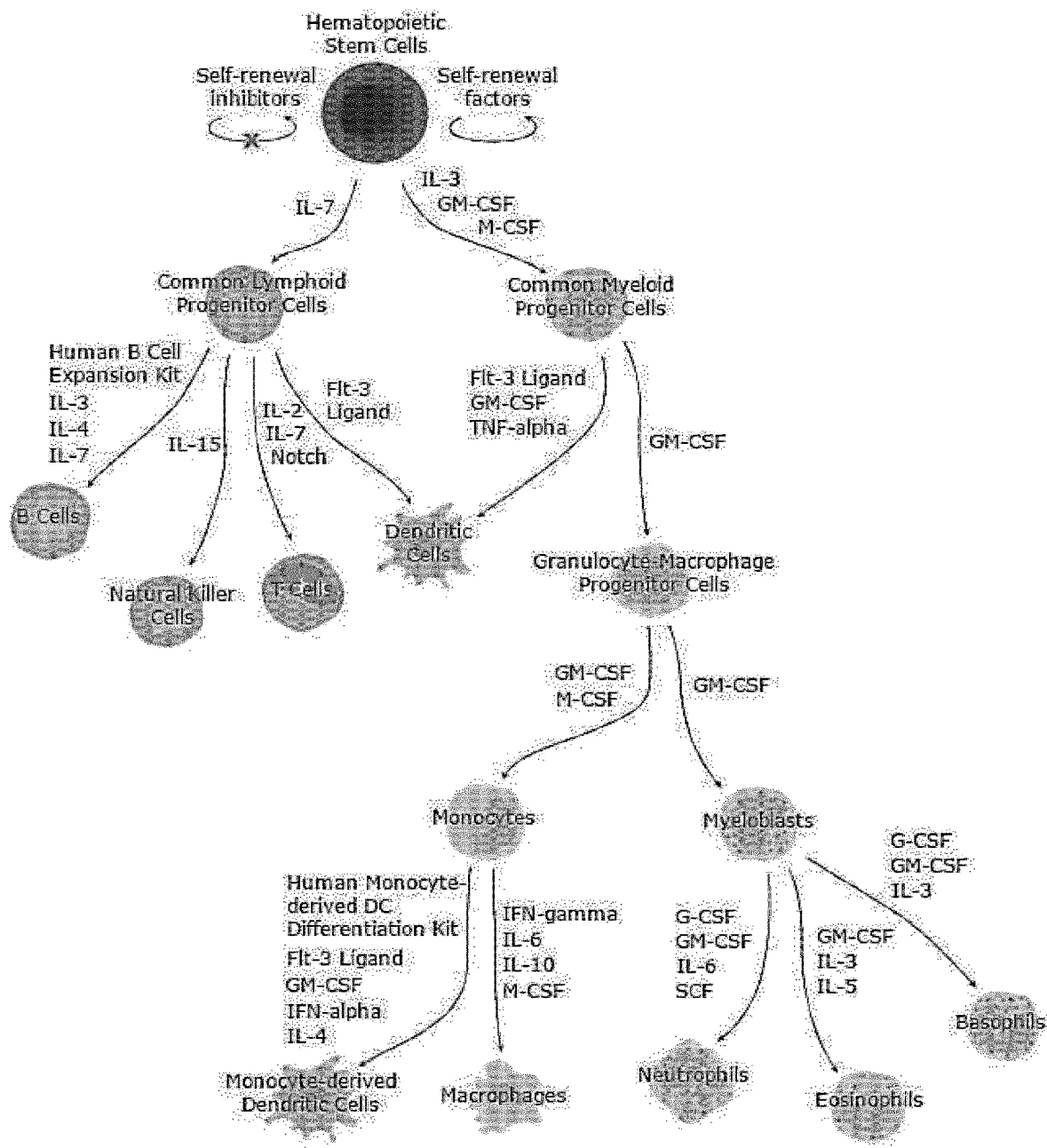

Specification includes a Sequence Listing.

(56) References Cited

OTHER PUBLICATIONS

Chu et al., Efficient CRISPR-mediated mutagenesis in primary immune cells using CrispRGold and a C57BL/6 Cas9 transgenic mouse line, PNAS, Nov. 1, 2016, vol. 113, No. 44, 12514-12519.
Sather et al., Efficient modification of CCR5 in primary human hematopoietic cells using a megaTAL nuclease and AAV donor template, Sci Transl Med. Sep. 30, 2015; 7(307):1-29.
Wang et al., Homology-driven genome editing in hematopoietic stem and progenitor cells using zinc finger nuclease mRNA and AAV6 donors, Nat Biotechnol. Dec. 2015 ; 33(12): 1256-1263.
Rongvaux et al. Human thrombopoietin knockin mice efficiently support human hematopoiesis in vivo. Proceedings of the National Academy of Sciences. 2011, 108(6), 2378-83.
Willinger et al. Human IL-3/GM-CSF knock-in mice support human alveolar macrophage development and human immune responses in the lung. Proceedings of the National Academy of Sciences. Feb. 8, 2011; 108(6): 2390-5. (Year: 2011).
Willinger et al. Improving human hemato-lymphoid-system mice by cytokine knock-in gene replacement. Trends in immunology, 2011, 32(7), 321-7.
Fesnak et al. Engineered T cells: the promise and challenges of cancer immunotherapy. Nature reviews cancer, 2016, 16(9), 566-81.
Chmielewski et al. IL-12 release by engineered T cells expressing chimeric antigen receptors can effectively muster an antigen-independent macrophage response on tumor cells that have shut down tumor antigen expression. Cancer Res, 2011, 71, 5697-706.
Pegram et al. Tumor-targeted T cells modified to secrete IL-12 eradicate systemic tumors without need for prior conditioning. Blood, The Journal of the American Society of Hematology. 2012, 119(18), 4133-41.
Austin et al. STAT3, STAT4, NFATc1, and CTCF regulate PD-1 through multiple novel regulatory regions in murine T cells. The Journal of Immunology, 2014, 192(10), 4876-86.
Bally et al. Genetic and epigenetic regulation of PD-1 expression. The Journal of Immunology. 2016, 196(6), 2431-7.
Tsai et al. Producer T cells: Using genetically engineered T cells as vehicles to generate and deliver therapeutics to tumors, Oncoimmunology, 2016, 5(5), e1122158.

\* cited by examiner

A

B

A

B

TARGETED GENE INSERTION FOR IMPROVED IMMUNE CELLS THERAPY

CROSS-REFERENCE TO RELATED APPLICATIONS

This application is a divisional of U.S. application Ser. No. 16/340,222 filed on Apr. 8, 2019, which is a U.S. Natl. Stage of International Application PCT/EP2017/076798 filed Oct. 19, 2017, which claims the benefit of U.S. provisional application 62/410,187 filed Oct. 19, 2016, and Danish Application PA201670840 filed Oct. 27, 2016.

REFERENCE TO SEQUENCE USING SUBMITTED ELECTRONICALLY

The instant application contains a Sequence Listing which has been submitted electronically in XML file format and is hereby incorporated by reference in its entirety. Said XML copy, created on Dec. 13, 2023, is named D12016-11US2_SL.xml and is 215,538 bytes in size.

FIELD OF THE INVENTION

The invention pertains to the field of adaptive cell immunotherapy. It aims to enhance the functionality of primary immune cells against pathologies that develop immune resistance, such as tumors, thereby improving the therapeutic potential of these immune cells. The method of the invention provides with the genetic insertion of exogenous coding sequence(s) that help the immune cells to direct their immune response against infected or malignant cells. These exogenous coding sequences are more particularly inserted under the transcriptional control of endogenous gene promoters that are up or downregulated upon immune cells activation, upon tumor microenvironment or life threatening inflammatory conditions or promoters that are insensitive to immune cells activation. The invention also provides with sequence-specific endonuclease reagents and donor DNA vectors, such as AAV vectors, to perform such targeted insertions at said particular loci. The method of the invention contributes to improving the therapeutic potential and safety of engineered primary immune cells for their efficient use in cell therapy

BACKGROUND OF THE INVENTION

Effective clinical application of primary immune cell populations including hematopoietic cell lineages has been established by a number of clinical trials over a decade against a range of pathologies, in particular HIV infection and Leukemia (Tristen S. J. et al. (2011) Treating cancer with genetically engineered T cells. *Trends in Biotechnology.* 29(11):550-557).

However, most of these clinical trials have used immune cells, mainly NK and T-cells, obtained from the patients themselves or from compatible donors, bringing some limitations with respect to the number of available immune cells, their fitness, and their efficiency to overcome diseases that have already developed strategies to get around or reduce patient's immune system.

As a primary advance into the procurement of allogeneic immune cells, universal immune cells, available as "off-the-shelf" therapeutic products, have been produced by gene editing (Poirot et al. (2015) Multiplex Genome-Edited T-cell Manufacturing Platform for "Off-the-Shelf" Adoptive T-cell Immunotherapies *Cancer Res.* 75: 3853-64). These universal immune cells are obtainable by expressing specific rare-cutting endonuclease into immune cells originating from donors, with the effect of disrupting, by double strand-break, their self-recognition genetic determinants.

Since the emergence of the first programmable sequence-specific reagents by the turn of the century, initially referred to as Meganucleases (Smith et al. (2006) A combinatorial approach to create artificial homing endonucleases cleaving chosen sequences. *Nucl. Acids Res.* 34 (22):e149), different types of sequence-specific endonucleases reagents have been developed offering improved specificity, safety and reliability.

TALE-nucleases (WO2011072246), which are fusions of a TALE binding domain with a cleavage catalytic domain have been successfully applied to primary immune cells, in particular T-cells from peripheral blood mononuclear cell (PBMC). Such TALE-nucleases, marketed under the name TALEN®, are those currently used to simultaneously inactivate gene sequences in T-cells originating from donors, in particular to produce allogeneic therapeutic T-Cells in which the genes encoding TCR (T-cell receptor) and CD52 are disrupted. These cells can be endowed with chimeric antigen receptors (CAR) for treating cancer patients (US2013/0315884). TALE-nucleases are very specific reagents because they need to bind DNA by pairs under obligatory heterodimeric form to obtain dimerization of the cleavage domain Fok-1. Left and right heterodimer members each recognizes a different nucleic sequences of about 14 to 20 bp, together spanning target sequences of 30 to 50 bp overall specificity.

Other endonucleases reagents have been developed based on the components of the type II prokaryotic CRISPR (Clustered Regularly Interspaced Short palindromic Repeats) adaptive immune system of the bacteria *S. pyogenes*. This multi-component system referred to as RNA-guided nuclease system (Gasiunas, Barrangou et al. 2012; Jinek, Chylinski et al. 2012), involves members of Cas9 or Cpf1 endonuclease families coupled with a guide RNA molecules that have the ability to drive said nuclease to some specific genome sequences (Zetsche et al. (2015). Cpf1 is a single RNA-guided endonuclease that provides immunity in bacteria and can be adapted for genome editing in mammalian cells. *Cell* 163:759-771). Such programmable RNA-guided endonucleases are easy to produce because the cleavage specificity is determined by the sequence of the RNA guide, which can be easily designed and cheaply produced. The specificity of CRISPR/Cas9 although stands on shorter sequences than TAL-nucleases of about 10 pb, which must be located near a particular motif (PAM) in the targeted genetic sequence. Similar systems have been described using a DNA single strand oligonucleotide (DNA guide) in combination with Argonaute proteins (Gao, F. et al. DNA-guided genome editing using the *Natronobacterum gregoryi* Argonaute (2016) doi:10.1038/nbt.3547).

Other endonuclease systems derived from homing endonucleases (ex: I-OnuI, or I-CreI), combined or not with TAL-nuclease (ex: MegaTAL) or zing-finger nucleases have also proven specificity, but to a lesser extend so far.

In parallel, novel specificities can be conferred to immune cells through the genetic transfer of transgenic T-cell receptors or so-called chimeric antigen receptors (CARs) (Jena et al. (2010) Redirecting T-cell specificity by introducing a tumor-specific chimeric antigen receptor. *Blood.* 116:1035-1044). CARs are recombinant receptors comprising a targeting moiety that is associated with one or more signaling domains in a single fusion molecule. In general, the binding moiety of a CAR consists of an antigen-binding domain of a single-chain antibody (scFv), comprising the light and heavy variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), ICOS and 4-1BB (CD137) have been added alone (second generation) or in combination (third generation) to enhance survival and increase proliferation of CAR modified T cells. CARs have successfully allowed T cells to be redirected against antigens expressed at the surface of tumor cells from various malignancies including lymphomas and solid tumors.

Recently engineered T-cells disrupted in their T-cell receptor (TCR) using TALE-nucleases, endowed with chimeric antigen receptor (CAR) targeting CD19 malignant antigen, referred to as "UCART19" product, have shown therapeutic potential in at least two infants who had refractory leukemia (Leukaemia success heralds wave of gene-editing therapies (2015) *Nature* 527:146-147). To obtain such UCART19 cells, the TALE-nuclease was transiently expressed into the cells upon electroporation of capped mRNA to operate TCR gene disruption, whereas a cassette encoding the chimeric antigen receptor (CAR CD19) was introduced randomly into the genome using a retroviral vector.

In this later approach, the steps of gene inactivation and of expressing the chimeric antigen receptor are independently performed after inducing activation of the T-Cell "ex-vivo".

However, engineering primary immune cells is not without any consequences on the growth/physiology of such cells. In particular one major challenge is to ovoid cells exhaustion/anergy that significantly reduces their immune reaction and life span. This is more likely to happen when the cells are artificially activated ahead of their infusion into the patient. It is also the case when a cell is endowed with a CAR that is too reactive.

To avoid these pitfalls, the inventors have thought about taking advantage of the transcriptional regulation of some key genes during T-cell activation to express exogenous genetic sequences increasing the therapeutic potential of the immune cells. The exogenous genetic sequences to be expressed or co-expressed upon immune cell activation are introduced by gene targeted insertion using sequence-specific endonuclease reagents, so that their coding sequences are transcribed under the control of the endogenous promoters present at said loci. Alternatively, loci that are not expressed during immune cell activation can be used as "safe-harbor loci" for the integration of expression cassettes without any adverse consequences on the genome.

These cell engineering strategies, as per the present invention, tend to reinforce the therapeutic potential of primary immune cells in general, in particular by increasing their life span, persistence and immune activity, as well as by limiting cell exhaustion. The invention may be carried out on primary cells originating from patients as part of autologous treatment strategies, as well as from donors, as part of allogeneic treatment strategies.

SUMMARY OF THE INVENTION

Non-homologous end-joining (NHEJ) and homology-directed repair (HDR) are the two major pathways used to repair in vivo DNA breaks. The latter pathway repairs the break in a template-dependent manner (HDR naturally utilizes the sister chromatid as a DNA repair template). Homologous recombination has been used for decades to precisely edit genomes with targeted DNA modifications using exogenously supplied donor template. The artificial generation of a double strand break (DSB) at the target location using rare-cutting endonucleases considerably enhances the efficiency of homologous recombination (e.g. U.S. Pat. No. 8,921,332). Also the co-delivery of a rare-cutting endonuclease along with a donor template containing DNA sequences homologous to the break site enables HDR-based gene editing such as gene correction or gene insertion. However, such techniques have not been widely used in primary immune cells, especially CAR T-cells, due to several technical limitations: difficulty of transfecting DNA into such types of cells leading to apoptosis, immune cells have a limited life span and number of generations, homologous recombination occurs at a low frequency in general.

So far, sequence specific endonuclease reagents have been mainly used in primary immune cells for gene inactivation (e.g. WO2013176915) using the NHEJ pathway.

In a general aspect, the present invention relies on performing site directed gene editing, in particular gene insertion (or multi gene insertions) in a target cell in order to have the integrated gene transcription be under the control of an endogenous promoter.

In a general aspect the invention relies on performing gene editing in primary immune cells to have integrated genes transcription be under the control of an endogenous promoter while maintaining the expression of the native gene through the use of cis-regulatory elements (e.g. 2A cis-acting hydrolase elements) or of internal ribosome entry site (IRES) in the donor template.

In a general aspect the invention relies, as non-limiting examples, on controlling the expression, in primary T-cells, of chimeric antigen receptors (CAR), of critical cytokines to drive an anti-tumor response, of stimulatory cytokines to increase proliferative potential, of chemokine receptors to encourage trafficking to the tumor, or of different protective or inhibitory genes to block the immune inhibition provided by the tumor. Indeed, one major advantage of the present invention is to place such exogenous sequences under control of endogenous promoters, which transcriptional activity is not reduced by the effects of the immune cells activation.

By contrast to previous method for engineering therapeutic immune cells, where for instance an exogenous coding sequence was integrated and expressed at the TCR locus for constitutive gene expression, the inventors have integrated coding sequence at loci, which are specifically transcribed during T-cells activation, preferably on a CAR dependent fashion.

In one aspect, the invention relies on expressing a chimeric antigen receptor (CAR) at selected gene loci that are upregulated upon immune cells activation. The exogenous sequence(s) encoding the CAR and the endogenous gene coding sequence (s) may be co-transcribed, for instance by being separated by cis-regulatory elements (e.g. 2A cis-acting hydrolase elements) or by an internal ribosome entry site (IRES), which are also introduced. For instance, the exogenous sequences encoding a CAR can be placed under transcriptional control of the promoter of endogenous genes that are activated by the tumor microenvironment, such as HIF1a, transcription factor hypoxia-inducible factor, or the aryl hydrocarbon receptor (AhR), which are gene sensors respectively induced by hypoxia and xenobiotics in the close environment of tumors.

The present invention is thus useful to improve the therapeutic outcome of CAR T-cell therapies by integrating exogenous genetic attributes/circuits under the control of endogenous T-cell promoters influenced by tumor microenvironment (TME). TME features, including as non-limiting examples, arginine, cysteine, tryptophan and oxygen deprivation as well as extracellular acidosis (lactate build up), are known to upregulate specific endogenous genes. Pursuant to the invention, upregulation of endogenous genes can be "hijacked" to re-express relevant exogenous coding sequences to improve the antitumor activity of CAR T-cells in certain tumor microenvironment.

In preferred embodiments, the method of the invention comprises the step of generating a double-strand break at a locus highly transcribed under tumor microenvironment, by expressing sequence-specific nuclease reagents, such as TALEN, ZFN or RNA-guided endonucleases as non-limiting examples, in the presence of a DNA repair matrix preferably set into an AAV6 based vector. This DNA donor template generally includes two homology arms embedding unique or multiple Open Reading Frames and regulatory genetic elements (stop codon and polyA sequences) referred to herein as exogenous coding sequences.

In another aspect, said exogenous sequence is introduced into the genome by deleting or modifying the endogenous coding sequence(s) present at said locus (knock-out by knock-in), so that a gene inactivation is combined with transgenesis.

Depending on the locus targeted and its involvement in immune cells activity, the targeted endogenous gene may be inactivated or maintained in its original function. Should the targeted gene be essential for immune cells activity, this insertion procedure can generate a single knock-in (KI) without gene inactivation. In the opposite, if the targeted gene is deemed involved in immune cells inhibition/exhaustion, the insertion procedure is designed to prevent expression of the endogenous gene, preferably by knocking-out the endogenous sequence, while enabling expression of the introduced exogenous coding sequence(s).

In more specific aspects, the invention relies on upregulating, with various kinetics, the target gene expression upon activation of the CAR signalling pathway by targeted integration (with or without the native gene disruption) at the specific loci such as, as non-limiting example, PD1, PDL1, CTLA-4, TIM3, LAG3, TNFa or IFNg.

In an even more specific aspect, it is herein described engineered immune cells, and preferably primary immune cells for infusion into patients, comprising exogenous sequences encoding IL-15 or IL-12 polypeptide(s), which are integrated at the PD1, CD25 or CD69 endogenous locus for their expression under the control of the endogenous promoters present at these loci.

The immune cells according to the present invention can be [CAR]$^{positive}$, [CAR]$^{negative}$, [TCR]$^{positive}$, or [TCR]$^{negative}$, depending on the therapeutic indications and recipient patients. In one preferred aspect, the immune cells are further made [TCR]$^{negative}$ for allogeneic transplantation. This can be achieved especially by genetic disruption of at least one endogenous sequence encoding at least one component of TCR, such as TRAC (locus encoding TCRalpha), preferably by integration of an exogenous sequence encoding a chimeric antigen receptor (CAR) or a recombinant TCR, or component(s) thereof.

According to a further aspect of the invention, the immune cells are transfected with an exogenous sequence coding for a polypeptide which can associate and preferably interfere with a cytokine receptor of the IL-6 receptor family, such as a mutated GP130, In particular, the invention provides immune cells, preferably T-cells, which secrete soluble mutated GP130, aiming at reducing cytokine release syndrome (CRS) by interfering, and ideally block, interleukine-6 (IL-6) signal transduction. CRS is a well-known complication of cell immunotherapy leading to auto immunity that appears when the transduced immune cells start to be active in-vivo. Following binding of IL-6 to its receptor IL-6R, the complex associate with the GP130 subunit, initiating signal transduction and a cascade of inflammatory responses. According to a particular aspect, a dimeric protein comprising the extracellular domain of GP130 fused to the Fc portion of an IgG1 antibody (sgp130Fc) is expressed in the engineered immune cells to bind specifically soluble IL-R/IL-6 complex to achieve partial or complete blockade of IL-6 trans signaling. The present invention thus refers to a method for limiting CRS in immunotherapy, wherein immune cells are genetically modified to express a soluble polypeptide which can associate and preferably interfere with a cytokine receptor of the IL-6 receptor family, such as sgp130Fc. According to a preferred aspect, this sequence encoding said soluble polypeptide which can associate and preferably interfere with a cytokine receptor of the IL-6 receptor family, is integrated under control of an endogenous promoter, preferably at one locus responsive to T-cells activation, such as one selected from Tables 6, 8 or 9, more especially PD1, CD25 or CD69. Polynucleotide sequences of the vectors, donor templates comprising the exogenous coding sequences and/or sequences homologous to the endogenous loci, the sequences pertaining to the resulting engineered cells, as well as those permitting the detection of said engineered cells are all part of the present disclosure.

In a general aspect the invention relies, as non-limiting examples, on controlling the expression of components of biological "logic gates" ("AND" or "OR" or "NOT" or any combination of these) by targeted integration of genes. Similar to the electronic logic gates, cellular components expressed at different loci can exchange negative and positive signals that rule, for instance, the conditions of activation of an immune cell. Such component encompasses as non-limiting examples positive and negative chimeric antigen receptors that may be used to control T-cell activation and the resulting cytotoxicity of the engineered T-cells in which they are expressed.

According to a preferred embodiment, the invention relies on introducing the sequence specific endonuclease reagent and/or the donor template containing the gene of interest and sequences homologous to the target gene by transfecting ssDNA (oligonucleotides as non-limiting example), dsDNA (plasmid DNA as non-limiting example), and more particularly adeno-associated virus (AAV) as non-limiting example.

The invention also relates to the vectors, donor templates, reagents and resulting engineered cells pertaining to the above methods, as well as their use in therapy.

BRIEF DESCRIPTION OF THE FIGURES AND TABLES

FIG. 1: Strategies for engineering hematopoietic stem cells (HSCs) by introducing exogenous sequences at specific loci under transcriptional control of endogenous promoters specifically activated in specific immune cell types. The figure lists examples of specific endogenous genes, at which loci the exogenous coding sequence(s) can be inserted for expression in the desired hematopoietic lineages as per the present invention. The goal is to produce ex-vivo engineered HSCs to be engrafted into patients, in order for them to produce immune cells in-vivo, which will express selected transgenes while they get differentiated into a desired lineage.

Figure 2:
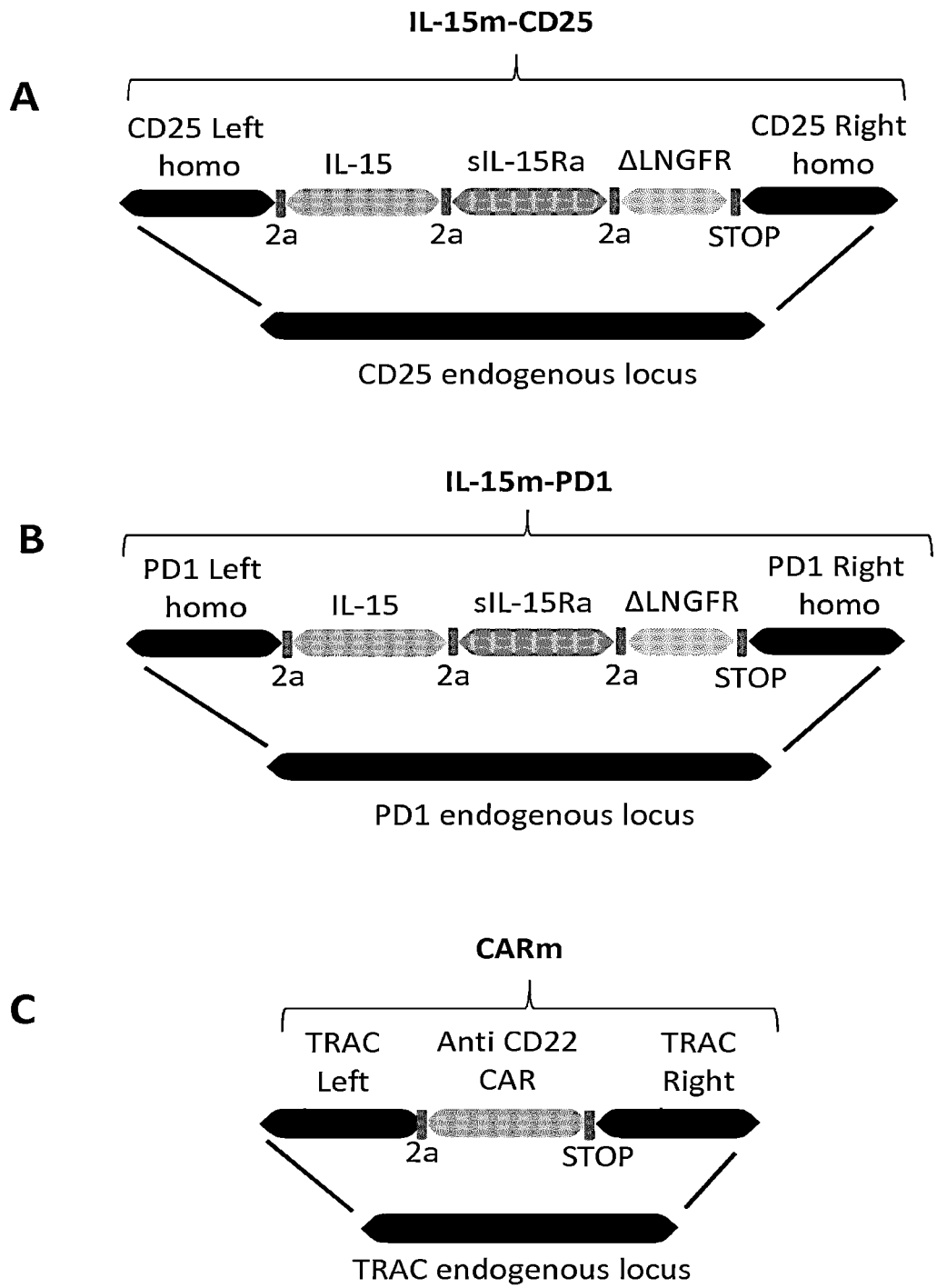

FIG. 2: Schematic representation of the donor sequences used in the experimental section to insert IL-15 exogenous coding sequence at the CD25 and PD1 loci and also the anti-CD22 CAR exogenous coding sequence at the TRAC locus. A: donor template (designated IL-15m-CD25) designed for site directed insertion of IL-15 at the CD25 locus for obtaining co-transcription of CD25 and IL-15 polypeptides by the immune cell. Sequences are detailed in the examples. B: donor template (designated IL-15m-PD1) designed for site directed insertion of IL-15 at the PD1 locus for obtaining transcription of IL-15 under the transcriptional activity of the promoter of PD1 endogenous gene. The PD1 right and Left border sequences can be selected so as to keep the PD1 endogenous coding sequence intact or disrupted. In this later case, PD1 is knocked-out while IL-15 is Knocked-in and transcribed. C: donor template designed for site directed insertion of a chimeric antigen receptor (ex: anti-CD22 CAR) into the TCR locus (ex: TRAC). In general, the left and right borders are chosen so as to disrupt the TCR in order to obtain $[TCR]^{neg}[CAR]^{pos}$ engineered immune cells suitable for allogeneic transplant into patients.

Figure 3:
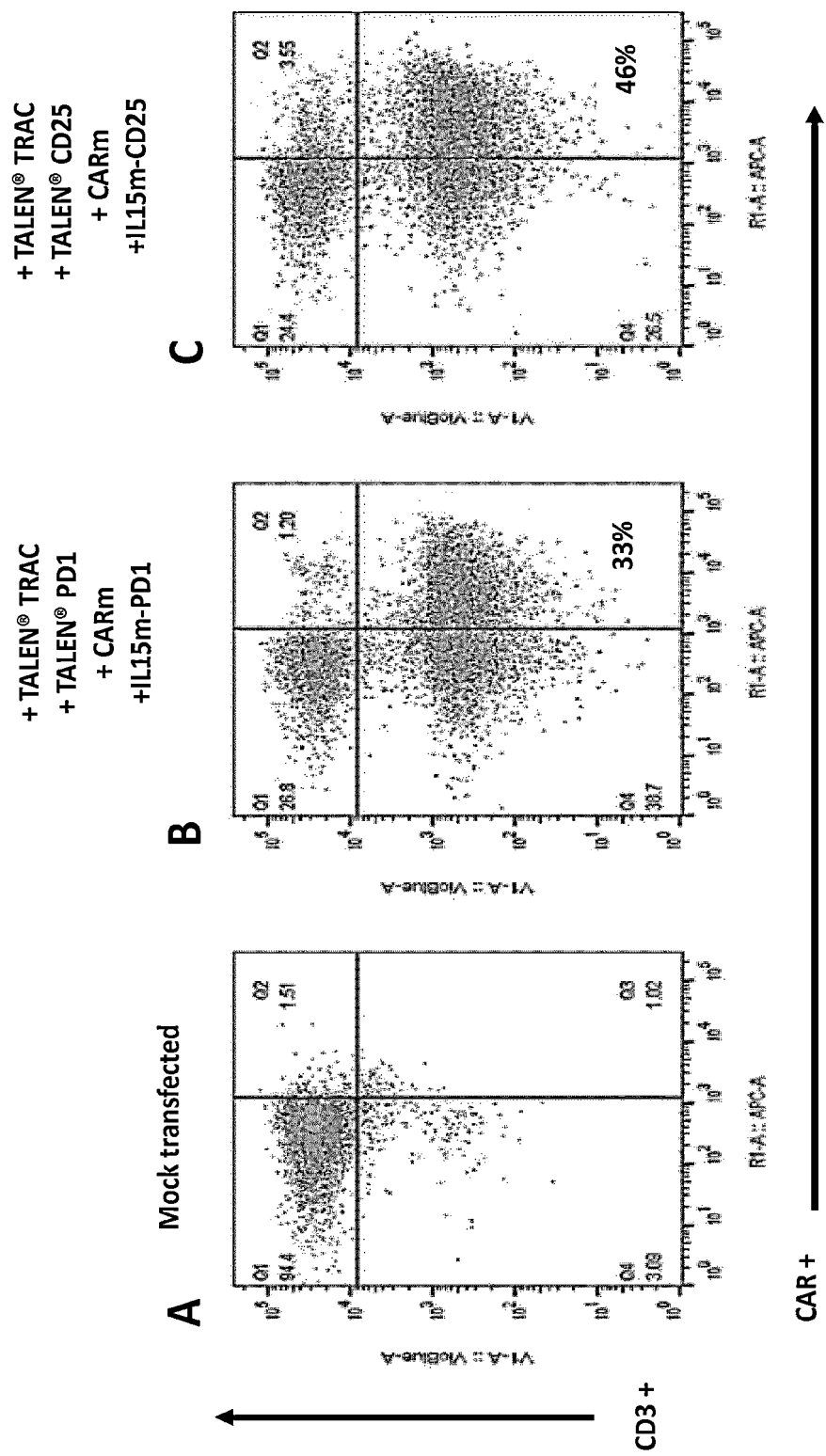

FIG. 3: Flow cytometry measures of the frequency of targeted integration of IL-15m at either the PD1 or CD25 locus by using respectively PD1 or CD25 TALEN®, in a context where an anti-CD22 CAR is also integrated at the TRAC locus using TRAC TALEN®. These results show efficient targeted integration of both the CAR anti-CD22 at the TRAC locus together and the IL-15 coding sequence at the PD1 or CD25 loci. A: mock transfected primary T-cells. B: primary T-cells transfected with the donor sequences described in FIGS. 1 (B and C) and specific TALEN® for the double integration at the TCR and PDI loci. C: primary T-cells transfected with the donor sequences described in FIG. 1 (A and C) and specific TALEN® for the double integration at the TCR and CD25 loci.

Figure 4:
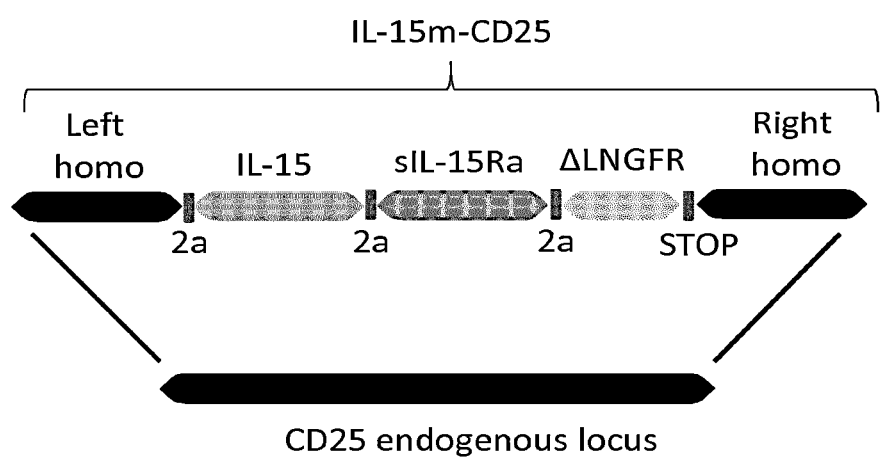
Figure 4:
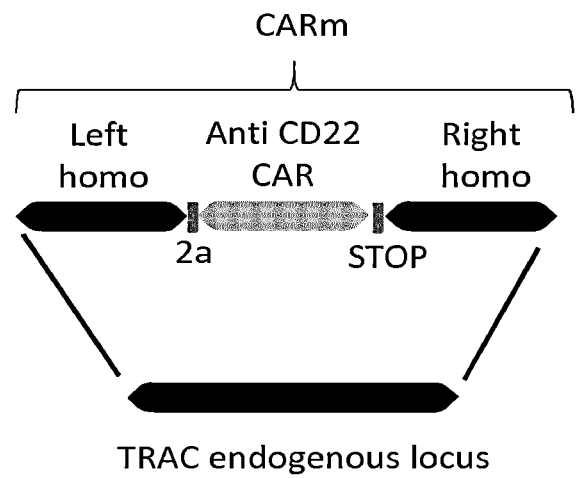

FIG. 4: Schematic representation of the exogenous sequences used in the experimental section to transfect the primary immune cells to obtain the results shown in FIGS. 5 and 6.

Figure 5:
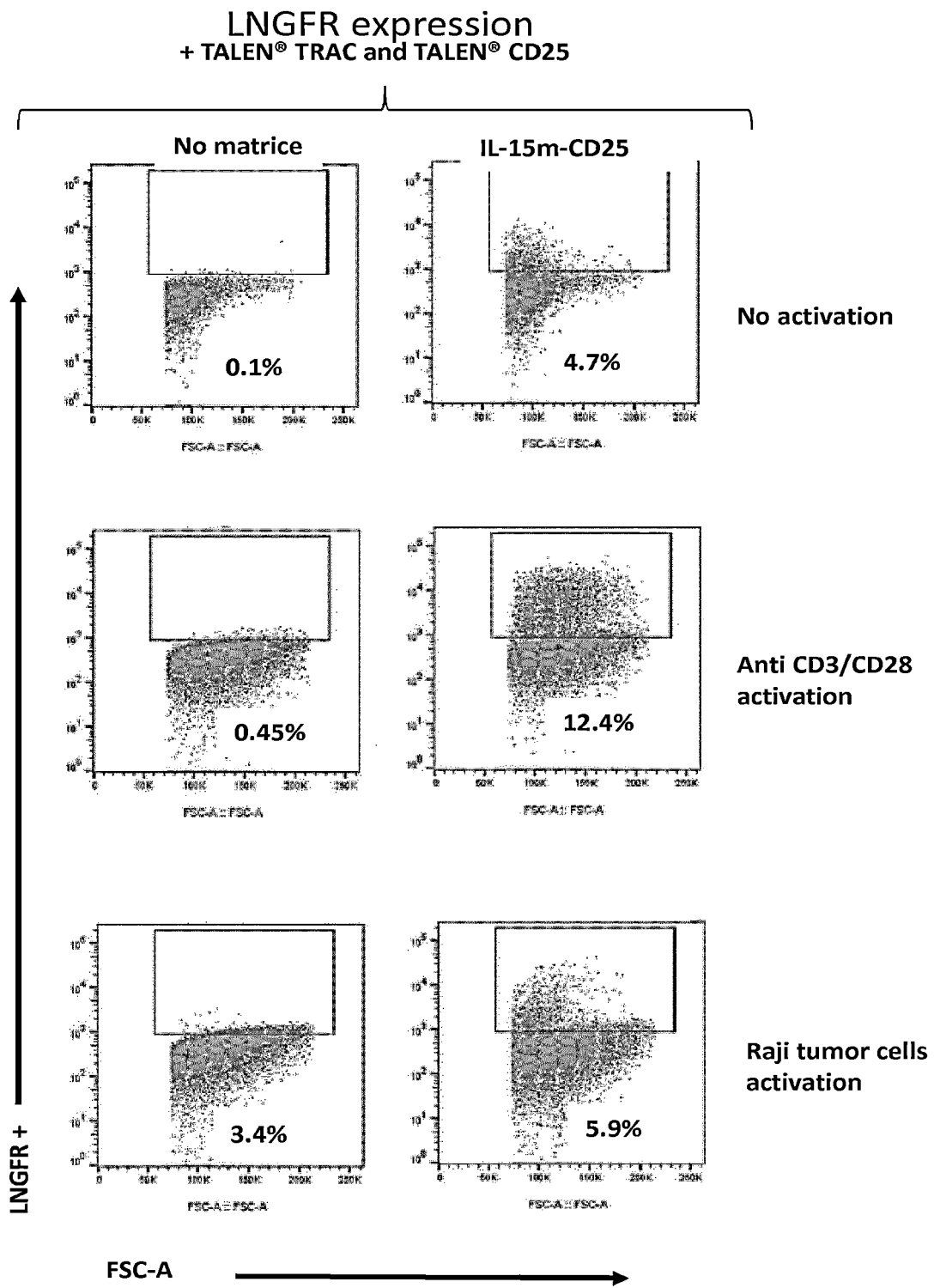
Figure 6:
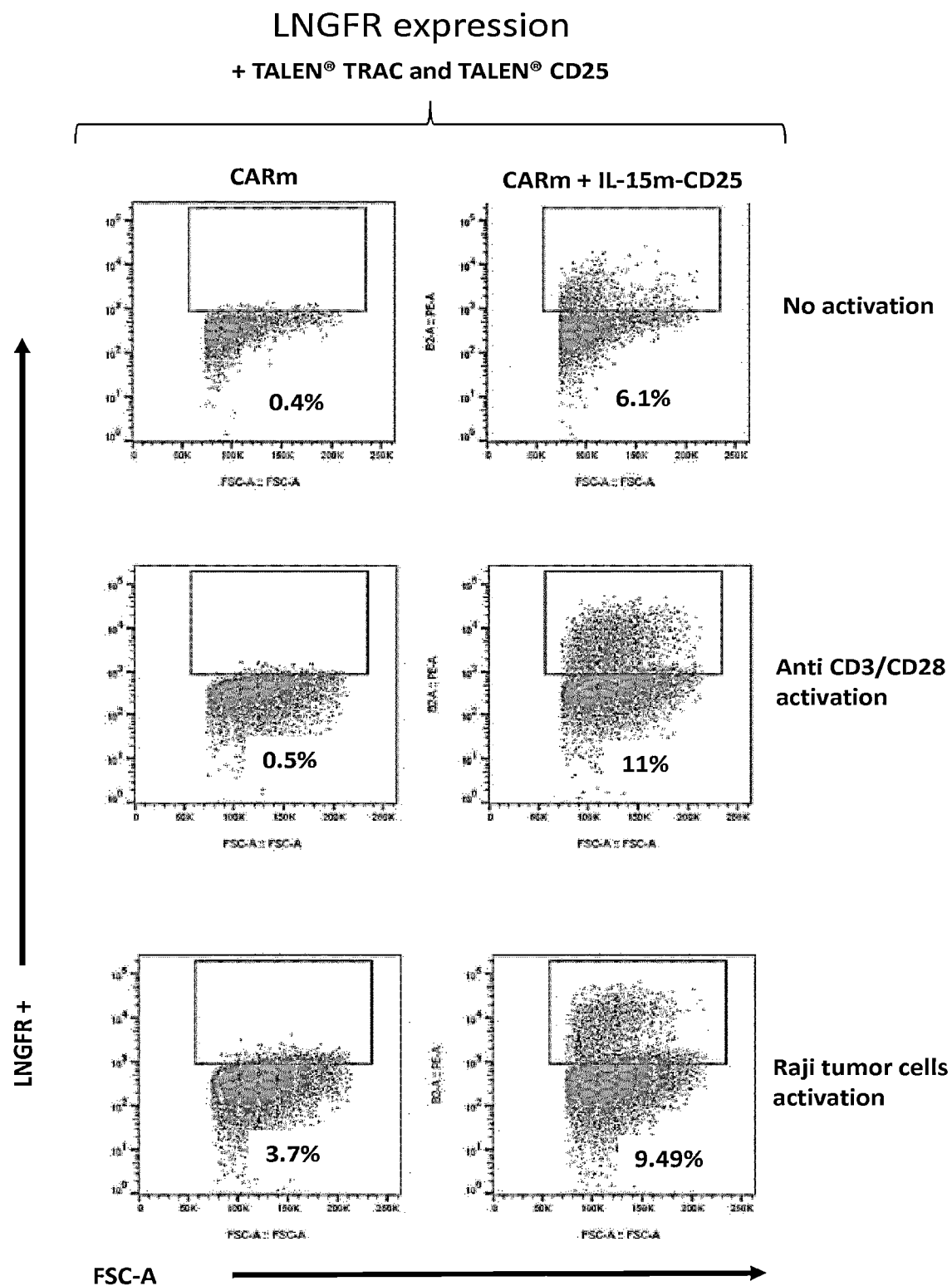

FIGS. 5 and 6: Flow cytometry measures for LNGFR expression among viable T-cells transfected with donor templates of FIG. 4 and specific TALEN® (TCR and CD25), upon antiCD3/CD28 non-specific activation (Dynabeads®) and upon CAR dependent tumor cell activation (raji tumor cells). As shown in FIG. 6, LNGFR expression was specifically induced in $[CAR\ anti-CD22]^{positive}$ cells upon CAR/tumor engagement.

Figure 7:
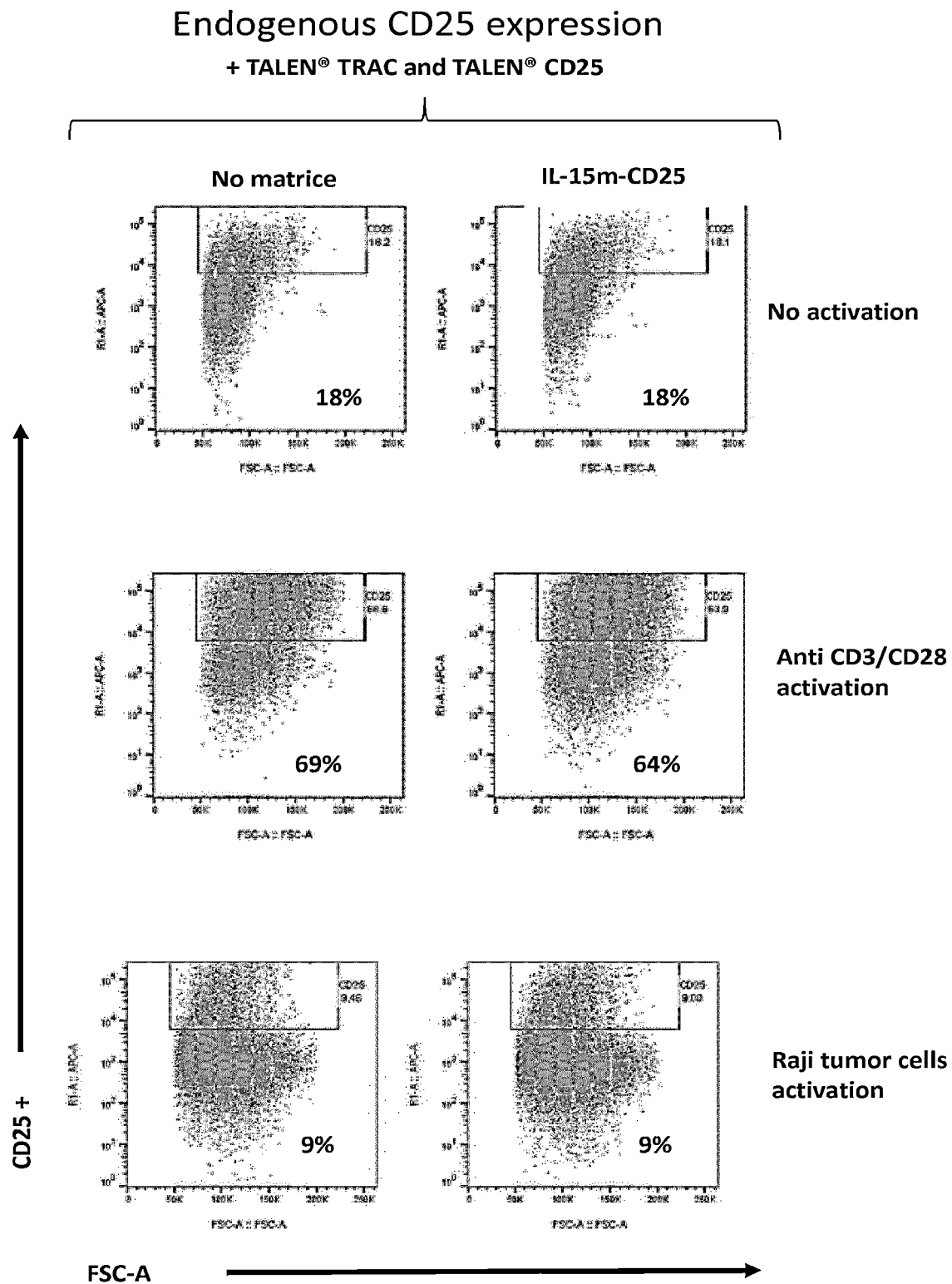
Figure 8:
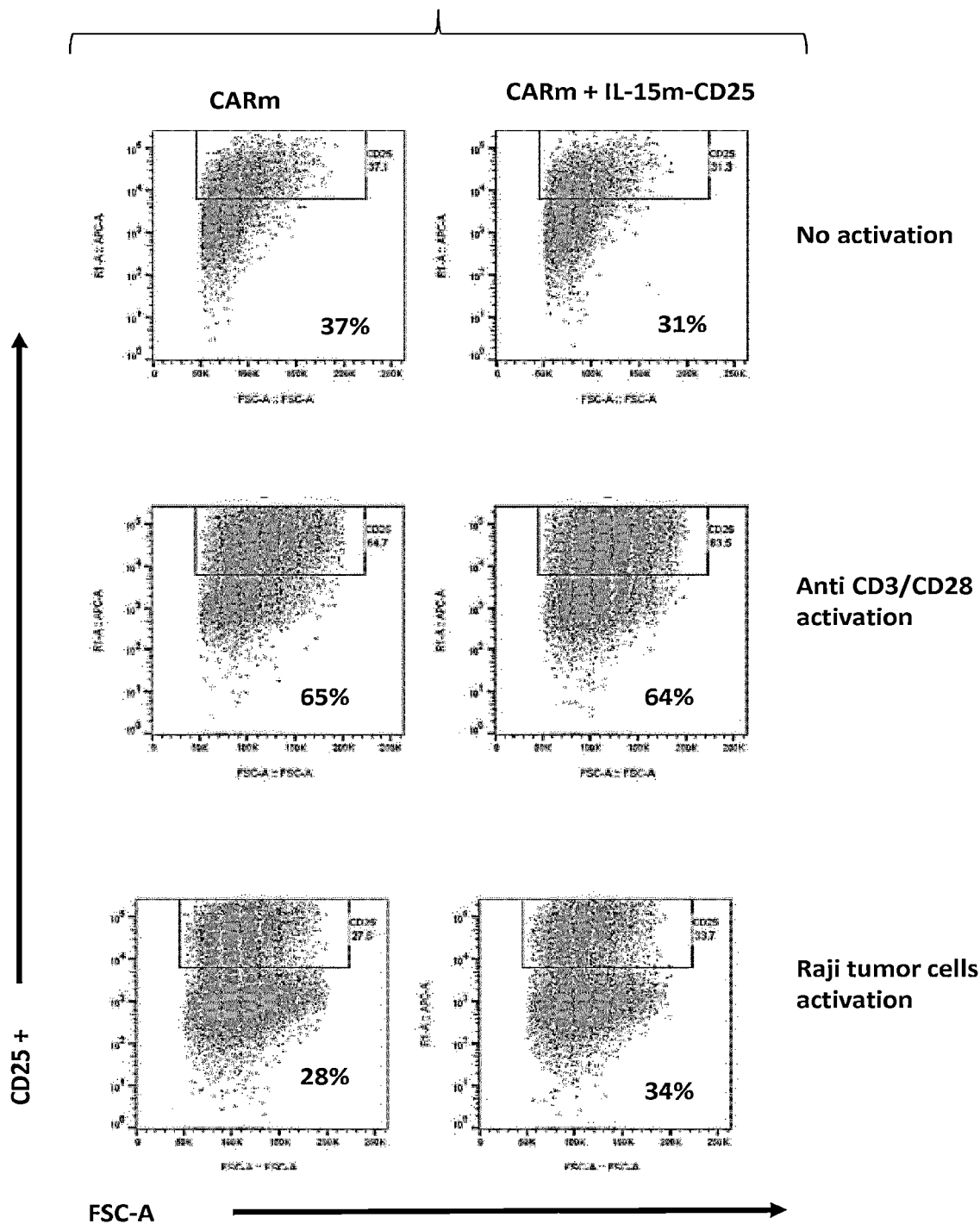

FIGS. 7 and 8: Flow cytometry measures for CD25 expression among viable T-cells transfected with donor templates of FIG. 4 and specific TALEN® (TCR and CD25) upon antiCD3/CD28 non-specific activation (Dynabeads®) and Tumor cell activation (raji tumor cells). As shown in FIG. 8, CD25 expression was specifically induced in $[CAR\ anti-CD22]^{positive}$ cells upon CAR/tumor engagement.

Figure 9:
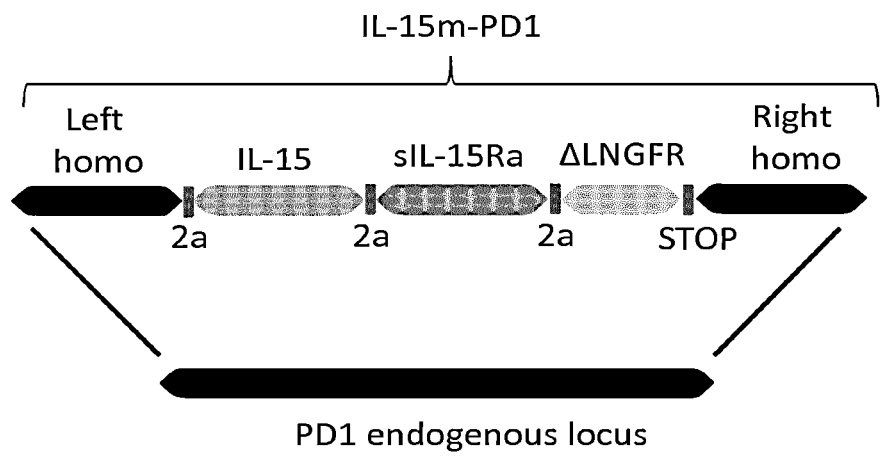
Figure 9:
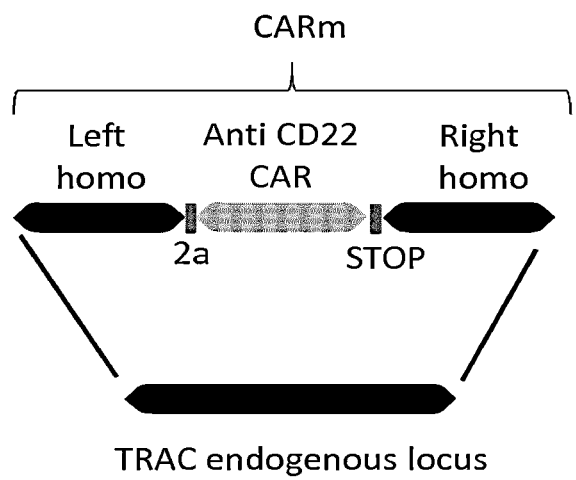

FIG. 9: Schematic representation of the exogenous sequences used in the experimental section to transfect the primary immune cells to obtain the results shown in FIGS. 11 and 12.

Figure 10:
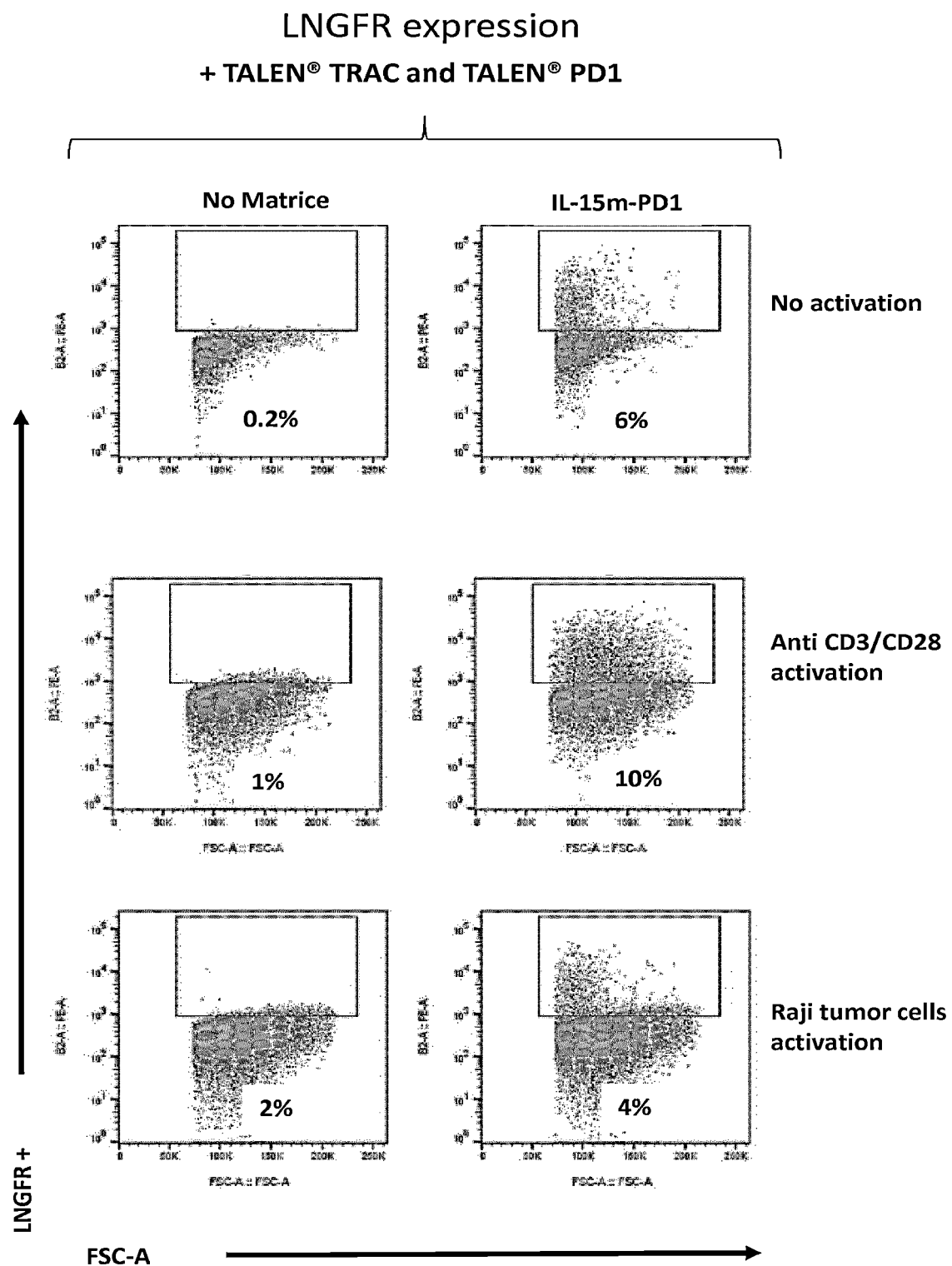
Figure 11:
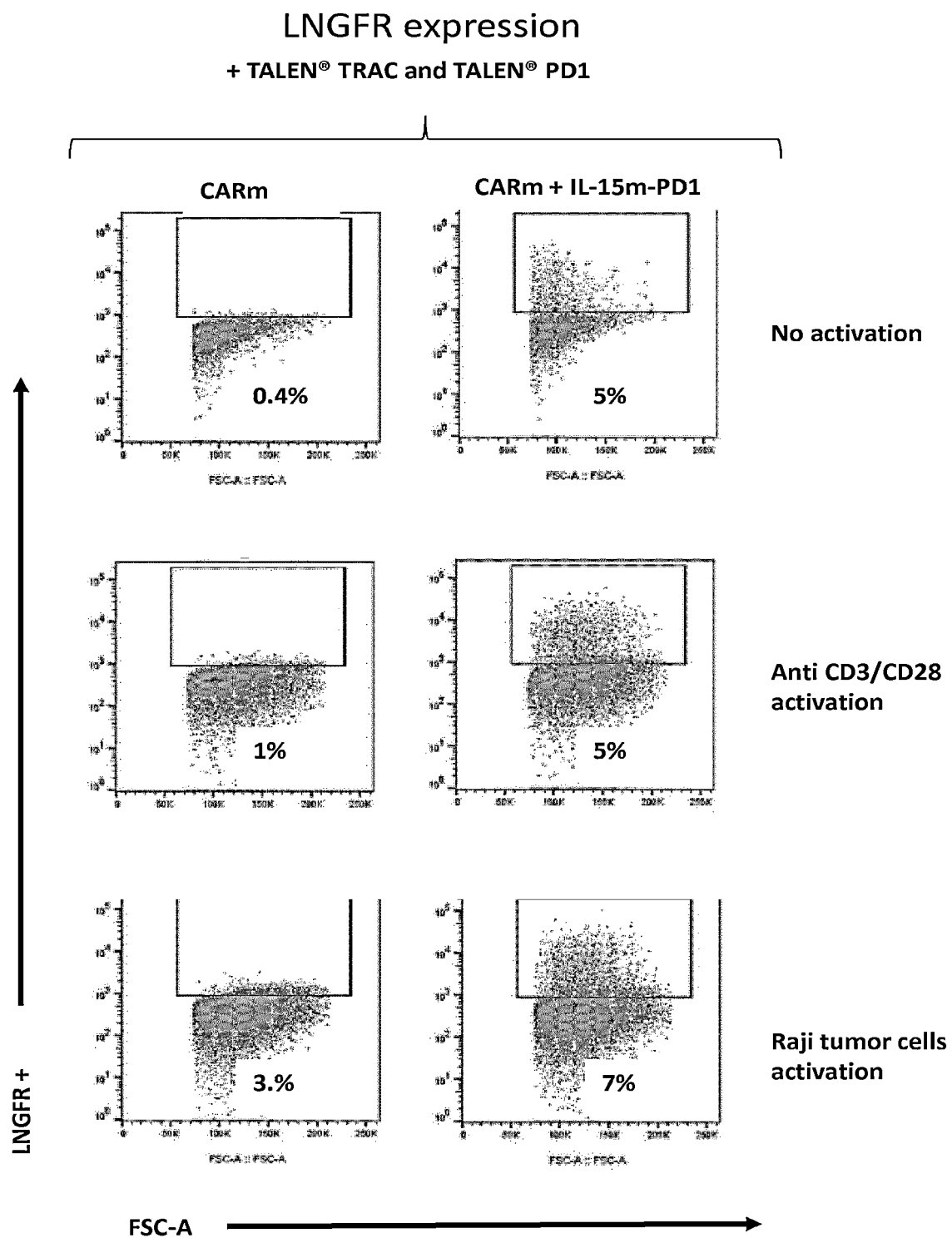

FIGS. 10 and 11: Flow cytometry measures for LNGFR expression among viable T-cells transfected with donor templates of FIG. 9 and specific TALEN® (TCR and PD1) upon antiCD3/CD28 non-specific activation (Dynabeads®) and Tumor cell activation (raji tumor cells). As shown in FIG. 11, LNGFR expression was specifically induced in $[CAR\ anti-CD22]^{positive}$ cells upon CAR/tumor engagement.

Figure 12:
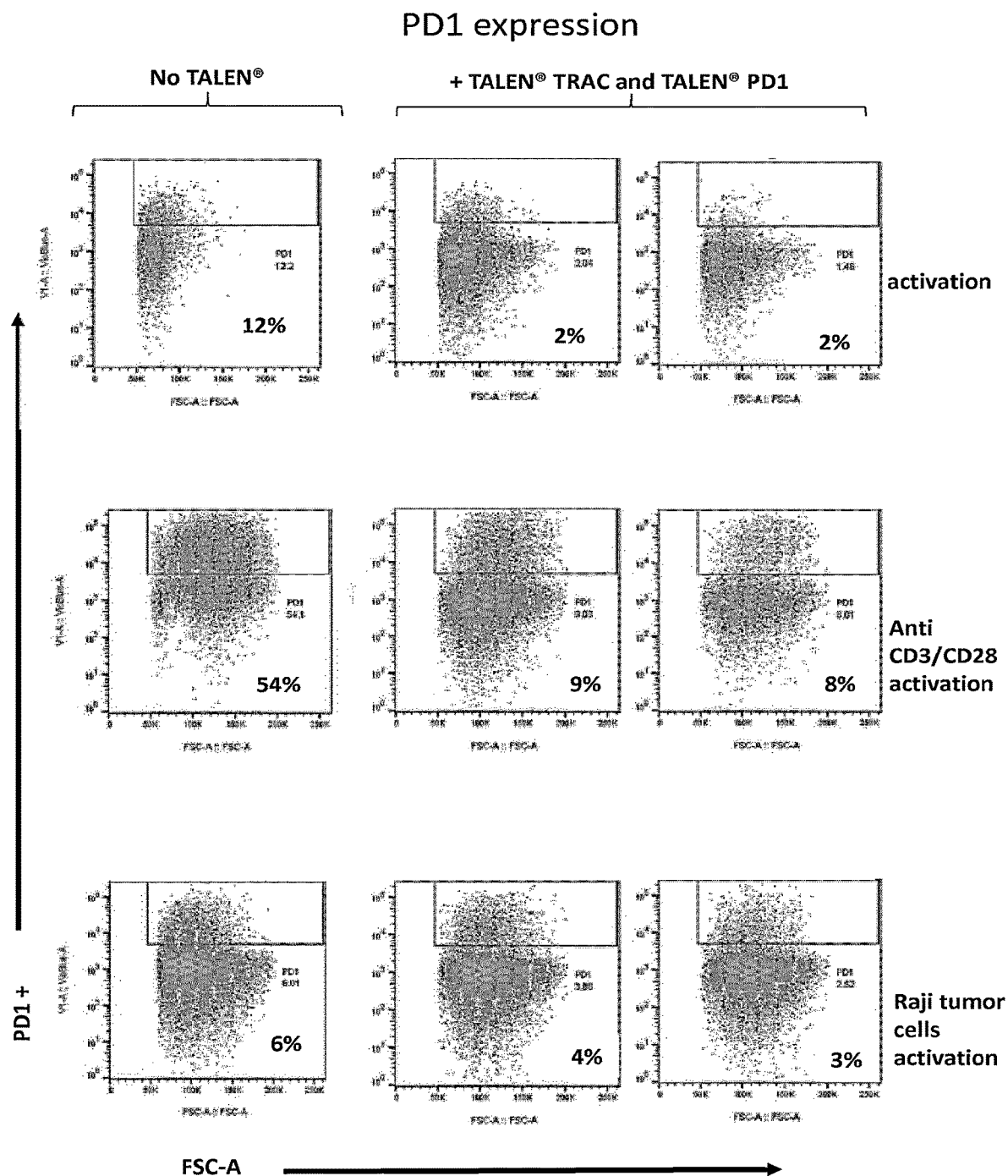

FIG. 12: Flow cytometry measures for endogenous PD1 expression among viable T-cells transfected with donor templates of FIG. 9 upon antiCD3/CD28 non-specific activation (Dynabeads®) and Tumor cell activation (raji tumor cells) with and without using TALEN® (TCR and PD1). PD1 was efficiently Knocked-out by TALEN treatment (8% remaining expression of PD1 out of 54%).

Figure 13:
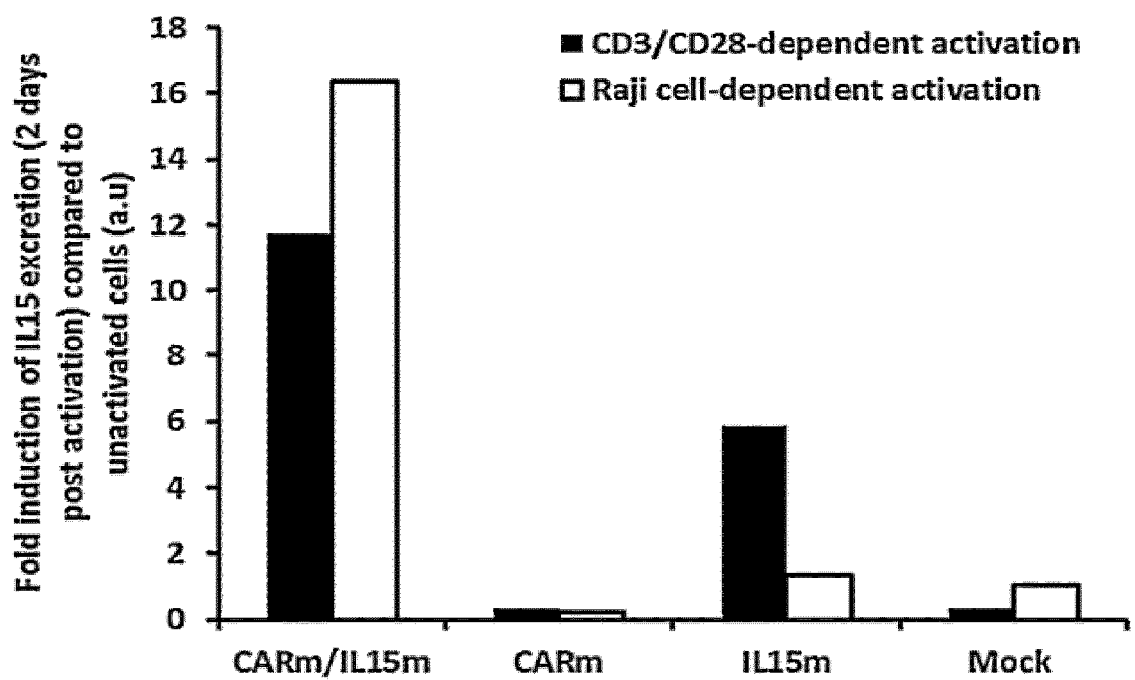

FIG. 13: Diagram showing IL-15 production in $[CAR]^{positive}$ (CARm) and $[CAR]^{negative}$ engineered immune cells according to the invention transfected with the donor template described in FIG. 2 (B) and TALEN® for insertion of IL-15 exogenous coding sequences into the PD1 locus. IL15, which transcription was under control of endogenous PD1 promoter, was efficiently induced upon antiCD3/CD28 non-specific activation (Dynabeads®) and Tumor cell activation (raji tumor cells) and secreted in the culture media.

Figure 14:
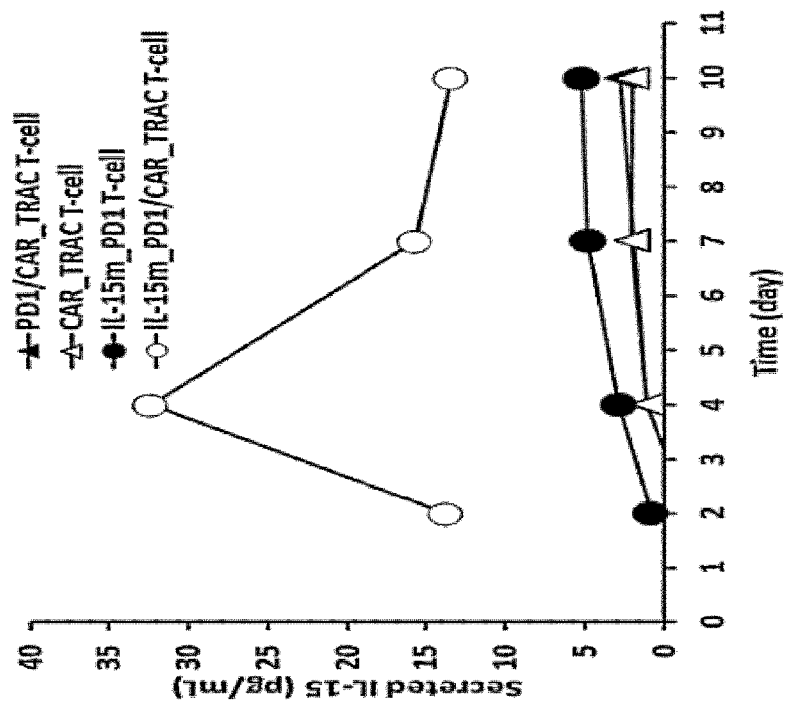
Figure 14:
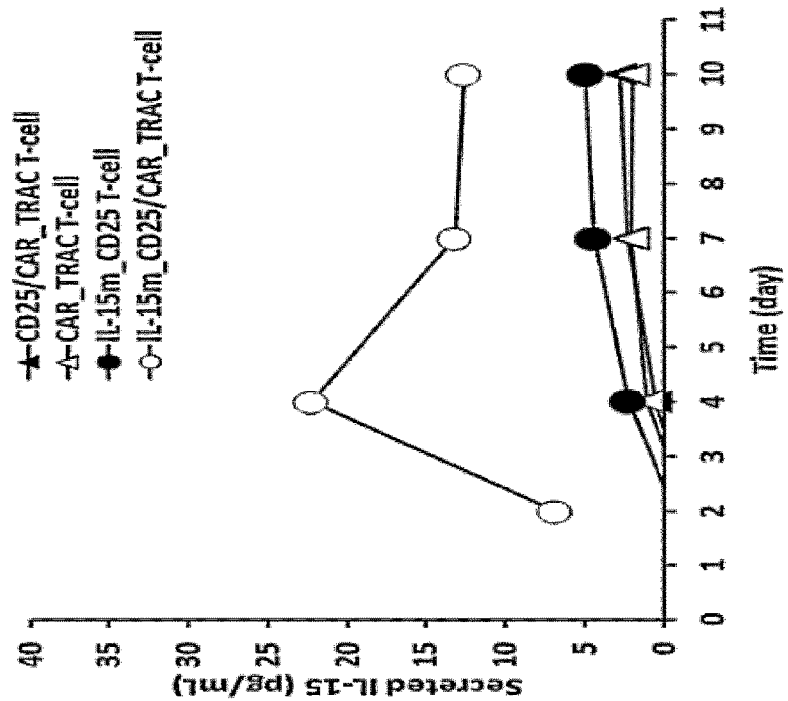

FIG. 14: Graph showing the amount of IL-15 secreted over time (days) post activation by the immune cells engineered according to the invention. A: Cells engineered by integration of the IL-15 coding sequence at the CD25 locus using the DNA donor templates described in FIGS. 2A (IL-15m_CD25) and/or 2C (CARm). B: Cells engineered by integration of the IL-15 coding sequence at the PD1 locus using the DNA donor templates described in FIGS. 2B (IL-15m_PD1) and/or 2C (CARm). Integrations at both loci show similar IL-15 secretion profiles. Secretion of IL-15 is significant increased by tumor specific activation of CAR.

Figure 15:
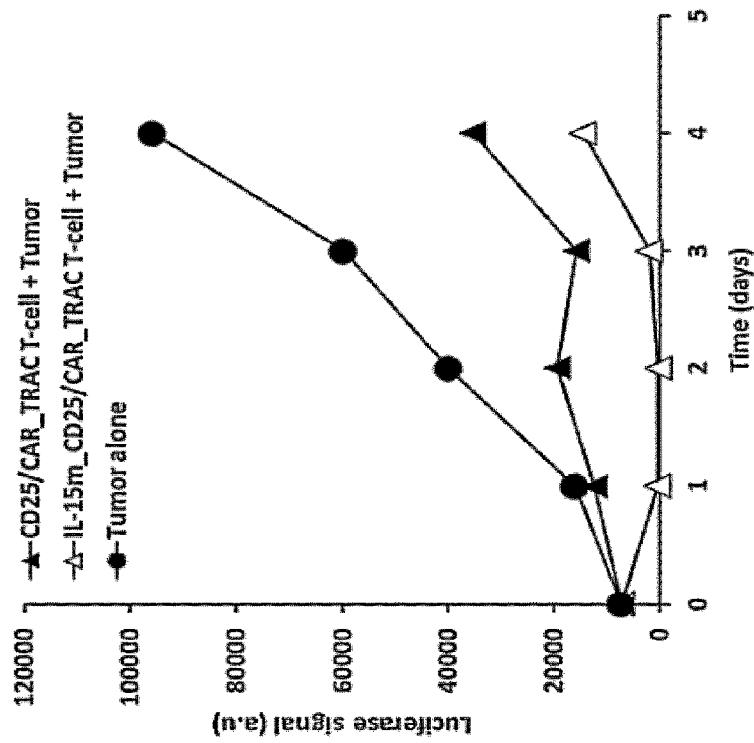
Figure 15:
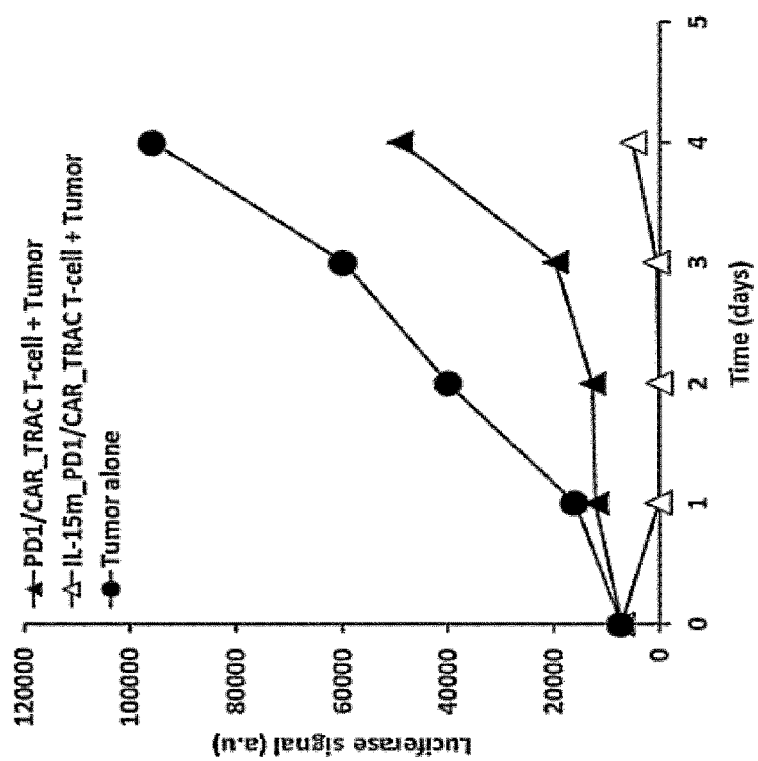

FIG. 15: Graph reporting number of Raji-Luc tumor cells expressing CD22 antigen (luciferase signal) over time in a survival assay (serial killing assay) as described in Example 2. The immune cells (PBMCs) have been engineered to integrate IL-15 coding sequences at the PD1 (A) or CD25 locus (B) and to express anti-CD22-CAR at the TCR locus (thereby disrupting TCR expression). In this assay, tumor cells are regularly added to the culture medium, while being partially or totally eliminated by the CAR positive cells. The re-expression of IL-15 at either PD1 or CD25 cells dramatically helps the elimination of the tumor cells by the CAR positive cells.

Figure 16:
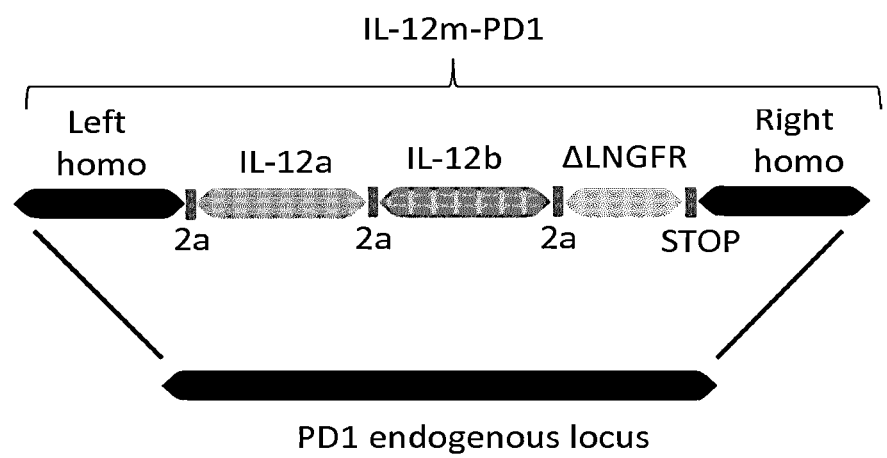
Figure 16:
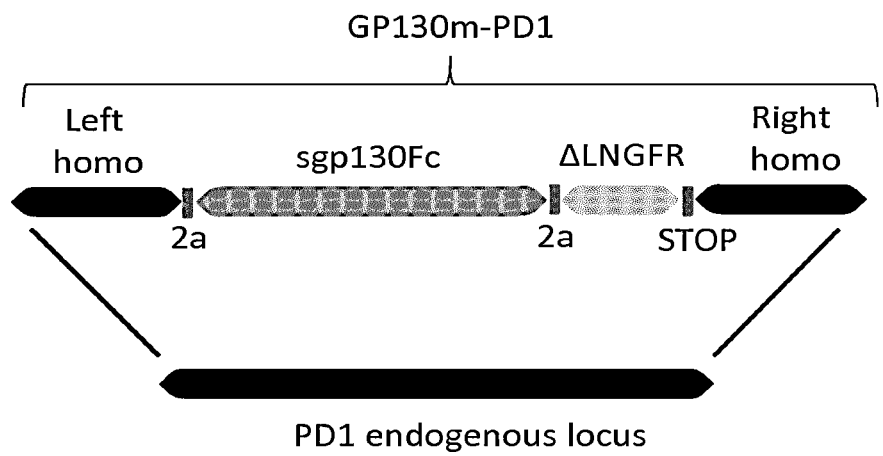

FIG. 16: Schematic representation of the donor sequences used in the experimental section to insert at the PD1 locus the exogenous sequences encoding IL-12 and gp130Fc. A: donor template (designated IL-12m-PD1) designed for site directed insertion of IL-12a and IL-12b coding sequences (SEQ ID NO:47 and 48) at the PD1 locus for obtaining co-transcription of IL-12a and IL-12b, while disrupting PD1 endogenous coding sequence. The right and left border sequences homologous to the PD1 locus sequences are at least 100 pb long, preferably at least 200 pb long, and more preferably at least 300 pb long and comprising SEQ ID NO:45 and 46. Sequences are detailed in Table 5. B: donor template (designated gp130Fcm-PD1) designed for site directed insertion of gp130Fc coding sequences (SEQ ID NO:51) for obtaining transcription at the PD1 locus under PD1 promoter, while disrupting PD1 endogenous coding sequence. The right and left border sequences homologous to the PD1 locus sequences are at least 100 pb long, preferably at least 200 pb long, and more preferably at least 300 pb long and comprising SEQ ID NO:45 and 46. Sequences are detailed in Table 5.

Table 1: ISU domain variants from diverse viruses.

Table 2: Amino acid sequences of FP polypeptide from natural and artificial origins.

Table 3: List of genes involved into immune cells inhibitory pathways, which can be advantageously modified or inactivated by inserting exogenous coding sequence according to the invention.

Table 4: sequences referred to in example 1.

Table 5: sequences referred to in example 2.

Table 6: List of human genes that are up-regulated upon T-cell activation (CAR activation sensitive promoters), in which gene targeted insertion is sought according to the present invention to improve immune cells therapeutic potential.

Table 7: Selection of genes that are steadily transcribed during immune cell activation (dependent or independent from T-cell activation).

Table 8: Selection of genes that are transiently upregulated upon T-cell activation.

Table 9: Selection of genes that are upregulated over more than 24 hours upon T-cell activation.

Table 10: Selection of genes that are down-regulated upon immune cell activation.

Table 11: Selection of genes that are silent upon T-cell activation (safe harbor gene targeted integration loci).

Table 12: List of gene loci upregulated in tumor exhausted infiltrating lymphocytes (compiled from multiple tumors) useful for gene integration of exogenous coding sequences as per the present invention.

Table 13: List of gene loci upregulated in hypoxic tumor conditions useful for gene integration of exogenous coding sequences as per the present invention.

DETAILED DESCRIPTION OF THE INVENTION

Unless specifically defined herein, all technical and scientific terms used herein have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

The present invention is drawn to a general method of preparing primary immune cells for cell immunotherapy involving gene targeted integration of an exogenous coding sequence into the chromosomal DNA of said immune cells. According to some aspects, this integration is performed in such a way that said coding sequence is placed under the transcriptional control of at least one promoter endogenous to said cells, said endogenous promoter being preferably not a constitutive promoter, such as the one transcribing T-cell receptor alpha constant (TRAC—NCBI Gene ID #28755) A constitutive promoter as per the present invention is for instance a promoter that is active independently from CAR activation—ex: when T-cells are not yet activated.

Improving the Therapeutic Potential of Immune Cells by Gene Targeted Integration Gene editing techniques using polynucleotide sequence-specific reagents, such as rare-cutting endonucleases, have become the state of the art for the introduction of genetic modifications into primary cells. However, they have not been used so far in immune cells to introduce exogenous coding sequences under the transcriptional control of endogenous promoters.

The present invention aims to improve the therapeutic potential of immune cells through gene editing techniques, especially by gene targeted integration.

By "gene targeting integration" is meant any known site-specific methods allowing to insert, replace or correct a genomic sequence into a living cell. According to a preferred aspect of the present invention, said gene targeted integration involves homologous gene recombination at the locus of the targeted gene to result the insertion or replacement of at least one exogenous nucleotide, preferably a sequence of several nucleotides (i.e. polynucleotide), and more preferably a coding sequence.

By "sequence-specific reagent" is meant any active molecule that has the ability to specifically recognize a selected polynucleotide sequence at a genomic locus, preferably of at least 9 bp, more preferably of at least 10 bp and even more preferably of at least 12 pb in length, in view of modifying said genomic locus. According to a preferred aspect of the invention, said sequence-specific reagent is preferably a sequence-specific nuclease reagent.

By "immune cell" is meant a cell of hematopoietic origin functionally involved in the initiation and/or execution of innate and/or adaptative immune response, such as typically CD3 or CD4 positive cells. The immune cell according to the present invention can be a dendritic cell, killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and from tumors, such as tumor infiltrating lymphocytes. In some embodiments, said immune cell can be derived from a healthy donor, from a patient diagnosed with cancer or from a patient diagnosed with an infection. In another embodiment, said cell is part of a mixed population of immune cells which present different phenotypic characteristics, such as comprising CD4, CD8 and CD56 positive cells.

By "primary cell" or "primary cells" are intended cells taken directly from living tissue (e.g. biopsy material) and established for growth in vitro for a limited amount of time, meaning that they can undergo a limited number of population doublings. Primary cells are opposed to continuous tumorigenic or artificially immortalized cell lines. Non-limiting examples of such cell lines are CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells. Primary cells are generally used in cell therapy as they are deemed more functional and less tumorigenic.

In general, primary immune cells are provided from donors or patients through a variety of methods known in the art, as for instance by leukapheresis techniques as reviewed by Schwartz J. et al. (Guidelines on the use of therapeutic apheresis in clinical practice-evidence-based approach from the Writing Committee of the American Society for Apheresis: the sixth special issue (2013) *J Clin Apher.* 28(3):145-284).

The primary immune cells according to the present invention can also be differentiated from stem cells, such as cord blood stem cells, progenitor cells, bone marrow stem cells, hematopoietic stem cells (HSC) and induced pluripotent stem cells (iPS).

By "nuclease reagent" is meant a nucleic acid molecule that contributes to an nuclease catalytic reaction in the target cell, preferably an endonuclease reaction, by itself or as a subunit of a complex such as a guide RNA/Cas9, preferably leading to the cleavage of a nucleic acid sequence target.

The nuclease reagents of the invention are generally "sequence-specific reagents", meaning that they can induce DNA cleavage in the cells at predetermined loci, referred to by extension as "targeted gene". The nucleic acid sequence which is recognized by the sequence specific reagents is referred to as "target sequence". Said target sequence is usually selected to be rare or unique in the cell's genome, and more extensively in the human genome, as can be determined using software and data available from human genome databases, such as ensembl. org/index. html.

"Rare-cutting endonucleases" are sequence-specific endonuclease reagents of choice, insofar as their recognition sequences generally range from 10 to 50 successive base pairs, preferably from 12 to 30 bp, and more preferably from 14 to 20 bp.

According to a preferred aspect of the invention, said endonuclease reagent is a nucleic acid encoding an "engineered" or "programmable" rare-cutting endonuclease, such as a homing endonuclease as described for instance by Arnould S., et al. (WO2004067736), a zing finger nuclease (ZFN) as described, for instance, by Umov F., et al. (Highly efficient endogenous human gene correction using designed zinc-finger nucleases (2005) *Nature* 435:646-651), a TALE-Nuclease as described, for instance, by Mussolino et al. (A novel TALE nuclease scaffold enables high genome editing activity in combination with low toxicity (2011) *Nucl. Acids Res.* 39(21):9283-9293), or a MegaTAL nuclease as described, for instance by Boissel et al. (MegaTALs: a rare-cleaving nuclease architecture for therapeutic genome engineering (2013) Nucleic Acids Research 42 (4):2591-2601).

According to another embodiment, the endonuclease reagent is a RNA-guide to be used in conjunction with a RNA guided endonuclease, such as Cas9 or Cpf1, as per, inter alia, the teaching by Doudna, J., and Chapentier, E., (The new frontier of genome engineering with CRISPR-Cas9 (2014) *Science* 346 (6213):1077), which is incorporated herein by reference.

According to a preferred aspect of the invention, the endonuclease reagent is transiently expressed into the cells, meaning that said reagent is not supposed to integrate into the genome or persist over a long period of time, such as be the case of RNA, more particularly mRNA, proteins or complexes mixing proteins and nucleic acids (eg: Ribonucleoproteins).

In general, 80% the endonuclease reagent is degraded by 30 hours, preferably by 24, more preferably by 20 hours after transfection.

An endonuclease under mRNA form is preferably synthetized with a cap to enhance its stability according to techniques well known in the art, as described, for instance, by Kore A. L., et al. (Locked nucleic acid (LNA)-modified dinucleotide mRNA cap analogue: synthesis, enzymatic incorporation, and utilization (2009) *J Am Chem Soc.* 131 (18):6364-5).

In general, electroporation steps that are used to transfect immune cells are typically performed in closed chambers comprising parallel plate electrodes producing a pulse electric field between said parallel plate electrodes greater than 100 volts/cm and less than 5,000 volts/cm, substantially uniform throughout the treatment volume such as described in WO/2004/083379, which is incorporated by reference, especially from page 23, line 25 to page 29, line 11. One such electroporation chamber preferably has a geometric factor ($cm^{-1}$) defined by the quotient of the electrode gap squared (cm2) divided by the chamber volume ($cm^3$), wherein the geometric factor is less than or equal to 0.1 $cm^{-1}$, wherein the suspension of the cells and the sequence-specific reagent is in a medium which is adjusted such that the medium has conductivity in a range spanning 0.01 to 1.0 milliSiemens. In general, the suspension of cells undergoes one or more pulsed electric fields. With the method, the treatment volume of the suspension is scalable, and the time of treatment of the cells in the chamber is substantially uniform.

Due to their higher specificity, TALE-nuclease have proven to be particularly appropriate sequence specific nuclease reagents for therapeutic applications, especially under heterodimeric forms—i.e. working by pairs with a "right" monomer (also referred to as "5'" or "forward") and 'left' monomer (also referred to as "3'"" or "reverse") as reported for instance by Mussolino et al. (TALEN® facilitate targeted genome editing in human cells with high specificity and low cytotoxicity (2014) *Nucl. Acids Res.* 42(10): 6762-6773).

As previously stated, the sequence specific reagent is preferably under the form of nucleic acids, such as under DNA or RNA form encoding a rare cutting endonuclease a subunit thereof, but they can also be part of conjugates involving polynucleotide(s) and polypeptide(s) such as so-called "ribonucleoproteins". Such conjugates can be formed with reagents as Cas9 or Cpf1 (RNA-guided endonucleases) or Argonaute (DNA-guided endonucleases) as recently respectively described by Zetsche, B. et al. (Cpf1 Is a Single RNA-Guided Endonuclease of a Class 2 CRISPR-Cas System (2015) *Cell* 163(3): 759-771) and by Gao F. et al. (DNA-guided genome editing using the *Natronobacterum*

*gregoryi* Argonaute (2016) *Nature Biotech*), which involve RNA or DNA guides that can be complexed with their respective nucleases.

"Exogenous sequence" refers to any nucleotide or nucleic acid sequence that was not initially present at the selected locus. This sequence may be homologous to, or a copy of, a genomic sequence, or be a foreign sequence introduced into the cell. By opposition "endogenous sequence" means a cell genomic sequence initially present at a locus. The exogenous sequence preferably codes for a polypeptide which expression confers a therapeutic advantage over sister cells that have not integrated this exogenous sequence at the locus. A endogenous sequence that is gene edited by the insertion of a nucleotide or polynucleotide as per the method of the present invention, in order to express a different polypeptide is broadly referred to as an exogenous coding sequence The method of the present invention can be associated with other methods involving physical of genetic transformations, such as a viral transduction or transfection using nanoparticles, and also may be combined with other gene inactivation and/or transgene insertions.

According to one aspect, the method according to the invention comprises the steps of:
  providing a population of primary immune cells;
  introducing into a proportion of said primary immune cells:
    i) At least one nucleic acid comprising an exogenous nucleotide or polynucleotide sequence to be integrated at a selected endogenous locus to encode at least one molecule improving the therapeutic potential of said immune cells population;
    ii) At least one sequence-specific reagent that specifically targets said selected endogenous locus,
  wherein said exogenous nucleotide or polynucleotide sequence is inserted by targeted gene integration into said endogenous locus, so that said exogenous nucleotide or polynucleotide sequence forms an exogenous coding sequence under transcriptional control of an endogenous promoter present at said locus.

According to one aspect of the method, the sequence specific reagent is a nuclease and the targeted gene integration is operated by homologous recombination or NHEJ into said immune cells.

According to a further aspect of the invention, said endogenous promoter is selected to be active during immune cell activation and preferably up-regulated. More specifically, the invention is drawn to a method for preparing engineered primary immune cells for cell immunotherapy, said method comprising:
  providing a population of primary immune cells;
  introducing into a proportion of said primary immune cells:
    i) At least one exogenous nucleic acid comprising an exogenous coding sequence encoding at least one molecule improving the therapeutic potential of said immune cells population;
    ii) At least one sequence-specific nuclease reagent that specifically targets a gene which is under control of an endogenous promoter active during immune cell activation;
  wherein said coding sequence is introduced into the primary immune cells genome by targeted homologous recombination, so that said coding sequence is placed under the transcriptional control of at least one endogenous promoter of said gene.

By "improving therapeutic potential" is meant that the engineered immune cells gain at least one advantageous property for their use in cell therapy by comparison to their sister non-engineered immune cells. The therapeutic properties sought by the invention maybe any measurable one as referred to in the relevant scientific literature.

Improved therapeutic potential can be more particularly reflected by a resistance of the immune cells to a drug, an increase in their persistence in-vitro or in-vivo, or a safer/more convenient handling during manufacturing of therapeutic compositions and treatments.

In general said molecule improving the therapeutic potential is a polypeptide, but it can also be a nucleic acid able to direct or repress expression of other genes, such as interference RNAs or guide-RNAs. The polypeptides may act directly or indirectly, such as signal transducers or transcriptional regulators.

According to one embodiment of the present method, the exogenous sequence is introduced into the endogenous chromosomal DNA by targeted homologous recombination. Accordingly, the exogenous nucleic acid introduced into the immune cell comprises at least one coding sequence(s), along with sequences that can hybridize endogenous chromosomal sequences under physiological conditions. In general, such homologous sequences show at least 70%, preferably 80% and more preferably 90% sequence identity with the endogenous gene sequences located at the insertion locus. These homologous sequences may flank the coding sequence to improve the precision of recombination as already taught for instance in U.S. Pat. No. 6,528,313. Using available software and on-line genome databases, it is possible to design vectors that includes said coding sequence (s), in such a way that said sequence(s) is (are) introduced at a precise locus, under transcriptional control of at least one endogenous promoter, which is a promoter of an endogenous gene. The exogenous coding sequence(s) is (are) then preferably inserted "in frame" with said endogenous gene. The sequences resulting from the integration of the exogenous polynucleotide sequence(s) can encode many different types of proteins, including fusion proteins, tagged protein or mutated proteins. Fusion proteins allow adding new functional domains to the proteins expressed in the cell, such as a dimerization domain that can be used to switch-on or switch-off the activity of said protein, such as caspase-9 switch. Tagged proteins can be advantageous for the detection of the engineered immune cells and the follow-up of the patients treated with said cells. Introducing mutation into proteins can confer resistance to drugs or immune depletion agents as further described below.

Conferring Resistance to Drugs or Immune Depletion Agents

According to one aspect of the present method, the exogenous sequence that is integrated into the immune cells genomic locus encodes a molecule that confers resistance of said immune cells to a drug.

Examples of preferred exogenous sequences are variants of dihydrofolate reductase (DHFR) conferring resistance to folate analogs such as methotrexate, variants of inosine monophosphate dehydrogenase 2 (IMPDH2) conferring resistance to IMPDH inhibitors such as mycophenolic acid (MPA) or its prodrug mycophenolate mofetil (MMF), variants of calcineurin or methylguanine transferase (MGMT) conferring resistance to calcineurin inhibitor such as FK506 and/or CsA, variants of mTOR such as mTORmut conferring resistance to rapamycin) and variants of Lck, such as Lckmut conferring resistance to Imatinib and Gleevec.

The term "drug" is used herein as referring to a compound or a derivative thereof, preferably a standard chemotherapy agent that is generally used for interacting with a cancer cell, thereby reducing the proliferative or living status of the cell. Examples of chemotherapeutic agents include, but are not limited to, alkylating agents (e.g., cyclophosphamide, ifosamide), metabolic antagonists (e.g., purine nucleoside antimetabolite such as clofarabine, fludarabine or 2'-deoxyadenosine, methotrexate (MTX), 5-fluorouracil or derivatives thereof), antitumor antibiotics (e.g., mitomycin, adriamycin), plant-derived antitumor agents (e.g., vincristine, vindesine, Taxol), cisplatin, carboplatin, etoposide, and the like. Such agents may further include, but are not limited to, the anti-cancer agents TRIMETHOTRIXATE™ (TMTX), TEMOZOLOMIDE™, RALTRITREXED™, S-(4-Nitrobenzyl)-6-thioinosine (NBMPR), 6-benzyguanidine (6-BG), bis-chloronitrosourea (BCNU) and CAMPTOTHECIN™, or a therapeutic derivative of any thereof.

As used herein, an immune cell is made "resistant or tolerant" to a drug when said cell, or population of cells is modified so that it can proliferate, at least in-vitro, in a culture medium containing half maximal inhibitory concentration (IC50) of said drug (said IC50 being determined with respect to an unmodified cell(s) or population of cells).

In a particular embodiment, said drug resistance can be conferred to the immune cells by the expression of at least one "drug resistance coding sequence". Said drug resistance coding sequence refers to a nucleic acid sequence that confers "resistance" to an agent, such as one of the chemotherapeutic agents referred to above. A drug resistance coding sequence of the invention can encode resistance to anti-metabolite, methotrexate, vinblastine, cisplatin, alkylating agents, anthracyclines, cytotoxic antibiotics, anti-immunophilins, their analogs or derivatives, and the like (Takebe, N., S. C. Zhao, et al. (2001) "Generation of dual resistance to 4-hydroperoxycyclophosphamide and methotrexate by retroviral transfer of the human aldehyde dehydrogenase class 1 gene and a mutated dihydrofolate reductase gene". *Mol. Ther.* 3(1): 88-96), (Zielske, S. P., J. S. Reese, et al. (2003) "In vivo selection of MGMT(P140K) lentivirus-transduced human NOD/SCID repopulating cells without pretransplant irradiation conditioning." *J. Clin. Invest.* 112 (10): 1561-70) (Nivens, M. C., T. Felder, et al. (2004) "Engineered resistance to camptothecin and antifolates by retroviral coexpression of tyrosyl DNA phosphodiesterase-I and thymidylate synthase" Cancer Chemother Pharmacol 53(2): 107-15), (Bardenheuer, W., K. Lehmberg, et al. (2005). "Resistance to cytarabine and gemcitabine and in vitro selection of transduced cells after retroviral expression of cytidine deaminase in human hematopoietic progenitor cells". *Leukemia* 19(12): 2281-8), (Kushman, M. E., S. L. Kabler, et al. (2007) "Expression of human glutathione S-transferase P1 confers resistance to benzo[a]pyrene or benzo[a]pyrene-7,8-dihydrodiol mutagenesis, macromolecular alkylation and formation of stable N2-Gua-BPDE adducts in stably transfected V79MZ cells co-expressing hCYP1A1" *Carcinogenesis* 28(1): 207-14).

The expression of such drug resistance exogenous sequences in the immune cells as per the present invention more particularly allows the use of said immune cells in cell therapy treatment schemes where cell therapy is combined with chemotherapy or into patients previously treated with these drugs.

Several drug resistance coding sequences have been identified that can potentially be used to confer drug resistance according to the invention. One example of drug resistance coding sequence can be for instance a mutant or modified form of Dihydrofolate reductase (DHFR). DHFR is an enzyme involved in regulating the amount of tetrahydrofolate in the cell and is essential to DNA synthesis. Folate analogs such as methotrexate (MTX) inhibit DHFR and are thus used as anti-neoplastic agents in clinic. Different mutant forms of DHFR which have increased resistance to inhibition by anti-folates used in therapy have been described. In a particular embodiment, the drug resistance coding sequence according to the present invention can be a nucleic acid sequence encoding a mutant form of human wild type DHFR (GenBank: AAH71996.1), which comprises at least one mutation conferring resistance to an anti-folate treatment, such as methotrexate. In particular embodiment, mutant form of DHFR comprises at least one mutated amino acid at position G15, L22, F31 or F34, preferably at positions L22 or F31 (Schweitzer et al. (1990) "Dihydrofolate reductase as a therapeutic target" *Faseb J* 4(8): 2441-52; International application WO94/24277; and U.S. Pat. No. 6,642,043). In a particular embodiment, said DHFR mutant form comprises two mutated amino acids at position L22 and F31. Correspondence of amino acid positions described herein is frequently expressed in terms of the positions of the amino acids of the form of wild-type DHFR polypeptide. In a particular embodiment, the serine residue at position 15 is preferably replaced with a tryptophan residue. In another particular embodiment, the leucine residue at position 22 is preferably replaced with an amino acid which will disrupt binding of the mutant DHFR to antifolates, preferably with uncharged amino acid residues such as phenylalanine or tyrosine. In another particular embodiment, the phenylalanine residue at positions 31 or 34 is preferably replaced with a small hydrophilic amino acid such as alanine, serine or glycine.

Another example of drug resistance coding sequence can also be a mutant or modified form of ionisine-5'-monophosphate dehydrogenase II (IMPDH2), a rate-limiting enzyme in the de novo synthesis of guanosine nucleotides. The mutant or modified form of IMPDH2 is a IMPDH inhibitor resistance gene. IMPDH inhibitors can be mycophenolic acid (MPA) or its prodrug mycophenolate mofetil (MMF). The mutant IMPDH2 can comprises at least one, preferably two mutations in the MAP binding site of the wild type human IMPDH2 (Genebank: NP_000875.2) leading to a significantly increased resistance to IMPDH inhibitor. Mutations in these variants are preferably at positions T333 and/or S351 (Yam, P., M. Jensen, et al. (2006) "Ex vivo selection and expansion of cells based on expression of a mutated inosine monophosphate dehydrogenase 2 after HIV vector transduction: effects on lymphocytes, monocytes, and CD34+ stem cells" *Mol. Ther.* 14(2): 236-44)(Jonnalagadda, M., et al. (2013) "Engineering human T cells for resistance to methotrexate and mycophenolate mofetil as an in vivo cell selection strategy." *PLoS One* 8(6): e65519).

Another drug resistance coding sequence is the mutant form of calcineurin. Calcineurin (PP2B—NCBI: ACX34092.1) is an ubiquitously expressed serine/threonine protein phosphatase that is involved in many biological processes and which is central to T-cell activation. Calcineurin is a heterodimer composed of a catalytic subunit (CnA; three isoforms) and a regulatory subunit (CnB; two isoforms). After engagement of the T-cell receptor, calcineurin dephosphorylates the transcription factor NFAT, allowing it to translocate to the nucleus and active key target gene such as IL2. FK506 in complex with FKBP12, or cyclosporine A (CsA) in complex with CyPA block NFAT access to calcineurin's active site, preventing its dephosphorylation and thereby inhibiting T-cell activation (Brewin et al. (2009) "Generation of EBV-specific cytotoxic T cells that are resistant to calcineurin inhibitors for the treatment of posttransplantation lymphoproliferative disease" *Blood* 114(23):

4792-803). In a particular embodiment, said mutant form can comprise at least one mutated amino acid of the wild type calcineurin heterodimer a at positions: V314, Y341, M347, T351, W352, L354, K360, preferably double mutations at positions T351 and L354 or V314 and Y341. In a particular embodiment, the valine residue at position 341 can be replaced with a lysine or an arginine residue, the tyrosine residue at position 341 can be replaced with a phenylalanine residue; the methionine at position 347 can be replaced with the glutamic acid, arginine or tryptophane residue; the threonine at position 351 can be replaced with the glutamic acid residue; the tryptophane residue at position 352 can be replaced with a cysteine, glutamic acid or alanine residue, the serine at position 353 can be replaced with the histidine or asparagines residue, the leucine at position 354 can be replaced with an alanine residue; the lysine at position 360 can be replaced with an alanine or phenylalanine residue. In another particular embodiment, said mutant form can comprise at least one mutated amino acid of the wild type calcineurin heterodimer b at positions: V120, N123, L124 or K125, preferably double mutations at positions L124 and K125. In a particular embodiment, the valine at position 120 can be replaced with a serine, an aspartic acid, phenylalanine or leucine residue; the asparagines at position 123 can be replaced with a tryptophan, lysine, phenylalanine, arginine, histidine or serine; the leucine at position 124 can be replaced with a threonine residue; the lysine at position 125 can be replaced with an alanine, a glutamic acid, tryptophan, or two residues such as leucine-arginine or isoleucine-glutamic acid can be added after the lysine at position 125 in the amino acid sequence. Correspondence of amino acid positions described herein is frequently expressed in terms of the positions of the amino acids of the form of wild-type human calcineurin heterodimer b polypeptide (NCBI: ACX34095.1).

Another drug resistance coding sequence is 0(6)-methyl-guanine methyltransferase (MGMT—UniProtKB: P16455) encoding human alkyl guanine transferase (hAGT). AGT is a DNA repair protein that confers resistance to the cytotoxic effects of alkylating agents, such as nitrosoureas and temozolomide (TMZ). 6-benzylguanine (6-BG) is an inhibitor of AGT that potentiates nitrosourea toxicity and is co-administered with TMZ to potentiate the cytotoxic effects of this agent. Several mutant forms of MGMT that encode variants of AGT are highly resistant to inactivation by 6-BG, but retain their ability to repair DNA damage (Maze, R. et al. (1999) "Retroviral-mediated expression of the P140A, but not P140A/G156A, mutant form of O6-methylguanine DNA methyltransferase protects hematopoietic cells against O6-benzylguanine sensitization to chloroethylnitrosourea treatment" J. Pharmacol. Exp. Ther. 290(3): 1467-74). In a particular embodiment, AGT mutant form can comprise a mutated amino acid of the wild type AGT position P140. In a preferred embodiment, said proline at position 140 is replaced with a lysine residue.

Another drug resistance coding sequence can be multidrug resistance protein (MDR1) gene. This gene encodes a membrane glycoprotein, known as P-glycoprotein (P-GP) involved in the transport of metabolic byproducts across the cell membrane. The P-Gp protein displays broad specificity towards several structurally unrelated chemotherapy agents. Thus, drug resistance can be conferred to cells by the expression of nucleic acid sequence that encodes MDR-1 (Genebank NP_000918).

Another drug resistance coding sequence can contribute to the production of cytotoxic antibiotics, such as those from ble or mcrA genes. Ectopic expression of ble gene or mcrA in an immune cell gives a selective advantage when exposed to the respective chemotherapeutic agents bleomycine and mitomycin C (Belcourt, M. F. (1999) "Mitomycin resistance in mammalian cells expressing the bacterial mitomycin C resistance protein MCRA". PNAS. 96(18):10489-94).

Another drug resistance coding sequence can come from genes encoded mutated version of drug targets, such as mutated variants of mTOR (mTOR mut) conferring resistance to rapamycin such as described by Lorenz M. C. et al. (1995) "TOR Mutations Confer Rapamycin Resistance by Preventing Interaction with FKBP12-Rapamycin" The Journal of Biological Chemistry 270, 27531-27537, or certain mutated variants of Lck (Lckmut) conferring resistance to Gleevec as described by Lee K. C. et al. (2010) "Lck is a key target of imatinib and dasatinib in T-cell activation", Leukemia, 24: 896-900.

As described above, the genetic modification step of the method can comprise a step of introduction into cells of an exogeneous nucleic acid comprising at least a sequence encoding the drug resistance coding sequence and a portion of an endogenous gene such that homologous recombination occurs between the endogenous gene and the exogeneous nucleic acid. In a particular embodiment, said endogenous gene can be the wild type "drug resistance" gene, such that after homologous recombination, the wild type gene is replaced by the mutant form of the gene which confers resistance to the drug.

Enhancing Persistence of the Immune Cells In-Vivo

According to one aspect of the present method, the exogeneous sequence that is integrated into the immune cells genomic locus encodes a molecule that enhances persistence of the immune cells, especially in-vivo persistence in a tumor environment.

By "enhancing persistence" is meant extending the survival of the immune cells in terms of life span, especially once the engineered immune cells are injected into the patient. For instance, persistence is enhanced, if the mean survival of the modified cells is significantly longer than that of non-modified cells, by at least 10%, preferably 20%, more preferably 30%, even more preferably 50%.

This especially relevant when the immune cells are allogeneic. This may be done by creating a local immune protection by introducing coding sequences that ectopically express and/or secrete immunosuppressive polypeptides at, or through, the cell membrane. A various panel of such polypeptides in particular antagonists of immune checkpoints, immunosuppressive peptides derived from viral envelope or NKG2D ligand can enhance persistence and/or an engraftment of allogeneic immune cells into patients.

According to one embodiment, the immunosuppressive polypeptide to be encoded by said exogenous coding sequence is a ligand of Cytotoxic T-Lymphocyte Antigen 4 (CTLA-4 also known as CD152, GenBank accession number AF414120.1). Said ligand polypeptide is preferably an anti-CTLA-4 immunoglobulin, such as CTLA-4a Ig and CTLA-4b Ig or a functional variant thereof.

According to one embodiment, the immunosuppressive polypeptide to be encoded by said exogenous coding sequence is an antagonist of PD1, such as PD-L1 (other names: CD274, Programmed cell death 1 ligand; ref. UniProt for the human polypeptide sequence Q9NZQ7), which encodes a type I transmembrane protein of 290 amino acids consisting of a Ig V-like domain, a Ig C-like domain, a hydrophobic transmembrane domain and a cytoplasmic tail of 30 amino acids. Such membrane-bound form of PD-L1 ligand is meant in the present invention under a native form (wild-type) or under a truncated form such as, for instance, by removing the intracellular domain, or with one or more mutation(s) (Wang S et al., 2003, *J Exp Med.* 2003; 197(9): 1083-1091). Of note, PD1 is not considered as being a membrane-bound form of PD-L1 ligand according to the present invention. According to another embodiment, said immunosuppressive polypeptide is under a secreted form. Such recombinant secreted PD-L1 (or soluble PD-L1) may be generated by fusing the extracellular domain of PD-L1 to the Fc portion of an immunoglobulin (Haile S T et al., 2014, *Cancer Immunol. Res.* 2(7): 610-615; Song M Y et al., 2015, Gut. 64(2):260-71). This recombinant PD-L1 can neutralize PD-1 and abrogate PD-1-mediated T-cell inhibition. PD-L1 ligand may be co-expressed with CTLA4 Ig for an even enhanced persistence of both.

According to another embodiment, the exogenous sequence encodes a polypeptide comprising a viral env immusuppressive domain (ISU), which is derived for instance from HIV-1, HIV-2, SIV, MoMuLV, HTLV-I, -II, MPMV, SRV-1, Syncitin 1 or 2, HERV-K or FELV.

The following Table 1 shows variants of ISU domain from diverse virus which can be expressed within the present invention.

described by Margalit A. et al. (2003) "Chimeric β2 microglobulin/CD3ζ polypeptides expressed in T cells convert MHC class I peptide ligands into T cell activation receptors: a potential tool for specific targeting of pathogenic CD8+ T cells" *Int. Immunol.* 15 (11): 1379-1387.

According to one embodiment, the exogenous sequence encodes NKG2D ligand. Some viruses such as cytomegaloviruses have acquired mechanisms to avoid NK cell mediate immune surveillance and interfere with the NKG2D pathway by secreting a protein able to bind NKG2D ligands and prevent their surface expression (Welte, S. A et al. (2003) "Selective intracellular retention of virally induced NKG2D ligands by the human cytomegalovirus UL16 glycoprotein". *Eur. J. Immunol.,* 33, 194-203). In tumors cells, some mechanisms have evolved to evade NKG2D response by secreting NKG2D ligands such as ULBP2, MICB or MICA (Salih H R, Antropius H, Gieseke F, Lutz S Z, Kanz L, et al. (2003) Functional expression and release of ligands for the activating immunoreceptor NKG2D in leukemia. *Blood* 102: 1389-1396)

According to one embodiment, the exogenous sequence encodes a cytokine receptor, such as an IL-12 receptor.

TABLE 1

ISU domain variants from diverse viruses
ISU Amino acids sequences

| | | | | | Amino acid positions | | | | | | | | | Virus origin | |
|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | Origin | SEQ ID NO |
| L | Q | A | R | I/V | L | A | V | E | R | Y | L | K/R/Q | D | HIV-1 | SEQ ID NO: 68 |
| L | Q | A | R | V | T | A | I | E | K | Y | L | K/A/Q | D/H | HIV-2 | SEQ ID NO: 69 |
| L | Q | A | R | L | L | A | V | E | R | Y | L | K | D | SIV | SEQ ID NO: 70 |
| L | Q | N | R | R | G | L | D | L | L | F | L | K | E | MoMuLV | SEQ ID NO: 71 |
| A | Q | N | R | R | G | L | D | L | L | F | W | E | Q | HTLV-I, -II | SEQ ID NO: 72 |
| L | Q | N | R | R | G | L | D | L | L | T | A | E | Q | MPMV, SRV-1 | SEQ ID NO: 73 |
| L | Q | N | R | R | A | L | D | L | L | T | A | E | R | Syncitin 1 | SEQ ID NO: 74 |
| L | Q | N | R | R | G | L | D | M | L | T | A | A | Q | Syncitin 2 | SEQ ID NO: 75 |
| L | A | N | Q | I | N | D | L | R | Q | T | V | I | W | HERV-K | SEQ ID NO: 76 |
| L | Q | N | R | R | G | L | D | I | L | F | L | Q | E | FELV | SEQ ID NO: 77 |

According to another embodiment, the exogenous sequence encodes a FP polypeptide such as gp41. The following Table 2 represents several FP polypeptide from natural and artificial origins.

TABLE 2

Amino acid sequences of FP polypeptide from
natural and artificial origins
FP Amino acids sequences

| | | Amino acid positions | | | | | | | | SEQ ID NO |
|---|---|---|---|---|---|---|---|---|---|---|
| 1 | 2 | 3 | 4 | 5 | 6 | 7 | 8 | 9 | Origin | |
| G | A | L | F | L | G | F | L | G | HIV-1 gp41 | SEQ ID NO: 78 |
| A | G | F | G | L | L | L | G | F | Synthetic | SEQ ID NO: 79 |
| A | G | L | F | L | G | F | L | G | Synthetic | SEQ ID NO: 80 |

According to another embodiment, the exogenous sequence encodes a non-human MHC homolog, especially a viral MHC homolog, or a chimeric β2m polypeptide such as IL-12 is a well known activator of immune cells activation (Curtis J. H. (2008) "IL-12 Produced by Dendritic Cells Augments CD8+ T Cell Activation through the Production of the Chemokines CCL1 and CCL171". *The Journal of Immunology.* 181 (12): 8576-8584.

According to one embodiment the exogenous sequence encodes an antibody that is directed against inhibitory peptides or proteins. Said antibody is preferably be secreted under soluble form by the immune cells. Nanobodies from shark and camels are advantageous in this respect, as they are structured as single chain antibodies (Muyldermans S. (2013) "Nanobodies: Natural Single-Domain Antibodies" *Annual Review of Biochemistry* 82: 775-797). Same are also deemed more easily to fuse with secretion signal polypeptides and with soluble hydrophilic domains.

The different aspects developed above to enhance persistence of the cells are particularly preferred, when the exogenous coding sequence is introduced by disrupting an endogenous gene encoding β2m or another MHC component, as detailed further on.

Enhancing the Therapeutic Activity of Immune Cells

According to one aspect of the present method, the exogenous sequence that is integrated into the immune cells genomic locus encodes a molecule that enhances the therapeutic activity of the immune cells.

By "enhancing the therapeutic activity" is meant that the immune cells, or population of cells, engineered according to the present invention, become more aggressive than non-engineered cells or population of cells with respect to a selected type of target cells. Said target cells generally belong to a defined type of cells, or population of cells, preferably characterized by common surface marker(s). In the present specification, "therapeutic potential" reflects the therapeutic activity, as measured through in-vitro experiments. In general sensitive cancer cell lines, such as Daudi cells, are used to assess whether the immune cells are more or less active towards said cells by performing cell lysis or growth reduction measurements. This can also be assessed by measuring levels of degranulation of immune cells or chemokines and cytokines production. Experiments can also be performed in mice with injection of tumor cells, and by monitoring the resulting tumor expansion. Enhancement of activity is deemed significant when the number of developing cells in these experiments is reduced by the immune cells by more than 10%, preferably more than 20%, more preferably more than 30%, even more preferably by more than 50%.

According to one aspect of the invention, said exogenous sequence encodes a chemokine or a cytokine, such as IL-12. It is particularly advantageous to express IL-12 as this cytokine is extensively referred to in the literature as promoting immune cell activation (Colombo M. P. et al. (2002) "Interleukin-12 in anti-tumor immunity and immunotherapy" *Cytokine Growth Factor Rev.* 13(2):155-68).

According to a preferred aspect of the invention the exogenous coding sequence encodes or promote secreted factors that act on other populations of immune cells, such as T-regulatory cells, to alleviate their inhibitory effect on said immune cells.

According to one aspect of the invention, said exogenous sequence encodes an inhibitor of regulatory T-cell activity is a polypeptide inhibitor of forkhead/winged helix transcription factor 3 (FoxP3), and more preferably is a cell-penetrating peptide inhibitor of FoxP3, such as that referred as P60 (Casares N. et al. (2010) "A peptide inhibitor of FoxP3 impairs regulatory T cell activity and improves vaccine efficacy in mice." *J Immunol* 185(9):5150-9).

By "inhibitor of regulatory T-cells activity" is meant a molecule or precursor of said molecule secreted by the T-cells and which allow T-cells to escape the down regulation activity exercised by the regulatory T-cells thereon. In general, such inhibitor of regulatory T-cell activity has the effect of reducing FoxP3 transcriptional activity in said cells.

According to one aspect of the invention, said exogenous sequence encodes a secreted inhibitor of Tumor Associated Macrophages (TAM), such as a CCR2/CCL2 neutralization agent. Tumor-associated macrophages (TAMs) are critical modulators of the tumor microenvironment. Clinicopathological studies have suggested that TAM accumulation in tumors correlates with a poor clinical outcome. Consistent with that evidence, experimental and animal studies have supported the notion that TAMs can provide a favorable microenvironment to promote tumor development and progression. (Theerawut C. et al. (2014) "Tumor-Associated Macrophages as Major Players in the Tumor Microenvironment" *Cancers* (Basel) 6(3): 1670-1690). Chemokine ligand 2 (CCL2), also called monocyte chemoattractant protein 1 (MCP1—NCBI NP_002973.1), is a small cytokine that belongs to the CC chemokine family, secreted by macrophages, that produces chemoattraction on monocytes, lymphocytes and basophils. CCR2 (C-C chemokine receptor type 2—NCBI NP_001116513.2), is the receptor of CCL2.

Enhancing Specificity and Safety of Immune Cells

Expressing chimeric antigen receptors (CAR) have become the state of the art to direct or improve the specificity of primary immune cells, such as T-Cells and NK-cells for treating tumors or infected cells. CARs expressed by these immune cells specifically target antigen markers at the surface of the pathological cells, which further help said immune cells to destroy these cells in-vivo (Sadelain M. et al. "The basic principles of chimeric antigen receptor design" (2013) *Cancer Discov.* 3(4):388-98). CARs are usually designed to comprise activation domains that stimulate immune cells in response to binding to a specific antigen (so-called positive CAR), but they may also comprise an inhibitory domain with the opposite effect (so-called negative CAR)(Fedorov, V. D. (2014) "Novel Approaches to Enhance the Specificity and Safety of Engineered T Cells" *Cancer Journal* 20 (2):160-165. Positive and negative CARs may be combined or co-expressed to finely tune the cells immune specificity depending of the various antigens present at the surface of the target cells.

The genetic sequences encoding CARs are generally introduced into the cells genome using retroviral vectors that have elevated transduction efficiency but integrate at random locations. Here, according to the present invention, components of chimeric antigen receptor (CAR) car be introduced at selected loci, more particularly under control of endogenous promoters by targeted gene recombination.

According to one aspect, while a positive CAR is introduced into the immune cell by a viral vector, a negative CAR can be introduced by targeted gene insertion and vice-versa, and be active preferably only during immune cells activation. Accordingly, the inhibitory (i.e. negative) CAR contributes to an improved specificity by preventing the immune cells to attack a given cell type that needs to be preserved. Still according to this aspect, said negative CAR can be an apoptosis CAR, meaning that said CAR comprise an apoptosis domain, such as FasL (CD95—NCBI: NP_000034.1) or a functional variant thereof, that transduces a signal inducing cell death (Eberstadt M; et al. "NMR structure and mutagenesis of the FADD (Mort1) death-effector domain" (1998) *Nature.* 392 (6679): 941-5).

Accordingly, the exogenous coding sequence inserted according to the invention can encode a factor that has the capability to induce cell death, directly, in combination with, or by activating other compound(s).

As another way to enhance the safety of us of the primary immune cells, the exogenous coding sequence can encodes molecules that confer sensitivity of the immune cells to drugs or other exogenous substrates. Such molecules can be cytochrome(s), such as from the P450 family (Preissner S et al. (2010) "SuperCYP: a comprehensive database on Cytochrome P450 enzymes including a tool for analysis of CYP-drug interactions". *Nucleic Acids Res* 38 (Database issue): D237-43), such as CYP2D6-1 (NCBI—NP_000097.3), CYP2D6-2 (NCBI—NP_001020332.2), CYP2C9( ), CYP3A4 (NCBI—NP_000762.2), CYP2C19 (NCBI—NP_000760.1) or CYP1A2 (NCBI—NP_000752.2), conferring hypersensitivity of the immune cells to a drug, such as cyclophosphamide and/or isophosphamide.

According to a further aspect of the invention, an exogenous sequence is introduced in the immune cells for its expression, especially in vivo, to reduce IL-6 or IL-8 trans signalling in view of controlling potential Cyokine Release Syndrome (CRS).

Such an exogenous sequence can encode for instance antibodies directed against IL-6 or IL-8 or against their receptors IL-6R or IL-8R.

According to a preferred aspect said exogenous sequence can encode soluble extracellular domain of GP130, such as one showing at least 80% identity with SEQ ID NO:61.

Such soluble extracellular domain of GP130 is described for instance by Rose-John S. [The Soluble Interleukine Receptor Advanced Therapeutic Options in Inflammation (2017) *Clinical Pharmacology & Therapeutics,* 102(4):591-598] can be fused with fragments of immunoglobulins, such as sgp130Fc (SEQ ID NO:62). As stated before, said exogenous sequence can be stably integrated into the genome by site directed mutagenesis (i.e. using sequence specific nuclease reagents) and be placed under the transcriptional activity of an endogenous promoter at a locus which is active during immune cell activation, such as one listed in Tables 6, 8 or 9, and preferably up-regulated upon CAR activation or being CAR dependent.

According to a more preferred embodiment, the exogenous sequence is introduced into a CAR positive immune cell, such as one expressing an anti-CD22 CAR T-cell polynucleotide sequence such as SEQ ID NO:31. According to some more specific embodiments, said exogenous sequence coding for a polypeptide which can associate, and preferably interfere, with a cytokine receptor of the IL-6 receptor family, such as said soluble extracellular domain of GP130, is integrated at a PD1, CD25 or CD69 locus. As per the present invention, the endogenous sequence encoding PD1 locus is preferably disrupted by said exogenous sequence.

The invention thus provides with a method for treating or reducing CRS in cell immunotherapy, wherein cells or a therapeutic composition thereof are administered to patients, said cells being genetically modified to secrete polypeptide(s) comprising a soluble extracellular domain of GP130, sGP130Fc, an anti-IL-6 or anti-IL6R antibody, an anti-IL-8 or anti-IL8R antibody, or any fusion thereof.

Examples of preferred genotypes of the engineered immune cells are:

[CAR]$^{positive}$[GP130]$^{positive}$
[CAR]$^{positive}$[GP130]$^{positive}$
[CAR]$^{positive}$[TCR]$^{negative}$[GP130]$^{positive}$[PD1]$^{negative}$
[CAR]$^{positive}$[TCR]$^{negative}$[GP130]$^{positive}$[PD1]$^{negative}$
[CAR]$^{positive}$[GP130]$^{positive}$[CD25]$^{negative}$
[CAR]$^{positive}$[TCR]$^{negative}$[GP130]$^{positive}$[CD25]$^{negative}$ Improving the Efficiency of Gene Targeted Insertion in Primary Immune Cells Using AAV Vectors The present specification provides with donor templates and sequence specific reagents as illustrated in the figures that are useful to perform efficient insertion of a coding sequence in frame with endogenous promoters, in particular PD1 and CD25, as well as means and sequences for detecting proper insertion of said exogenous sequences at said loci.

The donor templates according to the present invention are generally polynucleotide sequences which can be included into a variety of vectors described in the art prompt to deliver the donor templates into the nucleus at the time the endonuclease reagents get active to obtain their site directed insertion into the genome generally by NHEJ or homologous recombination, Specifically, the present invention provides specific donor polynucleotides for expression of IL-15 (SEQ ID NO:59) at the PD1 locus comprising one or several of the following sequences:

Sequence encoding IL-15, such as one presenting identity with SEQ ID NO:50;
Upstream and downstream (also referred to left and right) sequences homologous to the PD1 locus, comprising preferably polynucleotide sequences SEQ ID NO:45 and SEQ ID NO:46;
optionally, a sequence encoding soluble form of an IL-15 receptor (sIL-15R), such as one presenting identity with SEQ ID NO:50;
optionally, at least one_2A peptide cleavage site such as one of SEQ ID NO:53 (F2A), SEQ ID NO:54 (P2A) and/or SEQ ID NO:55 (T2A), Specifically, the present invention provides specific donor polynucleotides for expression of IL-12 (SEQ ID NO:58) at the PD1 locus comprising one or several of the following sequences:

Sequence encoding IL-12a, such as one presenting identity with SEQ ID NO:47;
Upstream and downstream (also referred to left and right) sequences homologous to the PD1 locus, comprising preferably polynucleotide sequences SEQ ID NO:45 and SEQ ID NO:46;
optionally, a sequence encoding IL-12b, such as one presenting identity with SEQ ID NO:48;
optionally, at least one 2A peptide cleavage site such as one of SEQ ID NO:53 (F2A), SEQ ID NO:54 (P2A) and/or SEQ ID NO:55 (T2A), Specifically, the present invention provides specific donor polynucleotides for expression of soluble GP130 (comprising SEQ ID NO:61) at the PD1 locus comprising one or several of the following sequences:

Sequence encoding soluble GP130, preferably a soluble gp130 fused to a Fc, such as one presenting identity with SEQ ID NO:62;
Upstream and downstream (also referred to left and right) sequences homologous to the PD1 locus, comprising preferably polynucleotide sequences SEQ ID NO:45 and SEQ ID NO:46;
optionally, at least one_2A peptide cleavage site such as one of SEQ ID NO:53 (F2A), SEQ ID NO:54 (P2A) and/or SEQ ID NO:55 (T2A), Specifically, the present invention provides specific donor polynucleotides for expression of IL-15 (SEQ ID NO:59) at the CD25 locus comprising one or several of the following sequences:

Sequence encoding IL-15, such as one presenting identity with SEQ ID NO:50;
Upstream and downstream (also referred to left and right) sequences homologous to the CD25 locus, comprising preferably polynucleotide sequences SEQ ID NO:43 and SEQ ID NO:44;
optionally, a sequence encoding soluble form of an IL-15 receptor (sIL-15R), such as one presenting identity with SEQ ID NO:50;
optionally, at least one 2A peptide cleavage site such as one of SEQ ID NO:53 (F2A), SEQ ID NO:54 (P2A) and/or SEQ ID NO:55 (T2A), Specifically, the present invention provides specific donor polynucleotides for expression of IL-12 (SEQ ID NO:58) at the CD25 locus comprising one or several of the following sequences:

Sequence encoding IL-12a, such as one presenting identity with SEQ ID NO:47;
Upstream and downstream (also referred to left and right) sequences homologous to the CD25 locus, comprising preferably polynucleotide sequences SEQ ID NO:43 and SEQ ID NO:44;

optionally, a sequence encoding IL-12b, such as one presenting identity with SEQ ID NO:48;

optionally, at least one_2A peptide cleavage site such as one of SEQ ID NO:53 (F2A), SEQ ID NO:54 (P2A) and/or SEQ ID NO:55 (T2A), Specifically, the present invention provides specific donor polynucleotides for expression of soluble GP130 (comprising SEQ ID NO:61) at the CD25 locus comprising one or several of the following sequences:

Sequence encoding soluble GP130, preferably a soluble gp130 fused to a Fc, such as one presenting identity with SEQ ID NO:62;

Upstream and downstream (also referred to left and right) sequences homologous to the CD25 locus, comprising preferably polynucleotide sequences SEQ ID NO:43 and SEQ ID NO:44;

optionally, at least one_2A peptide cleavage site such as one of SEQ ID NO:53 (F2A), SEQ ID NO:54 (P2A) and/or SEQ ID NO:55 (T2A), As illustrated in the examples herein, the inventors have significantly improved the rate of gene targeted insertion into human cells by using AAV vectors, especially vectors from the AAV6 family.

One broad aspect of the present invention is thus the transduction of AAV vectors in human primary immune cells, in conjunction with the expression of sequence specific endonuclease reagents, such as TALE endonucleases, more preferably introduced under mRNA form, to increase homologous recombination events in these cells.

According to one aspect of this invention, sequence specific endonuclease reagents can be introduced into the cells by transfection, more preferably by electroporation of mRNA encoding said sequence specific endonuclease reagents, such as TALE nucleases.

Still according to this broad aspect, the invention more particularly provides a method of insertion of an exogenous nucleic acid sequence into an endogenous polynucleotide sequence in a cell, comprising at least the steps of transducing into said cell an AAV vector comprising said exogenous nucleic acid sequence and sequences homologous to the targeted endogenous DNA sequence, and Inducing the expression of a sequence specific endonuclease reagent to cleave said endogenous sequence at the locus of insertion.

The obtained insertion of the exogenous nucleic acid sequence may result into the introduction of genetic material, correction or replacement of the endogenous sequence, more preferably "in frame" with respect to the endogenous gene sequences at that locus.

According to another aspect of the invention, from $10^5$ to $10^7$ preferably from $10^6$ to $10^7$, more preferably about $5 \cdot 10^6$ viral genomes are transduced per cell.

According to another aspect of the invention, the cells can be treated with proteasome inhibitors, such as Bortezomib to further help homologous recombination.

As one object of the present invention, the AAV vector used in the method can comprise a promoterless exogenous coding sequence as any of those referred to in this specification in order to be placed under control of an endogenous promoter at one loci selected among those listed in the present specification.

As one object of the present invention, the AAV vector used in the method can comprise a 2A peptide cleavage site followed by the cDNA (minus the start codon) forming the exogenous coding sequence.

As one object of the present invention, said AAV vector comprises an exogenous sequence coding for a chimeric antigen receptor, especially an anti-CD19 CAR, an anti-CD22 CAR, an anti-CD123 CAR, an anti-CS1 CAR, an anti-CCL1 CAR, an anti-HSP70 CAR, an anti-GD3 CAR or an anti-ROR1 CAR.

The invention thus encompasses any AAV vectors designed to perform the method herein described, especially vectors comprising a sequence homologous to a locus of insertion located in any of the endogenous gene responsive to T-cell activation referred to in Table 4.

Many other vectors known in the art, such as plasmids, episomal vectors, linear DNA matrices, etc. . . . can also be used following the teachings to the present invention.

As stated before, the DNA vector used according to the invention preferably comprises: (1) said exogenous nucleic acid comprising the exogenous coding sequence to be inserted by homologous recombination, and (2) a sequence encoding the sequence specific endonuclease reagent that promotes said insertion. According to a more preferred aspect, said exogenous nucleic acid under (1) does not comprise any promoter sequence, whereas the sequence under (2) has its own promoter. According to an even more preferred aspect, the nucleic acid under (1) comprises an Internal Ribosome Entry Site (IRES) or "self-cleaving" 2A peptides, such as T2A, P2A, E2A or F2A, so that the endogenous gene where the exogenous coding sequence is inserted becomes multi-cistronic. The IRES of 2A Peptide can precede or follow said exogenous coding sequence.

Preferred vectors of the present invention are vectors derived from AAV6, comprising donor polynucleotides as previously described herein or illustrated in the experimental section and figures. Examples of vectors according to the invention comprise or consist of polynucleotides having identity with sequences SEQ ID NO:37 (matrix for integration of sequence coding for IL-15 into the CD25 locus), SEQ ID NO:38 (matrix for integration of sequence coding for IL-15 into the PD1 locus) SEQ ID NO:39 (matrix for integration of sequence coding for IL-12 into the CD25 locus) and SEQ ID NO:40 (matrix for integration of sequence coding for IL-12 into the PD1 locus).

Gene Targeted Integration in Immune Cells Under Transcriptional Control of Endogenous Promoters The present invention, in one of its main aspects, is taking advantage of the endogenous transcriptional activity of the immune cells to express exogenous sequences that improve their therapeutic potential.

The invention provides with several embodiments based on the profile of transcriptional activity of the endogenous promoters and on a selection of promoter loci useful to carry out the invention. Preferred loci are those, which transcription activity is generally high upon immune cell activation, especially in response to CAR activation (CAR-sensitive promoters) when the cells are endowed with CARs.

Accordingly, the invention provides with a method for producing allogeneic therapeutic immune cells by expressing a first exogenous sequence encoding a CAR at the TCR locus, thereby disrupting TCR expression, and expressing a second exogenous coding sequence under transcriptional activity of an endogenous locus, preferably dependent from either:

CD3/CD28 activation, such as dynabeads, which is useful for instance for promoting cells expansion;

CAR activation, such as through the CD3zeta pathway, which is useful for instance to activate immune cells functions on-target;

Transcriptional activity linked to the appearance of disease symptom or molecular marker, which is useful for instance for activating the cells in-situ in ill organs.

Cell differentiation, which is useful for conferring therapeutic properties to cells at a given level of differentiation or to express protein into a particular lineage (see FIG. 1), for instance at the time hematopoietic cells gain their immune functions; or/and TME (Tumor microoenvironment), which is useful for redirect cells activity and their amplification to specific tumor conditions (hypoxia, low glucose . . . ), or for preventing exhaustion and/or sustaining activation;

CRS (cytokine release syndrome), which is useful to mitigate adverse events related to CAR T-cell activity The inventors have established a first list of endogenous genes (Table 6) which have been found to be particularly appropriate for applying the targeted gene recombination as per the present invention. To draw this list, they have come across several transcriptome murine databases, in particular that from the Immunological Genome Project Consortium referred to in Best J. A. et al. (2013) "Transcriptional insights into the CD8(+) T cell response to infection and memory T cell formation" *Nat. Immunol.* 14(4):404-12., which allows comparing transcription levels of various genes upon T-cell activation, in response to ovalbumin antigens. Also, because very few data is available with respect to human T-cell activation, they had to make some extrapolations and analysis from these data and compare with the human situation by studying available literature related to the human genes. The selected loci are particularly relevant for the insertion of sequences encoding CARs. Based on the first selection of Table 6, they made subsequent selections of genes based on their expected expression profiles (Tables 7 to 10).

On another hand, the inventors have identified a selection of transcriptional loci that are mostly inactive, which would be most appropriate to insert expression cassette(s) to express exogenous coding sequence under the transcriptional control of exogenous promoters. These loci are referred to as "safe harbor loci" as those being mostly transcriptionally inactive, especially during T-Cell activation. They are useful to integrate a coding sequence by reducing at the maximum the risk of interfering with genome expression of the immune cells.

Gene Targeted Insertion Under Control of Endogenous Promoters that are Steadily Active During Immune Cell Activation A selection of endogenous gene loci related to this embodiment is listed in Table 7.

Accordingly the method of the present invention provides with the step of performing gene targeted insertion under control of an endogenous promoter that is constantly active during immune cell activation, preferably from of an endogenous gene selected from CD3G, Rn28s1, Rn18s, Rn7sk, Actg1, β2m, Rpl18a, Pabpc1, Gapdh, Rpl17, Rpl19, Rplp0, Cfl1 and Pfn1.

By "steadily active" means that the transcriptional activity observed for these promoters in the primary immune cell is not affected by a negative regulation upon the activation of the immune cell.

As reported elsewhere (Acuto, O. (2008) "Tailoring T-cell receptor signals by proximal negative feedback mechanisms". *Nature Reviews Immunology* 8:699-712), the promoters present at the TCR locus are subjected to different negative feedback mechanisms upon TCR engagement and thus may not be steadily active or up regulated during for the method of the present invention. The present invention has been designed to some extend to avoid using the TCR locus as a possible insertion site for exogenous coding sequences to be expressed during T-cell activation. Therefore, according to one aspect of the invention, the targeted insertion of the exogenous coding sequence is not performed at a TCRalpha or TCRbeta gene locus.

Examples of exogenous coding sequence that can be advantageously introduced at such loci under the control of steadily active endogenous promoters, are those encoding or positively regulating the production of a cytokine, a chemokine receptor, a molecule conferring resistance to a drug, a co-stimulation ligand, such as 4-1BRL and OX40L, or of a secreted antibody.

Gene Integration Under Endogenous Promoters that are Dependent from Immune Cell Activation or Dependent from CAR Activation As stated before, the method of the present invention provides with the step of performing gene targeted insertion under control of an endogenous promoter, which transcriptional activity is preferably up-regulated upon immune cell activation, either transiently or over more than 10 days.

By "immune cell activation" is meant production of an immune response as per the mechanisms generally described and commonly established in the literature for a given type of immune cells. With respect to T-cell, for instance, T-cell activation is generally characterized by one of the changes consisting of cell surface expression by production of a variety of proteins, including CD69, CD71 and CD25 (also a marker for Treg cells), and HLA-DR (a marker of human T cell activation), release of perforin, granzymes and granulysin (degranulation), or production of cytokine effectors IFN-γ, TNF and LT-alpha.

According to a preferred embodiment of the invention, the transcriptional activity of the endogenous gene is up-regulated in the immune cell, especially in response to an activation by a CAR. The CAR can be independently expressed in the immune cell. By "independently expressed" is meant that the CAR can be transcribed in the immune cell from an exogenous expression cassette introduced, for instance, using a retroviral vector, such as a lentiviral vector, or by transfecting capped messenger RNAs by electroporation encoding such CAR Many methods are known in the art to express a CAR into an immune cell as described for instance by (REF.)

Said endogenous gene whose transcriptional activity is up regulated are particularly appropriate for the integration of exogenous sequences to encode cytokine(s), such as IL-12 and IL-15, immunogenic peptide(s), or a secreted antibody, such as an anti-IDO1, anti-IL10, anti-PD1, anti-PDL1, anti-IL6 or anti-PGE2 antibody.

According to a preferred embodiment of the invention, the endogenous promoter is selected for its transcriptional activity being responsive to, and more preferably being dependent from CAR activation.

As shown herein, CD69, CD25 and PD1 are such loci, which are particularly appropriate for the insertion of expression of an exogenous coding sequences to be expressed when the immune cells get activated, especially into CAR positive immune cells.

The present invention thus combines any methods of expressing a CAR into an immune cell with the step of performing a site directed insertion of an exogenous coding sequence at a locus, the transcriptional activity of which is responsive to or dependent from the engagement of said CAR with a tumor antigen. Especially, the method comprises the step of introducing into a CAR positive or Recombinant TCR positive immune cell an exogenous sequence encoding IL-12 or IL-15 under transcriptional control of one promoter selected from PD1, CD25 and CD69 promoters.

In particular, CAR positive cells can obtained by following the steps of co-expressing into an immune cell, preferably a primary cell, and more preferably into a primary T-cell, at least one exogenous sequence encoding a CAR and another exogenous sequence placed under an endogenous promoter dependent, which transcriptional activity is dependent from said CAR, such a PD1, CD25 or CD71.

The expression "dependent from said CAR" means that the transcriptional activity of said endogenous promoter is necessary increased by more than 10%, preferably by more than 20%, more preferably by more than 50% and even more preferably more than 80%, as a result of the engagement of the CAR with its cognate antigen, in a situation where, in general, the antigens are exceeding the number of CARs present at the cell surface and the number of CARs expressed at the cell surface is more than 10 per cell, preferably more than 100, and more preferably more than 1000 molecules per cells.

The present invention thus teaches the expression of a CAR sequence, preferably inserted at the TCR locus and constitutively expressed, whereas another exogenous sequence integrated at another locus is co-expressed, in response to, or dependent from, the engagement of said CAR with its cognate antigen. Said another locus is for instance CD25, PD1 or CD71 or any loci being specifically transcribed upon CAR activation.

In other words, the invention provides the co-expression of a CAR and at least one exogenous coding sequence, the expression of said exogenous sequence being under control of an endogenous promoter the transcriptional activity of which is influenced by the CAR activity, this being done in view of obtaining engineered immune cells offering a better immune response.

As previously described, this can be performed by transfecting the cells with sequence-specific nuclease reagents targeting the coding regions of such loci being specifically CAR dependent, along with donor templates comprising sequences homologous to said genomic regions. The sequence specific nuclease reagents help the donor templates to be integrated by homologous recombination or NHEJ.

According to a preferred embodiment, the exogenous coding sequence is integrated in frame with the endogenous gene, so that the expression of said endogenous gene is preserved. This is the case for instance with respect to CD25 and CD69 in at least one example of the experimental section herein.

According to a preferred embodiment, the exogenous sequence disrupts the endogenous coding sequence of the gene to prevent its expression of one endogenous coding sequence, especially when this expression has a negative effect on the immune cell functions, as it the case for instance with PD1 in the experimental section herein.

According to an even more preferred embodiments, the exogenous coding sequence, which disrupts the endogenous gene sequence is placed in frame with the endogenous promoter, so that its expression is made dependent from the endogenous promoter as also shown in the experimental section.

The present invention is also drawn to the polynucleotide and polypeptide sequences encoding the different TAL-nucleases exemplified in the present patent application, especially those permitting the site directed insertion at the CD25 locus (SEQ ID NO:18 and 19), as well as their respective target and RVD sequences.

The present invention also encompasses kits for immune cells transfection comprising polynucleotides encoding the sequence-specific endonuclease reagents and the donor sequences designed to integrate the exogenous sequence at the locus targeted by said reagents. Examples of such kits are a kit comprising mRNA encoding rare-cutting endonuclease targeting PD1 locus (ex: PD1 TALEN®) and an AAV vector comprising an exogenous sequence encoding IL-12, a kit comprising mRNA encoding rare-cutting endonuclease targeting PD1 locus (ex: PD1 TALEN®) and an AAV vector comprising an exogenous sequence encoding IL-15, a kit comprising mRNA encoding rare-cutting endonuclease targeting CD25 locus (ex: CD25 TALEN®) and an AAV vector comprising an exogenous sequence encoding IL-12, a kit comprising mRNA encoding rare-cutting endonuclease targeting CD25 locus (ex: CD25 TALEN®) and an AAV vector comprising an exogenous sequence encoding IL-15, a kit comprising mRNA encoding rare-cutting endonuclease targeting PD1 locus (ex: PD1 TALEN®) and an AAV vector comprising an exogenous sequence encoding soluble gp130, a kit comprising mRNA encoding rare-cutting endonuclease targeting CD25 locus (ex: CD25 TALEN®) and an AAV vector comprising an exogenous sequence encoding soluble gp130, and any kits involving endonuclease reagents targeting a gene listed in table 6, and a donor matrix for introducing a coding sequence referred to in the present specification.

According to one aspect of the invention, the endogenous gene is selected for a weak up-regulation. The exogenous coding sequence introduced into said endogenous gene whose transcriptional activity is weakly up regulated, can be advantageously a constituent of an inhibitory CAR, or of an apoptotic CAR, which expression level has generally to remain lower than that of a positive CAR. Such combination of CAR expression, for instance one transduced with a viral vector and the other introduced according to the invention, can greatly improve the specificity or safety of CAR immune cells Some endogenous promoters are transiently up-regulated, sometimes over less than 12 hours upon immune cell activation, such as those selected from the endogenous gene loci Spata6, Itga6, Rcbtb2, Cdld1, St8sia4, Itgae and Fam214a (Table 8). Other endogenous promoters are up-regulated over less than 24 hours upon immune cell activation, such as those selected from the endogenous gene loci IL3, IL2, Ccl4, IL21, Gp49a, Nr4a3, Lirb4, Cd200, Cdkn1a, Gzmc, Nr4a2, Cish, Ccr8, Lad1 and Crabp2 (Table 9) and others over more than 24 hours, more generally over more than 10 days, upon immune cell activation. Such as those selected from Gzmb, Tbx21, Plek, Chek1, Slamf7, Zbtb32, Tigit, Lag3, Gzma, Wee1, IL12rb2, Eea1 and DtU (Table 9).

Alternatively, the inventors have found that endogenous gene under transcriptional control of promoters that are down-regulated upon immune cell activation, could also be of interest for the method according to the present invention. Indeed they have conceived that exogenous coding sequences encoding anti-apoptotic factors, such as of Bcl2 family, BcIXL, NF-kB, Survivin, or anti-FAP (fibroblast activation protein), such as a constituent of a CAR anti-FAP, could be introduced at said loci. Said endogenous gene under transcriptional control of promoters that are down-regulated upon immune cell activation can be more particularly selected from Slc6a19, Cd55, Xkrx, Mtum, H2-Ob, Cnr2, Itgae, Raver2, Zbtb20, Arrb1, Abca1, Tet1, Sic16a5 and Ampd3 (Table 10)

Gene Integration Under Endogenous Promoters Activated Under Tumor Microenvironment (TME) Conditions One aspect of the present invention more particularly concerns methods to prevent immune cells exhaustion in tumor microenvironment (TME) conditions. Immune cells often get exhausted in response to nutrient depletion or molecular signals found in the microoenvironment of tumors, which helps tumor resistance. The method comprises the steps of engineering immune cells by integrating exogenous coding sequences under control of endogenous promoters which are up-regulated under arginine, cysteine, tryptophan and oxygen deprivation as well as extracellular acidosis (lactate build up).

Such exogenous sequences may encode chimeric antigen receptors, interleukins, or any polypeptide given elsewhere in this specification to bolster immune cells function or activation and/or confer a therapeutic advantage.

The inventors have listed a number of loci which have been found to be upregulated in a large number of exhausted tumor infiltrating lymphocytes (TIL), which are listed in tables 12 and 13. The invention provides with the step of integrating exogenous coding sequences at these preferred loci to prevent exhaustion of the immune cells, in particular T-cells, in tumor microoenvironment.

For instance, the exogenous sequences encoding a CAR can be placed under transcriptional control of the promoter of endogenous genes that are activated by the tumor microenvironment, such as HIF1a, transcription factor hypoxia-inducible factor, or the aryl hydrocarbon receptor (AhR), These gene are sensors respectively induced by hypoxia and xenobiotics in the close environment of tumors.

The present invention is thus useful to improve the therapeutic outcome of CAR T-cell therapies by integrating exogenous coding sequences, and more generally genetic attributes/circuits, under the control of endogenous T-cell promoters influenced by tumor microenvironment (TME).

Pursuant to the invention, upregulation of endogenous genes can be "hijacked" to re-express relevant exogenous coding sequences to improve the antitumor activity of CAR T-cells in certain tumor microenvironment Gene Targeted Insertion and Expression in Hematopoietic Stem Cells (HSCs)

One aspect of the present invention more particularly concerns the insertion of transgenes into hematopoietic stem cells (HSCs).

Hematopoietic stem cells (HSCs) are multipotent, self-renewing progenitor cells from which all differentiated blood cell types arise during the process of hematopoiesis. These cells include lymphocytes, granulocytes, and macrophages of the immune system as well as circulating erythrocytes and platelets. Classically, HSCs are thought to differentiate into two lineage-restricted, lymphoid and myelo-erythroid, oligopotent progenitor cells. The mechanisms controlling HSC self-renewal and differentiation are thought to be influenced by a diverse set of cytokines, chemokines, receptors, and intracellular signaling molecules. Differentiation of HSCs is regulated, in part, by growth factors and cytokines including colony-stimulating factors (CSFs) and interleukins (ILs) that activate intracellular signaling pathways. The factors depicted below are known to influence HSC multipotency, proliferation, and lineage commitment. HSCs and their differentiated progeny can be identified by the expression of specific cell surface lineage markers such as cluster of differentiation (CD) proteins and cytokine receptors into hematopoietic stem cells.

Gene therapy using HSCs has enormous potential to treat diseases of the hematopoietic system including immune diseases. In this approach, HSCs are collected from a patient, gene-modified ex-vivo using integrating retroviral vectors, and then infused into a patient To date retroviral vectors have been the only effective gene delivery system for HSC gene therapy. Gene delivery to HSCs using integrating vectors thereby allowing for efficient delivery to HSC-derived mature hematopoietic cells. However, the gene-modified cells that are infused into a patient are a polyclonal population, where the different cells have vector proviruses integrated at different chromosomal locations, which can result into many adverse mutations, which may be amplified due to some proliferative/survival advantage of these mutations (Powers and Trobridge (2013) "Identification of Hematopoietic Stem Cell Engraftment Genes in Gene Therapy Studies" *J Stem Cell Res Ther* S3:004. doi:10.4172/2157-7633.S3-00).

HSCs are commonly harvested from the peripheral blood after mobilization (patients receive recombinant human granulocyte-colony stimulating factor (G-CSF)). The patient's peripheral blood is collected and enriched for HSCs using the CD34+ marker. HSCs are then cultured ex vivo and exposed to viral vectors. The ex vivo culture period varies from 1 to 4 days. Prior to the infusion of gene-modified HSCs, patients may be treated with chemotherapy agents or irradiation to help enhance the engraftment efficiency. Gene-modified HSCs are re-infused into the patient intravenously. The cells migrate into the bone marrow before finally residing in the sinusoids and perivascular tissue. Both homing and hematopoiesis are integral aspects of engraftment. Cells that have reached the stem cell niche through homing will begin producing mature myeloid and lymphoid cells from each blood lineage. Hematopoiesis continues through the action of long-term HSCs, which are capable of self-renewal for life-long generation of the patient's mature blood cells, in particular the production of common lymphoid progenitor cells, such as T cells and NK cells, which are key immune cells for eliminating infected and malignant cells.

The present invention provides with performing gene targeted insertion in HSCs to introduce exogenous coding sequences under the control of endogenous promoters, especially endogenous promoters of genes that are specifically activated into cells of a particular hematopoietic lineage or at particular differentiation stage, preferably at a late stage of differentiation. The HSCs can be transduced with a polynucleotide vector (donor template), such as an AAV vector, during an ex-vivo treatment as referred to in the previous paragraph, whereas a sequence specific nuclease reagent is expressed as to promote the insertion of the coding sequences at the selected locus. The resulting engineered HSCs can be then engrafted into a patient in need thereof for a long term in-vivo production of engineered immune cells that will comprise said exogenous coding sequences. Depending on the activity of the selected endogenous promoter, the coding sequences will be selectively expressed in certain lineages or in response to the local environment of the immune cells in-vivo, thereby providing adoptive immunotherapy.

According to one preferred aspect of the invention, the exogenous coding sequences are placed under the control of promoters of a gene, which transcriptional activity is specifically induced in common lymphoid progenitor cells, such as CD34, CD43, Flt-3/Flk-2, IL-7 R alpha/CD127 and Neprilysin/CD10.

More preferably, the exogenous coding sequences are placed under the control of promoters of a gene, which transcriptional activity is specifically induced in NK cells, such as CD161, CD229/SLAMF3, CD96, DNAM-1/CD226, Fc gamma RII/CD32, Fc gamma RII/RIII (CD32/CD16), Fc gamma RIII (CD16), IL-2 R beta, Integrin alpha 2/CD49b, KIR/CD158, NCAM-1/CD56, NKG2A/CD159a, NKG2C/CD159c, NKG2D/CD314, NKp30/NCR3, NKp44/NCR2, NKp46/NCR1, NKp80/KLRF1, Siglec-7/CD328 and TIGIT, or induced in T-cells, such as CCR7, CD2, CD3, CD4, CD8, CD28, CD45, CD96, CD229/SLAMF3, DNAM-1/CD226, CD25/AL-2 R alpha, L-Selectin/CD62L and TIGIT.

The invention comprises as a preferred aspect the introduction of an exogenous sequence encoding a CAR, or a component thereof, into HSCs, preferably under the transcriptional control of a promoter of a gene that is not expressed in HSC, more preferably a gene that is only expressed in the hematopoietic cells produced by said HSC, and even more preferably of a gene that is only expressed in T-cells or NK cells.

Conditional CAR Expression in HSCs to Overpass the Thymus Barrier

A particular aspect of the present invention concerns the in-vivo production by the above engineered HSCs of hematopoietic immune cells, such as T-cells or NK-cells, expressing exogenous coding sequences, in particular a CAR or a component thereof.

One major bar of the production of hematopoietic CAR positive cells by engineered HSCs, for instance, is the rejection of the CAR positive cells by the immune system itself, especially by the thymus.

The blood-thymus barrier regulates exchange of substances between the circulatory system and thymus, providing a sequestered environment for immature T cells to develop. The barrier also prevents the immature T cells from contacting foreign antigens (since contact with antigens at this stage will cause the T cells to die by apoptosis).

One solution provided by the present invention is to place the sequences encoding the CAR components in the HSCs under the transcriptional control of promoters which are not significantly transcribed into the hematopoietic cells when they pass through the thymus barrier. One example of a gene that offers a conditional expression of the CAR into the hematopoietic cells with reduced or no significant transcriptional activity in the thymus is LCK (Uniprot P06239).

According to a preferred aspect of the invention the exogenous sequence encoding a CAR, or a component thereof, is introduced into the HSC under the transcriptional control of a gene that is described as being specifically expressed in T-cells or NK cells, preferably in these types of cells only.

The invention thereby provides with a method of producing HSCs comprising an exogenous coding sequences to be expressed exclusively in selected hematopoietic lineage(s), said coding sequences encoding preferably at least one component of a CAR or of an antigen in order to stimulate the immune system.

More broadly, the invention provides with a method of engineering HSCs by gene targeted insertion of an exogenous coding sequences to be selectively expressed in the hematopoietic cells produced by said HSCs. As a preferred embodiment, said hematopoietic cells produced by said engineered HSCs express said exogenous coding sequences in response to selected environmental factors or in-vivo stimuli to improve their therapeutic potential.

Combining Targeted Sequence Insertion(s) in Immune Cells with the Inactivation of Endogenous Genomic Sequences One particular focus of the present invention is to perform gene inactivation in primary immune cells at a locus, by integrating exogenous coding sequence at said locus, the expression of which improves the therapeutic potential of said engineered cells. Examples of relevant exogenous coding sequences that can be inserted according to the invention have been presented above in connection with their positive effects on the therapeutic potential of the cells. Here below are presented the endogenous gene that are preferably targeted by gene targeted insertion and the advantages associated with their inactivation.

According to a preferred aspect of the invention, the insertion of the coding sequence has the effect of reducing or preventing the expression of genes involved into self and non-self recognition to reduce host versus graft disease (GVHD) reaction or immune rejection upon introduction of the allogeneic cells into a recipient patient. For instance, one of the sequence-specific reagents used in the method can reduce or prevent the expression of TCR in primary T-cells, such as the genes encoding TCR-alpha or TCR-beta.

As another preferred aspect, one gene editing step is to reduce or prevent the expression of the 182m protein and/or another protein involved in its regulation such as C2TA (Uniprot P33076) or in MHC recognition, such as HLA proteins. This permits the engineered immune cells to be less alloreactive when infused into patients.

By "allogeneic therapeutic use" is meant that the cells originate from a donor in view of being infused into patients having a different haplotype. Indeed, the present invention provides with an efficient method for obtaining primary cells, which can be gene edited in various gene loci involved into host-graft interaction and recognition.

Other loci may also be edited in view of improving the activity, the persistence of the therapeutic activity of the engineered primary cells as detailed here after Inactivation of Checkpoint Receptors and Immune Cells Inhibitory Pathways:

According to a preferred aspect of the invention, the inserted exogenous coding sequence has the effect of reducing or preventing the expression of a protein involved in immune cells inhibitory pathways, in particular those referred to in the literature as "immune checkpoint" (Pardoll, D. M. (2012) The blockade of immune checkpoints in cancer immunotherapy, Nature Reviews Cancer, 12:252-264). In the sense of the present invention, "immune cells inhibitory pathways" means any gene expression in immune cells that leads to a reduction of the cytotoxic activity of the lymphocytes towards malignant or infected cells. This can be for instance a gene involved into the expression of FOXP3, which is known to drive the activity of Tregs upon T cells (moderating T-cell activity).

"Immune checkpoints" are molecules in the immune system that either turn up a signal (co-stimulatory molecules) or turn down a signal of activation of an immune cell. As per the present invention, immune checkpoints more particularly designate surface proteins involved in the ligand-receptor interactions between T cells and antigen-presenting cells (APCs) that regulate the T cell response to antigen (which is mediated by peptide-major histocompatibility complex (MHC) molecule complexes that are recognized by the T cell receptor (TCR)). These interactions can occur at the initiation of T cell responses in lymph nodes (where the major APCs are dendritic cells) or in peripheral tissues or tumours (where effector responses are regulated). One important family of membrane-bound ligands that bind both co-stimulatory and inhibitory receptors is the B7 family. All of the B7 family members and their known ligands belong to the immunoglobulin superfamily. Many of the receptors for more recently identified B7 family members have not yet been identified. Tumour necrosis factor (TNF) family members that bind to cognate TNF receptor family molecules represent a second family of regulatory ligand-receptor pairs. These receptors predominantly deliver co-stimulatory signals when engaged by their cognate ligands. Another major category of signals that regulate the activation of T cells comes from soluble cytokines in the microenvironment. In other cases, activated T cells upregulate ligands, such as CD40L, that engage cognate receptors on APCs. A2aR, adenosine A2a receptor; B7RP1, B7-related protein 1; BTLA, B and T lymphocyte attenuator; GAL9, galectin 9; HVEM, herpesvirus entry mediator; ICOS, inducible T cell co-stimulator; IL, interleukin; KIR, killer cell immunoglobulin-like receptor; LAG3, lymphocyte activation gene 3; PD1, programmed cell death protein 1; PDL, PD1 ligand; TGFβ, transforming growth factor-β; TIM3, T cell membrane protein 3.

Examples of further endogenous genes, which expression could be reduced or suppressed to turn-up activation in the engineered immune cells according the present invention are listed in Table 3.

For instance, the inserted exogenous coding sequence(s) can have the effect of reducing or preventing the expression, by the engineered immune cell of at least one protein selected from PD1 (Uniprot Q15116), CTLA4 (Uniprot P16410), PPP2CA (Uniprot P67775), PPP2CB (Uniprot P62714), PTPN6 (Uniprot P29350), PTPN22 (Uniprot Q9Y2R2), LAG3 (Uniprot P18627), HAVCR2 (Uniprot Q8TDQ0), BTLA (Uniprot Q7Z6A9), CD160 (Uniprot O95971), TIGIT (Uniprot Q495A1), CD96 (Uniprot P40200), CRTAM (Uniprot O95727), LAIR1 (Uniprot Q6GTX8), SIGLEC7 (Uniprot Q9Y286), SIGLEC9 (Uniprot Q9Y336), CD244 (UniprotQ9BZWC), TNFRSF1B (Uniprot014763), TNFRSF10A (Uniprot000220), CASP8 (Uniprot Q14790), CASP10 (Uniprot Q92851), CASP3 (Uniprot P42574), CASP6 (Uniprot P55212), CASP7 (Uniprot P55210), FADD (Uniprot Q13158), FAS (Uniprot P25445), TGFBRII (Uniprot P37173), TGFRBRI (Uniprot Q15582), SMAD2 (Uniprot Q15796), SMAD3 (Uniprot P84022), SMAD4 (Uniprot Q13485), SMAD10 (Uniprot B7ZSB5), SKI (Uniprot P12755), SKIL (Uniprot P12757), TGIF1 (Uniprot Q15583), IL10RA (Uniprot Q13651), IL10RB (Uniprot Q08334), HMOX2 (Uniprot P30519), IL6R (Uniprot P08887), IL6ST (Uniprot P40189), EIF2AK4 (Uniprot Q9P2K8), CSK (Uniprot P41240), PAG1 (Uniprot Q9NWQ8), SIT1 (Uniprot Q9Y3P8), FOXP3 (Uniprot Q9BZS1), PRDM1 (Uniprot Q60636), BATF (Uniprot Q16520), GUCY1A2 (Uniprot P33402), GUCY1A3 (Uniprot Q02108), GUCY1B2 (Uniprot Q8BXH3) and GUCYB3 (Uniprot Q02153). The gene editing introduced in the genes encoding the above proteins is preferably combined with an inactivation of TCR in CAR T cells.

Preference is given to inactivation of PD1 and/or CTLA4, in combination with the expression of non-endogenous immunosuppressive polypeptide, such as a PD-L1 ligand and/or CTLA-4 Ig (see also peptides of Table 1 and 2).

TABLE 3

List of genes involved into immune cells inhibitory pathways

| Pathway | | Genes that can be inactivated In the pathway |
|---|---|---|
| Co-inhibitory receptors | CTLA4 (CD152) | CTLA4, PPP2CA, PPP2CB, PTPN6, PTPN22 |
| | PDCD1 (PD-1, CD279) | PDCD1 |
| | CD223 (lag3) | LAG3 |
| | HAVCR2 (tim3) | HAVCR2 |
| | BTLA(cd272) | BTLA |
| | CD160(by55) | CD160 |
| | IgSF family | TIGIT |
| | | CD96 |
| | | CRTAM |
| | LAIR1(cd305) | LAIR1 |
| | SIGLECs | SIGLEC7 |
| | | SIGLEC9 |
| | CD244(2b4) | CD244 |
| Death receptors | TRAIL | TNFRSF10B, TNFRSF10A, CASP8, CASP10, CASP3, CASP6, CASP7 |
| | FAS | FADD, FAS |
| Cytokine signalling | TGF-beta signaling | TGFBRII, TGFBRI, SMAD2, SMAD3, SMAD4, SMAD10, SKI, SKIL, TGIF1 |
| | IL10 signalling | IL10RA, IL10RB, HMOX2 |
| | IL6 signalling | IL6R, IL6ST |
| Prevention of TCR signalling | | CSK, PAG1 SIT1 |
| Induced Treg | induced Treg | FOXP3 |
| Transcription factors controlling exhaustion | transcription factors controlling exhaustion | PRDM1 BATF |
| Hypoxia mediated tolerance | iNOS induced guanylated cyclase | GUCY1A2, GUCY1A3, GUCY1B2, GUCY1B3 |

Inhibiting Suppressive Cytokines/Metabolites

According to another aspect of the invention, the inserted exogenous coding sequence has the effect of reducing or preventing the expression of genes encoding or positively regulating suppressive cytokines or metabolites or receptors thereof, in particular TGFbeta (Uniprot:P01137), TGFbR (UniprotP37173), IL10 (Uniprot:P22301), IL10R (Uniprot: Q13651 and/or Q08334), A2aR (Uniprot: P29274), GCN2 (Uniprot: P15442) and PRDM1 (Uniprot: O75626).

Preference is given to engineered immune cells in which a sequence encoding IL-2, IL-12 or IL-15 replaces the sequence of at least one of the above endogenous genes.

Inducing Resistance to Chemotherapy Drugs

According to another aspect of the present method, the inserted exogenous coding sequence has the effect of reducing or preventing the expression of a gene responsible for the sensitivity of the immune cells to compounds used in standard of care treatments for cancer or infection, such as drugs purine nucleotide analogs (PNA) or 6-Mercaptopurine (6MP) and 6 thio-guanine (6TG) commonly used in chemotherapy. Reducing or inactivating the genes involved into the mode of action of such compounds (referred to as "drug sensitizing genes") improves the resistance of the immune cells to same.

Examples of drug sensitizing gene are those encoding DCK (Uniprot P27707) with respect to the activity of PNA, such a clorofarabine et fludarabine, HPRT (Uniprot P00492) with respect to the activity of purine antimetabolites such as 6MP and 6TG, and GGH (Uniprot Q92820) with respect to the activity of antifolate drugs, in particular methotrexate.

This enables the cells to be used after or in combination with conventional anti-cancer chemotherapies.

Resistance to Immune-Suppressive Treatments

According to another aspect of the present invention, the inserted exogenous coding sequence has the effect of reducing or preventing the expression of receptors or proteins, which are drug targets, making said cells resistant to immune-depletion drug treatments. Such target can be glucocorticoids receptors or antigens, to make the engineered immune cells resistant to glucocorticoids or immune depletion treatments using antibodies such as Alemtuzumab, which is used to deplete CD52 positive immune cells in many cancer treatments.

Also the method of the invention can comprise gene targeted insertion in endogenous gene(s) encoding or regulating the expression of CD52 (Uniprot P31358) and/or GR (Glucocorticoids receptor also referred to as NR3C1—Uniprot P04150).

Improving CAR Positive Immune Cells Activity and Survival

According to another aspect of the present invention, the inserted exogenous coding sequence can have the effect of reducing or preventing the expression of a surface antigen, such as BCMA, CS1 and CD38, wherein such antigen is one targeted by a CAR expressed by said immune cells.

This embodiment can solve the problem of CAR targeting antigens that are present at the surface of infected or malignant cells, but also to some extent expressed by the immune cell itself.

According to a preferred embodiment the exogenous sequence encoding the CAR or one of its constituents is integrated into the gene encoding the antigen targeted by said CAR to avoid self-destruction of the immune cells.

Engineered Immune Cells and Populations of Immune Cells

The present invention is also drawn to the variety of engineered immune cells obtainable according to one of the method described previously under isolated form or as part of populations of cells.

According to a preferred aspect of the invention the engineered cells are primary immune cells, such as NK cells or T-cells, which are generally part of populations of cells that may involve different types of cells. In general, population deriving from patients or donors isolated by leukapheresis from PBMC (peripheral blood mononuclear cells).

According to a preferred aspect of the invention, more than 50% of the immune cells comprised in said population are TCR negative T-cells. According to a more preferred aspect of the invention, more than 50% of the immune cells comprised in said population are CAR positive T-cells.

The present invention encompasses immune cells comprising any combinations of the different exogenous coding sequences and gene inactivation, which have been respectively and independently described above. Among these combinations are particularly preferred those combining the expression of a CAR under the transcriptional control of an endogenous promoter that is steadily active during immune cell activation and preferably independently from said activation, and the expression of an exogenous sequence encoding a cytokine, such as IL-2, IL-12 or IL-15, under the transcriptional control of a promoter that is up-regulated during the immune cell activation.

Another preferred combination is the insertion of an exogenous sequence encoding a CAR or one of its constituents under the transcription control of the hypoxia-inducible factor 1 gene promoter (Uniprot: Q16665).

The invention is also drawn to a pharmaceutical composition comprising an engineered primary immune cell or immune cell population as previously described for the treatment of infection or cancer, and to a method for treating a patient in need thereof, wherein said method comprises:
 preparing a population of engineered primary immune cells according to the method of the invention as previously described;
 optionally, purifying or sorting said engineered primary immune cells;
 activating said population of engineered primary immune cells upon or after infusion of said cells into said patient.

Activation and Expansion of T Cells

Whether prior to or after genetic modification, the immune cells according to the present invention can be activated or expanded, even if they can activate or proliferate independently of antigen binding mechanisms. T-cells, in particular, can be activated and expanded using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo. T cells are generally expanded by contact with an agent that stimulates a CD3 TCR complex and a co-stimulatory molecule on the surface of the T cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell.

As non-limiting examples, T cell populations may be stimulated in vitro such as by contact with an anti-CD3 antibody, or antigen-binding fragment thereof, or an anti- CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, IL-4, IL-7, GM-CSF, -10, -2, IL-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% C02). T cells that have been exposed to varied stimulation times may exhibit different characteristics In another particular embodiment, said cells can be expanded by co-culturing with tissue or cells. Said cells can also be expanded in vivo, for example in the subject's blood after administrating said cell into the subject.

Therapeutic Compositions and Applications

The method of the present invention described above allows producing engineered primary immune cells within a limited time frame of about 15 to 30 days, preferably between 15 and 20 days, and most preferably between 18 and 20 days so that they keep their full immune therapeutic potential, especially with respect to their cytotoxic activity.

These cells form a population of cells, which preferably originate from a single donor or patient. These populations of cells can be expanded under closed culture recipients to comply with highest manufacturing practices requirements and can be frozen prior to infusion into a patient, thereby providing "off the shelf" or "ready to use" therapeutic compositions.

As per the present invention, a significant number of cells originating from the same Leukapheresis can be obtained, which is critical to obtain sufficient doses for treating a patient. Although variations between populations of cells originating from various donors may be observed, the number of immune cells procured by a leukapheresis is generally about from $10^8$ to $10^{10}$ cells of PBMC. PBMC comprises several types of cells: granulocytes, monocytes and lymphocytes, among which from 30 to 60% of T-cells, which generally represents between $10^8$ to $10^9$ of primary T-cells from one donor. The method of the present invention generally ends up with a population of engineered cells that reaches generally more than about $10^8$ T-cells, more generally more than about $10^9$ T-cells, even more generally more than about $10^{10}$ T-cells, and usually more than $10^{11}$ T-cells.

The invention is thus more particularly drawn to a therapeutically effective population of primary immune cells, wherein at least 30%, preferably 50%, more preferably 80% of the cells in said population have been modified according to any one the methods described herein. Said therapeutically effective population of primary immune cells, as per the present invention, comprises immune cells that have integrated at least one exogenous genetic sequence under the transcriptional control of an endogenous promoter from at least one of the genes listed in Table 6.

Such compositions or populations of cells can therefore be used as medicaments; especially for treating cancer, particularly for the treatment of lymphoma, but also for solid tumors such as melanomas, neuroblastomas, gliomas or carcinomas such as lung, breast, colon, prostate or ovary tumors in a patient in need thereof.

The invention is more particularly drawn to populations of primary TCR negative T-cells originating from a single donor, wherein at least 20%, preferably 30%, more preferably 50% of the cells in said population have been modified using sequence-specific reagents in at least two, preferably three different loci.

In another aspect, the present invention relies on methods for treating patients in need thereof, said method comprising at least one of the following steps:
(a) Determining specific antigen markers present at the surface of patients tumors biopsies;
(b) providing a population of engineered primary immune cells engineered by one of the methods of the present invention previously described expressing a CAR directed against said specific antigen markers;
(c) Administrating said engineered population of engineered primary immune cells to said patient, Generally, said populations of cells mainly comprises CD4 and CD8 positive immune cells, such as T-cells, which can undergo robust in vivo T cell expansion and can persist for an extended amount of time in-vitro and in-vivo.

The treatments involving the engineered primary immune cells according to the present invention can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

In another embodiment, said isolated cell according to the invention or cell line derived from said isolated cell can be used for the treatment of liquid tumors, and preferably of T-cell acute lymphoblastic leukemia.

Adult tumors/cancers and pediatric tumors/cancers are also included.

The treatment with the engineered immune cells according to the invention may be in combination with one or more therapies against cancer selected from the group of antibodies therapy, chemotherapy, cytokines therapy, dendritic cell therapy, gene therapy, hormone therapy, laser light therapy and radiation therapy.

According to a preferred embodiment of the invention, said treatment can be administrated into patients undergoing an immunosuppressive treatment. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^8$ cells/kg body weight including all integer values of cell numbers within those ranges. The present invention thus can provide more than 10, generally more than 50, more generally more than 100 and usually more than 1000 doses comprising between $10^8$ to $10^8$ gene edited cells originating from a single donor's or patient's sampling.

The cells or population of cells can be administered in one or more doses. In another embodiment, said effective amount of cells are administered as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or composition comprising those cells are administered parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Henderson, Naya et al. 1991; Liu, Albers et al. 1992; Bierer, Hollander et al. 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

When CARs are expressed in the immune cells or populations of immune cells according to the present invention, the preferred CARs are those targeting at least one antigen selected from CD22, CD38, CD123, CS1, HSP70, ROR1, GD3, and CLL1.

The engineered immune cells according to the present invention endowed with a CAR or a modified TCR targeting CD22 are preferably used for treating leukemia, such as acute lymphoblastic leukemia (ALL), those with a CAR or a modified TCR targeting CD38 are preferably used for treating leukemia such as T-cell acute lymphoblastic leukemia (T-ALL) or multiple myeloma (MM), those with a CAR or a modified TCR targeting CD123 are preferably used for treating leukemia, such as acute myeloid leukemia (AML), and blastic plasmacytoid dendritic cells neoplasm (BPDCN), those with a CAR or a modified TCR targeting CS1 are preferably used for treating multiple myeloma (MM).

The present invention also encompasses means for detecting the engineered cells of the present invention comprising the desired genetic insertions, especially by carrying out steps of using PCR methods for detecting insertions of exogenous coding sequences at the endogenous loci referred to in the present specification, especially at the PD1, CD25, CD69 and TCR loci, by using probes or primers hybridizing any sequences represented by SEQ ID NO:36 to 40.

Immunological assays may also be performed for detecting the expression by the engineered cells of CARs, GP130, and to check absence or reduction of the expression of TCR, PD1, IL-6 or IL-8 in the cells where such genes have been knocked-out or their expression reduced.

Other Definitions

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site greater than 10 base pairs (bp) in length, more preferably of 14-55 bp. Rare-cutting endonucleases significantly increase homologous recombination by inducing DNA double-strand breaks (DSBs) at a defined locus thereby allowing gene repair or gene insertion therapies (Pingoud, A. and G. H. Silva (2007). Precision genome surgery. *Nat. Biotechnol.* 25(7): 743-4).

By "DNA target", "DNA target sequence", "target DNA sequence", "nucleic acid target sequence", "target sequence", or "processing site" is intended a polynucleotide sequence that can be targeted and processed by a rare-cutting endonuclease according to the present invention. These terms refer to a specific DNA location, preferably a genomic location in a cell, but also a portion of genetic material that can exist independently to the main body of genetic material such as plasmids, episomes, virus, transposons or in organelles such as mitochondria as non-limiting example. As non-limiting examples of RNA guided target sequences, are those genome sequences that can hybridize the guide RNA which directs the RNA guided endonuclease to a desired locus.

By "mutation" is intended the substitution, deletion, insertion of up to one, two, three, four, five, six, seven, eight, nine, ten, eleven, twelve, thirteen, fourteen, fifteen, twenty, twenty five, thirty, forty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

By "vector" is meant a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available. Viral vectors include retrovirus, adenovirus, parvovirus (e. g. adenoassociated viruses (AAV), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

As used herein, the term "locus" is the specific physical location of a DNA sequence (e.g. of a gene) into a genome. The term "locus" can refer to the specific physical location of a rare-cutting endonuclease target sequence on a chromosome or on an infection agent's genome sequence. Such a locus can comprise a target sequence that is recognized and/or cleaved by a sequence-specific endonuclease according to the invention. It is understood that the locus of interest of the present invention can not only qualify a nucleic acid sequence that exists in the main body of genetic material (i.e. in a chromosome) of a cell but also a portion of genetic material that can exist independently to said main body of genetic material such as plasmids, episomes, virus, transposons or in organelles such as mitochondria as non-limiting examples.

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

The term "subject" or "patient" as used herein includes all members of the animal kingdom including non-human primates and humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

Having generally described this invention, a further understanding can be obtained by reference to certain specific examples, which are provided herein for purposes of illustration only, and are not intended to limit the scope of the claimed invention.

EXAMPLES

Example 1: AAV Driven Homologous Recombination in Human Primary T-Cells at Various Loci Under Control of Endogenous Promoters with Knock-Out of the Endogenous Gene Introduction Sequence specific endonuclease reagents, such as TALEN® (Cellectis, 8 rue de la Croix Jarry, 75013 PARIS) enable the site-specific induction of double-stranded breaks (DSBs) in the genome at desired loci. Repair of DSBs by cellular enzymes occurs mainly through two pathways: non-homologous end joining (NHEJ) and homology directed repair (HDR). HDR uses a homologous piece of DNA (template DNA) to repair the DSB by recombination and can be used to introduce any genetic sequence comprised in the template DNA. As shown therein, said template DNA can be delivered by recombinant adeno-associated virus (rAAV) along with an engineered nuclease such as TALEN® to introduce a site-specific DSB.

Design of the Integration Matrices 1.1. Insertion of an Apoptosis CAR in an Upregulated Locus with Knock-Out of the Endogenous PD1 Gene Coding Sequence The location of the TALEN target site has been designed to be located in the targeted endogenous PDCD1 gene (Programmed cell death protein 1 referred to as PD1—Uniprot #Q15116). The sequence encompassing 1000 bp upstream and downstream the TALEN targets is given in SEQ ID NO:1 and SEQ ID NO:2. Target sequences of the TALEN (SEQ ID NO:3 and SEQ ID NO:4) is given in SEQ ID NO:5. The integration matrix is designed to be composed of a sequence (300 bp) homologous to the endogenous gene upstream of the TALEN site (SEQ ID NO:1), followed by a 2A regulatory element (SEQ ID NO:6), followed by a sequence encoding an apoptosis inducing CAR without the start codon (SEQ ID NO:7), followed by a STOP codon (TAG), followed by a polyadenylation sequence (SEQ ID NO:8), followed by a sequence (1000 bp) homologous to the endogenous gene downstream of the TALEN site (SEQ ID NO:2). The insertion matrix is subsequently cloned into a promoterless rAAV vector and used to produce AAV6.

1.2 Insertion of an Interleukin in an Upregulated Locus with Knock-Out of the Endogenous Gene The location of the TALEN target site is designed to be located in the targeted endogenous PDCD1 gene (Programmed cell death protein 1, PD1). The sequence encompassing 1000 bp upstream and downstream the TALEN targets is given in SEQ ID NO:1 and SEQ ID NO:2. Target sequences of the TALEN (SEQ ID NO:3 and SEQ ID NO:4) is given in SEQ ID NO:5. The integration matrix is designed to be composed of a sequence (300 bp) homologous to the endogenous gene upstream of the TALEN site (SEQ ID NO:1), followed by a 2A regulatory element (SEQ ID NO:6), followed by a sequence encoding an engineered single-chained human IL-12 p35 (SEQ ID NO:9) and p40 (SEQ ID NO:10) subunit fusion protein, followed by a STOP codon (TAG), followed by a polyadenylation sequence (SEQ ID NO:8), followed by a sequence (1000 bp) homologous to the endogenous gene downstream of the TALEN site (SEQ ID NO:2). The insertion matrix is subsequently cloned into a promoterless rAAV vector and used to produce AAV6.

1.3 Insertion of an Apoptosis CAR in a Weakly Expressed Locus without Knocking Out the Endogenous Gene—N-Terminal Insertion The location of the TALEN target site is designed to be located as close as possible to the start codon of the targeted endogenous LCK gene (LCK, LCK proto-oncogene, Src family tyrosine kinase [*Homo sapiens* (human)]). The sequence encompassing 1000 bp upstream and downstream the start codon is given in SEQ ID NO:11 and SEQ ID NO:12. The integration matrix is designed to be composed of a sequence (1000 bp) homologous to the endogenous gene upstream of the start codon, followed by a sequence encoding an apoptosis inducing CAR containing a start codon (SEQ ID NO:13), followed by a 2A regulatory element (SEQ ID NO:8), followed by a sequence (1000 bp) homologous to the endogenous gene downstream of the start codon (SEQ ID NO:12). The insertion matrix is subsequently cloned into a promoterless rAAV vector and used to produce AAV6.

1.4 Insertion of an Apoptosis CAR in a Weakly Expressed Locus without Knocking Out the Endogenous Gene—C-Terminal Insertion The location of the TALEN target site is designed to be located as close as possible to the stop codon of the targeted endogenous LCK gene (LCK, LCK proto-oncogene, Src family tyrosine kinase [*Homo sapiens* (human)]). The sequence encompassing 1000 bp upstream and downstream the stop codon is given in SEQ ID NO:14 and SEQ ID NO:15. The integration matrix is designed to be composed of a sequence (1000 bp) homologous to the endogenous gene upstream of the stop codon, followed by a 2A regulatory element (SEQ ID NO:8), followed by a sequence encoding an apoptosis inducing CAR without the start codon (SEQ ID NO:7), followed by a STOP codon (TAG), followed by a sequence (1000 bp) homologous to the endogenous gene downstream of the stop codon (SEQ ID NO:15). The insertion matrix is subsequently cloned into a promoterless rAAV vector and used to produce AAV6.

Expression of the Sequence-Specific Nuclease Reagents in the Transduced Cells

TALEN® mRNA is synthesized using the mMessage mMachine T7 Ultra kit (Thermo Fisher Scientific, Grand Island, NY) as each TALEN is cloned downstream of a T7 promoter, purified using RNeasy columns (Qiagen, Valencia, CA) and eluted in "cytoporation medium T" (Harvard Apparatus, Holliston, MA). Human T-cells are collected and activated from whole peripheral blood provided by ALL-CELLS (Alameda, CA) in X-Vivo-15 medium (Lonza, Basel, Switzerland) supplemented with 20 ng/ml human IL-2 (Miltenyi Biotech, San Diego, CA), 5% human AB serum (Gemini Bio-Products, West San Francisco, CA) and Dynabeads Human T-activator CD3/CD28 at a 1:1 bead:cell ratio (Thermo Fisher Scientific, Grand Island, NY). Beads are removed after 3 days and 5×10⁶ cells are electroporated with 10 μg mRNA of each of the two adequate TALEN® using Cytopulse (BTX Harvard Apparatus, Holliston, MA) by applying two 0.1 mS pulses at 3,000 V/cm followed by four 0.2 mS pulses at 325 V/cm in 0.4 cm gap cuvettes in a final volume of 200 μl of "cytoporation medium T" (BTX Harvard Apparatus, Holliston, Massachusetts). Cells are immediately diluted in X-Vivo-15 media with 20 ng/mL IL-2 and incubated at 37° C. with 5% CO₂. After two hours, cells are incubated with AAV6 particles at 3×10⁵=viral genomes (vg) per cell (37° C., 16 hours). Cells are passaged and maintained in X-Vivo-15 medium supplemented with 5% human AB serum and 20 ng/mL IL-2 until examined by flow cytometry for expression of the respective inserted gene sequences.

TABLE 4

Sequences referred to in example 1

| Sequence name | Ref. sequences | Polynucleotide or polypeptide sequences |
|---|---|---|
| PD1 left homology | SEQ ID NO: 1 | CCAAGCCCTGACCCTGGCAGGCATATGTTTCAGGAGGTCCTTGTCTTGGGA<br>GCCCAGGGTCGGGGGCCCCGTGTCTGTCCACATCCGAGTCAATGGCCCAT<br>CTCGTCTCTGAAGCATCTTTGCTGTGAGCTCTAGTCCCCACTGTCTTGCTGG<br>AAAATGTGGAGGCCCCACTGCCCACTGCCCAGGGCAGCAATGCCCATACC<br>ACGTGGTCCCAGCTCCGAGCTTGTCCTGAAAAGGGGGCAAAGACTGGACC<br>CTGAGCCTGCCAAGGGGCCACACTCCTCCCAGGGCTGGGGTCTCCATGGG<br>CAGCCCCCCACCCACCCAGACCAGTTACACTCCCCTGTGCCAGAGCAGTGC<br>AGACAGGACCAGGCCAGGATGCCCAAGGGTCAGGGGCTGGGGATGGGT<br>AGCCCCCAAACAGCCCTTTCTGGGGGAACTGGCCTCAACGGGGAAGGGG<br>GTGAAGGCTCTTAGTAGGAAATCAGGGAGACCCAAGTCAGAGCCAGGTG<br>CTGTGCAGAAGCTGCAGCCTCACGTAGAAGGAAGAGGCTCTGCAGTGGA<br>GGCCAGTGCCCATCCCCGGGTGGCAGAGGCCCCAGCAGAGACTTCTCAAT<br>GACATTCCAGCTGGGGTGGCCCTTCCAGAGCCCTTGCTGCCCGAGGGATG<br>TGAGCAGGTGGCCGGGGAGGCTTTGTGGGGCCACCCAGCCCCTTCCTCAC<br>CTCTCTCCATCTCTCAGACTCCCCAGACAGGCCCTGGAACCCCCCACCTTC<br>TCCCCAGCCCTGCTCGTGGTGACCGAAGGGGACAACGCCACCTTCACCTGC<br>AGCTTCTCCAACACATCGGAGAGCTTCGTGCTAAACTGGTACCGCATGAGC<br>CCCAGCAACCAGACGGACAAGCTGGCCGCCTTCCCCGAGGACCGCAGCCA<br>GCCCGGCCAGGACTGCCGCTTCCGTGTCACACAACTGCCCAACGGGCGTG<br>ACTTCCACATGAGCGTGGTCAGGGCCCGGCGCAATGACAGCGGCACC |
| PD1 right homology | SEQ ID NO: 2 | GCCTGCGGGCAGAGCTCAGGGTGACAGGTGCGGCCTCGGAGGCCCCGGG<br>GCAGGGGTGAGCTGAGCCGGTCCTGGGGTGGGTGTCCCCTCCTGCACAG<br>GATCAGGAGCTCCAGGGTCGTAGGGCAGGGACCCCCCAGCTCCAGTCCAG<br>GGCTCTGTCCTGCACCTGGGGAATGGTGACCGGCATCTCTGTCCTCTAGCT<br>CTGGAAGCACCCCAGCCCCTCTAGTCTGCCCTCACCCCTGACCCTGACCCTC<br>CACCCTGACCCCGTCCTAACCCCTGACCTTTGTGCCCTTCCAGAGAGAAGG<br>GCAGAAGTGCCCACAGCCCACCCCAGCCCCTCACCCAGGCCAGCCGGCCA<br>GTTCCAAACCCTGGTGGTTGGTGTCGTGGGCGGCCTGCTGGGCAGCCTGG<br>TGCTGCTAGTCTGGGTCCTGGCCGTCATCTGCTCCCGGGCCGCACGAGGTA<br>ACGTCATCCCAGCCCCTCGGCCTGCCCTGCCCTAACCCTGCTGGCGGCCCT<br>CACTCCCGCCTCCCCTTCCTCCACCCTTCCCTCACCCCACCCCACCTCCCCCC<br>ATCTCCCCGCCAGGCTAAGTCCCTGATGAAGGCCCCTGGACTAAGACCCCC<br>CACCTAGGAGCACGGCTCAGGGTCGGCCTGGTGACCCCAAGTGTGTTTCT<br>CTGCAGGGACAATAGGAGCCAGGCGCACCGGCCAGCCCCTGGTGAGTCTC<br>ACTCTTTTCCTGCATGATCCACTGTGCCTTCCTTCCTGGGTGGGCAGAGGT<br>GGAAGGACAGGCTGGGACCACACGGCCTGCAGGACTCACATTCTATTATA<br>GCCAGGACCCCACCTCCCCAGCCCCCAGGCAGCAACCTCAATCCCTAAAGC<br>CATGATCTGGGGCCCCAGCCCACCTGCGGTCTCCGGGGGTGCCCGGCCCA<br>TGTGTGTGCCTGCCTGCGGTCTCCAGGGGTGCCTGGCCCACGCGTGTGCC<br>CGCCTGCGGTCTCTGGGGGTGCCCGGCCCACATATGTGCC |
| PD1_T3C-L2 | SEQ ID NO: 3 | ATGGGCGATCCTAAAAAGAAACGTAAGGTCATCGATATCGCCGATCTACG<br>CACGCTCGGCTACAGCCAGCAGCAACAGGAGAAGATCAAACCGAAGGTTC<br>GTTCGACAGTGGCGCAGCACCACGAGGCACTGGTCGGCCACGGGTTTACA<br>CACGCGCACATCGTTGCGTTAAGCCAACACCCGGCAGCGTTAGGGACCGT<br>CGCTGTCAAGTATCAGGACATGATCGCAGCGTTGCCAGAGGCGACACACG<br>AAGCGATCGTTGGCGTCGGCAAACAGTGGTCCGGCGCACGCGCTCTGGA<br>GGCCTTGCTCACGGTGGCGGGAGAGTTGAGAGGTCCACCGTTACAGTTGG<br>ACACAGGCCAACTTCTCAAGATTGCAAAACGTGGCGGCGTGACCGCAGTG<br>GAGGCAGTGCATGCATGGCGCAATGCACTGACGGGTGCCCCGCTCAACTT<br>GACCCCCGAGCAAGTGGTGGCTATCGCTTCCAAGCTGGGGGGAAAGCAG<br>GCCCTGGAGACCGTCCAGGCCCTTCTCCCAGTGCTTTGCCAGGCTCACGGA<br>CTGACCCCTGAACAGGTGGTGGCAATTGCCTCACACGACGGGGGCAAGCA<br>GGCACTGGAGACTGTCCAGCGGCTGCTGCCTGTCCTCTGCCAGGCCCACG<br>GACTCACTCCTGAGCAGGTCGTGGCCATTGCCAGCCACGATGGGGGCAAA<br>CAGGCTCTGGAGACCGTGCAGCGCCTCCTCCCAGTGCTGTGCCAGGCTCAT<br>GGGCTGACCCCACACAGGTCGTCGCCATTGCCAGTAACGGCGGGGGA<br>AGCAGGCCCTCGAAACAGTGCAGAGGCTGCTGCCCGTCTTGTGCCAAGCA<br>CACGGCCTGACACCCGAGCAGGTGGTGGCCATCGCCTCTCATGACGGCGG<br>CAAGCAGGCCCTTGAGACAGTGCAGAGACTGTTGCCCGTGTTGTGTCAGG<br>CCCACGGGTTGACACCCCAGCAGGTGGTCGCCATCGCCAGCAATGGCGGG<br>GGAAAGCAGGCCCTTGAGACCGTGCAGCGGTTGCTTCCAGTGTTGTGCCA |

TABLE 4-continued

Sequences referred to in example 1

| Sequence name | Ref. sequences | Polynucleotide or polypeptide sequences |
|---|---|---|
| | | GGCACACGGACTGACCCCTCAACAGGTGGTCGCAATCGCCAGCTACAAGG<br>GCGGAAAGCAGGCTCTGGAGACAGTGCAGCGCCTCCTGCCCGTGCTGTGT<br>CAGGCTCACGGACTGACACCACAGCAGGTGGTCGCCATCGCCAGTAACGG<br>GGGCGGCAAGCAGGCTTTGGAGACCGTCCAGAGACTCCTCCCCGTCCTTT<br>GCCAGGCCCACGGGTTGACACCTCAGCAGGTCGTCGCCATTGCCTCCAAC<br>AACGGGGGCAAGCAGGCCCTCGAAACTGTGCAGAGGCTGCTGCCTGTGCT<br>GTGCCAGGCTCATGGGCTGACACCCCAGCAGGTGGTGGCCATTGCCTCTA<br>ACAACGGCGGCAAACAGGCACTGGAGACCGTGCAAAGGCTGCTGCCCGT<br>CCTCTGCCAAGCCCACGGGCTCACTCCACAGCAGGTCGTGGCCATCGCCTC<br>AAACAATGGCGGGAAGCAGGCCCTGGAGACTGTGCAAAGGCTGCTCCCT<br>GTGCTCTGCCAGGCACACGGACTGACCCCTCAGCAGGTGGTGGCAATCGC<br>TTCCAACAACGGGGGAAAGCAGGCCCTCGAAACCGTGCAGCGCCTCCTCC<br>CAGTGCTGTGCCAGGCACATGGCCTCACACCCGAGCAAGTGGTGGCTATC<br>GCCAGCCACGACGGAGGGAAGCAGGCTCTGGAGACCGTGCAGAGGCTGC<br>TGCCTGTCCTGTGCCAGGCCCACGGGCTTACTCCAGAGCAGGTCGTCGCCA<br>TCGCCAGTCATGATGGGGGGAAGCAGGCCCTTGAGACAGTCCAGCGGCT<br>GCTGCCAGTCCTTTGCCAGGCTCACGGCTTGACTCCCGAGCAGGTCGTGGC<br>CATTGCCTCAAACATTGGGGGCAAACAGGCCCTGGAGACAGTGCAGGCCC<br>TGCTGCCCGTGTTGTGTCAGGCCCACGGCTTGACACCCCAGCAGGTGGTC<br>GCCATTGCCTCTAATGGCGGCGGGAGACCCGCCTTGGAGAGCATTGTTGC<br>CCAGTTATCTCGCCCTGATCCGGCGTTGGCCGCGTTGACCAACGACCACCT<br>CGTCGCCTTGGCCTGCCTCGGCGGGCGTCCTGCGCTGGATCAGTGAAAA<br>AGGGATTGGGGGATCCTATCAGCCGTTCCCAGCTGGTGAAGTCCGAGCTG<br>GAGGAGAAGAAATCCGAGTTGAGGCACAAGCTGAAGTACGTGCCCCACG<br>AGTACATCGAGCTGATCGAGATCGCCCGGAACAGCACCCAGGACCGTATC<br>CTGGAGATGAAGGTGATGGAGTTCTTCATGAAGGTGTACGGCTACAGGG<br>GCAAGCACCTGGGCGGCTCCAGGAAGCCCGACGGCGCCATCTACACCGTG<br>GGCTCCCCCATCGACTACGGCGTGATCGTGGACACCAAGGCCTACTCCGG<br>CGGCTACAACCTGCCCATCGGCCAGGCCGACGAAATGCAGAGGTACGTGG<br>AGGAGAACCAGACCAGGAACAAGCACATCAACCCCAACGAGTGGTGGAA<br>GGTGTACCCCTCCAGCGTGACCGAGTTCAAGTTCCTGTTCGTGTCCGGCCA<br>CTTCAAGGGCAACTACAAGGCCCAGCTGACCAGGCTGAACCACATCACCA<br>ACTGCAACGGCGCCGTGCTGTCCGTGGAGGAGCTCCTGATCGGCGGCGA<br>GATGATCAAGGCCGGCACCCTGACCCTGGAGGAGGTGAGGAGGAAGTTC<br>AACAACGGCGAGATCAACTTCGCGGCCGACTGATAA |
| PD1T3R | SEQ ID<br>NO: 4 | ATGGGCGATCCTAAAAAGAAACGTAAGGTCATCGATATCGCCGATCTACG<br>CACGCTCGGCTACAGCCAGCAGCAACAGGAGAAGATCAAACCGAAGGTTC<br>GTTCGACAGTGGCGCAGCACCACGAGGCACTGGTCGGCCACGGGTTTACA<br>CACGCGCACATCGTTGCGTTAAGCCAACACCCGGCAGCGTTAGGGACCGT<br>CGCTGTCAAGTATCAGGACATGATCGCAGCGTTGCCAGAGGCGACACACG<br>AAGCGATCGTTGGCGTCGGCAAACAGTGGTCCGGCGCACGCGCTCTGGA<br>GGCCTTGCTCACGGTGGCGGGAGAGTTGAGAGGTCCACCGTTACAGTTGG<br>ACACAGGCCAACTTCTCAAGATTGCAAAACGTGGCGGCGTGACCGCAGTG<br>GAGGCAGTGCATGCATGGCGCAATGCACTGACGGGTGCCCCGCTCAACTT<br>GACCCCCGAGCAAGTCGTCGCAATCGCCAGCCATGATGGAGGGAAGCAA<br>GCCCTCGAAACCGTGCAGCGGTTGCTTCCTGTGCTCTGCCAGGCCCACGGC<br>CTTACCCCTCAGCAGGTGGTGGCCATCGCAAGTAACGGAGGAGGAAAGCA<br>AGCCTTGGAGACAGTGCAGCGCCTGTTGCCCGTGCTGTGCCAGGCACACG<br>GCCTCACACCAGAGCAGGTCGTGGCCATTGCCTCCCATGACGGGGGGAAA<br>CAGGCTCTGGAGACCGTCCAGAGGCTGCTGCCCGTCCTCTGTCAAGCTCAC<br>GGCCTGACTCCCCAACAAGTGGTCGCCATCGCCTCTAATGGCGGCGGGAA<br>GCAGGCACTGGAAACAGTGCAGAGATGCTCCCTGTGCTTTGCCAAGCTC<br>ATGGGTTGACCCCCAACAGGTCGTCGCTATTGCCTCAAACGGGGGGGGC<br>AAGCAGGCCCTTGAGACTGTGCAGAGGCTGTTGCCAGTGCTGTGTCAGGC<br>TCACGGGCTCACTCCACAACAGGTGGTCGCAATTGCCAGCAACGGCGGCG<br>GAAAGCAAGCTCTTGAAACCGTGCAACGCCTCCTGCCCGTGCTCTGTCAGG<br>CTCATGGCCTGACACCACAACAAGTCGTGGCCATCGCCAGTAATAATGGC<br>GGGAAACAGGCTCTTGAGACCGTCCAGAGGCTGCTCCCAGTGCTCTGCCA<br>GGCACACGGGCTGACCCCGAGCAGGTGGTGGCTATCGCCAGCAATATTG<br>GGGGCAAGCAGGCCCTGGAAACAGTCCAGGCCCTGCTGCCAGTGCTTTGC<br>CAGGCTCACGGGCTCACTCCCCAACGGTCGTGGCAATCGCCTCCAACGG<br>CGGAGGGAAGCAGGCTCTGGAGACCGTGCAGAGACTGCTGCCCGTCTTGT<br>GCCAGGCCCACGGACTCACACCTGAACAGGTCGTCGCCATTGCCTCTCACG<br>ATGGGGGCAAACAAGCCCTGGAGACAGTGCAGCGGCTGTTGCCTGTGTTG<br>TGCCAAGCCCACGGCTTGACTCCTCAACAAGTGGTCGCCATCGCCTCAAAT<br>GGCGGCGGAAAACAAGCTCTGGAGACAGTGCAGAGGTTGCTGCCCGTCC<br>TCTGCCAAGCCCACGGCCTGACTCCCAACAGGTCGTCGCCATTGCCAGCA<br>ACAACGGAGGAAAGCAGGCTCTCGAAACTGTGCAGCGGCTGCTTCCTGTG<br>CTGTGTCAGGCTCATGGGCTGACCCCGAGCAAGTGGTGGCTATTGCCTCT<br>AATGGAGGCAAGCAAGCCCTTGAGACAGTCCAGAGGCTGTTGCCAGTGCT<br>GTGCCAGGCCCACGGGCTCACACCCCAGCAGGTGGTCGCCATCGCCAGTA<br>CAACGGGGGCAAACAGGCATTGGAAACCGTCCAGCGCCTGCTTCCAGTG<br>CTCTGCCAGGCACACGGACTGACACCCGAACAGGTGGTGGCCATTGCATC<br>CCATGATGGGGGCAAGCAGGCCCTGGAGACCGTGCAGAGACTCCTGCCA |

TABLE 4-continued

Sequences referred to in example 1

| Sequence name | Ref. sequences | Polynucleotide or polypeptide sequences |
|---|---|---|
| | | GTGTTGTGCCAAGCTCACGGCCTCACCCCTCAGCAAGTCGTGGCCATCGCC<br>TCAAACGGGGGGGGCCGGCCTGCACTGGAGAGCATTGTTGCCCAGTTATC<br>TCGCCCTGATCCGGCGTTGGCCGCGTTGACCAACGACCACCTCGTCGCCTT<br>GGCCTGCCTCGGCGGGCGTCCTGCGCTGGATGCAGTGAAAAAGGGATTG<br>GGGGATCCTATCAGCCGTTCCCAGCTGGTGAAGTCCGAGCTGGAGGAGAA<br>GAAATCCGAGTTGAGGCACAAGCTGAAGTACGTGCCCCACGAGTACATCG<br>AGCTGATCGAGATCGCCCGGAACAGCACCCAGGACCGTATCCTGGAGATG<br>AAGGTGATGGAGTTCTTCATGAAGGTGTACGGCTACAGGGGCAAGCACCT<br>GGGCGGCTCCAGGAAGCCCGACGGCGCCATCTACACCGTGGGCTCCCCCA<br>TCGACTACGGCGTGATCGTGGACACCAAGGCCTACTCCGGCGGCTACAAC<br>CTGCCCATCGGCCAGGCCGACGAAATGCAGAGGTACGTGGAGGAGAACC<br>AGACCAGGAACAAGCACATCAACCCCAACGAGTGGTGGAAGGTGTACCCC<br>TCCAGCGTGACCGAGTTCAAGTTCCTGTTCGTGTCCGGCCACTTCAAGGGC<br>AACTACAAGGCCCAGCTGACCAGGCTGAACCACATCACCAACTGCAACGG<br>CGCCGTGCTGTCCGTGGAGGAGCTCCTGATCGGCGGCGAGATGATCAAG<br>GCCGGCACCCTGACCCTGGAGGAGGTGAGGAGGAAGTTCAACAACGGCG<br>AGATCAACTTCGCGGCCGACTGATAA |
| PD1-T3 | SEQ ID NO: 5 | TACCTCTGTGGGGCCATCTCCCTGGCCCCCAAGGCGCAGATCAAAGAGA |
| 2A-element | SEQ ID NO: 6 | TCCGGTGAGGGCAGAGGAAGTCTTCTAACATGCGGTGACGTGGAGGAGA<br>ATCCGGGCCCC |
| apoptosis CAR<br>(without<br>start codon) | SEQ ID NO: 7 | GCTTTGCCTGTCACTGCCTTGCTGCTTCCACTTGCTCTGTTGTTGCACGCCG<br>CAAGACCCGAGGTCAAGCTCCAGGAAAGCGGACCAGGGCTGGTGGCCCC<br>TAGTCAGTCATTGAGCGTCACTTGCACCGTCAGCGGCGTGTCTCTGCCCGA<br>TTACGGCGTGAGCTGGATCAGACAGCCCCCAAGGAAGGGACTGGAGTGG<br>CTGGGCGTCATCTGGGGGAGCGAGACTACCTACTACAACAGCGCCCTGAA<br>GAGCAGGCTGACCATCATTAAGGACAACTCCAAGTCCCAGGTCTTTCTGAA<br>AATGAACAGCCTGCAGACTGATGACACTGCCATCTACTACTGCGCCAAGCA<br>TTACTACTACGGGGGCAGCTACGCTATGGACTACTGGGGCAGGGGACCT<br>CTGTCACAGTGTCAAGTGGCGGAGGAGGCAGTGGCGGAGGGGGAAGTG<br>GGGGCGGCGGCAGCGACATCCAGATGACCCAGAACATCCAGCCTCTCC<br>GCCTCTCTGGGCGACAGAGTGACAATCAGCTGCCGGGCCAGTCAGGACAT<br>CAGCAAGTATCTCAATTGGTACCAGCAGAAACCAGACGGGACAGTGAAAT<br>TGCTGATCTACCACACATCCAGGCTGCACTCAGGAGTCCCCAGCAGGTTTT<br>CCGGCTCCGGCTCCGGGACAGATTACAGTCTGACCATTTCCAACCTGGAGC<br>AGGAGGATATTGCCACATACTTTTGCCAGCAAGGCAACACTCTGCCCTATA<br>CCTTCGGCGGAGGCACAAAACTGGAGATTACTCGGTCGGATCCCGAGCCC<br>AAATCTCCTGACAAAACTCACACATGCCCACCGTGCCCAGCACCTCCCGTG<br>GCCGGCCCGTCAGTGTTCCTCTTCCCCCCAAAACCCAAGGACACCCTCATG<br>ATCGCCCGGACCCCTGAGGTCACATGCGTGGTGGTGGACGTGAGCCACGA<br>GGACCCTGAGGTCAAGTTCAACTGGTACGTGGACGGCGTGGAGGTGCAT<br>AATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTGTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAACCGGAGAACAACTACAAGACCACGCCTCCCGTGCTGGACTCCGACG<br>GCTCCTTCTTCCTCTACAGCAAGCTCACCGTGGACAAGAGCAGGTGGCAGC<br>AGGGGAACGTGTTCTCATGCTCCGTGATGCATGAGGCCCTGCACAATCACT<br>ATACCCAGAAATCTCTGAGTCTGAGCCCAGGCAAGAAGGATATTTTGGGG<br>TGGCTTTGCCTTCTTCTTTTGCCAATTCCACTAATTGTTTGGGTGAAGAGAA<br>AGGAAGTACAGAAAACATGCAGAAAGCACAGAAAGGAAAACCAAGGTTC<br>TCATGAATCTCCAACCTTAAATCCTGAAACAGTGGCAATAAATTTATCTGAT<br>GTTGACTTGAGTAAATATATCACCACTATTGCTGGAGTCATGACACTAAGT<br>CAAGTTAAAGGCTTTGTTCGAAAGAATGGTGTCAATGAAGCCAAAATAGA<br>TGAGATCAAGAATGACAATGTCCAAGACACAGCAGAACAGAAAGTTCAAC<br>TGCTTCGTAATTGGCATCAACTTCATGGAAAGAAAGAAGCGTATGACACAT<br>TGATTGCAGATCTCAAAAAAGCCAATCTTTGTACTCTTGCAGAGAAAATTC<br>AGACTATCATCCTCAAGGACATTACTAGTGACTCAGAAAATTCAAACTTCA<br>GAAATGAAATCCAGAGCTTGGTCGAA |
| BGH polyA | SEQ ID NO: 8 | TCTAGAGGGCCCGTTTAAACCCGCTGATCAGCCTCGACTGTGCCTTCTAGT<br>TGCCAGCCATCTGTTGTTTGCCCCTCCCCCGTGCCTTCCTTGACCCTGGAAG<br>GTGCCACTCCCACTGTCCTTTCCTAATAAAATGAGGAAATTGCATCGCATT<br>GTCTGAGTAGGTGTCATTCTATTCTGGGGGGTGGGGTGGGGCAGGACAG<br>CAAGGGGGAGGATTGGGAAGACAATAGCAGGCATGCTGGGGATGCGGT<br>GGGCTCTATGACTAGTGGCGAATTC |
| Interleukin-<br>12 subunit<br>alpha | SEQ ID NO: 9 | MCPARSLLLVATLVLLDHLSLARNLPVATPDPGMFPCLHHSQNLLRAVSNML<br>QKARQTLEFYPCTSEEIDHEDITKDKTSTVEACLPLELTKNESCLNSRETSF<br>ITNGSCLASRKTSFMMALCLSSIYEDLKMYQVEFKTMNAKLLMDPKRQIFLD |

TABLE 4-continued

Sequences referred to in example 1

| Sequence name | Ref. sequences | Polynucleotide or polypeptide sequences |
|---|---|---|
| | | QNMLAVIDELMQALNFNSETVPQKSSLEEPDFYKTKIKLCILLHAFRIRAVT IDRVMSYLNAS |
| Interleukin-12 subunit beta | SEQ ID NO: 10 | MCHQQLVISWFSLVFLASPLVAIWELKKDVYVVELDWYPDAPGEMVVLTCDT PEEDGITWTLDQSSEVLGSGKTLTIQVKEFGDAGQYTCHKGGEVLSHSLLLLHK KEDGIWSTDILKDQKEPKNKTFLRCEAKNYSGRFTCWWLTTISTDLTFSVKSSR GSSDPQGVTCGAATLSAERVRGDNKEYEYSVECQEDSACPAAEESLPIEVMV DAVHKLKYENYTSSFFIRDIIKPDPPKNLQLKPLKNSRQVEVSWEYPDTWSTPH SYFSLTFCVQVQGKSKREKKDRVFTDKTSATVICRKNASISVRAQDRYYSSSWS EWASVPCS |
| Lck left homology | SEQ ID NO: 11 | GGGATAGGGGGTGCCTCTGTGTGTGTGTGAGAGTGTGTGTGTGTAGG GTGTGTATATGTATAGGGTGTGTGTGAGTGTGTGTGTGTGAGAGAGTGTG TGTGTGGCAGAATAGACTGCGGAGGTGGATTTCATCTTGATATGAAAGGT CTGGAATGCATGGTACATTAAACTTTGAGGACAGCGCTTTCCAAGCACTCT GAGGAGCAGCCCTAGAGAAGGAGGAGCTGCAGGGACTCCGGGGGCTTCA AAGTGAGGGCCCCACTCTGCTTCAGGCAAAACAGGCACACATTTATCACTT TATCTATGGAGTTCTGCTTGATTTCATCAGACAAAAAATTTCCACTGCTAAA ACAGGCAAATAAACAAAAAAAAAGTTATGGCCAACAGAGTCACTGGAGG GTTTTCTGCTGGGGAGAAGCAAGCCCGTGTTTGAAGGAACCCTGTGAGAT GACTGTGGGCTGTGTGAGGGGAACAGCGGGGGCTTGATGGTGGACTTCG GGAGCAGAAGCCTCTTTCTCAGCCTCCTCAGCTAGACAGGGGAATTATAAT AGGAGGTGTGGCGTGCACACCTCTCCAGTAGGGGAGGGTCTGATAAGTC AGGTCTCTCCCAGGCTTGGGAAAGTGTGTGTCATCTCTAGGAGGTGGTCCT CCCAACACAGGGTACTGGCAGAGGGAGAGGGAGGGGGCAGAGGCAGGA AGTGGGTAACTAGACTAACAAAGGTGCCTGTGGCGGTTTGCCCATCCCAG GTGGGAGGGTGGGGCTAGGGCTCAGGGGCCGTGTGTGAATTTACTTGTA GCCTGAGGGCTCAGAGGGAGCACCGGTTTGGAGCTGGGACCCCCTATTTT AGCTTTTCTGTGGCTGGTGAATGGGGATCCCAGGATCTCACAATCTCAGGT ACTTTTGGAACTTTCCAGGGCAAGGCCCCATTATATCTGATGTTGGGGGAG CAGATCTTGGGGGAGCCCCTTCAGCCCCCTCTTCCATTCCCTCAGGGACC |
| lck right homology | SEQ ID NO: 12 | GGCTGTGGCTGCAGCTCACACCCGGAAGATGACTGGATGGAAAACATCGA TGTGTGTGAGAACTGCCATTATCCCATAGTCCCACTGGATGGCAAGGGCA CGGTAAGAGGCGAGACAGGGGCCTTGGTGAGGGAGTTGGGTAGAGAAT GCAACCCAGGAGAAAGAAATGACCAGCACTACAGGCCCTTGAAAGAATA GAGTGGCCCTCTCCCCTGAAATACAGAAAGGAAAAGAGGCCCAGAGAGG GGAAGGGAATCTCCTAAGATCACACAGAAAGTAGTTGGTAAACTCAGGGA TAACATCTAACCAGGCTGGAGAGGCTGAGAGCAGAGCAGGGGGAAGG GGGCCAGGGTCTGACCCAATCTTCTGCTTTCTGACCCCACCCTCATCCCCCA CTCCACAGCTGCTCATCCGAAATGGCTCTGAGGTGCGGGACCCACTGGTTA CCTACGAAGGCTCCAATCCGCCGGCTTCCCCACTGCAAGGTGACCCCAGGC AGCAGGGCCTGAAAGACAAGGCCTGCGGATCCCTGGCTGTTGGCTTCCAC CTCTCCCCCACCTACTTTCTCCCCGGTCTTGCCTTCTTGTCCCCCACCCTGT AACTCCAGGCTTCCTGCCGATCCCAGCTCGGTTCTCCCTGATGCCCCTTGTC TTTACAGACAACCTGGTTATCGCTCTGCACAGCTATGAGCCCTCTCACGAC GGAGATCTGGGCTTTGAGAAGGGGAACAGCTCCGCATCCTGGAGCAGT GAGTCCCTCTCCACCTTGCTCTGGCGGAGTCCGTGAGGGAGCGGCGATCT CCGCGACCCGCAGCCCTCCTGCGGCCCTTGACCAGCTCGGGGTGGCCGCC CTTGGGACAAAATTCGAGGCTCAGTATTGCTGAGCCAGGGTTGGGGGAG GCTGGCTTAAGGGGTGGAGGGGTCTTTGAGGGAGGGTCTCAGGTCGACG GCTGAGCGAGCCACACTGACCCACCTCCGTGGCGCAGGAGCGGCGAGTG |
| apoptosis CAR (with start codon) | SEQ ID NO: 13 | ATGGCTTTGCCTGTCACTGCCTTGCTGCTTCCACTTGCTCTGTTGTTGCACG CCGCAAGACCCGAGGTCAAGCTCCAGGAAAGCGGACCAGGGCTGGTGGC CCCTAGTCAGTCATTGAGCGTCACTTGCACCGTCAGCGGCGTGTCTCTGCC CGATTACGGCGTGAGCTGGATCAGACAGCCCCCAAGGAAGGGACTGGAG TGGCTGGGCGTCATCTGGGGGAGCGAGACTACCTACTACAACAGCGCCCT GAAGAGCAGGCTGACCATCATTAAGGACAACTCCAAGTCCCAGGTCTTTCT GAAAATGAACAGCCTGCAGACTGATGACACTGCCATCTACTACTGCGCCAA GCATTACTACTACGGGGGCAGCTACGCTATGGACTACTGGGGCCAGGGG ACCTCTGTCACAGTGTCAAGTGGCGGAGGAGGCAGTGGCGGAGGGGGAA GTGGGGGCGGCGGCAGCGACATCCAGATGACCCAGACAACATCCAGCCTC TCCGCCTCTCTGGGCGACAGAGTGACAATCAGCTGCCGGGCCAGTCAGGA CATCAGCAAGTATCTCAATTGGTACCAGCAGAAACCAGACGGGACAGTGA AATTGCTGATCTACCACACATCCAGGCTGCACTCAGGAGTCCCCAGCAGGT TTTCCGGCTCCGGCTCCGGGACAGATTACAGTCTGACCATTTCCAACCTGG AGCAGGAGGATATTGCCACATACTTTTGCCAGCAAGGCAACACTCTGCCCT ATACCTTCGGCGGAGGCACAAAACTGGAGATTACTGGTCGGATCCCGAG CCCAAATCTCCTGACAAAACTCACACATGCCCACCGTGCCCAGCCACCTCCC GTGGCCGGCCCGTCAGTGTTCCTCTTCCCCCCAAAACCCAAGGACACCCTC ATGATCGCCCGGACCCCTGAGGTCACATGCGTGGTGGTGGACGTGAGCCA CGAGGACCCTGAGGTCAAGTTCAACTGGTACGTGGACGGCGTGGAGGTG CATAATGCCAAGACAAAGCCGCGGGAGGAGCAGTACAACAGCACGTACC GTGTGGTCAGCGTCCTCACCGTCCTGCACCAGGACTGGCTGAATGGCAAG |

TABLE 4-continued

Sequences referred to in example 1

| Sequence name | Ref. sequences | Polynucleotide or polypeptide sequences |
|---|---|---|
|  |  | GAGTACAAGTGCAAGGTGTCCAACAAAGCCCTCCCAGCCCCCATCGAGAA<br>AACCATCTCCAAAGCCAAAGGGCAGCCCCGAGAACCACAGGTGTACACCC<br>TGCCCCCATCCCGGGATGAGCTGACCAAGAACCAGGTCAGCCTGACCTGC<br>CTGGTCAAAGGCTTCTATCCCAGCGACATCGCCGTGGAGTGGGAGAGCAA<br>TGGGCAACCGGAGAACAACTACAAGACCACGCCTCCCGTGCTGGACTCCG<br>ACGGCTCCTTCTTCCTCTACAGCAAGCTCACCGTGGACAAGAGCAGGTGGC<br>AGCAGGGGAACGTGTTCTCATGCTCCGTGATGCATGAGGCCCTGCACAAT<br>CACTATACCCAGAAATCTCTGAGTCTGAGCCCAGGCAAGAAGGATATTTTG<br>GGGTGGCTTTGCCTTCTTCTTTTGCCAATTCCACTAATTGTTTGGGTGAAGA<br>GAAAGGAAGTACAGAAAACATGCAGAAAGCACAGAAAGGAAAACCAAGG<br>TTCTCATGAATCTCCAACCTTAAATCCTGAAACAGTGGCAATAAATTTATCT<br>GATGTTGACTTGAGTAAATATATCACCACTATTGCTGGAGTCATGACACTA<br>AGTCAAGTTAAAGGCTTTGTTCGAAAGAATGGTGTCAATGAAGCCAAAAT<br>AGATGAGATCAAGAATGACAATGTCCAAGACACAGCAGAACAGAAAGTTC<br>AACTGCTTCGTAATTGGCATCAACTTCATGGAAAGAAAGAAGCGTATGAC<br>ACATTGATTGCAGATCTCAAAAAAGCCAATCTTTGTACTCTTGCAGAGAAA<br>ATTCAGACTATCATCCTCAAGGACATTACTAGTGACTCAGAAAATTCAAAC<br>TTCAGAAATGAAATCCAGAGCTTGGTCGAA |
| Lck left homology | SEQ ID NO: 14 | CTCATAACAATTCTATGAGGTAGGAACAGTTATTTACTCTATTTTCCAAATA<br>AGGAAACTGGGCTCGCCCAAGGTTCCACAACTAACATGTGTGTATTATTGA<br>GCATTTAATTTACACCAGGGAAGCAGGTTGTGGTGGTGTGCACCTGTTGTC<br>CAGCTATTTAGGAGGCTGAGGTGAAAGGATCACTTGAACGGAGGAGTTCA<br>AATTTGCAATGTGCTATGATTGTGCCTGTGAACAGCTGCTGCACTCCAGCC<br>TGGGCAACATAGTGAGATCCCTTATCTAAAACATTTTTTTTAAGTAAATAAT<br>CAGGTGGGCACGGTGGCTCACGCCTGTAATCCAGCACTTTGGGAGGCTGA<br>GGCGGGCGGATCACCTGAGGTCAGGAGTTCAAGACCAGCCTGACCAACAT<br>GGAGAAACCCGTCTCTACTAAAAATACAAAATTAGCTTGGCGTGGTGGTG<br>CATGCCTGTAATCCCAGCTACTCGAGAAGCTGAGGCAGGAGAATTGTTTG<br>AACCTGGGAGGTGGAGGTTGCGGTGAGCCGAGATCGCACCATTGCACTCC<br>AGCCTGGGCAACAAGAGTGAAATTGCATCTCAAAAAAAAAGAAAAGGAA<br>ATAATCTATACCAGGCACTCCAAGTGGTGTGACTGATATTCAACAAGTACC<br>TCTAGTGTGACCTTACCATTGATGAAGACCAAGATTCTTTTGGATTGGTGC<br>TCACACTGTGCCAGTTAAATATTCCGAACATTACCCTTGCCTGTGGGCTTCC<br>AGTGCCTGACCTTGATGTCCTTTCACCCATCAACCCGTAGGGATGACCAAC<br>CCGGAGGTGATTCAGAACCTGGAGCGAGGCTACCGCATGGTGCGCCCTGA<br>CAACTGTCCAGAGGAGCTGTACCAACTCATGAGGCTGTGCTGGAAGGAGC<br>GCCCAGAGGACCGGCCCACCTTTGACTACCTGCGCAGTGTGCTGGAGGAC<br>TTCTTCACGGCCACAGAGGGCCAGTACCAGCCTCAGCCT |
| lck right homology | SEQ ID NO: 15 | GAGGCCTTGAGAGGCCCTGGGGTTCTCCCCCTTTCTCTCCAGCCTGACTTG<br>GGGAGATGGAGTTCTTGTGCCATAGTCACATGGCCTATGCACATATGGAC<br>TCTGCACATGAATCCCACCCACATGTGACACATATGCACCTTGTGTCTGTAC<br>ACGTGTCCTGTAGTTGCGTGGACTCTGCACATGTCTTGTACATGTGTAGCC<br>TGTGCATGTATGTCTTGGACACTGTACAAGGTACCCCTTTCTGGCTCTCCCA<br>TTTCCTGAGACCACAGAGAGAGGGGAGAAGCCTGGGATTGACAGAAGCT<br>TCTGCCCACCTACTTTTCTTTCCTCAGATCATCCAGAAGTTCCTCAAGGGCC<br>AGGACTTTATCTAATACCTCTGTGTGCTCCTCCTTGGTGCCTGGCCTGGCAC<br>ACATCAGGAGTTCAATAAATGTCTGTTGATGACTGTTGTACATCTCTTTGCT<br>GTCCACTCTTTGTGGGTGGGCAGTGGGGGTTAAGAAAATGGTAATTAGGT<br>CACCCTGAGTTGGGGTGAAAGATGGGATGAGTGGATGTCTGGAGGCTCT<br>GCAGACCCCTTCAAATGGGACAGTGCTCCTCACCCCTCCCCAAAGGATTCA<br>GGGTGACTCCTACCTGGAATCCCTTAGGGAATGGGTGCGTCAAAGGACCT<br>TCCTCCCCATTATAAAGGGCAACAGCATTTTTTACTGATTCAAGGGCTATA<br>TTTGACCTCAGATTTTGTTTTTTAAGGCTAGTCAAATGAAGCGGCGGGAA<br>TGGAGGAGGAACAAATAAATCTGTAACTATCCTCAGATTTTTTTTTTTTTT<br>GAGACTGGGTCTCACTTTTTCATCCAGGCTGGAGTGCAGTCGCATGATCAC<br>GGCTCACTGTAGCCTCAACCTCTCCAGCTCAAATGCTCCTCCTGTCTCAGCC<br>TCCCGAGTACCTGGGACTACTTTCTTGAGGCCAGGAATTCAAGAACAGAG<br>TAAGATCCTGGTCTCCAAAAAAAGTTTTAAA |

Example 2: TALEN®-Mediated Double Targeted Integration of IL-15 and CAR Encoding Matrices in T-Cells Materials X-vivo-15 was obtained for Lonza (cat #BE04-418Q), IL-2 from Miltenyi Biotech (cat #130-097-748), human serum AB from Seralab (cat #GEM-100-318), human T activator CD3/CD28 from Life Technology (cat #11132D), QBEND10-APC from R&D Systems (cat #FAB7227A), vioblue-labeled anti-CD3, PE-labeled anti-LNGFR, APC-labeled anti-CD25 and PE-labeled anti-PD1 from Miltenyi (cat #130-094-363, 130-112-790, 130-109-021 and 130-104-892 respectively) 48 wells treated plates (CytoOne, cat #CC7682-7548), human IL-15 Quantikine ELISA kit from R&D systems (cat #S1500), ONE-Glo from Promega (cat #E6110). AAV6 batches containing the different matrices were obtained from Virovek, PBMC cells were obtained from Allcells, (cat #PB004F) and Raji-Luciferase cells were obtained after Firefly Luciferase-encoding lentiviral particles transduction of Raji cells from ATCC (cat #CCL-86).

Methods 2.1-Transfection-Transduction

The double targeted integration at TRAC and PD1 or CD25 loci were performed as follows. PBMC cells were first thawed, washed, resuspended and cultivated in X-vivo-15 complete media (X-vivo-15, 5% AB serum, 20 ng/mL IL-2). One day later, cells were activated by Dynabeads human T activator CD3/CD28 (25 uL of beads/$1E^6$ CD3 positive cells) and cultivated at a density of $1E^6$ cells/mL for 3 days in X-vivo complete media at 37° C. in the presence of 5% $CO_2$. Cells were then split in fresh complete media and transduced/transfected the next day according to the following procedure. On the day of transduction-transfection, cells were first de-beaded by magnetic separation (EasySep), washed twice in Cytoporation buffer T (BTX Harvard Apparatus, Holliston, Massachusetts) and resuspended at a final concentration of $28E^6$ cells/mL in the same solution. Cellular suspension was mixed with 5 µg mRNA encoding TRAC TALEN® arms (SEQ ID NO:16 and 17) in the presence or in the absence of 15 µg of mRNA encoding arms of either CD25 or PD1 TALEN® (SEQ ID NO:18 and 19 and SEQ ID NO:20 and 21 respectively) in a final volume of 200 µl. TALEN® is a standard format of TALE-nucleases resulting from a fusion of TALE with Fok-1 Transfection was performed using Pulse Agile technology, by applying two 0.1 mS pulses at 3,000 V/cm followed by four 0.2 mS pulses at 325 V/cm in 0.4 cm gap cuvettes and in a final volume of 200 µl of Cytoporation buffer T (BTX Harvard Apparatus, Holliston, Massachusetts). Electroporated cells were then immediately transferred to a 12-well plate containing 1 mL of prewarm X-vivo-15 serum-free media and incubated for 37° C. for 15 min. Cells were then concentrated to $8E^6$ cells/mL in 250 µL of the same media in the presence of AAV6 particles (MOI=$3E^5$ vg/cells) comprising the donor matrices in 48 wells regular treated plates. After 2 hours of culture at 30° C., 250 µL of Xvivo-15 media supplemented by 10% AB serum and 40 ng/ml IL-2 was added to the cell suspension and the mix was incubated 24 hours in the same culture conditions. One day later, cells were seeded at $1E^6$ cells/mL in complete X-vivo-15 media and cultivated at 37° C. in the presence of 5% $CO_2$.

2.2-Activation-Dependent Expression of ΔLNGFR and Secretion of IL15

Engineered T-cells were recovered from the transfection-transduction process described earlier and seeded at $1E^6$ cells/mL alone or in the presence of Raji cells (E:T=1:1) or Dynabeads (12.5 uL/$1E^6$ cells) in 100 µL final volume of complete X-vivo-15 media. Cells were cultivated for 48 hours before being recovered, labeled and analyzed by flow cytometry. Cells were labeled with two independent sets of antibodies. The first sets of antibodies, aiming at detecting the presence of ΔLNGFR, CAR and CD3 cells, consisted in QBEND10-APC (diluted 1/10), vioblue-labeled anti CD3 (diluted 1/25) and PE-labeled anti-ΔLNGFR (diluted 1/25). The second sets of antibodies, aiming at detecting expression of endogenous CD25 and PD1, consisted in APC-labeled anti-CD25 (diluted 1/25) and vioblue-labeled anti PD1 (diluted 1/25).

The same experimental set up was used to study IL-15 secretion in the media. Cells mixture were kept in co-culture for 2, 4, 7 and 10 days before collecting and analyzing supernatant using an IL-15 specific ELISA kit.

2.3-Serial Killing Assay

To assess the antitumor activity of engineered CAR T-cells, a serial killing assay was performed. The principle of this assay is to challenge CAR T-cell antitumor activity everyday by a daily addition of a constant amount of tumor cells. Tumor cell proliferation, control and relapse could be monitored via luminescence read out thanks to a Luciferase marker stably integrated in Tumor cell lines.

Typically, CAR T-cells are mixed to a suspension of $2.5 \times 10^5$ Raji-luc tumor cells at variable E:T ratio (E:T=5:1 or 1:1) in a total volume of 1 mL of Xvivo 5% AB, 20 ng/uL IL-2. The mixture is incubated 24 hours before determining the luminescence of 25 uL of cell suspension using ONE-Glo reagent. Cells mixture are then spun down, the old media is discarded and substituted with 1 mL of fresh complete X-vivo-15 media containing $2.5 \times 10^5$ Raji-Luc cells and the resulting cell mixture is incubated for 24 hours. This protocol is repeated 4 days.

EXPERIMENTS AND RESULTS

This example describes methods to improve the therapeutic outcome of CAR T-cell therapies by integrating an IL-15/soluble IL-15 receptor alpha heterodimer (IL15/sIL15rα) expression cassette under the control of the endogenous T-cell promoters regulating PD1 and CD25 genes. Because both genes are known to be upregulated upon tumor engagement by CAR T-cells, they could be hijacked to re-express IL-IL15/sIL15rα only in vicinity of a tumor. This method aims to reduce the potential side effects of IL15/sIL15rα systemic secretion while maintaining its capacity to reduced activation induced T-cell death (AICD), promote T-cell survival, enhance T-cell antitumor activity and to reverse T-cell anergy.

The method developed to integrate IL15/sIL15rα at PD1 and CD25 loci consisted in generating a double-strand break at both loci using TALEN in the presence of a DNA repair matrix vectorized by AAV6. This matrix consists of two homology arms embedding IL15/sIL15rα coding regions separated by a 2A cis acting elements and regulatory elements (stop codon and polyA sequences). Depending on the locus targeted and its involvement in T-cell activity, the targeted endogenous gene could be inactivated or not via specific matrix design. When CD25 gene was considered as targeted locus, the insertion matrix was designed to knock-in (KI) IL15/sIL15rα without inactivating CD25 because the protein product of this gene is regarded as essential for T-cell function. By contrast, because PD1 is involved in T-cell inhibition/exhaustion of T-cells, the insertion matrix was designed to prevent its expression while enabling the expression and secretion of IL15/sIL15rα.

To illustrate this approach and demonstrate the feasibility of double targeted insertion in primary T-cells, three different matrices were designed (FIGS. 2A, 2B and 2C). The first one named CARm represented by SEQ ID NO:36 was designed to insert an anti-CD22 CAR cDNA at the TRAC locus in the presence of TRAC TALEN® (SEQ ID NO:16 and 17). The second one, IL-15_CD25m (SEQ ID NO:37) was designed to integrate IL15, sIL15rα and the surface marker named ΔLNGFR cDNAs separated by 2A cis-acting elements just before the stop codon of CD25 endogenous coding sequence using CD25 TALEN® (SEQ ID NO:18 and 19). The third one, IL-15_PD1m (SEQ ID NO:38), contained the same expression cassette and was designed to integrate in the middle of the PD1 open reading frame using PD1 TALEN® (SEQ ID NO:20 and 21). The three matrices contained an additional 2A cis-acting element located upstream expression cassettes to enable co-expression of IL15/sIL15rα and CAR with the endogenous gene targeted.

We first assessed the efficiency of double targeted insertion in T-cells by transducing them with one of the AAV6 encoding IL15/sIL15rα matrices (SEQ ID NO:41; pCLS30519) along with the one encoding the CAR and subsequently transfected the corresponding TALEN®. AAV6-assisted vectorization of matrices in the presence of mRNA encoding TRAC TALEN® (SEQ ID NO:22 and 23) and PD1 TALEN® (SEQ ID NO:24 and 25) or CD25 TALEN® (SEQ ID NO:26 and 27) enabled expression of the anti CD22 CAR in up to 46% of engineered T-cells (FIG. 3).

To determine the extent of IL15m integration at CD25 and PD1 locus, engineered T-cells were activated with either antiCD3/CD28 coated beads or with CD22 expressing Raji tumor cells. 2 days post activation, cells were recovered and analyzed by FACS using LNGFR expression as IL15/sIL15rα secretion surrogate (FIGS. 4 and 5). Our results showed that antiCD3/CD28 coated beads induced expression of ΔLNGFR by T-cells containing IL-15m_CD25 or IL-15m_PD1, independently of the presence of the anti CD22 CAR (FIG. 4A-B). Tumor cells however, only induced expression of ΔLNGFR by T-cell treated by both CARm and IL-15m. This indicated that expression of ΔLNGFR could be specifically induced through tumor cell engagement by the CAR (FIGS. 5 and 6).

As expected the endogenous CD25 gene was still expressed in activated treated T-cells (FIGS. 7 and 8) while PD1 expression was strongly impaired (FIG. 12).

To verify that expression of ΔLNGFR correlated with secretion of IL15 in the media, T-cells expressing the anti-CD22 CAR and ΔLNGFR were incubated in the presence of CD22 expressing Raji tumor cells (E:T ratio=1:1) for a total of 10 days. Supernatant were recovered at day 2, 4, 7 and 10 and the presence of IL15 was quantified by ELISA assay. Our results showed that IL15 was secreted in the media only by T-cells that were co-treated by both CARm and IL15m matrices along with their corresponding TALEN® (FIG. 13). T-cell treated with either one of these matrices were unable to secrete any significant level of IL15 with respect to resting T-cells. Interestingly, IL-15 secretion level was found transitory, with a maximum peak centered at day 4 (FIG. 14).

To assess whether the level of secreted IL-15 (SEQ ID NO:59) could impact CAR T-cell activity, CAR T-cell were co-cultured in the presence of tumor cells at E:T ratio of 5:1 for 4 days. Their antitumor activity was challenged everyday by pelleting and resuspended them in a culture media lacking IL-2 and containing fresh tumor cells. Antitumor activity of CAR T-cell was monitored everyday by measuring the luminescence of the remaining Raji tumor cells expressing luciferase. Our results showed that CAR T-cells co-expressing IL-15 had a higher antitumor activity than those lacking IL15 at all time points considered (FIG. 15).

Thus, together our results showed that we have developed a method allowing simultaneous targeted insertions of CAR and IL15 cDNA at TRAC and CD25 or PD1 loci. This double targeted insertion led to robust expression of an antiCD22 CAR and to the secretion of IL15 in the media. Levels of secreted IL15 were sufficient to enhance the activity of CAR T-cells.

TABLE 5

Sequences referred to in example 2.

| SEQ ID NO# | Sequence Name | Polypeptide sequence | RVD sequence |
|---|---|---|---|
| 16 | TALEN right TRAC | MGDPKKKRKVIDYPYDVPDYAIDIADLRTLGYSQQQQEKIKPKVRSTVA QHHEALVGHGFTHAHIVALSQHPAALGTVAVKYQDMIAALPEATHEAIV GVGKQWSGARALEALLTVAGELRGPPLQLDTGQLLKIAKRGGVTAVEA VHAWRNALTGAPLNLTPQQVVAIASNGGGKQALETVQRLLPVLCQAHG LTPQQVVAIASNNGGKQALETVQRLLPVLCQAHGLTPQQVVAIASNGG GKQALETVQRLLPVLCQAHGLTPEQVVAIASHDGGKQALETVQRLLPVL CQAHGLTPEQVVAIASHDGGKQALETVQRLLPVLCQAHGLTPEQVVAIA SHDGGKQALETVQRLLPVLCQAHGLTPEQVVAIASNIGGKQALETVQAL LPVLCQAHGLTPEQVVAIASHDGGKQALETVQRLLPVLCQAHGLTPEQ VVAIASNIGGKQALETVQALLPVLCQAHGLTPQQVVAIASNNGGKQALE TVQRLLPVLCQAHGLTPEQVVAIASNIGGKQALETVQALLPVLCQAHGL TPQQVVAIASNGGGKQALETVQRLLPVLCQAHGLTPEQVVAIASNIGGK QALETVQALLPVLCQAHGLTPQQVVAIASNGGGKQALETVQRLLPVLC QAHGLTPEQVVAIASHDGGKQALETVQRLLPVLCQAHGLTPQQVVAIAS NGGGRPALESIVAQLSRPDPALAALTNDHLVALACLGGRPALDAVKKGL GDPISRSQLVKSELEEKKSELRHKLKYVPHEYIELIEIARNSTQDRILEMK VMEFFMKVYGYRGKHLGGSRKPDGAIYTVGSPIDYGVIVDTKAYSGGY NLPIGQADEMQRYVEENQTRNKHINPNEWWKVYPSSVTEFKFLFVSGH FKGNYKAQLTRLNHITNCNGAVLSVEELLIGGEMIKAGTLTLEEVRRKFN NGEINFAAD | NG-NN-NG-HD- HD-HD-NI-HD-NI- NN-NI-NG-NI-NG- HD-NG# |

TABLE 5-continued

Sequences referred to in example 2.

| 17 | TALEN Left TRAC | MGDPKKKRKVIDKETAAAKFERQHMDSIDIADLRTLGYSQQQEKIKPK VRSTVAQHHEALVGHGFTHAHIVALSQHPAALGTVAVKYQDMIAALPEA THEAIVGVGKQWSGARALEALLTVAGELRGPPLQLDTGQLLKIAKRGGV TAVEAVHAWRNALTGAPLNLTPEQVVAIASHDGGKQALETVQRLLPVL CQAHGLTPQQVVAIASNGGGKQALETVQRLLPVLCQAHGLTPEQVVAI ASHDGGKQALETVQRLLPVLCQAHGLTPEQVVAIASNIGGKQALETVQA LLPVLCQAHGLTPQQVVAIASNNGGKQALETVQRLLPVLCQAHGLTPE QVVAIASHDGGKQALETVQRLLPVLCQAHGLTPQQVVAIASNGGGKQA LETVQRLLPVLCQAHGLTPQQVVAIASNNGGKQALETVQRLLPVLCQA HGLTPQQVVAIASNNGGKQALETVQRLLPVLCQAHGLTPQQVVAIASN GGGKQALETVQRLLPVLCQAHGLTPEQVVAIASNIGGKQALETVQALLP VLCQAHGLTPEQVVAIASHDGGKQALETVQRLLPVLCQAHGLTPEQVV AIASNIGGKQALETVQALLPVLCQAHGLTPEQVVAIASHDGGKQALETV QRLLPVLCQAHGLTPQQVVAIASNNGGKQALETVQRLLPVLCQAHGLT PQQVVAIASNGGGRPALESIVAQLSRPDPALAALTNDHLVALACLGGRP ALDAVKKGLGDPISRSQLVKSELEEKKSELRHKLKYVPHEYIELIEIARNS TQDRILEMKVMEFFMKVYGYRGKHLGGSRKPDGAIYTVGSPIDYGVIVD TKAYSGGYNLPIGQADEMQRYVEENQTRNKHINPNEWWKVYPSSVTE FKFLFVSGHFKGNYKAQLTRLNHITNCNGAVLSVEELLIGGEMIKAGTLT LEEVRRKFNNGEINFAAD | HD-NG-HD-NI-NN-<br>HD-NG-NN-NN-<br>NG-NI-HD-NI-HD-<br>NN-NG# |
|---|---|---|---|
| 18 | TALEN right CD25 | MGDPKKKRKVIDYPYDVPDYAIDIADLRTLGYSQQQEKIKPKVRSTVA QHHEALVGHGFTHAHIVALSQHPAALGTVAVKYQDMIAALPEATHEAIV GVGKQWSGARALEALLTVAGELRGPPLQLDTGQLLKIAKRGGVTAVEA VHAWRNALTGAPLNLTPQQVVAIASNNGGKQALETVQRLLPVLCQAHG LTPQQVVAIASNGGGKQALETVQRLLPVLCQAHGLTPQQVVAIASNGG GKQALETVQRLLPVLCQAHGLTPEQVVAIASHDGGKQALETVQRLLPVL CQAHGLTPQQVVAIASNGGGKQALETVQRLLPVLCQAHGLTPQQVVAI ASNGGGKQALETVQRLLPVLCQAHGLTPQQVVAIASNGGGKQALETVQ RLLPVLCQAHGLTPQQVVAIASNGGGKQALETVQRLLPVLCQAHGLTP QQVVAIASNNGGKQALETVQRLLPVLCQAHGLTPQQVVAIASNNGGKQ ALETVQRLLPVLCQAHGLTPQQVVAIASNGGGKQALETVQRLLPVLCQ AHGLTPQQVVAIASNGGGKQALETVQRLLPVLCQAHGLTPQQVVAIAS NGGGKQALETVQRLLPVLCQAHGLTPQQVVAIASNGGGKQALETVQRL LPVLCQAHGLTPEQVVAIASHDGGKQALETVQRLLPVLCQAHGLTPQQ VVAIASNGGGRPALESIVAQLSRPDPSGSGSGGDPISRSQLVKSELEEK KSELRHKLKYVPHEYIELIEIARNSTQDRILEMKVMEFFMKVYGYRGKHL GGSRKPDGAIYTVGSPIDYGVIVDTKAYSGGYNLPIGQADEMQRYVEEN QTRNKHINPNEWWKVYPSSVTEFKFLFVSGHFKGNYKAQLTRLNHITN CNGAVLSVEELLIGGEMIKAGTLTLEEVRRKFNNGEINFAAD | NN-NG-NG-HD-<br>NG-NG-NG-NG-<br>NN-NN-NG-NG-<br>NG-NG-HD-NG# |
| 19 | TALEN left CD25 | MGDPKKKRKVIDYPYDVPDYAIDIADLRTLGYSQQQEKIKPKVRSTVA QHHEALVGHGFTHAHIVALSQHPAALGTVAVKYQDMIAALPEATHEAIV GVGKQWSGARALEALLTVAGELRGPPLQLDTGQLLKIAKRGGVTAVEA VHAWRNALTGAPLNLTPEQVVAIASNIGGKQALETVQALLPVLCQAHGL TPEQVVAIASHDGGKQALETVQRLLPVLCQAHGLTPEQVVAIASNIGGK QALETVQALLPVLCQAHGLTPQQVVAIASNNGGKQALETVQRLLPVLC QAHGLTPQQVVAIASNNGGKQALETVQRLLPVLCQAHGLTPEQVVAIAS NIGGKQALETVQALLPVLCQAHGLTPQQVVAIASNNGGKQALETVQRLL PVLCQAHGLTPQQVVAIASNNGGKQALETVQRLLPVLCQAHGLTPEQV VAIASNIGGKQALETVQALLPVLCQAHGLTPEQVVAIASNIGGKQALETV QALLPVLCQAHGLTPQQVVAIASNNGGKQALETVQRLLPVLCQAHGLT PEQVVAIASNIGGKQALETVQALLPVLCQAHGLTPQQVVAIASNNGGKQ ALETVQRLLPVLCQAHGLTPQQVVAIASNGGGKQALETVQRLLPVLCQ AHGLTPEQVVAIASNIGGKQALETVQALLPVLCQAHGLTPQQVVAIASN GGGRPALESIVAQLSRPDPSGSGSGGDPISRSQLVKSELEEKKSELRH KLKYVPHEYIELIEIARNSTQDRILEMKVMEFFMKVYGYRGKHLGGSRK PDGAIYTVGSPIDYGVIVDTKAYSGGYNLPIGQADEMQRYVEENQTRNK HINPNEWWKVYPSSVTEFKFLFVSGHFKGNYKAQLTRLNHITNCNGAV LSVEELLIGGEMIKAGTLTLEEVRRKFNNGEINFAAD | NI-HD-NI-NN-NN-<br>NI-HD-NI-NN-NI-NI-<br>NN-NI-NN-NG-NI-<br>NG# |
| 20 | TALEN right PD1 | MGDPKKKRKVIDYPYDVPDYAIDIADLRTLGYSQQQEKIKPKVRSTVA QHHEALVGHGFTHAHIVALSQHPAALGTVAVKYQDMIAALPEATHEAIV GVGKQWSGARALEALLTVAGELRGPPLQLDTGQLLKIAKRGGVTAVEA VHAWRNALTGAPLNLTPEQVVAIASKLGGKQALETVQALLPVLCQAHGL TPEQVVAIASHDGGKQALETVQRLLPVLCQAHGLTPEQVVAIASHDGG KQALETVQRLLPVLCQAHGLTPQQVVAIASNGGGKQALETVQRLLPVL CQAHGLTPEQVVAIASHDGGKQALETVQRLLPVLCQAHGLTPQQVVAI ASNGGGKQALETVQRLLPVLCQAHGLTPQQVVAIASYKGGKQALETVQ RLLPVLCQAHGLTPQQVVAIASNGGGKQALETVQRLLPVLCQAHGLTP QQVVAIASNNGGKQALETVQRLLPVLCQAHGLTPQQVVAIASNGGGKQ ALETVQRLLPVLCQAHGLTPQQVVAIASNNGGKQALETVQRLLPVLCQA HGLTPQQVVAIASNNGGKQALETVQRLLPVLCQAHGLTPEQVVAIASHD GGKQALETVQRLLPVLCQAHGLTPEQVVAIASHDGGKQALETVQRLLP VLCQAHGLTPEQVVAIASNIGGKQALETVQALLPVLCQAHGLTPQQVVA IASNGGGRPALESIVAQLSRPDPALAALTNDHLVALACLGGRPALDAVK KGLGDPISRSQLVKSELEEKKSELRHKLKYVPHEYIELIEIARNSTQDRIL | KL-HD-HD-NG-HD-<br>NG-YK-NG-NN-<br>NN-NN-NN-HD-<br>HD-NI-NG# |

TABLE 5-continued

Sequences referred to in example 2.

| | | | |
|---|---|---|---|
| | | EMKVMEFFMKVYGYRGKHLGGSRKPDGAIYTVGSPIDYGVIVDTKAYS<br>GGYNLPIGQADEMQRYVEENQTRNKHINPNEWWKVYPSSVTEFKFLFV<br>SGHFKGNYKAQLTRLNHITNCNGAVLSVEELLIGGEMIKAGTLTLEEVRR<br>KFNNGEINFAAD | |
| 21 | TALEN<br>Left PD1 | MGDPKKKRKVIDKETAAAKFERQHMDSIDIADLRTLGYSQQQQEKIKPK<br>VRSTVAQHHEALVGHGFTHAHIVALSQHPAALGTVAVKYQDMIAALPEA<br>THEAIVGVGKQWSGARALEALLTVAGELRGPPLQLDTGQLLKIAKRGGV<br>TAVEAVHAWRNALTGAPLNLTPEQVVAIASHDGGKQALETVQRLLPVL<br>CQAHGLTPQQVVAIASNGGGKQALETVQRLLPVLCQAHGLTPEQVVAI<br>ASHDGGKQALETVQRLLPVLCQAHGLTPQQVVAIASNGGGKQALETVQ<br>RLLPVLCQAHGLTPQQVVAIASNGGGKQALETVQRLLPVLCQAHGLTP<br>QQVVAIASNGGGKQALETVQRLLPVLCQAHGLTPQQVVAIASNNGGKQ<br>ALETVQRLLPVLCQAHGLTPEQVVAIASNIGGKQALETVQALLPVLCQA<br>HGLTPQQVVAIASNGGGKQALETVQRLLPVLCQAHGLTPEQVVAIASH<br>DGGKQALETVQRLLPVLCQAHGLTPQQVVAIASNGGGKQALETVQRLL<br>PVLCQAHGLTPQQVVAIASNNGGKQALETVQRLLPVLCQAHGLTPEQV<br>VAIASNGGKQALETVQRLLPVLCQAHGLTPQQVVAIASNNGGKQALETV<br>QRLLPVLCQAHGLTPEQVVAIASHDGGKQALETVQRLLPVLCQAHGLT<br>PQQVVAIASNGGGRPALESIVAQLSRPDPALAALTNDHLVALACLGGRP<br>ALDAVKKGLGDPISRSQLVKSELEEKKSELRHKLKYVPHEYIELIEIARNS<br>TQDRILEMKVMEFFMKVYGYRGKHLGGSRKPDGAIYTVGSPIDYGVIVD<br>TKAYSGGYNLPIGQADEMQRYVEENQTRNKHINPNEWWKVYPSSVTE<br>FKFLFVSGHFKGNYKAQLTRLNHITNCNGAVLSVEELLIGGEMIKAGTLT<br>LEEVRRKFNNGEINFAAD | HD-NG-HD-NG-<br>NG-NG-NN-NI-NG-<br>HD-NG-NN-N-NN-<br>HD-NG# |

| SEQ<br>ID<br>NO# | Sequence<br>Name | Polynucleotide sequence |
|---|---|---|
| 22 | TALEN TRAC<br>pCLS11370 | ATGGGCGATCCTAAAAAGAAACGTAAGGTCATCGATTACCCATACGATGTTCCAGATTACGCTAT<br>CGATATCGCCGATCTACGCACGCTCGGCTACAGCCAGCAGCAACAGGAGAAGATCAAACCGAA<br>GGTTCGTTCGACAGTGGCGCAGCACCACGAGGCACTGGTCGGCCACGGGTTTACACACGCGC<br>ACATCGTTGCGTTAAGCCAACACCCGGCAGCGTTAGGGACCGTCGCTGTCAAGTATCAGGACA<br>TGATCGCAGCGTTGCCAGAGGCGACACACGAAGCGATCGTTGGCGTCGGCAAACAGTGGTCC<br>GGCGCACGCGCTCTGGAGGCCTTGCTCACGGTGGCGGGAGAGTTGAGAGGTCCACCGTTACA<br>GTTGGACACAGGCCAACTTCTCAAGATTGCAAAACGTGGCGGCGTGACCGCAGTGGAGGCAGT<br>GCATGCATGGCGCAATGCACTGACGGGTGCCCCGCTCAACTTGACCCCCCAGCAGGTGGTGG<br>CCATCGCCAGCAATGGCGGTGGCAAGCAGGCGCTGGAGACGGTCCAGCGGCTGTTGCCGGTG<br>CTGTGCCAGGCCCACGGCTTGACCCCCCAGCAGGTGGTGGCCATCGCCAGCAATAATGGTGG<br>CAAGCAGGCGCTGGAGACGGTCCAGCGGCTGTTGCCGGTGCTGTGCCAGGCCCACGGCTTGA<br>CCCCCCAGCAGGTGGTGGCCATCGCCAGCAATGGCGGTGGCAAGCAGGCGCTGGAGACGGT<br>CCAGCGGCTGTTGCCGGTGCTGTGCCAGGCCCACGGCTTGACCCCGGAGCAGGTGGTGGCCA<br>TCGCCAGCCACGATGGCGGCAAGCAGGCGCTGGAGACGGTCCAGCGGCTGTTGCCGGTGCTG<br>TGCCAGGCCCACGGCTTGACCCCGGAGCAGGTGGTGGCCATCGCCAGCCACGATGGCGGCAA<br>GCAGGCGCTGGAGACGGTCCAGCGGCTGTTGCCGGTGCTGTGCCAGGCCCACGGCTTGACCC<br>CGGAGCAGGTGGTGGCCATCGCCAGCCACGATGGCGGCAAGCAGGCGCTGGAGACGGTCCA<br>GCGGCTGTTGCCGGTGCTGTGCCAGGCCCACGGCTTGACCCCGGAGCAGGTGGTGGCCATCG<br>CCAGCAATATTGGTGGCAAGCAGGCGCTGGAGACGGTGCAGGCGCTGTTGCCGGTGCTGTGC<br>CAGGCCCACGGCTTGACCCCGGAGCAGGTGGTGGCCATCGCCAGCCACGATGGCGGCAAGCA<br>GGCGCTGGAGACGGTCCAGCGGCTGTTGCCGGTGCTGTGCCAGGCCCACGGCTTGACCCCCG<br>AGCAGGTGGTGGCCATCGCCAGCAATATTGGTGGCAAGCAGGCGCTGGAGACGGTGCAGGC<br>GCTGTTGCCGGTGCTGTGCCAGGCCCACGGCTTGACCCCCCAGCAGGTGGTGGCCATCGCCA<br>GCAATAATGGTGGCAAGCAGGCGCTGGAGACGGTCCAGCGGCTGTTGCCGGTGCTGTGCCAG<br>GCCCACGGCTTGACCCCGGAGCAGGTGGTGGCCATCGCCAGCAATATTGGTGGCAAGCAGGC<br>GCTGGAGACGGTGCAGGCGCTGTTGCCGGTGCTGTGCCAGGCCCACGGCTTGACCCCCCAGC<br>AGGTGGTGGCCATCGCCAGCAATGGCGGTGGCAAGCAGGCGCTGGAGACGGTCAGCGGCT<br>GTTGCCGGTGCTGTGCCAGGCCCACGGCTTGACCCCGGAGCAGGTGGTGGCCATCGCCAGCA<br>ATATTGGTGGCAAGCAGGCGCTGGAGACGGTGCAGGCGCTGTTGCCGGTGCTGTGCCAGGCC<br>CACGGCTTGACCCCCCAGCAGGTGGTGGCCATCGCCAGCAATGGCGGTGGCAAGCAGGCGCT<br>GGAGACGGTCCAGCGGCTGTTGCCGGTGCTGTGCCAGGCCCACGGCTTGACCCCGGAGCAG<br>GTGGTGGCCATCGCCAGCCACGATGGCGGCAAGCAGGCGCTGGAGACGGTCCAGCGGCTGTT<br>GCCGGTGCTGTGCCAGGCCCACGGCTTGACCCCTCAGCAGGTGGTGGCCATCGCCAGCAATG<br>GCGGCGGCAGGCCGGCGCTGGAGAGCATTGTTGCCCAGTTATCTCGCCCTGATCCGGCGTTG<br>GCCGCGTTGACCAACGACCACCTCGTCGCCTTGGCCTGCCTCGGCGGGCGTCCTGCGCTGGA<br>TGCAGTGAAAAAGGGATTGGGGGATCCTATCAGCCGTTCCCAGCTGGTGAAGTCCGAGCTGGA<br>GGAGAAGAAATCCGAGTTGAGGCACAAGCTGAAGTACGTGCCCCACGAGTACATCGAGCTGAT<br>CGAGATCGCCCGGAACAGCACCCAGGACCGTATCCTGGAGATGAAGGTGATGGAGTTCTTCAT<br>GAAGGTGTACGGCTACAGGGGCAAGCACCTGGGCGGCTCCAGGAAGCCCGACGGCGCCATCT<br>ACACCGTGGGCTCCCCCATCGACTACGGCGTGATCGTGGACACCAAGGCCTACTCCGGCGGC<br>TACAACCTGCCCATCGGCCAGGCCGACGAAATGCAGAGGTACGTGGAGGAGAACCAGACCAG<br>GAACAAGCACATCAACCCCAACGAGTGGTGGAAGGTGTACCCCTCCAGCGTGACCGAGTTCAA<br>GTTCCTGTTCGTGTCCGGCCACTTCAAGGGCAACTACAAGGCCCAGCTGACCAGGCTGAACCA<br>CATCACCAACTGCAACGGCGCCGTGCTGTCCGTGGAGGAGCTCCTGATCGGCGGCGAGATGA<br>TCAAGGCCGGCACCCTGACCCTGGAGGAGGTGAGGAGGAAGTTCAACAACGGCGAGATCAAC<br>TTCGCGGCCGACTGATAA |

TABLE 5-continued

Sequences referred to in example 2.

| 23 | TALEN TRAC pCLS11369 | ATGGGCGATCCTAAAAAGAAACGTAAGGTCATCGATAAGGAGACCGCCGCTGCCAAGTTCGAG
AGACAGCACATGGACAGCATCGATATCGCCGATCTACGCACGCTCGGCTACAGCCAGCAGCAA
CAGGAGAAGATCAAACCGAAGGTTCGTTCGACAGTGGCGCAGCACCACGAGGCACTGGTCGG
CCACGGGTTTACACACGCGCACATCGTTGCGTTAAGCCAACACCCGGCAGCGTTAGGGACCGT
CGCTGTCAAGTATCAGGACATGATCGCAGCGTTGCCAGAGGCGACACACGAAGCGATCGTTGG
CGTCGGCAAACAGTGGTCCGGCGCACGCGCTCTGGAGGCCTTGCTCACGGTGGCGGGAGAGT
TGAGAGGTCCACCGTTACAGTTGGACACAGGCCAACTTCTCAAGATTGCAAAACGTGGCGGCG
TGACCGCAGTGGAGGCAGTGCATGCATGGCGCAATGCACTGACGGGTGCCCCGCTCAACTTG
ACCCCGGAGCAGGTGGTGGCCATCGCCAGCCACGATGGCGGCAAGCAGGCGCTGGAGACGG
TCCAGCGGCTGTTGCCGGTGCTGTGCCAGGCCCACGGCTTGACCCCCCAGCAGGTGGTGGCC
ATCGCCAGCAATGGCGGTGGCAAGCAGGCGCTGGAGACGGTCCAGCGGCTGTTGCCGGTGCT
GTGCCAGGCCCACGGCTTGACCCCGGAGCAGGTGGTGGCCATCGCCAGCCACGATGGCGGC
AAGCAGGCGCTGGAGACGGTCCAGCGGCTGTTGCCGGTGCTGTGCCAGGCCCACGGCTTGAC
CCCGGAGCAGGTGGTGGCCATCGCCAGCAATATTGGTGGCAAGCAGGCGCTGGAGACGGTGC
AGGCGCTGTTGCCGGTGCTGTGCCAGGCCCACGGCTTGACCCCCCAGCAGGTGGTGGCCATC
GCCAGCAATAATGGTGGCAAGCAGGCGCTGGAGACGGTCCAGCGGCTGTTGCCGGTGCTGTG
CCAGGCCCACGGCTTGACCCCGGAGCAGGTGGTGGCCATCGCCAGCCACGATGGCGGCAAG
CAGGCGCTGGAGACGGTCCAGCGGCTGTTGCCGGTGCTGTGCCAGGCCCACGGCTTGACCCC
CCAGCAGGTGGTGGCCATCGCCAGCAATGGCGGTGGCAAGCAGGCGCTGGAGACGGTCCAG
CGGCTGTTGCCGGTGCTGTGCCAGGCCCACGGCTTGACCCCCCAGCAGGTGGTGGCCATCGC
CAGCAATAATGGTGGCAAGCAGGCGCTGGAGACGGTCCAGCGGCTGTTGCCGGTGCTGTGCC
AGGCCCACGGCTTGACCCCCCAGCAGGTGGTGGCCATCGCCAGCAATAATGGTGGCAAGCAG
GCGCTGGAGACGGTCCAGCGGCTGTTGCCGGTGCTGTGCCAGGCCCACGGCTTGACCCCCCA
GCAGGTGGTGGCCATCGCCAGCAATGGCGGTGGCAAGCAGGCGCTGGAGACGGTCCAGCGG
CTGTTGCCGGTGCTGTGCCAGGCCCACGGCTTGACCCCGGAGCAGGTGGTGGCCATCGCCAG
CAATATTGGTGGCAAGCAGGCGCTGGAGACGGTCCAGCGGCTGTTGCCGGTGCTGTGCCAGG
CCCACGGCTTGACCCCGGAGCAGGTGGTGGCCATCGCCAGCCACGATGGCGGCAAGCAGGC
GCTGGAGACGGTCCAGCGGCTGTTGCCGGTGCTGTGCCAGGCCCACGGCTTGACCCCGGAGC
AGGTGGTGGCCATCGCCAGCAATATTGGTGGCAAGCAGGCGCTGGAGACGGTGCAGGCGCTG
TTGCCGGTGCTGTGCCAGGCCCACGGCTTGACCCCGGAGCAGGTGGTGGCCATCGCCAGCA
CGATGGCGGCAAGCAGGCGCTGGAGACGGTCCAGCGGCTGTTGCCGGTGCTGTGCCAGGCC
CACGGCTTGACCCCCCAGCAGGTGGTGGCCATCGCCAGCAATAATGGTGGCAAGCAGGCGCT
GGAGACGGTCCAGCGGCTGTTGCCGGTGCTGTGCCAGGCCCACGGCTTGACCCCTCAGCAGG
TGGTGGCCATCGCCAGCAATGGCGGCGGCAGGCCGGCGCTGGAGAGCATTGTTGCCCAGTTA
TCTCGCCCTGATCCGGCGTTGGCCGCGTTGACCAACGACCACCTCGTCGCCTTGGCCTGCCTC
GGCGGGCGTCCTGCGCTGGATGCAGTGAAAAAGGGATTGGGGGATCCTATCAGCCGTTCCCA
GCTGGTGAAGTCCGAGCTGGAGGAGAAGAAATCCGAGTTGAGGCACAAGCTGAAGTACGTGCC
CCACGAGTACATCGAGCTGATCGAGATCGCCCGGAACAGCACCCAGGACCGTATCCTGGAGAT
GAAGGTGATGGAGTTCTTCATGAAGGTGTACGGCTACAGGGGCAAGCACCTGGGCGGCTCCA
GGAAGCCCGACGGCGCCATCTACACCGTGGGCTCCCCCATCGACTACGGCGTGATCGTGGAC
ACCAAGGCCTACTCCGGCGGCTACAACCTGCCCATCGGCCAGGCCGACGAAATGCAGAGGTA
CGTGGAGGAGAACCAGACCAGGAACAAGCACATCAACCCCAACGAGTGGTGGAAGGTGTACC
CCTCCAGCGTGACCGAGTTCAAGTTCCTGTTCGTGTCCGGCCACTTCAAGGGCAACTACAAGG
CCCAGCTGACCAGGCTGAACCACATCACCAACTGCAACGGCGCCGTGCTGTCCGTGGAGGAG
CTCCTGATCGGCGGCGAGATGATCAAGGCCGGCACCCTGACCCTGGAGGAGGTGAGGAGGAA
GTTCAACAACGGCGAGATCAACTTCGCGGCCGACTGATAA |
| 24 | TALEN CD25 pCLS30480 | ATGGGCGATCCTAAAAAGAAACGTAAGGTCATCGATTACCCATACGATGTTCCAGATTACGCTAT
CGATATCGCCGATCTACGCACGCTCGGCTACAGCCAGCAGCAACAGGAGAAGATCAAACCGAA
GGTTCGTTCGACAGTGGCGCAGCACCACGAGGCACTGGTCGGCCACGGGTTTACACACGCGC
ACATCGTTGCGTTAAGCCAACACCCGGCAGCGTTAGGGACCGTCGCTGTCAAGTATCAGGACA
TGATCGCAGCGTTGCCAGAGGCGACACACGAAGCGATCGTTGGCGTCGGCAAACAGTGGTCC
GGCGCACGCGCTCTGGAGGCCTTGCTCACGGTGGCGGGAGAGTTGAGAGGTCCACCGTTACA
GTTGGACACAGGCCAACTTCTCAAGATTGCAAAACGTGGCGGCGTGACCGCAGTGGAGGCAGT
GCATGCATGGCGCAATGCACTGACGGGTGCCCCGCTCAACTTGACCCCCCAGCAGGTGGTGG
CCATCGCCAGCAATAATGGTGGCAAGCAGGCGCTGGAGACGGTCCAGCGGCTGTTGCCGGTG
CTGTGCCAGGCCCACGGCTTGACCCCCCAGCAGGTGGTGGCCATCGCCAGCAATGGCGGTGG
CAAGCAGGCGCTGGAGACGGTCCAGCGGCTGTTGCCGGTGCTGTGCCAGGCCCACGGCTTGA
CCCCCCAGCAGGTGGTGGCCATCGCCAGCAATGGCGGTGGCAAGCAGGCGCTGGAGACGGT
CCAGCGGCTGTTGCCGGTGCTGTGCCAGGCCCACGGCTTGACCCCGGAGCAGGTGGTGGCCA
TCGCCAGCCACGATGGCGGCAAGCAGGCGCTGGAGACGGTCCAGCGGCTGTTGCCGGTGCTG
TGCCAGGCCCACGGCTTGACCCCCCAGCAGGTGGTGGCCATCGCCAGCAATGGCGGTGGCAA
GCAGGCGCTGGAGACGGTCCAGCGGCTGTTGCCGGTGCTGTGCCAGGCCCACGGCTTGACCC
CCCAGCAGGTGGTGGCCATCGCCAGCAATGGCGGTGGCAAGCAGGCGCTGGAGACGGTCCA
GCGGCTGTTGCCGGTGCTGTGCCAGGCCCACGGCTTGACCCCCCAGCAGGTGGTGGCCATCG
CCAGCAATGGCGGTGGCAAGCAGGCGCTGGAGACGGTCAGCGGCTGTTGCCGGTGCTGTGC
CAGGCCCACGGCTTGACCCCCAGCAGGTGGTGGCCATCGCCAGCAATGGCGGTGGCAAGCA
GGCGCTGGAGACGGTCCAGCGGCTGTTGCCGGTGCTGTGCCAGGCCCACGGCTTGACCCCC
AGCAGGTGGTGGCCATCGCCAGCAATAATGGTGGCAAGCAGGCGCTGGAGACGGTCCAGCGG
CTGTTGCCGGTGCTGTGCCAGGCCCACGGCTTGACCCCCAGCAGGTGGTGGCCATCGCCAG
CAATAATGGTGGCAAGCAGGCGCTGGAGACGGTCCAGCGGCTGTTGCCGGTGCTGTGCCAGG
CCCACGGCTTGACCCCCAGCAGGTGGTGGCCATCGCCAGCAATGGCGGTGGCAAGCAGGCG
CTGGAGACGGTCCAGCGGCTGTTGCCGGTGCTGTGCCAGGCCCACGGCTTGACCCCCCAGCA
GGTGGTGGCCATCGCCAGCAATGGCGGTGGCAAGCAGGCGCTGGAGACGGTCCAGCGGCTG
TTGCCGGTGCTGTGCCAGGCCCACGGCTTGACCCCCCAGCAGGTGGTGGCCATCGCCAGCAA
TGGCGGTGGCAAGCAGGCGCTGGAGACGGTCCAGCGGCTGTTGCCGGTGCTGTGCCAGGCC
CACGGCTTGACCCCCCAGCAGGTGGTGGCCATCGCCAGCAATGGCGGTGGCAAGCAGGCGCT |

TABLE 5-continued

Sequences referred to in example 2.

| | | |
|---|---|---|
| | | GGAGACGGTCCAGCGGCTGTTGCCGGTGCTGTGCCAGGCCCACGGCTTGACCCCGGAGCAG<br>GTGGTGGCCATCGCCAGCCACGATGGCGGCAAGCAGGCGCTGGAGACGGTCCAGCGGCTGTT<br>GCCGGTGCTGTGCCAGGCCCACGGCTTGACCCCTCAGCAGGTGGTGGCCATCGCCAGCAATG<br>GCGGCGGCAGGCCGGCGCTGGAGAGCATTGTTGCCCAGTTATCTCGCCCTGATCCGAGTGGC<br>AGCGGAAGTGGCGGGGATCCTATCAGCCGTTCCCAGCTGGTGAAGTCCGAGCTGGAGGAGAA<br>GAAATCCGAGTTGAGGCACAAGCTGAAGTACGTGCCCCACGAGTACATCGAGCTGATCGAGAT<br>CGCCCGGAACAGCACCCAGGACCGTATCCTGGAGATGAAGGTGATGGAGTTCTTCATGAAGGT<br>GTACGGCTACAGGGGCAAGCACCTGGGCGGCTCCAGGAAGCCCGACGGCGCCATCTACACCG<br>TGGGCTCCCCCATCGACTACGGCGTGATCGTGGACACCAAGGCCTACTCCGGCGGCTACAACC<br>TGCCCATCGGCCAGGCCGACGAAATGCAGAGGTACGTGGAGGAGAACCAGACCAGGAACAAG<br>CACATCAACCCCAACGAGTGGTGGAAGGTGTACCCCTCCAGCGTGACCGAGTTCAAGTTCCTG<br>TTCGTGTCCGGCCACTTCAAGGGCAACTACAAGGCCCAGCTGACCAGGCTGAACCACATCACC<br>AACTGCAACGGCGCCGTGCTGTCCGTGGAGGAGCTCCTGATCGGCGGCGAGATGATCAAGGC<br>CGGCACCCTGACCCTGGAGGAGGTGAGGAGGAAGTTCAACAACGGCGAGATCAACTTCGCGG<br>CCGACTGATAA |
| 25 | TALEN CD25<br>pCLS30479 | ATGGGCGATCCTAAAAAGAAACGTAAGGTCATCGATTACCCATACGATGTTCCAGATTACGCTAT<br>CGATATCGCCGATCTACGCACGCTCGGCTACAGCCAGCAGCAACAGGAGAAGATCAAACCGAA<br>GGTTCGTTCGACAGTGGCGCAGCACCACGAGGCACTGGTCGGCGCACGGGTTTACACACGCGC<br>ACATCGTTGCGTTAAGCCAACACCCGGCAGCGTTAGGGACCGTCGCTGTCAAGTATCAGGACA<br>TGATCGCAGCGTTGCCAGAGGCGACACACGAAGCGATCGTTGGCGTCGGCAAACAGTGGTCC<br>GGCGCACGCGCTCTGGAGGCCTTGCTCACGGTGGCGGGAGAGTTGAGAGGTCCACCGTTACA<br>GTTGGACACAGGCCAACTTCTCAAGATTGCAAAACGTGGCGGCGTGACCGCAGTGGAGGCAGT<br>GCATGCATGGCGCAATGCACTGACGGGTGCCCCGCTCAACTTGACCCCGGAGCAGGTGGTGG<br>CCATCGCCAGCAATATTGGTGGCAAGCAGGCGCTGGAGACGGTGCAGGCGCTGTTGCCGGTG<br>CTGTGCCAGGCCCACGGCTTGACCCCGGAGCAGGTGGTGGCCATCGCCAGCCACGATGGCGG<br>CAAGCAGGCGCTGGAGACGGTCCAGCGGCTGTTGCCGGTGCTGTGCCAGGCCCACGGCTTGA<br>CCCCGGAGCAGGTGGTGGCCATCGCCAGCAATATTGGTGGCAAGCAGGCGCTGGAGACGGTG<br>CAGGCGCTGTTGCCGGTGCTGTGCCAGGCCCACGGCTTGACCCCCAGCAGGTGGTGGCCAT<br>CGCCAGCAATAATGGTGGCAAGCAGGCGCTGGAGACGGTCCAGCGGCTGTTGCCGGTGCTGT<br>GCCAGGCCCACGGCTTGACCCCCAGCAGGTGGTGGCCATCGCCAGCAATAATGGTGGCAAG<br>CAGGCGCTGGAGACGGTCCAGCGGCTGTTGCCGGTGCTGTGCCAGGCCCACGGCTTGACCCC<br>GGAGCAGGTGGTGGCCATCGCCAGCAATATTGGTGGCAAGCAGGCGCTGGAGACGGTGCAGG<br>CGCTGTTGCCGGTGCTGTGCCAGGCCCACGGCTTGACCCCCAGCAGGTGGTGGCCATCGCC<br>AGCAATAATGGTGGCAAGCAGGCGCTGGAGACGGTCCAGCGGCTGTTGCCGGTGCTGTGCCA<br>GGCCCACGGCTTGACCCCCAGCAGGTGGTGGCCATCGCCAGCAATAATGGTGGCAAGCAGG<br>CGCTGGAGACGGTCCAGCGGCTGTTGCCGGTGCTGTGCCAGGCCCACGGCTTGACCCCGGAG<br>CAGGTGGTGGCCATCGCCAGCAATAATGGTGGCAAGCAGGCGCTGGAGACGGTGCAGGCGCT<br>GTTGCCGGTGCTGTGCCAGGCCCACGGCTTGACCCCCAGCAGGTGGTGGCCATCGCCAGCA<br>ATATTGGTGGCAAGCAGGCGCTGGAGACGGTGCAGGCGCTGTTGCCGGTGCTGTGCCAGGCC<br>CACGGCTTGACCCCCAGCAGGTGGTGGCCATCGCCAGCAATAATGGTGGCAAGCAGGCGCT<br>GGAGACGGTCCAGCGGCTGTTGCCGGTGCTGTGCCAGGCCCACGGCTTGACCCCGGAGCAG<br>GTGGTGGCCATCGCCAGCAATATTGGTGGCAAGCAGGCGCTGGAGACGGTGCAGGCGCTGTT<br>GCCGGTGCTGTGCCAGGCCCACGGCTTGACCCCCAGCAGGTGGTGGCCATCGCCAGCAATA<br>ATGGTGGCAAGCAGGCGCTGGAGACGGTCCAGCGGCTGTTGCCGGTGCTGTGCCAGGCCCAC<br>GGCTTGACCCCCAGCAGGTGGTGGCCATCGCCAGCAATGGCGGTGGCAAGCAGGCGCTGGA<br>GACGGTCCAGCGGCTGTTGCCGGTGCTGTGCCAGGCCCACGGCTTGACCCCGGAGCAGGTGG<br>TGGCCATCGCCAGCAATATTGGTGGCAAGCAGGCGCTGGAGACGGTGCAGGCGCTGTTGCCG<br>GTGCTGTGCCAGGCCCACGGCTTGACCCCTCAGCAGGTGGTGGCCATCGCCAGCAATGGCGG<br>CGGCAGGCCGGCGCTGGAGAGCATTGTTGCCCAGTTATCTCGCCCTGATCCGAGTGGCAGCG<br>GAAGTGGCGGGGATCCTATCAGCCGTTCCCAGCTGGTGAAGTCCGAGCTGGAGGAGAAGAAAT<br>CCGAGTTGAGGCACAAGCTGAAGTACGTGCCCCACGAGTACATCGAGCTGATCGAGATCGCCC<br>GGAACAGCACCCAGGACCGTATCCTGGAGATGAAGGTGATGGAGTTCTTCATGAAGGTGTACG<br>GCTACAGGGGCAAGCACCTGGGCGGCTCCAGGAAGCCCGACGGCGCCATCTACACCGTGGGC<br>TCCCCCATCGACTACGGCGTGATCGTGGACACCAAGGCCTACTCCGGCGGCTACAACCTGCCC<br>ATCGGCCAGGCCGACGAAATGCAGAGGTACGTGGAGGAGAACCAGACCAGGAACAAGCACAT<br>CAACCCCAACGAGTGGTGGAAGGTGTACCCCTCCAGCGTGACCGAGTTCAAGTTCCTGTTCGT<br>GTCCGGCCACTTCAAGGGCAACTACAAGGCCCAGCTGACCAGGCTGAACCACATCACCAACTG<br>CAACGGCGCCGTGCTGTCCGTGGAGGAGCTCCTGATCGGCGGCGAGATGATCAAGGCCGGCA<br>CCCTGACCCTGGAGGAGGTGAGGAGGAAGTTCAACAACGGCGAGATCAACTTCGCGGCCGAC<br>TGATAA |
| 26 | TALEN PD1<br>pCLS28959 | ATGGGCGATCCTAAAAAGAAACGTAAGGTCATCGATTACCCATACGATGTTCCAGATTACGCTAT<br>CGATATCGCCGATCTACGCACGCTCGGCTACAGCCAGCAGCAACAGGAGAAGATCAAACCGAA<br>GGTTCGTTCGACAGTGGCGCAGCACCACGAGGCACTGGTCGGCGCACGGGTTTACACACGCGC<br>ACATCGTTGCGTTAAGCCAACACCCGGCAGCGTTAGGGACCGTCGCTGTCAAGTATCAGGACA<br>TGATCGCAGCGTTGCCAGAGGCGACACACGAAGCGATCGTTGGCGTCGGCAAACAGTGGTCC<br>GGCGCACGCGCTCTGGAGGCCTTGCTCACGGTGGCGGGAGAGTTGAGAGGTCCACCGTTACA<br>GTTGGACACAGGCCAACTTCTCAAGATTGCAAAACGTGGCGGCGTGACCGCAGTGGAGGCAGT<br>GCATGCATGGCGCAATGCACTGACGGGTGCCCCGCTCAACTTGACCCCGGAGCAAGTGGTGG<br>CTATCGCTTCCAAGCTGGGGGAAAGCAGGCCCTGGAGACCGTCCAGGCCCTTCTCCCAGTG<br>CTTTGCCAGGCTCACGGACTGACCCCTGAACAGGTGGTGGCAATTGCCTCACACGACGGGGG<br>CAAGCAGGCACTGGAGACTGTCCAGCGGCTGCTTCCTGTCCTGTGCCAGGCCCACGGACTCA<br>CTCCTGAGCAGGTCGTGGCCATTGCCAGCCACGATGGGGGCAAACAGGCTCTGGAGACCGTG<br>CAGCGCCTCCTCCCAGTGCTGTGCCAGGCTCATGGGCTGACCCCACAGCAGGTCGTCGCCATT<br>GCCAGTAACGGCGGGGGAAGCAGGCCCTCGAAACAGTGCAGAGGCTGCTGCCCGTCTTGTG<br>CCAAGCACACGGCCTGACACCCGAGCAGGTGGTGGCCATCGCCTCTCATGACGGCGGCAAGC<br>AGGCCCTTGAGACAGTGCAGAGACTGTTGCCCGTGTTGTGTCAGGCCCACGGGTTGACACCCC |

TABLE 5-continued

Sequences referred to in example 2.

| | | |
|---|---|---|
| | | AGCAGGTGGTCGCCATCGCCAGCAATGGCGGGGGAAAGCAGGCCCTTGAGACCGTGCAGCGG
TTGCTTCCAGTGTTGTGCCAGGCACACGGACTGACCCCTCAACAGGTGGTCGCAATCGCCAGC
TACAAGGGCGGAAAGCAGGCTCTGGAGACAGTGCAGCGCCTCCTGCCCGTGCTGTGTCAGGC
TCACGGACTGACACCACAGCAGGTGGTCGCCATCGCCAGTAACGGGGGCGGCAAGCAGGCTT
TGGAGACCGTCCAGAGACTCCTCCCCGTCCTTTGCCAGGCCCACGGGTTGACACCTCAGCAGG
TCGTCGCCATTGCCTCCAACAACGGGGGCAAGCAGGCCCTCGAAACTGTGCAGAGGCTGCTG
CCTGTGCTGTGCCAGGCTCATGGGCTGACACCCCAGCAGGTGGTGGCCATTGCCTCTAACAAC
GGCGGCAAACAGGCACTGGAGACCGTGCAAAGGCTGCTGCCCGTCCTCTGCCAAGCCCACGG
GCTCACTCCACAGCAGGTCGTGGCCATCGCCTCAAACAATGGCGGGAAGCAGGCCCTGGAGA
CTGTGCAAAGGCTGCTCCCTGTGCTCTGCCAGGCACACGGACTGACCCCTCAGCAGGTGGTG
GCAATCGCTTCCAACAACGGGGGAAAGCAGGCCCTCGAAACCGTGCAGCGCCTCCTGCCCAGT
GCTGTGCCAGGCACATGGCCTCACACCCGAGCAAGTGGTGGCTATCGCCAGCCACGACGGAG
GGAAGCAGGCTCTGGAGACCGTGCAGAGGCTGCTGCCTGTCCTGTGCCAGGCCCACGGGCTT
ACTCCAGAGCAGGTCGTCGCCATCGCCAGTCATGATGGGGGAAGCAGGCCCTTGAGACAGT
CCAGCGGCTGCTGCCAGTCCTTTGCCAGGCTCACGGCTTGACTCCCGAGCAGGTCGTGGCCAT
TGCCTCAAACATTGGGGGCAAACAGGCCCTGGACAGTGCAGGCCCTGCTGCCCGTGTTGTG
TCAGGCCCACGGCTTGACACCCCAGCAGGTGGTCGCCATTGCCTCTAATGGCGGCGGGAGAC
CCGCCTTGGAGAGCATTGTTGCCCAGTTATCTCGCCCTGATCCGGCGTTGGCCGCGTTGACCA
ACGACCACCTCGTCGCCTTGGCCTGCCTCGGCGGCGTCCTGCGCTGGATGCAGTGAAAAAG
GGATTGGGGGATCCTATCAGCCGTTCCCAGCTGGTGAAGTCCGAGCTGGAGGAGAAGAAATCC
GAGTTGAGGCACAAGCTGAAGTACGTGCCCCACGAGTACATCGAGCTGATCGAGATCGCCCGG
AACAGCACCCAGGACCGTATCCTGGAGATGAAGGTGATGGAGTTCTTCATGAAGGTGTACGGC
TACAGGGGCAAGCACCTGGGCGGCTCCAGGAAGCCCGACGGCGCCATCTACACCGTGGGCTC
CCCCATCGACTACGGCGTGATCGTGGACACCAAGGCCTACTCCGGCGGCTACAACCTGCCCAT
CGGCCAGGCCGACGAAATGCAGAGGTACGTGGAGGAGAACCAGACCAGGAACAAGCACATCA
ACCCCAACGAGTGGTGGAAGGTGTACCCCTCCAGCGTGACCGAGTTCAAGTTCCTGTTCGTGT
CCGGCCACTTCAAGGGCAACTACAAGGCCCAGCTGACCAGGCTGAACCACATCACCAACTGCA
ACGGCGCCGTGCTGTCCGTGGAGGAGCTCCTGATCGGCGGCGAGATGATCAAGGCCGGCACC
CTGACCCTGGAGGAGGTGAGGAGGAAGTTCAACAACGGCGAGATCAACTTCGCGGCCGACTG
ATAA |
| 27 | TALEN PD1
pCLS18792 | ATGGGCGATCCTAAAAAGAAACGTAAGGTCATCGATAAGGAGACCGCCGCTGCCAAGTTCGAG
AGACAGCACATGGACAGCATCGATATCGCCGATCTACGCACGCTCGGCTACAGCCAGCAGCAA
CAGGAGAAGATCAAACCGAAGGTTCGTTCGACAGTGGCGCAGCACCACGAGGCACTGGTCGG
CCACGGGTTTACACACGCGCACATCGTTGCGTTAAGCCAACACCCGGCAGCGTTAGGGACCGT
CGCTGTCAAGTATCAGGACATGATCGCAGCGTTGCCAGAGGCGACACACGAAGCGATCGTTGG
CGTCGGCAAACAGTGGTCCGGCGCACGCGCTCTGGAGGCCTTGCTCACGGTGGCGGGAGAGT
TGAGAGGTCCACCGTTACAGTTGGACACAGGCCAACTTCTCAAGATTGCAAAACGTGGCGGCG
TGACCGCAGTGGAGGCAGTGCATGCATGGCGCAATGCACTGACGGGTGCCCCGCTCAACTTG
ACCCCCGAGCAAGTCGTCGCAATCGCCAGCCATGATGGAGGGAAGCAAGCCCTCGAAACCGT
GCAGCGGTTGCTTCCTGTGCTCTGCCAGGCCCACGGCCTTACCCCTCAGCAGGTGGTGGCCAT
CGCAAGTAACGGAGGAGGAAAGCAAGCCTTGGAGACAGTGCAGCGCCTGTTGCCCGTGCTGT
GCCAGGCACACGGCCTCACACCAGAGCAGGTCGTGGCCATTGCCTCCCATGACGGGGGGAAA
CAGGCTCTGGAGACCGTCCAGAGGCTGCTGCCCGTCCTCTGTCAAGCTCACGGCCTGACTCCC
CAACAAGTGGTCGCCATCGCCTCTAATGGCGGCGGGAAGCAGGCACTGGAAACAGTGCAGAG
ACTGCTCCCTGTGCTTTGCCAAGCTCATGGGTTGACCCCCAACAGGTCGTCGCTATTGCCTCA
AACGGGGGGGGCAAGCAGGCCCTTGAGACTGTGCAGAGGCTGTTGCCAGTGCTGTGTCAGGC
TCACGGGCTCACTCCACAACAGGTGGTCGCAATTGCCAGCAACGGCGGCGGAAAGCAAGCTCT
TGAAACCGTGCAACGCCTCCTGCCCGTGCTCTGTCAGGCTCATGGCCTGACACCACAACAAGT
CGTGGCCATCGCCAGTAATAATGGCGGGAAACAGGCTCTTGAGACCGTCCAGAGGCTGCTCCC
AGTGCTCTGCCAGGCACACGGCTGACCCCCGAGCAGGTGGTGGCTATCGCCAGCAATATTG
GGGGCAAGCAGGCCCTGGAAACAGTCCAGGCCCTGCTGCCAGTGCTTTGCCAGGCTCACGGG
CTCACTCCCCAGCAGGTCGTGGCAATCGCCTCCAACGGCGGAGGGAAGCAGGCTCTGGAGAC
CGTGCAGAGACTGCTGCCCGTCTTGTGCCAGGCCCACGGACTCACACCTGAACAGGTCGTCGC
CATTGCCTCTCACGATGGGGGCAAACAAGCCCTGGAGACAGTGCAGCGGCTGTTGCCTGTGTT
GTGCCAAGCCCACGGCTTGACTCCTCAACAAGTGGTCGCCATCGCCTCAAATGGCGGCGGAAA
ACAAGCTCTGGAGACAGTGCAGAGGTTGCTGCCCGTCCTCTGCCAAGCCCACGGCCTGACTCC
CCAACAGGTCGTCGCCATTGCCAGCAACAACGGAGGAAAGCAGGCTCTCGAAACTGTGCAGCG
GCTGCTTCCTGTGCTGTGTCAGGCTCATGGGCTGACCCCCGAGCAAGTGGTGGCTATTGCCTC
TAATGGAGGCAAGCAAGCCCTTGAGACAGTCCAGAGGCTGTTGCCAGTGCTGTGCCAGGCCCA
CGGGCTCACACCCCAGCAGGTGGTCGCCATCGCCAGTAACAACGGGGGCAAACAGGCATTGG
AAACCGTCCAGCGCCTGCTTCCAGTGCTCTGCCAGGCACACGGACTGACACCCGAACAGGTGG
TGGCCATTGCATCCCATGATGGGGGCAAGCAGGCCCTGGAGACCGTGCAGAGACTCCTGCCA
GTGTTGTGCCAAGCTCACGGCCTCACCCCTCAGCAAGTCGTGGCCATCGCCTCAAACGGGGG
GGGCCGGCCTGCACTGGAGAGCATTGTTGCCCAGTTATCTCGCCCTGATCCGGCGTTGGCCG
CGTTGACCAACGACCACCTCGTCGCCTTGGCCTGCCTCGGCGGCGTCCTGCGCTGGATGCA
GTGAAAAAGGGATTGGGGGATCCTATCAGCCGTTCCCAGCTGGTGAAGTCCGAGCTGGAGGAG
AAGAAATCCGAGTTGAGGCACAAGCTGAAGTACGTGCCCCACGAGTACATCGAGCTGATCGAG
ATCGCCCGGAACAGCACCCAGGACCGTATCCTGGAGATGAAGGTGATGGAGTTCTTCATGAAG
GTGTACGGCTACAGGGGCAAGCACCTGGGCGGCTCCAGGAAGCCCGACGGCGCCATCTACAC
CGTGGGCTCCCCCATCGACTACGGCGTGATCGTGGACACCAAGGCCTACTCCGGCGGCTACA
ACCTGCCCATCGGCCAGGCCGACGAAATGCAGAGGTACGTGGAGGAGAACCAGACCAGGAAC
AAGCACATCAACCCCAACGAGTGGTGGAAGGTGTACCCCTCCAGCGTGACCGAGTTCAAGTTC
CTGTTCGTGTCCGGCCACTTCAAGGGCAACTACAAGGCCCAGCTGACCAGGCTGAACCACATC
ACCAACTGCAACGGCGCCGTGCTGTCCGTGGAGGAGCTCCTGATCGGCGGCGAGATGATCAA
GGCCGGCACCCTGACCCTGGAGGAGGTGAGGAGGAAGTTCAACAACGGCGAGATCAACTTCG
CGGCCGACTGATAA |

TABLE 5-continued

Sequences referred to in example 2.

| | | |
|---|---|---|
| 28 | TALEN target TRAC | TTGTCCCACAGATATCCAGAACCCTGACCCTGCCGTGTACCAGCTGAGA |
| 29 | TALEN target CD25 | TACAGGAGGAAGAGTAGAAGAACAATCTAGAAAACCAAAAGAACA |
| 30 | TALEN target PD1 | TACCTCTGTGGGGCCATCTCCCTGGCCCCCAAGGCGCAGATCAAAGAGA |
| 31 | Matrice TRAC locus_CubiCAR CD22 pCLS30056 | TTGCTGGGCCTTTTTCCCATGCCTGCCTTTACTCTGCCAGAGTTATATTGCTGGGGTTTTGAAGA<br>AGATCCTATTAAATAAAAGAATAAGCAGTATTATTAAGTAGCCCTGCATTTCAGGTTTCCTTGAGT<br>GGCAGGCCAGGCCTGGCCGTGAACGTTCACTGAAATCATGGCCTCTTGGCCAAGATTGATAGC<br>TTGTGCCTGTCCCTGAGTCCCAGTCCATCACGAGCAGCTGGTTTCTAAGATGCTATTTCCCGTA<br>TAAAGCATGAGACCGTGACTTGCCAGCCCCACAGAGCCCCGCCCTTGTCCATCACTGGCATCT<br>GGACTCCAGCCTGGGTTGGGGCAAAGAGGGAAATGAGATCATGTCCTAACCCTGATCCTCTTG<br>TCCCACAGATATCCAGTACCCCTACGACGTGCCCGACTACGCCTCCGGTGAGGGCAGAGGAAG<br>TCTTCTAACATGCGGTGACGTGGAGGAGAATCCGGGCCCCGGATCCGCTCTGCCCGTCACCGC<br>TCTGCTGCTGCCACTGGCACTGCTGCTGCACGCTGCTAGGCCCGGAGGGGGAGGCAGCTGCC<br>CCTACAGCAACCCCAGCCTGTGCAGCGGAGGCGGCGGCAGCGGCGGAGGGGGTAGCCAGGT<br>GCAGCTGCAGCAGAGCGGCCCTGGCCTGGTGAAGCCAAGCCAGACACTGTCCCTGACCTGCG<br>CCATCAGCGGCGATTCCGTGAGCTCCAACTCCGCCGCCTGGAATTGGATCAGGCAGTCCCCTT<br>CTCGGGGCCTGGAGTGGCTGGGAAGGACATACTATCGGTCTAAGTGGTACAACGATTATGCCG<br>TGTCTGTGAAGAGCAGAATCACAATCAACCCTGACACCTCCAAGAATCAGTTCTCTCTGCAGCT<br>GAATAGCGTGACACCAGAGGACACCGCCGTGTACTATTGCGCCAGGGAGGTGACCGGCGACC<br>TGGAGGATGCCTTTGACATCTGGGGCCAGGGCACAATGGTGACCGTGAGCTCCGGAGGCGGC<br>GGATCTGGCGGAGGAGGAAGTGGGGGCGGCGGGAGTGATATCCAGATGACACAGTCCCCATC<br>CTCTCTGAGCGCCTCCGTGGGCGACAGAGTGACAATCACCTGTAGGGCCTCCCAGACCATCTG<br>GTCTTACCTGAACTGGTATCAGCAGAGGCCCGGCAAGGCCCCTAATCTGCTGATCTACGCAGC<br>AAGCTCCCTGCAGAGCGGAGTGCCATCCAGATTCTCTGGCAGGGGCTCCGGCACAGACTTCAC<br>CCTGACCATCTCTAGCCTGCAGGCCGAGGACTTCGCCACCTACTATTGCCAGCAGTCTTATAGC<br>ATCCCCCAGACATTTGGCCAGGGCACCAAGCTGGAGATCAAGTCGGATCCCGGAAGCGGAGG<br>GGGAGGCAGCTGCCCCTACAGCAACCCCAGCCTGTGCAGCGGAGGCGGCGGCAGCGAGCTG<br>CCCACCCAGGGCACCTTCTCCAACGTGTCCACCAACGTGAGCCCAGCCAAGCCCACCACCACC<br>GCCTGTCCTTATTCCAATCCTTCCCTGTGTGCTCCACCACAACCCCCGCTCCAAGGCCCCCTA<br>CCCCCGCACCAACTATTGCCTCCCAGCCACTCTCACTGCGGCCTGAGGCCTGTCGGCCCGCTG<br>CTGGAGGCGCAGTGCATACAAGGGGCCTCGATTTCGCCTGCGATATTTACATCTGGGCACCCC<br>TCGCCGGCACCTGCGGGGTGCTTCTCCTCTCCCTGGTGATTACCCTGTATTGCAGACGGGGCC<br>GGAAGAAGCTCCTCTACATTTTTAAGCAGCCTTTCATGCGGCCAGTGCAGACAACCCAAGAGGA<br>GGATGGGTGTTCCTGCAGATTCCCTGAGGAAGAGGAAGGCGGGTGCGAGCTGAGAGTGAAGT<br>TCTCCAGGAGCGCAGATGCCCCCGCCTATCAACAGGGCCAGAACCAGCTCTACAACGAGCTTA<br>ACCTCGGGAGGCGCGAAGAATACGACGTGTTGGATAAGAGAAGGGGGCGGGACCCCGAGATG<br>GGAGGAAAGCCCCGGAGGAAGAACCCTCAGGAGGGCCTGTACAACGAGCTGCAGAAGGATAA<br>GATGGCCGAGGCCTACTCAGAGATCGGGATGAAGGGGGAGCGGCGCCGCGGGAAGGGGCAC<br>GATGGGCTCTACCAGGGGCTGAGCACAGCCACAAAGGACACATACGACGCTTGCACATGCAG<br>GCCCTTCCACCCCGGGAATAGTCTAGAGGGCCCGTTTAAACCCGCTGATCAGCCTCGACTGTG<br>CCTTCTAGTTGCCAGCCATCTGTTGTTTGCCCCTCCCCGTGCCTTCCTTGACCCTGGAAGGTG<br>CCACTCCCACTGTCCTTTCCTAATAAAATGAGGAAATTGCATCGCATTGTCTGAGTAGGTGTCAT<br>TCTATTCTGGGGGGTGGGGTGGGGCAGGACAGCAAGGGGGAGGATTGGGAAGACAATAGCAG<br>GCATGCTGGGGATGCGGTGGGCTCTATGACTAGTGGCGAATTCCCGTGTACCAGCTGAGAGAC<br>TCTAAATCCAGTGACAAGTCTGTCTGCCTATTCACCGATTTTGATTCTCAAACAAATGTGTCACA<br>AAGTAAGGATTCTGATGTGTATATCACAGACAAAACTGTGCTAGACATGAGGTCTATGGACTTCA<br>AGAGCAACAGTGCTGTGGCCTGGAGCAACAAATCTGACTTTGCATGTGCAAACGCCTTCAACAA<br>CAGCATTATTCCAGAAGACACCTTCTTCCCCAGCCCAGGTAAGGGCAGCTTTGGTGCCTTCGCA<br>GGCTGTTTCCTTGCTTCAGGAATGGCCAGGTTCTGCCCAGAGCTCTGGTCAATGATGTCTAAAA<br>CTCCTCTGATTGGTGGTCTCGGCCTTATCCATTGCCACCAAAACCCTCTTTTTACTAA |
| 32 | Matrice CD25 locus_IL15_ 2A_sIL15Ra pCLS30519 | GTTTATTATTCCTGTTCCACAGCTATTGTCTGCCATATAAAAACTTAGGCCAGGCACAGTGGCTC<br>ACACCTGTAATCCCAGCACTTTGGAAGGCCGAGGCAGGCAGATCACAAGGTCAGGAGTTCGAG<br>ACCAGCCTGGCCAACATAGCAAAACCCCATCTCTACTAAAAATACAAAAATTAGCCAGGCATGG<br>TGGCGTGTGCACTGGTTTAGAGTGAGGACCACATTTTTTGGTGCCGTGTTACACATATGACCG<br>TGACTTTGTTACACCACTACAGGAGGAAGAGTAGAAGAACAATCTAGAAAACCAAAAGAACAGAC<br>TTTGAATTTTGACCTTCTCAAGTTGGCGGGAGACGTGGAGTCCAACCCAGGGCCCGGTACCGG<br>GTCCGCCACCATGGACTGACCTGGATTCTGTTCCTCGTGGCTGCTGCTACAAGAGTGCACAG<br>CGGCATTCATGTCTTCATTTTGGGCTGTTTCAGTGCAGGGCTTCCTAAAACAGAAGCCAACTGG<br>GTGAATGTAATAAGTGATTTGAAAAAAATTGAAGATCTTATTCAATCTATGCATATTGATGCTACT<br>TTATATACGGAAAGTGATGTTCACCCCAGTTGCAAAGTAACAGCAATGAAGTGCTTTCTCTTGGA<br>GTTACAAGTTATTCACTTGAGTCCGGAGATGCAAGTATTCATGATACAGTAGAAAATCTGATCA<br>TCCTAGCAAACAACAGTTTGTCTTCTAATGGGAATGTAACAGAATCTGGATGCAAAGAATGTGAG<br>GAACTGGAGGAAAAAAATATTAAAGAATTTTTGCAGAGTTTTGTACATATTGTCCAAATGTTCATC<br>AACACTTCTGAAGCGGAGCTACTAACTTCAGCCTGCTGAAGCAGGCTGGAGACGTGGAGGAG<br>AACCCTGGACCTGGGACCGGCTCTGCAACCATGGATTGGACGTGGATCCTGTTTCTCGTGGCA<br>GCTGCCACAAGAGTTCACAGTATCACGTGCCCTCCCCCATGTCCGTGGAACACGCAGACATC<br>TGGGTCAAGAGCTACAGCTTGTACTCCAGGGAGCGGTACATTTGTAACTCTGGTTTCAAGCGTA<br>AAGCCGGCACGTCCAGCCTGACGGAGTGCGTGTTGAACAAGGCCACGAATGTCGCCCACTGG<br>ACAACCCCAGTCTCAAATGCATTAGAGACCCTGCCCTGGTTCACCAAAGGCCAGCGCCACCC<br>TCCACAGTAACGACGGCAGGGGTGACCCCACAGCCAGAGAGCCTCTCCCCTTCTGGAAAAGAG<br>CCCGCAGCTTCATCTCCCAGCTCAAACAACACAGCGGCCACAACAGCAGCTATTGTCCCGGGC<br>TCCCAGCTGATGCCTTCAAAATCACCTTCCACAGGAACCACAGAGATAAGCAGTCATGAGTCCT |

TABLE 5-continued

Sequences referred to in example 2.

|  |  |  |
|---|---|---|
|  |  | CCCACGGCACCCCCTCTCAGACAACAGCCAAGAACTGGGAACTCACAGCATCCGCCTCCCACC<br>AGCCGCCAGGTGTGTATCCACAGGGCCACAGCGACACCACTGAGGGCAGAGGCAGCCTGCTG<br>ACCTGCGGCGACGTCGAGGAGAACCCCGGGCCCATGGGGGCAGGTGCCACCGGCCGCGCCA<br>TGGACGGGCCGCGCCTGCTGCTGTTGCTGCTTCTGGGGGTGTCCCTTGGAGGTGCCAAGGAG<br>GCATGCCCCACAGGCCTGTACACACACAGCGGTGAGTGCTGCAAAGCCTGCAACCTGGGCGA<br>GGGTGTGGCCCAGCCTTGTGGAGCCAACCAGACCGTGTGTGAGCCCTGCCTGGACAGCGTGA<br>CGTTCTCCGACGTGGTGAGCGCGACCGAGCCGTGCAAGCCGTGCACCGAGTGCGTGGGGCTC<br>CAGAGCATGTCGGCGCCGTGCGTGGAGGCCGATGACGCCGTGTGCCGCTGCGCCTACGGCTA<br>CTACCAGGATGAGACGACTGGGCGCTGCGAGGCGTGCCGCGTGTGCGAGGCGGGCTCGGGC<br>CTCGTGTTCTCCTGCCAGGACAAGCAGAACACCGTGTGCGAGGAGTGCCCCGACGGCACGTAT<br>TCCGACGAGGCCAACCACGTGGACCCGTGCCTGCCCTGCACCGTGTGCGAGGACACCGAGCG<br>CCAGCTCCGCGAGTGCACACGCTGGGCCGACGCCGAGTGCGAGGAGATCCCTGGCCGTTGGA<br>TTACACGGTCCACACCCCAGAGGGCTCGGACAGCACAGCCCCAGCACCCAGGAGCCTGAG<br>GCACCTCCAGAACAAGACCTCATAGCCAGCACGGTGGCAGGTGTGGTGACCACAGTGATGGG<br>CAGCTCCCAGCCCGTGGTGACCCGAGGCACCACCGACAACCTCATCCCTGTCTATTGCTCCAT<br>CCTGGCTGCTGTGGTTGTGGGTCTTGTGGCCTACATAGCCTTCAAGAGGTGAAAAACCAAAGA<br>ACAAGAATTTCTTGGTAAGAAGCCGGGAACAGACAACAGAAGTCATGAAGCCCAAGTGAAATCA<br>AAGGTGCTAAATGGTCGCCCAGGAGACATCCGTTGTGCTTGCCTGCGTTTTGGAAGCTCTGAA<br>GTCACATCACAGGACACGGGGCAGTGGCAACCTTGTCTCTATGCCAGCTCAGTCCCATCAGAG<br>AGCGAGCGCTACCCACTTCTAAATAGCAATTTCGCCGTTGAAGAGGAAGGGCAAAACCACTAGA<br>ACTCTCCATCTTATTTTCATGTATATGTGTTCAT |
| 33 | Matrice PD1<br>locus_IL15_<br>2A_sIL15Ra<br>pCLS30513 | GACTCCCCAGACAGGCCCTGGAACCCCCCCACCTTCTCCCCAGCCCTGCTCGTGGTGACCGAA<br>GGGGACAACGCCACCTTCACCTGCAGCTTCTCCAACACATCGGAGAGCTTCGTGCTAAACTGG<br>TACCGCATGAGCCCCAGCAACCAGACGGACAAGCTGGCCGCCTTCCCCGAGGACCGCAGCCA<br>GCCCGGCCAGGACTGCCGCTTCCGTGTCACACAACTGCCCAACGGGCGTGACTTCCACATGAG<br>CGTGGTCAGGGCCCGGCGCAATGACAGCGGCACCTACCTCTGTGGGGCCGGTTCTGGCGTGA<br>AACAGACTTTGAATTTTGACCTTCTCAAGTTGGCGGGAGACGTGGAGTCCAACCCAGGGCCCG<br>GTACCGGGTCCGCCACCATGGACTGGACCTGGATTCTGTTCCTCGTGGCTGCTGCTACAAGAG<br>TGCACAGCGGCATTCATGTCTTCATTTTGGGCTGTTTCAGTGCAGGGCTTCCTAAAACAGAAGC<br>CAACTGGGTGAATGTAATAAGTGATTTGAAAAAAATTGAAGATCTTATTCAATCATGCATATTGA<br>TGCTACTTTATATACGGAAAGTGATGTTCACCCCAGTTGCAAAGTAACAGCAATGAAGTGCTTTC<br>TCTTGGAGTTACAAGTTATTTCACTTGAGTCCGGAGATGCAAGTATTCATGATACAGTAGAAAAT<br>CTGATCATCCTAGCAAACAACAGTTTGTCTTCTAATGGGAATGTAACAGAATCTGGATGCAAAGA<br>ATGTGAGGAACTGGAGGAAAAAAATATTAAAGAATTTTTGCAGAGTTTTGTACATATTGTCCAAAT<br>GTTCATCAACACTTCTGGAAGCGGAGCTACTAACTTCAGCCTGCTGAAGCAGGCTGGAGCAGT<br>GGGAGGAGAACCCTGGACCTGGGACCGGCTCTGCAACCATGGATTGGACGTGGATCCTGTTTCT<br>CGTGGCAGCTGCCACAAGAGTTCACAGTATCACGTGCCCTCCCCCCATGTCCGTGGAACACGC<br>AGACATCTGGGTCAAGAGCTACAGCTTGTACTCCAGGGAGCGGTACATTTGTAACTCTGGTTTC<br>AAGCGTAAAGCCGGCACGTCCAGCCTGACGGAGTGCGTGTTGAACAAGGCCACGAATGTCGC<br>CCACTGGACAACCCCCAGTCTCAAATGCATTAGAGACCCTGCCCTGGTTCACCAAAGGCCAGC<br>GCCACCCTCCACAGTAACGACGGCAGGGGTGACCCCACAGCCAGAGAGCCTCTCCCCTTCTG<br>GAAAAGAGCCCGCAGCTTCATCTCCCAGCTCAAACAACACAGCGGCCACAACAGCAGCTATTG<br>TCCCGGGCTCCCAGCTGATGCCTTCAAAATCACCTTCCACGGAACCACAGAGATAAGCAGTCA<br>TGAGTCCTCCCACGGCACCCCCTCTCAGACAACAGCCAAGAACTGGGAACTCACAGCATCCGC<br>CTCCCACCAGCCGCCAGGTGTGTATCCACAGGGCCACAGCGACACCACTGAGGGCAGAGGCA<br>GCCTGCTGACCTGCGGCGACGTCGAGGAGAACCCCGGGCCCATGGGGGCAGGTGCCACCGG<br>CCGCGCCATGGACGGGCCGCGCCTGCTGCTGTTGCTGCTTCTGGGGGTGTCCCTTGGAGGTG<br>CCAAGGAGGCATGCCCCACAGGCCTGTACACACACAGCGGTGAGTGCTGCAAAGCCTGCAAC<br>CTGGGCGAGGGTGTGGCCCAGCCTTGTGGAGCCAACCAGACCGTGTGTGAGCCCTGCCTGGA<br>CAGCGTGACGTTCTCCGACGTGGTGAGCGCGACCGAGCCGTGCAAGCCGTGCACCGAGTGCG<br>TGGGGCTCCAGAGCATGTCGGCGCCGTGCGTGGAGGCCGATGACGCCGTGTGCCGCTGCGC<br>CTACGGCTACTACCAGGATGAGACGACTGGGCGCTGCGAGGCGTGCCGCGTGTGCGAGGCGG<br>GCTCGGGCCTCGTGTTCTCCTGCCAGGACAAGCAGAACACCGTGTGCGAGGAGTGCCCCGAC<br>GGCACGTATTCCGACGAGGCCAACCACGTGGACCCGTGCCTGCCCTGCACCGTGTGCGAGGA<br>CACCGAGCGCCAGCTCCGCGAGTGCACACGCTGGGCCGACGCCGAGTGCGAGGAGATCCCT<br>GGCCGTTGGATTACACGGTCCACACCCCAGAGGGCTCGGACAGCACAGCCCCAGCACCCA<br>GGAGCCTGAGGCACCTCCAGAACAAGACCTCATAGCCAGCACGGTGGCAGGTGTGGTGACCA<br>CAGTGATGGGCAGCTCCCAGCCCGTGGTGACCCGAGGCACCACCGACAACCTCATCCCTGTCT<br>ATTGCTCCATCCTGGCTGCTGTGGTTGTGGGTCTTGTGGCCTACATAGCCTTCAAGAGGTGATC<br>TAGAGGGCCCGTTTAAACCCGCTGATCAGCCTCGACTGTGCCTTCTAGTTGCCAGCCATCTGTT<br>GTTTGCCCCTCCCCCGTGCCTTCCTTGACCCTGGAAGGTGCCACTCCCACTGTCCTTTCCTAAT<br>AAAATGAGGAAATTGCATCGCATTGTCTGAGTAGGTGTCATTCTATTCTGGGGGGTGGGTGGG<br>GCAGGACAGCAAGGGGGAGGATTGGGAAGACAATAGCAGGCATGCTGGGGATGCGGTGGGCT<br>CTATGACTAGTGGCGAATTCGGCGCAGATCAAAGAGAGCCTGCGGGCAGAGCTCAGGGTGACA<br>GGTGCGGCCTCGGAGGCCCCGGGCAGGGGTGAGCTGAGCCGGTCCTGGGGTGGGTGTCCC<br>CTCCCTGCACAGGATCAGGAGCTCCAGGGTCGTAGGGCAGGGACCCCCAGCTCCAGTCCAGG<br>GCTCTGTCCTGCACCTGGGGAATGGTGACCGGCATCTCTGTCCTCTAGCTCTGGAAGCACCCC<br>AGCCCCTCTAGTCTGCCCTCACCCCTGACCCTGACCCTCCACCCTGACCCCGTCCTAACCCCT<br>GACCTTTG |
| 34 | Matrice CD25<br>locus_IL12a_<br>2A_IL12b<br>pCLS30520 | GTTTATTATTCCTGTTCCACAGCTATTGTCTGCCATATAAAAACTTAGGCCAGGCACAGTGGCTC<br>ACACCTGTAATCCCAGCACTTTGGAAGGCCGAGGCAGGCAGATCACAAGGTCAGGAGTTCGAG<br>ACCAGCCTGGCCAACATAGCAAAACCCCATCTCTACTAAAAATACAAAAATTAGCCAGGCATGG<br>TGGCGTGTGCACTGGTTTAGAGTGAGGACCACATTTTTTTGGTGCCGTGTTACACATATGACCG<br>TGACTTTGTTACACCACTACAGGAGGAAGAGTAGAAGAACAATCGGTTCTGGCGTGAAACAGAC<br>TTTGAATTTTGACCTTCTCAAGTTGGCGGGAGACGTGGAGTCCAACCCAGGGCCCATGTGGCC<br>CCTGGGTCAGCCTCCCAGCCACCGCCCTCACCTGCCGCGGCCACAGGTCTGCATCCAGCGG |

TABLE 5-continued

Sequences referred to in example 2.

```
CTCGCCCTGTGTCCCTGCAGTGCCGGCTCAGCATGTGTCCAGCGCGCAGCCTCCTCCTTGTGG
CTACCCTGGTCCTCCTGGACCACCTCAGTTTGGCCAGAAACCTCCCCGTGGCCACTCCAGACC
CAGGAATGTTCCCATGCCTTCACCACTCCCAAAACCTGCTGAGGGCCGTCAGCAACATGCTCCA
GAAGGCCAGACAAACTCTAGAATTTTACCCTTGCACTTCTGAAGAGATTGATCATGAAGATATCA
CAAAAGATAAAACCAGCACAGTGGAGGCCTGTTTACCATTGGAATTAACCAAGAATGAGAGTTG
CCTAAATTCCAGAGAGACCTCTTTCATAACTAATGGGAGTTGCCTGGCCTCCAGAAAGACCTCT
TTTATGATGGCCCTGTGCCTTAGTAGTATTTATGAAGACTTGAAGATGTACCAGGTGGAGTTCAA
GACCATGAATGCAAAGCTTCTGATGGATCCTAAGAGGCAGATCTTTCTAGATCAAAACATGCTG
GCAGTTATTGATGAGCTGATGCAGGCCCTGAATTTCAACAGTGAGACTGTGCCACAAAAATCCT
CCCTTGAAGAACCGGATTTTTATAAAACTAAAATCAAGCTCTGCATACTTCTTCATGCTTTCAGAA
TTCGGGCAGTGACTATTGATAGAGTGATGAGCTATCTGAATGCTTCCGGAAGCGGAGCTACTAA
CTTCAGCCTGCTGAAGCAGGCTGGAGACGTGGAGGAGAACCCTGGACCTATGTGTCACCAGCA
GTTGGTCATCTCTTGGTTTTCCCTGGTTTTTCTGGCATCTCCCCTCGTGGCCATATGGGAACTGA
AGAAAGATGTTTATGTCGTAGAATTGGATTGGTATCCGGATGCCCCTGGAGAAATGGTGGTCCT
CACCTGTGACACCCCTGAAGAAGATGGTATCACCTGGACCTTGGACCAGAGCAGTGAGGTCTT
AGGCTCTGGCAAAACCCTGACCATCCAAGTCAAAGAGTTTGGAGATGCTGGCCAGTACACCTGT
CACAAAGGAGGCGAGGTTCTAAGCCATTCGCTCCTGCTGCTTCACAAAAAGGAAGATGGAATTT
GGTCCACTGATATTTTAAAGGACCAGAAAGAACCCAAAAATAAGACCTTTCTAAGATGCGAGGC
CAAGAATTATTCTGGACGTTTCACCTGCTGGTGGCTGACGACAATCAGTACTGATTTGACATTCA
GTGTCAAAAGCAGCAGAGGCTCTTCTGACCCCCAAGGGGTGACGTGCGGAGCTGCTACACTCT
CTGCAGAGAGTCAGAGGGGACAACAAGGAGTATGAGTACTCAGTGGAGTGCCAGGAGGAC
AGTGCCTGCCCAGCTGCTGAGGAGAGTCTGCCCATTGAGGTCATGGTGGATGCCGTTCACAAG
CTCAAGTATGAAAACTACACCAGCAGCTTCTTCATCAGGGACATCATCAAACCTGACCCACCCA
AGAACTTGCAGCTGAAGCCATTAAAGAATTCTCGGCAGGTGGAGGTCAGCTGGGAGTACCCTG
ACACCTGGAGTACTCCACATTCCTACTTCTCCCTGACATTCTGCGTTCAGGTCAGGGCAAGAG
CAAGAGAGAAAAGAAAGATAGAGTCTTCACGGACAAGACCTCAGCCACGGTCATCTGCCGCAA
AAATGCCAGCATTAGCGTGCGGGCCCAGGACCGCTACTATAGCTCATCTTGGAGCAGAATGGGC
ATCTGTGCCCTGCAGTGAGGGCAGAGGCAGCCTGCTGACCTGCGGCGACGTCGAGGAGAACC
CCGGGCCCATGGGGGCAGGTGCCACCGGCCGCGCCATGGACGGGCCGCGCCTGCTGCTGTT
GCTGCTTCTGGGGGTGTCCCTTGGAGGTGCCAAGGAGGCATGCCCCACAGGCCTGTACACAC
ACAGCGGTGAGTGCTGCAAAGCCTGCAACCTGGGCGAGGGTGTGGCCCAGCCTTGTGGAGCC
AACCAGACCGTGTGTGAGCCCTGCCTGGACAGCGTGACGTTCTCCGACGTGGTGAGCGCGAC
CGAGCCGTGCAAGCCGTGCACCGAGTGCGTGGGGCTCCAGAGCATGTCGGCGCCGTGCGTG
GAGGCCGATGACGCCGTGTGCCGCTGCGCCTACGGCTACTACCAGGATGAGACGACTGGGCG
CTGCGAGGCGTGCCGCGTGTGCGAGGCGGGCTCGGGCCTCGTGTTCTCCTGCCAGGACAAGC
AGAACACCGTGTGCGAGGAGTGCCCCGACGGCACGTATTCCGACGAGGCCAACCACGTGGAC
CCGTGCCTGCCCTGCACCGTGTGCGAGGACACCGAGCGCCAGCTCCGCGAGTGCACACGCTG
GGCCGACGCCGAGTGCGAGGAGATCCCTGGCCGTTGGATTACACGGTCCACACCCCCAGAGG
GCTCGGACAGCACAGCCCCCAGCACCCAGGAGCCTGAGGCACCTCCAGAACAAGACCTCATA
GCCAGCACGGTGGCAGGTGTGGTGACCACAGTGATGGGCAGCTCCCAGCCCGTGGTGACCCG
AGGCACCACCGACAACCTCATCCCTGTCTATTGCTCCATCCTGGCTGCTGTGGTTGTGGGTCTT
GTGGCCTACATAGCCTTCAAGAGGTGAAAAACCAAAAGAACAAGAATTTCTTGGTAAGAAGCCG
GGAACAGACAACAGAAGTCATGAAGCCCAAGTGAAATCAAAGGTGCTAAATGGTCGCCCAGGA
GACATCCGTTGTGCTTGCCTGCGTTTTGGAAGCTCTGAAGTCACATCACAGGACACGGGCAG
TGGCAACCTTGTCTCTATGCCAGCTCAGTCCCATCAGAGAGCGAGCGCTACCCACTTCTAAATA
GCAATTTCGCCGTTGAAGAGGAAGGGCAAAACCACTAGAACTCTCCATCTTATTTTCATGTATAT
GTGTTCAT
```

35 Matrice PD1
locus_IL12a_
2A_IL12b
pCLS30511

```
GACTCCCCAGACAGGCCCTGGAACCCCCCACCTTCTCCCCAGCCCTGCTCGTGGTGACCGAA
GGGGACAACGCCACCTTCACCTGCAGCTTCTCCAACACATCGGAGAGCTTCGTGCTAAACTGG
TACCGCATGAGCCCCAGCAACCAGACGGACAAGCTGGCCGCCTTCCCCGAGGACCGCAGCCA
GCCCGGCCAGGACTGCCGCTTCCGTGTCACACAACTGCCCAACGGGCGTGACTTCCACATGAG
CGTGGTCAGGGCCCGGCGCAATGACAGCGGCACCTACCTCTGTGGGGCCGGTTCTGGCGTGA
AACAGACTTTGAATTTTGACCTTCTCAAGTTGGCGGGAGACGTGGAGTCCAACCCAGGGCCCAT
GTGGCCCCCTGGGTCAGCCTCCCAGCCACCGCCCTCACCTGCCGCGGCCACAGGTCTGCATC
CAGCGGCTCGCCCTGTGTCCCTGCAGTGCCGGCTCAGCATGTGTCCAGCGCGCAGCCTCCTC
CTTGTGGCTACCCTGGTCCTCCTGGACCACCTCAGTTTGGCCAGAAACCTCCCCGTGGCCACT
CCAGACCCAGGAATGTTCCCATGCCTTCACCACTCCCAAAACCTGCTGAGGGCCGTCAGCAAC
ATGCTCCAGAAGGCCAGACAAACTCTAGAATTTTACCCTTGCACTTCTGAAGAGATTGATCATGA
AGATATCACAAAAGATAAAACCAGCACAGTGGAGGCCTGTTTACCATTGGAATTAACCAAGAAT
GAGAGTTGCCTAAATTCCAGAGAGACCTCTTTCATAACTAATGGGAGTTGCCTGGCCTCCAGAA
AGACCTCTTTTATGATGGCCCTGTGCCTTAGTAGTATTTATGAAGACTTGAAGATGTACCAGGTG
GAGTTCAAGACCATGAATGCAAAGCTTCTGATGGATCCTAAGAGGCAGATCTTTCTAGATCAAA
CATGCTGGCAGTTATTGATGAGCTGATGCAGGCCCTGAATTTCAACAGTGAGACTGTGCCACAA
AAATCCTCCCTTGAAGAACCGGATTTTTATAAAACTAAAATCAAGCTCTGCATACTTCTTCATGCT
TTCAGAATTCGGGCAGTGACTATTGATAGAGTGATGAGCTATCTGAATGCTTCCGGAAGCGGAG
CTACTAACTTCAGCCTGCTGAAGCAGGCTGGAGACGTGGAGGAGAACCCTGGACCTATGTGTC
ACCAGCAGTTGGTCATCTCTTGGTTTTCCCTGGTTTTTCTGGCATCTCCCCTCGTGGCCATATGG
GAACTGAAGAAAGATGTTTATGTCGTAGAATTGGATTGGTATCCGGATGCCCCTGGAGAAATGG
TGGTCCTCACCTGTGACACCCCTGAAGAAGATGGTATCACCTGGACCTTGGACCAGAGCAGTG
AGGTCTTAGGCTCTGGCAAAACCCTGACCATCCAAGTCAAAGAGTTTGGAGATGCTGGCCAGTA
CACCTGTCACAAAGGAGGCGAGGTTCTAAGCCATTCGCTCCTGCTGCTTCACAAAAAGGAAGAT
GGAATTTGGTCCACTGATATTTTAAAGGACCAGAAAGAACCCAAAAATAAGACCTTTCTAAGATG
CGAGGCCAAGAATTATTCTGGACGTTTCACCTGCTGGTGGCTGACGACAATCAGTACTGATTTG
ACATTCAGTGTCAAAAGCAGCAGAGGCTCTTCTGACCCCCAAGGGGTGACGTGCGGAGCTGCT
ACACTCTCTGCAGAGAGTCAGAGGGGACAACAAGGAGTATGAGTACTCAGTGGAGTGCCAG
GAGGACAGTGCCTGCCCAGCTGCTGAGGAGAGTCTGCCCATTGAGGTCATGGTGGATGCCGTT
CACAAGCTCAAGTATGAAAACTACACCAGCAGCTTCTTCATCAGGGACATCATCAAACCTGACC
```

TABLE 5-continued

Sequences referred to in example 2.

| | | |
|---|---|---|
| | | CACCCAAGAACTTGCAGCTGAAGCCATTAAAGAATTCTCGGCAGGTGGAGGTCAGCTGGGAGT<br>ACCCTGACACCTGGAGTACTCCACATTCCTACTTCTCCCTGACATTCTGCGTTCAGGTCCAGGG<br>CAAGAGCAAGAGAGAAAAGAAAGATAGAGTCTTCACGGACAAGACCTCAGCCACGGTCATCTG<br>CCGCAAAAATGCCAGCATTAGCGTGCGGGCCCAGGACCGCTACTATAGCTCATCTTGGAGCGA<br>ATGGGCATCTGTGCCCTGCAGTGAGGGCAGAGGCAGCCTGCTGACCTGCGGCGACGTCGAGG<br>AGAACCCCGGGCCCATGGGGGCAGGTGCCACCGGCCGCGCCATGGACGGGCCGCGCCTGCT<br>GCTGTTGCTGCTTCTGGGGGTGTCCCTTGGAGGTGCCAAGGAGGCATGCCCCACAGGCCTGTA<br>CACACACAGCGGTGAGTGCTGCAAAGCCTGCAACCTGGGCGAGGGTGTGGCCCAGCCTTGTG<br>GAGCCAACCAGACCGTGTGTGAGCCCTGCCTGGACAGCGTGACGTTCTCCGACGTGGTGAGC<br>GCGACCGAGCCGTGCAAGCCGTGCACCGAGTGCGTGGGGCTCCAGAGCATGTCGGCGCCGT<br>GCGTGGAGGCCGATGACGCCGTGTGCCGCTGCGCCTACGGCTACTACCAGGATGAGACGACT<br>GGGCGCTGCGAGGCGTGCCGCGTGTGCGAGGCGGGCTCGGGCCTCGTGTTCTCCTGCCAGG<br>ACAAGCAGAACACCGTGTGCGAGGAGTGCCCCGACGGCACGTATTCCGACGAGGCCAACCAC<br>GTGGACCCGTGCCTGCCCTGCACCGTGTGCGAGGACACCGAGCGCCAGCTCCGCGAGTGCAC<br>ACGCTGGGCCGACGCCGAGTGCGAGGAGATCCCTGGCCGTTGGATTACACGGTCCACACCCC<br>CAGAGGGCTCGGACAGCACAGCCCCCAGCACCCAGGAGCCTGAGGCACCTCCAGAACAAGAC<br>CTCATAGCCAGCACGGTGGCAGGTGTGGTGACCACAGTGATGGGCAGCTCCCAGCCCGTGGT<br>GACCCGAGGCACCACCGACAACCTCATCCCTGTCTATTGCTCCATCCTGGCTGCTGTGGTTGT<br>GGGTCTTGTGGCCTACATAGCCTTCAAGAGGTGATCTAGAGGGCCCGTTTAAACCCGCTGATCA<br>GCCTCGACTGTGCCTTCTAGTTGCCAGCCATCTGTTGTTTGCCCCTCCCCCGTGCCTTCCTTGA<br>CCCTGGAAGGTGCCACTCCCACTGTCCTTTCCTAATAAAATGAGGAAATTGCATCGCATTGTCT<br>GAGTAGGTGTCATTCTATTCTGGGGGGTGGGGTGGGGCAGGACAGCAAGGGGGAGGATTGGG<br>AAGACAATAGCAGGCATGCTGGGGATCGGTGGGCTCTATGACTAGTGGCGAATTCGGCGCAG<br>ATCAAAGAGAGCCTGCGGGCAGAGCTCAGGGTGACAGGTGCGGCCTCGGAGGCCCCGGGGC<br>AGGGGTGAGCTGAGCCGGTCCTGGGGTGGGTGTCCCCTCCTGCACAGGATCAGGAGCTCCAG<br>GGTCGTAGGGCAGGGACCCCCCAGCTCCAGTCCAGGGCTCTGTCCTGCACCTGGGGAATGGT<br>GACCGGCATCTCTGTCCTCTAGCTCTGGAAGCACCCCAGCCCCTCTAGTCTGCCCTCACCCCT<br>GACCCTGACCCTCCACCCTGACCCGTCCTAACCCCTGACCTTTG |
| 36 | Inserted<br>matrice TRAC<br>locus_CubiCAR<br>CD22 (60<br>nucleotides<br>upstream and<br>downstream) | ATGAGATCATGTCCTAACCCTGATCCTCTTGTCCCACAGATATCCAGAACCCTGACCCTGTTGCT<br>GGGCCTTTTTCCCATGCCTGCCTTTACTCTGCCAGAGTTATATTGCTGGGGTTTTGAAGAAGATC<br>CTATTAAATAAAAGAATAAGCAGTATTATTAAGTAGCCCTGCATTTCAGGTTTCCTTGAGTGGCA<br>GGCCAGGCCTGGCCGTGAACGTTCACTGAAATCATGGCCTCTTGGCCAAGATTGATAGCTTGT<br>GCCTGTCCCTGAGTCCCAGTCCATCACGAGCAGCTGGTTTCTAAGATGCTATTTCCCGTATAAA<br>GCATGAGACCGTGACTTGCCAGCCCCACAGAGCCCCGCCCTTGTCCATCACTGGCATCTGGAC<br>TCCAGCCTGGGTTGGGGCAAAGAGGGAAATGAGATCATGTCCTAACCCTGATCCTCTTGTCCCA<br>CAGATATCCAGTACCCCTACGACGTGCCCGACTACGCCTCCGGTGAGGGCAGAGGAAGTCTTC<br>TAACATGCGGTGACGTGGAGGAGAATCCGGGCCCCGGATCCGCTCTGCCCGTCACCGCTCTG<br>CTGCTGCCACTGGCACTGCTGCTGCACGCTGCTAGGCCCGGAGGGGGAGGCAGCTGCCCCTA<br>CAGCAACCCCAGCCTGTGCAGCGGAGGCGGCGGCAGCGGCGGAGGGGGTAGCCAGGTGCAG<br>CTGCAGCAGAGCGGCCCTGGCCTGGTGAAGCCAAGCCAGACACTGTCCCTGACCTGCGCCAT<br>CAGCGGCGATTCCGTGAGCTCCAACTCCGCCGCCTGGAATTGGATCAGGCAGTCCCCTTCTCG<br>GGGCCTGGAGTGGCTGGGAAGGACATACTATCGGTCTAAGTGGTACAACGATTATGCCGTGTC<br>TGTGAAGAGCAGAATCACAATCAACCCTGACACCTCCAAGAATCAGTTCTCTCTGCAGCTGAAT<br>AGCGTGACACCAGAGGACACCGCCGTGTACTATTGCGCCAGGGAGGTGACCGGCGACCTGGA<br>GGATGCCTTTGACATCTGGGGCCAGGGCACAATGGTGACCGTGAGCTCCGGAGGCGGCGGAT<br>CTGGCGGAGGAGGAAGTGGGGGCGGCGGGAGTGATATCCAGATGACACAGTCCCCATCCTCT<br>CTGAGCGCCTCCGTGGGCGACAGAGTGACAATCACCTGTAGGGCCTCCCAGACCATCTGGTCT<br>TACCTGAACTGGTATCAGCAGAGGCCCGGCAAGGCCCCTAATCTGCTGATCTACGCAGCAAGC<br>TCCCTGCAGAGCGGAGTGCCATCCAGATTCTCTGGCAGGGGCTCCGGCACAGACTTCACCCTG<br>ACCATCTCTAGCCTGCAGGCCGAGGACTTCGCCACCTACTATTGCCAGCAGTCTTATAGCATCC<br>CCCAGACATTTGGCCAGGGCACCAAGCTGGAGATCAAGTCGGATCCCGGAAGCGGAGGGGGA<br>GGCAGCTGCCCCTACAGCAACCCCAGCCTGTGCAGCGGAGGCGGCGGCAGCGAGCTGCCCA<br>CCCAGGGCACCTTCTCCAACGTGTCCACCAACGTGAGCCCAGCCAAGCCCACCACCACCGCCT<br>GTCCTTATTCCAATCCTTCCCTGTGTGCTCCACCACAACCCCGCTCCAAGGCCCCCTACCCC<br>CGCACCAACTATTGCTCCCAGCCACTCTCACTGCGGCCTGAGGCCTGTCGGCCGCTGCTGG<br>AGGCGCAGTGCATACAAGGGGCCTCGATTTCGCCTGCGATATTTACATCTGGGCACCCCTCGC<br>CGGCACCTGCGGGGTGCTTCTCCTCTCCCTGGTGATTACCCTGTATTGCAGACGGGGCCGGAA<br>GAAGCTCCTCTACATTTTTAAGCAGCCTTTCATGCGGCCAGTGCAGACAACCCAAGAGGAGGAT<br>GGGTGTTCCTGCAGATTCCCTGAGGAAGAGGAAGGCGGGTGCGAGCTGAGAGTGAAGTTCTC<br>CAGGAGCGCAGATGCCCCCGCCTATCAACAGGGCCAGAACCAGCTCTACAACGAGCTTAACCT<br>CGGGAGGCGCAAGAATACGACGTGTTGGATAAGAGAAGGGGGCGGGACCCCGAGATGGGA<br>GGAAAGCCCCGGAGGAAGAACCCTCAGGAGGGCCTGTACAACGAGCTGCAGAAGGATAAGAT<br>GGCCGAGGCCTACTCAGAGATCGGGATGAAGGGGAGCGGCGCCGCGGGAAGGGGCACGAT<br>GGGCTCTACCAGGGGCTGAGCACAGCCACAAAGGACACATACGACGCCTTGCACATGCAGGC<br>CCTTCCACCCCGGGAATAGTCTAGAGGGCCCGTTTAAACCCGCTGATCAGCCTCGACTGTGCC<br>TTCTAGTTGCCAGCCATCTGTTGTTTGCCCCTCCCCCGTGCCTTCCTTGACCCTGGAAGGTGCC<br>ACTCCCACTGTCCTTTCCTAATAAAATGAGGAAATTGCATCGCATTGTCTGAGTAGGTGTCATTC<br>TATTCTGGGGGGTGGGGTGGGGCAGGACAGCAAGGGGGAGGATTGGGAAGACAATAGCAGGC<br>ATGCTGGGGATCGGTGGGCTCTATGACTAGTGGCGAATTCCCGTGTACCAGCTGAGAGACTC<br>TAAATCCAGTGACAAGTCTGTCTGCCTATTCACCGATTTTGATTCTCAAACAAATGTGTCACAAA<br>GTAAGGATTCTGATGTGTATATCACAGACAAAACTGTGCTAGACATGAGGTCTATGGACTTCAAG<br>AGCAACAGTGCTGTGGCCTGGAGCAACAAATCTGACTTTGCATGTGCAAACGCCTTCAACAACA<br>GCATTATTCCAGAAGACACCTTCTTCCCCAGCCCAGGTAAGGGCAGCTTTGGTGCCTTCGCAG<br>GCTGTTTCCTTGCTTCAGGAATGGCCAGGTTCTGCCCAGAGCTCTGGTCAATGATGTCTAAAAC<br>TCCTCTGATTGGTGGTCTCGGCCTTATCCATTGCCACCAAAACCCTCTTTTTACTAAGAAACAGT<br>GAGCCTTGTTCTGGCAGTCCAGAGAATGACACGGGAAAAAAGCAGATGAAGA |

TABLE 5-continued

Sequences referred to in example 2.

| | | |
|---|---|---|
| 37 | Inserted matrice CD25 locus_IL15_ 2A_sIL15Ra (60 nucleotides upstream and downstream) | AGTGCTGGCTAGAAACCAAGTGCTTTACTGCATGCACATCATTTAGCACAGTTAGTTGCTGTTTA<br>TTATTCCTGTTCCACAGCTATTGTCTGCCATATAAAAACTTAGGCCAGGCACAGTGGCTCACACC<br>TGTAATCCCAGCACTTTGGAAGGCCGAGGCAGGCAGATCACAAGGTCAGGAGTTCGAGACCAG<br>CCTGGCCAACATAGCAAAACCCCATCTCTACTAAAAATACAAAAATTAGCCAGGCATGGTGGCG<br>TGTGCACTGGTTTAGAGTGAGGACCACATTTTTTGGTGCCGTGTTACACATATGACCGTGACTT<br>TGTTACACCACTACAGGAGGAAGAGTAGAAGAACAATCGGTTCTGGCGTGAAACAGACTTTGAA<br>TTTTGACCTTCTCAAGTTGGCGGGAGACGTGGAGTCCAACCCAGGGCCCGGTACCGGGTCCGC<br>CACCATGGACTGGACCTGGATTCTGTTCCTCGTGGCTGCTGCTACAAGAGTGCACAGCGGCAT<br>TCATGTCTTCATTTTGGGCTGTTTCAGTGCAGGGCTTCCTAAAACAGAAGCCAACTGGGTGAAT<br>GTAATAAGTGATTTGAAAAAAATTGAAGATCTTATTCAATCTATGCATATTGATGCTACTTTATATA<br>CGGAAAGTGATGTTCACCCCAGTTGCAAAGTAACAGCAATGAAGTGCTTTCTCTTGGAGTTACA<br>AGTTATTTCACTTGAGTCCGGAGATGCAAGTATTCATGATACAGTAGAAAATCTGATCATCCTAG<br>CAAACAACAGTTTGTCTTCTAATGGGAATGTAACAGAATCTGGATGCAAAGAATGTGAGGAACT<br>GGAGGAAAAAAATATTAAAGAATTTTTGCAGAGTTTTGTACATATTGTCCAAATGTTCATCAACAC<br>TTCTGGAAGCGGAGCTACTAACTTCAGCCTGCTGAAGCAGGCTGGAGACGTGGAGGAGAACCC<br>TGGACCTGGGACCGGCTCTGCAACCATGGATTGGACGTGGATCCTGTTTCTCGTGGCAGCTGC<br>CACAAGAGTTCACAGTATCACGTGCCCTCCCCCCATGTCCGTGAACACGCAGACATCTGGGT<br>CAAGAGCTACAGCTTGTACTCCAGGGAGCGGTACATTTGTAACTCTGGTTTCAAGCGTAAAGCC<br>GGCACGTCCAGCCTGACGGAGTGCGTGTTGAACAAGGCCACGAATGTCGCCCACTGGACAAC<br>CCCCAGTCTCAAATGCATTAGAGACCCTGCCCTGGTTCACCAAAGGCCAGCGCCACCCTCCAC<br>AGTAACGACGGCAGGGGTGACCCCACAGCCAGAGAGCCTCTCCCCTTCTGGAAAAGAGCCCG<br>CAGCTTCATCTCCCAGCTCAAACAACACAGCGGCCACAACAGCAGCTATTGTCCCGGGCTCCC<br>AGCTGATGCCTTCAAAATCACCTTCCACAGGAACCACAGAGATAAGCAGTCATGAGTCCTCCCA<br>CGGCACCCCCTCTCAGACAACAGCCAAGAACTGGGAACTCACAGCATCCGCCTCCCACCAGCC<br>GCCAGGTGTGTATCCACAGGGCCACAGCGACACCACTGAGGGCAGAGGCAGCCTGCTGACCT<br>GCGGCGACGTCGAGGAGAACCCCGGGCCCATGGGGGCAGGTGCCACCGGCCGCGCCATGGA<br>CGGGCCGCGCCTGCTGCTGTTGCTGCTTCTGGGGGTGTCCCTTGGAGGTGCCAAGGAGGCAT<br>GCCCCACAGGCCTGTACACACACAGCGGTGAGTGCTGCAAAGCCTGCAACCTGGGCGAGGGT<br>GTGGCCCAGCCTTGTGGAGCCAACCAGACCGTGTGTGAGCCCTGCCTGGACAGCGTGACGTT<br>CTCCGACGTGGTGAGCGCGACCGAGCCGTGCAAGCCGTGCACCGAGTGCGTGGGGCTCCAGA<br>GCATGTCGGCGCCGTGCGTGGAGGCCGATGACGCCGTGTGCCGCTGCGCCTACGGCTACTAC<br>CAGGATGAGACGACTGGGCGCTGCGAGGCGTGCCGCGTGTGCGAGGCGGGCTCGGGCCTCG<br>TGTTCTCCTGCCAGGACAAGCAGAACACCGTGTGCGAGGAGTGCCCCGACGGCACGTATTCCG<br>ACGAGGCCAACCACGTGGACCCGTGCCTGCCCTGCACCGTGTGCGAGGACACCGAGCGCCAG<br>CTCCGCGAGTGCACACGCTGGGCCGACGCCGAGTGCGAGGAGATCCCTGGCCGTTGGATTAC<br>ACGGTCCACACCCCCAGAGGGCTCGGACAGCACAGCCCCCAGCACCCAGGAGCCTGAGGCAC<br>CTCCAGAACAAGACCTCATAGCCAGCACGGTGGCAGGTGTGGTGACCACAGTGATGGGCAGCT<br>CCCAGCCCGTGGTGACCCGAGGCACCACCGACAACCTCATCCCTGTCTATTGCTCCATCCTGG<br>CTGCTGTGGTTGTGGGTCTTGTGGCCTACATAGCCTTCAAGAGGTGAAAAACCAAAAGAACAAG<br>AATTTCTTGGTAAGAAGCCGGGAACAGACAACAGAAGTCATGAAGCCAAGTGAAATCAAAGGT<br>GCTAAATGGTCGCCCAGGAGACATCCGTTGTGCTTGCCTGCGTTTTGGAAGCTCTGAAGTCACA<br>TCACAGGACACGGGGCAGTGGCAACCTTGTCTCTATGCCAGCTCAGTCCCATCAGAGAGCGAG<br>CGCTACCCACTTCTAAATAGCAATTTCGCCGTTGAAGAGGAAGGGCAAAACCACTAGAACTCTC<br>CATCTTATTTTCATGTATATGTGTTCATTAAAGCATGAATGGTATGGAACTCTCTCCACCCTATAT<br>GTAGTATAAAGAAAAGTAGGTT |
| 38 | Inserted matrice PD1 locus_IL15_ 2A_sIL15Ra (60 nucleotides upstream and downstream) | GGTGGCCGGGGAGGCTTTGTGGGGCCACCCAGCCCCTTCCTCACCTCTCTCCATCTCTCAGAC<br>TCCCCAGACAGGCCCTGGAACCCCCCACCTTCTCCCCAGCCCTGCTCGTGGTGACCGAAGG<br>GGACAACGCCACCTTCACCTGCAGCTTCTCCAACACATCGGAGAGCTTCGTGCTAAACTGGTAC<br>CGCATGAGCCCCAGCAACCAGACGGACAAGCTGGCCGCCTTCCCCGAGGACCGCAGCCAGCC<br>CGGCCAGGACTGCCGCTTCCGTGTCACACAACTGCCCAACGGGCGTGACTTCCACATGAGCGT<br>GGTCAGGGCCCGGCGCAATGACAGCGGCACCTACCTCTGTGGGGTGGTTCTGGCGTGAAAC<br>AGACTTTGAATTTTGACCTTCTCAAGTTGGCGGGAGACGTGGAGTCCAACCCAGGGCCCGGTA<br>CCGGGTCCGCCACCATGGACTGGACCTGGATTCTGTTCCTCGTGGCTGCTGCTACAAGAGTGC<br>ACAGCGGCATTCATGTCTTCATTTTGGGCTGTTTCAGTGCAGGGCTTCCTAAAACAGAAGCCAA<br>CTGGGTGAATGTAATAAGTGATTTGAAAAAAATTGAAGATCTTATTCAATCTATGCATATTGATGC<br>TACTTTATATACGGAAAGTGATGTTCACCCCAGTTGCAAAGTAACAGCAATGAAGTGCTTTCTCT<br>TGGAGTTACAAGTTATTTCACTTGAGTCCGGAGATGCAAGTATTCATGATACAGTAGAAAATCTG<br>ATCATCCTAGCAAACAACAGTTTGTCTTCTAATGGGAATGTAACAGAATCTGGATGCAAAGAATG<br>TGAGGAACTGGAGGAAAAAAATATTAAAGAATTTTTGCAGAGTTTTGTACATATTGTCCAAATGTT<br>CATCAACACTTCTGGAAGCGGAGCTACTAACTTCAGCCTGCTGAAGCAGGCTGGAGACGTGGA<br>GGAGAACCCTGGACCTGGGACCGGCTCTGCAACCATGGATTGGACGTGGATCCTGTTTCTCGT<br>GGCAGCTGCCACAAGAGTTCACAGTATCACGTGCCCTCCCCCCATGTCCGTGGAACACGCAGA<br>CATCTGGGTCAAGAGCTACAGCTTGTACTCCAGGGAGCGGTACATTTGTAACTCTGGTTTCAAG<br>CGTAAAGCCGGCACGTCCAGCCTGACGGAGTGCGTGTTGAACAAGGCCACGAATGTCGCCCA<br>CTGGACAACCCCCAGTCTCAAATGCATTAGAGACCCTGCCCTGGTTCACCAAAGGCCAGCGCC<br>ACCCTCCACAGTAACGACGGCAGGGGTGACCCCACAGCCAGAGAGCCTCTCCCCTTCTGGAAA<br>AGAGCCCGCAGCTTCATCTCCCAGCTCAAACAACACAGCGGCCACAACAGCAGCTATTGTCCC<br>GGGCTCCCAGCTGATGCCTTCAAAATCACCTTCCACAGGAACCACAGAGATAAGCAGTCATGAG<br>TCCTCCCACGGCACCCCCTCTCAGACAACAGCCAAGAACTGGGAACTCACAGCATCCGCCTCC<br>CACCAGCCGCCAGGTGTGTATCCACAGGGCCACAGCGACACCACTGAGGGCAGAGGCAGCCT<br>GCTGACCTGCGGCGACGTCGAGGAGAACCCCGGGCCCATGGGGGCAGGTGCCACCGGCCGC<br>GCCATGGACGGGCCGCGCCTGCTGCTGTTGCTGCTTCTGGGGGTGTCCCTTGGAGGTGCCAA<br>GGAGGCATGCCCCACAGGCCTGTACACACACAGCGGTGAGTGCTGCAAAGCCTGCAACCTGG<br>GCGAGGGTGTGGCCCAGCCTTGTGGAGCCAACCAGACCGTGTGTGAGCCCTGCCTGGACAGC<br>GTGACGTTCTCCGACGTGGTGAGCGCGACCGAGCCGTGCAAGCCGTGCACCGAGTGCGTGGG<br>GCTCCAGAGCATGTCGGCGCCGTGCGTGGAGGCCGATGACGCCGTGTGCCGCTGCGCCTACG<br>GCTACTACCAGGATGAGACGACTGGGCGCTGCGAGGCGTGCCGCGTGTGCGAGGCGGGCTC |

TABLE 5-continued

Sequences referred to in example 2.

| | | |
|---|---|---|
| | | GGGCCTCGTGTTCTCCTGCCAGGACAAGCAGAACACCGTGTGCGAGGAGTGCCCCGACGGCA<br>CGTATTCCGACGAGGCCAACCACGTGGACCCGTGCCTGCCCTGCACCGTGTGCGAGGACACC<br>GAGCGCCAGCTCCGCGAGTGCACACGCTGGGCCGACGCCGAGTGCGAGGAGATCCCTGGCC<br>GTTGGATTACACGGTCCACACCCCCAGAGGGCTCGGACAGCACAGCCCCCAGCACCCAGGAG<br>CCTGAGGCACCTCCAGAACAAGACCTCATAGCCAGCACGGTGGCAGGTGTGGTGACCACAGTG<br>ATGGGCAGCTCCCAGCCCGTGGTGACCCGAGGCACCACCGACAACCTCATCCCTGTCTATTGC<br>TCCATCCTGGCTGCTGTGGTTGTGGGTCTTGTGGCCTACATAGCCTTCAAGAGGTGATCTAGAG<br>GGCCCGTTTAAACCCGCTGATCAGCCTCGACTGTGCCTTCTAGTTGCCAGCCATCTGTTGTTTG<br>CCCCTCCCCCGTGCCTTCCTTGACCCTGGAAGGTGCCACTCCCACTGTCCTTTCCTAATAAAAT<br>GAGGAAATTGCATCGCATTGTCTGAGTAGGTGTCATTCTATTCTGGGGGGTGGGGTGGGGCAG<br>GACAGCAAGGGGGAGGATTGGGAAGACAATAGCAGGCATGCTGGGGATGCGGTGGGCTCTAT<br>GACTAGTGGCGAATTCGGCGCAGATCAAAGAGAGCCTGCGGGCAGAGCTCAGGGTGACAGGT<br>GCGGCCTCGGAGGCCCCGGGGCAGGGTGAGCTGAGCCGGTCCTGGGGTGGGTGTCCCCTC<br>CTGCACAGGATCAGGAGCTCCAGGGTCGTAGGGCAGGGACCCCCAGCTCCAGTCCAGGGCT<br>CTGTCCTGCACCTGGGGAATGGTGACCGGCATCTCTGTCCTCTAGCTCTGGAAGCACCCCAGC<br>CCCTCTAGTCTGCCCTCACCCCTGACCCTGACCCTCCACCCTGACCCCGTCCTAACCCCTGAC<br>CTTTGTGCCCTTCCAGAGAGAAGGGCAGAAGTGCCCACAGCCCACCCCAGCCCCTCACCCAGG<br>CC |
| 39 | Inserted<br>matrice CD25<br>locus_IL12a_<br>2A_IL12b (60<br>nucleotides<br>upstream and<br>downstream) | AGTGCTGGCTAGAAACCAAGTGCTTTACTGCATGCACATCATTTAGCACAGTTAGTTGCTGTTTA<br>TTATTCCTGTTCCACAGCTATTGTCTGCCATATAAAACTTAGGCCAGGCACAGTGGCTCACACC<br>TGTAATCCCAGCACTTTGGAAGGCCGAGGCAGGCAGATCACAAGGTCAGGAGTTCGAGACCAG<br>CCTGGCCAACATAGCAAAACCCCATCTCTACTAAAAATACAAAAATTAGCCAGGCATGGTGGCG<br>TGTGCACTGGTTTAGAGTGAGGACCACATTTTTTGGTGCCGTGTTACACATATGACCGTGACTT<br>TGTTACACCACTACAGGAGGAAGAGTAGAAGAACAATCGGTTCTGGCGTGAAACAGACTTTGAA<br>TTTTGACCTTCTCAAGTTGGCGGGAGACGTGGAGTCCAACCCAGGGCCCATGTGGCCCCCTGG<br>GTCAGCCTCCCAGCCACCGCCCTCACCTGCCGCGGCCACAGGTCTGCATCCAGCGGCTCGCC<br>CTGTGTCCCTGCAGTGCCGGCTCAGCATGTGTCCAGCGCGCAGCCTCCTCCTTGTGGCTACCC<br>TGGTCCTCCTGGACCACCTCAGTTTGGCCAGAAACCTCCCCGTGGCCACTCCAGACCCAGGAA<br>TGTTCCCATGCCTTCACCACTCCCAAAACCTGCTGAGGGCCGTCAGCAACATGCTCCAGAAGG<br>CCAGACAAACTCTAGAATTTTACCCTTGCACTTCTGAAGAGATTGATCATGAAGATATCACAAAA<br>GATAAAACCAGCACAGTGGAGGCCTGTTTACCATTGGAATTAACCAAGAATGAGAGTTGCCTAA<br>ATTCCAGAGAGACCTCTTTCATAACTAATGGGAGTTGCCTGGCCTCCAGAAAGACCTCTTTTATG<br>ATGGCCCTGTGCCTTAGTAGTATTTATGAAGACTTGAAGATGTACCAGGTGGAGTTCAAGACCA<br>TGAATGCAAAGCTTCTGATGGATCCTAAGAGGCAGATCTTTCTAGATCAAAACATGCTGGCAGTT<br>ATTGATGAGCTGATGCAGGCCCTGAATTTCAACAGTGAGACTGTGCCACAAAAATCCTCCCTTG<br>AAGAACCGGATTTTTATAAAACTAAAATCAAGCTCTGCATACTTCTTCATGCTTTCAGAATTCGGG<br>CAGTGACTATTGATAGAGTGATGAGCTATCTGAATGCTTCCGGAAGCGGAGCTACTAACTTCAG<br>CCTGCTGAAGCAGGCTGGAGACGTGGAGGAGAACCCTGGACCTATGTGTCACCAGCAGTTGGT<br>CATCTCTTGGTTTTCCCTGGTTTTTCTGGCATCTCCCCTCGTGGCCATATGGGAACTGAAGAAA<br>GATGTTTATGTCGTAGAATTGGATTGGTATCCGGATGCCCCTGGAGAAATGGTGGTCCTCACCT<br>GTGACACCCCTGAAGAAGATGGTATCACCTGGACCTTGGACCAGAGCAGTGAGGTCTTAGGCT<br>CTGGCAAAACCCTGACCATCCAAGTCAAAGAGTTTGGAGATGCTGGCCAGTACACCTGTCACAA<br>AGGAGGCGAGGTTCTAAGCCATTCGCTCCTGCTGCTTCACAAAAAGGAAGATGGAATTTGGTCC<br>ACTGATATTTTAAAGGACCAGAAAGAACCCAAAAATAAGACCTTTCTAAGATGCGAGGCCAAGAA<br>TTATTCTGGACGTTTCACCTGCTGGTGGCTGACGACAATCAGTACTGATTTGACATTCAGTGTCA<br>AAAGCAGCAGAGGCTCTTCTGACCCCCAAGGGGTGACGTGCGGAGCTGCTACACTCTCTGCAG<br>AGAGAGTCAGAGGGGACAACAAGGAGTATGAGTACTCAGTGGAGTGCCAGGAGGACAGTGCC<br>TGCCCAGCTGCTGAGGAGAGTCTGCCCATTGAGGTCATGGTGGATGCCGTTCACAAGCTCAAG<br>TATGAAAACTACACCAGCAGCTTCTTCATCAGGGACATCATCAAACCTGACCCACCCAAGAACTT<br>GCAGCTGAAGCCATTAAAGAATTCTCGGCAGGTGGAGGTCAGCTGGGAGTACCCTGACACCTG<br>GAGTACTCCACATTCCTACTTCTCCCTGACATTCTGCGTTCAGGTCCAGGGCAAGAGCAAGAGA<br>GAAAAGAAAGATAGAGTCTTCACGGACAAGACCTCAGCCACGGTCATCTGCCGCAAAAATGCCA<br>GCATTAGCGTGCGGGCCCAGGACCGCTACTATAGCTCATCTTTGGAGCGAATGGGCATCGTGC<br>CCTGCAGTGAGGGCAGAGGCAGCCTGCTGACCTGCGGCGACGTCGAGGAGAACCCCGGGCC<br>CATGGGGGCAGGTGCCACCGGCCGCGCCATGGACGGGCCGCGCCTGCTGCTGTTGCTGCTTC<br>TGGGGGTGTCCCTTGGAGGTGCCAAGGAGGCATGCCCCACAGGCCTGTACACACACAGCGGT<br>GAGTGCTGCAAAGCCTGCAACCTGGGCGAGGGTGTGGCCCAGCCTTGTGGAGCCAACCAGAC<br>CGTGTGTGAGCCCTGCCTGGACAGCGTGACGTTCTCCGACGTGGTGAGCGCGACCGAGCCGT<br>GCAAGCCGTGCACCGAGTGCGTGGGGCTCCAGAGCATGTCGGCGCCGTGCGTGGAGGCCGA<br>TGACGCCGTGTGCCGCTGCGCCTACGGCTACTACCAGGATGAGACGACTGGGCGCTGCGAGG<br>CGTGCCGCGTGTGCGAGGCGGGCTCGGGCCTCGTGTTCTCCTGCCAGGACAAGCAGAACACC<br>GTGTGCGAGGAGTGCCCCGACGGCACGTATTCCGACGAGGCCAACCACGTGGACCCGTGCCT<br>GCCCTGCACCGTGTGCGAGGACACCGAGCGCCAGCTCCGCGAGTGCACACGCTGGGCCGAC<br>GCCGAGTGCGAGGAGATCCCTGGCCGTTGGATTACACGGTCCACACCCCCAGAGGGCTCGGA<br>CAGCACAGCCCCCAGCACCCAGGAGCCTGAGGCACCTCCAGAACAAGACCTCATAGCCAGCA<br>CGGTGGCAGGTGTGGTGACCACAGTGATGGGCAGCTCCCAGCCCGTGGTGACCCGAGGCACC<br>ACCGACAACCTCATCCCTGTCTATTGCTCCATCCTGGCTGCTGTGGTTGTGGGTCTTGTGGCCT<br>ACATAGCCTTCAAGAGGTGAAAAACAAAAGAACAAGAAATTTCTTGGTAAGAAGCCGGGAACAG<br>ACAACAGAAGTCATGAAGCCCAAGTGAAATCAAAGGTGCTAAATGGTCGCCAGGAGACATCC<br>GTTGTGCTTGCCTGCGTTTTGGAAGCTCTGAAGTCACATCACAGGACACGGGGCAGTGGCAAC<br>CTTGTCTCTATGCCAGCTCAGTCCCATCAGAGAGCGAGCGCTACCCACTTCTAAATAGCAATTT<br>CGCCGTTGAAGAGGAAGGGCAAAACCACTAGAACTCTCCATCTTATTTTCATGTATATGTGTTCA<br>TGAATGGTATGGAACTCTCTCACCCTATATGTAGTATAAAGAAAAGTAGGTT |
| 40 | Inserted<br>matrice PD1<br>locus_IL12a_ | GGTGGCCGGGGAGGCTTTGTGGGGCCACCCAGCCCCTTCCTCACCTCTCTCCATCTCTCAGAC<br>TCCCCAGACAGGCCCTGGAACCCCCCCACCTTCTCCCCAGCCCTGCTCGTGGTGACCGAAGG<br>GGACAACGCCACCTTCACCTGCAGCTTCTCCAACACATCGGAGAGCTTCGTGCTAAACTGGTAC |

TABLE 5-continued

Sequences referred to in example 2.

| | |
|---|---|
| 2A_IL12b (60 nucleotides upstream and downstream) | CGCATGAGCCCCAGCAACCAGACGGACAAGCTGGCCGCCTTCCCCGAGGACCGCAGCCAGCC<br>CGGCCAGGACTGCCGCTTCCGTGTCACACAACTGCCCAACGGGCGTGACTTCCACATGAGCGT<br>GGTCAGGGCCCGGCGCAATGACAGCGGCACCTACCTCTGTGGGGCCGGTTCTGGCGTGAAAC<br>AGACTTTGAATTTTGACCTTCTCAAGTTGGCGGGAGACGTGGAGTCCAACCCAGGGCCCATGT<br>GGCCCCCTGGGTCAGCCTCCCAGCCACCGCCCTCACCTGCCGCGGCCACAGGTCTGCATCCA<br>GCGGCTCGCCCTGTGTCCCTGCAGTGCCGGCTCAGCATGTGTCCAGCGCGCAGCCTCCTCCTT<br>GTGGCTACCCTGGTCCTCCTGGACCACCTCAGTTTGGCCAGAAACCTCCCCGTGGCCACTCCA<br>GACCCAGGAATGTTCCCATGCCTTCACCACTCCCAAAACCTGCTGAGGGCCGTCAGCAACATG<br>CTCCAGAAGGCCAGACAAACTCTAGAATTTTACCCTTGCACTTCTGAAGAGATTGATCATGAAGA<br>TATCACAAAAGATAAAACCAGCACAGTGGAGGCCTGTTTATCCATTGGAATTAACCAAGAATGAG<br>AGTTGCCTAAATTCCAGAGAGACCTCTTTCATAACTAATGGGAGTTGCCTGGCCTCCAGAAAGA<br>CCTCTTTTATGATGGCCCTGTGCCTTAGTAGTATTTATGAAGACTTGAAGATGTACCAGGTGGAG<br>TTCAAGACCATGAATGCAAAGCTTCTGATGGATCCTAAGAGGCAGATCTTTCTAGATCAAAACAT<br>GCTGGCAGTTATTGATGAGCTGATGCAGGCCCTGAATTTCAACAGTGAGACTGTGCCACAAAAA<br>TCCTCCCTTGAAGAACCGGATTTTTATAAAACTAAAATCAAGCTCTGCATACTTCTTCATGCTTTC<br>AGAATTCGGGCAGTGACTATTGATAGAGTGATGAGCTATCTGAATGCTTCCGGAAGCGGAGCTA<br>CTAACTTCAGCCTGCTGAAGCAGGCTGGAGACGTGGAGGAGAACCCTGGACCTATGTGTCACC<br>AGCAGTTGGTCATCTCTTGGTTTTCCCTGGTTTTTCTGGCATCTCCCCTCGTGGCCATATGGGAA<br>CTGAAGAAAGATGTTTATGTCGTAGAATTGGATTGGTATCCGGATGCCCCTGGAGAAATGGTGG<br>TCCTCACCTGTGACACCCCTGAAGAAGATGGTATCACCTGGACCTTGGACCAGAGCAGTGAGG<br>TCTTAGGCTCTGGCAAAACCCTGACCATCCAAGTCAAAGAGTTTGGAGATGCTGGCCAGTACAC<br>CTGTCACAAAGGAGGCGAGGTTCTAAGCCATTCGCTCCTGCTGCTTCACAAAAAGGAAGATGGA<br>ATTTGGTCCACTGATATTTTAAAGGACCAGAAAGAACCCAAAAATAAGACCTTTCTAAGATGCGA<br>GGCCAAGAATTATTCTGGACGTTTCACCTGCTGGTGGCTGACGACAATCAGTACTGATTTGACA<br>TTCAGTGTCAAAAGCAGCAGAGGCTCTTCTGACCCCCAAGGGGTGACGTGCGGAGCTGCTACA<br>CTCTCTGCAGAGAGAGTCAGAGGGGACAACAAGGAGTATGAGTACTCAGTGGAGTGCCAGGAG<br>GACAGTGCCTGCCCAGCTGCTGAGGAGAGTCTGCCCATTGAGGTCATGGTGGATGCCGTTCAC<br>AAGCTCAAGTATGAAAACTACACCAGCAGCTTCTTCATCAGGGACATCATCAAACCTGACCCAC<br>CCAAGAACTTGCAGCTGAAGCCATTAAAGAATTCTCGGCAGGTGGAGGTCAGCTGGGAGTACC<br>CTGACACCTGGAGTACTCCACATTCCTACTTCTCCCTGACATTCTGCGTTCAGGTCCAGGGCAA<br>GAGCAAGAGAGAAAAGAAAGATAGAGTCTTCACGGACAAGACCTCAGCCACGGTCATCTGCCG<br>CAAAAATGCCAGCATTAGCGTGCGGGCCCAGGACCGCTACTATAGCTCATCTTGGAGCGAATG<br>GGCATCTGTGCCCTGCAGTGAGGGCAGAGGCAGCCTGCTGACCTGCGGCGACGTCGAGGAGA<br>ACCCCGGGCCCATGGGGGCAGGTGCCACCGGCCGCGCCATGGACGGGCCGCGCCTGCTGCT<br>GTTGCTGCTTCTGGGGGTGTCCCTTGGAGGTGCCAAGGAGGCATGCCCCACAGGCCTGTACAC<br>ACACAGCGGTGAGTGCTGCAAAGCCTGCAACCTGGGCGAGGGTGTGGCCCAGCCTTGTGGAG<br>CCAACCAGACCGTGTGTGAGCCCTGCCTGGACAGCGTGACGTTCTCCGACGTGGTGAGCGCG<br>ACCGAGCCGTGCAAGCCGTGCACCGAGTGCGTGGGGCTCCAGAGCATGTCGGCGCCGTGCGT<br>GGAGGCCGATGACGCCGTGTGCCGCTGCGCCTACGGCTACTACCAGGATGAGACGACTGGGC<br>GCTGCGAGGCGTGCCGCGTGTGCGAGGCGGGCTCGGGCCTCGTGTTCTCCTGCCAGGACAAG<br>CAGAACACCGTGTGCGAGGAGTGCCCCGACGGCACGTATTCCGACGAGGCCAACCACGTGGA<br>CCCCGTGCCTGCCCTGCACCGTGTGCGAGGACACCGAGCGCCAGCTCCGCGAGTGCACACGCT<br>GGGCCGACGCCGAGTGCGAGGAGATCCCTGGCCGTTGGATTACACGGTCCACACCCCCAGAG<br>GGCTCGGACAGCACAGCCCCCAGCACCCAGGAGCCTGAGGCACCTCCAGAACAAGACCTCAT<br>AGCCAGCACGGTGGCAGGTGTGGTGACCACAGTGATGGGCAGCTCCCAGCCCGTGGTGACCC<br>GAGGCACCACCGACAACCTCATCCCTGTCTATTGCTCCATCCTGGCTGCTGTGGTTGTGGGTCT<br>TGTGGCCTACATAGCCTTCAAGAGGTGATCTAGAGGGCCCGTTTAAACCCGCTGATCAGCCTC<br>GACTGTGCCTTCTAGTTGCCAGCCATCTGTTGTTTGCCCCTCCCCCGTGCCTTCTTGACCCTG<br>GAAGGTGCCACTCCCACTGTCCTTTCCTAATAAAATGAGGAAATTGCATCGCATTGTCTGAGTA<br>GGTGTCATTCTATTCTGGGGGGTGGGGTGGGGCAGGACAGCAAGGGGGAGGATTGGGAAGAC<br>AATAGCAGGCATGCTGGGGATGCGGTGGGCTCTATGACTAGTGGCGAATTCGGCGCAGATCAA<br>AGAGAGCCTGCGGGCAGAGCTCAGGGTGACAGGTGCGGCCTCGGAGGCCCCGGGGCAGGGG<br>TGAGCTGAGCCGGTCCTGGGGTGGGTGTCCCCTCCTGCACAGGATCAGGAGCTCCAGGGTCG<br>TAGGGCAGGGACCCCCCAGCTCCAGTCCAGGGCTCTGTCCTGCACCTGGGGAATGGTGACCG<br>GCATCTCTGTCCTCTAGCTCTGGAAGCACCCCAGCCCCTCTAGTCTGCCCTCACCCCTGACCCT<br>GACCCTCCACCCTGACCCCGTCCTAACCCCTGACCTTTGTGCCCTTCCAGAGAGAAGGGCAGA<br>AGTGCCCACAGCCCACCCCAGCCCCTCACCCAGGCC |
| 41 upstream TRAC locus polynucleotide sequence | ATGAGATCATGTCCTAACCCTGATCCTCTTGTCCCACAGATATCCAGAACCCTGACC<br>CTG |
| 42 downstream TRAC locus polynucleotide sequence | GAAACAGTGAGCCTTGTTCTGGCAGTCCAGAGAATGACACGGGAAAAAAGCAGATG<br>AAGA |
| 43 upstream CD25 locus polynucleotide sequence | AGTGCTGGCTAGAAACCAAGTGCTTTACTGCATGCACATCATTTAGCACAGTTAGTT<br>GCT |
| 44 downstream CD25 locus polynucleotide sequence | GAATGGTATGGAACTCTCTCCACCCTATATGTAGTATAAAGAAAAGTAGGTT |

TABLE 5-continued

Sequences referred to in example 2.

| 45 | upstream PD1 locus polynucleotide sequence | GGTGGCCGGGGAGGCTTTGTGGGGCCACCCAGCCCCTTCCTCACCTCTCTCCATCTCTCA |
| --- | --- | --- |
| 46 | downstream PD1 locus polynucleotide sequence | TGCCCTTCCAGAGAGAAGGGCAGAAGTGCCCACAGCCCACCCCAGCCCCTCACCCAGGCC |
| 47 | IL-12a polynucleotide | ATGTGGCCCCCTGGGTCAGCCTCCCAGCCACCGCCCTCACCTGCCGCGGCCACAGGTCTGCATCCAGCGGCTCGCCCTGTGTCCCTGCAGTGCCGGCTCAGCATGTGTCCAGCGCGCAGCCTCCTCCTTGTGGCTACCCTGGTCCTCCTGGACCACCTCAGTTTGGCCAGAAACCTCCCCGTGGCCACTCCAGACCCAGGAATGTTCCCATGCCTTCACCACTCCCAAAACCTGCTGAGGGCCGTCAGCAACATGCTCCAGAAGGCCAGACAAACTCTAGAATTTTACCCTTGCACTTCTGAAGAGATTGATCATGAAGATATCACAAAAGATAAAACCAGCACAGTGGAGGCCTGTTTACCATTGGAATTAACCAAGAATGAGAGTTGCCTAAATTCCAGAGAGACCTCTTTCATAACTAATGGGAGTTGCCTGGCCTCCAGAAAGACCTCTTTTATGATGGCCCTGTGCCTTAGTAGTATTTATGAAGACTTGAAGATGTACCAGGTGGAGTTCAAGACCATGAATGCAAAGCTTCTGATGGATCCTAAGAGGCAGATCTTTCTAGATCAAAACATGCTGGCAGTTATTGATGAGCTGATGCAGGCCCTGAATTTCAACAGTGAGACTGTGCCACAAAAATCCTCCCTTGAAGAACCGGATTTTTATAAAACTAAAATCAAGCTCTGCATACTTCTTCATGCTTTCAGAATTCGGGCAGTGACTATTGATAGAGTGATGAGCTATCTGAATGCTTCC |
| 48 | IL12b polynucleotide | ATGTGTCACCAGCAGTTGGTCATCTCTTGGTTTTCCCTGGTTTTTCTGGCATCTCCCCTCGTGGCCATATGGGAACTGAAGAAAGATGTTTATGTCGTAGAATTGGATTGGTATCCGGATGCCCCTGGAGAAATGGTGGTCCTCACCTGTGACACCCCTGAAGAAGATGGTATCACCTGGACCTTGGACCAGAGCAGTGAGGTCTTAGGCTCTGGCAAAACCCTGACCATCCAAGTCAAAGAGTTTGGAGATGCTGGCCAGTACACCTGTCACAAAGGAGGCGAGGTTCTAAGCCATTCGCTCCTGCTGCTTCACAAAAAGGAAGATGGAATTTGGTCCACTGATATTTTAAAGGACCAGAAAGAACCCAAAAATAAGACCTTTCTAAGATGCGAGGCCAAGAATTATTCTGGACGTTTCACCTGCTGGTGGCTGACGACAATCAGTACTGATTTGACATTCAGTGTCAAAAGCAGCAGAGGCTCTTCTGACCCCCAAGGGGTGACGTGCGGAGCTGCTACACTCTCTGCAGAGAGAGTCAGAGGGGACAACAAGGAGTATGAGTACTCAGTGGAGTGCCAGGAGGACAGTGCCTGCCCAGCTGCTGAGGAGAGTCTGCCCATTGAGGTCATGGTGGATGCCGTTCACAAGCTCAAGTATGAAAACTACACCAGCAGCTTCTTCATCAGGGACATCATCAAACCTGACCCACCCAAGAACTTGCAGCTGAAGCCATTAAAGAATTCTCGGCAGGTGGAGGTCAGCTGGGAGTACCCTGACACCTGGAGTACTCCACATTCCTACTTCTCCCTGACATTCTGCGTTCAGGTCCAGGGCAAGAGCAAGAGAGAAAAGAAAGATAGAGTCTTCACGGACAAGACCTCAGCCACGGTCATCTGCCGCAAAAATGCCAGCATTAGCGTGCGGGCCCAGGACCGCTACTATAGCTCATCTTGGAGCGAATGGGCATCTGTGCCCTGCAGT |
| 49 | IL15 polynucleotide | GGCATTCATGTCTTCATTTTGGGCTGTTTCAGTGCAGGGCTTCCTAAAACAGAAGCCAACTGGGTGAATGTAATAAGTGATTTGAAAAAAATTGAAGATCTTATTCAATCTATGCATATTGATGCTACTTTATATACGGAAAGTGATGTTCACCCCAGTTGCAAAGTAACAGCAATGAAGTGCTTTCTCTTGGAGTTACAAGTTATTTCACTTGAGTCCGGAGATGCAAGTATTCATGATACAGTAGAAAATCTGATCATCCTAGCAAACAACAGTTTGTCTTCTAATGGGAATGTAACAGAATCTGGATGCAAAGAATGTGAGGAACTGGAGGAAAAAAATATTAAAGAATTTTTGCAGAGTTTTGTACATATTGTCCAAATGTTCATCAACACTTCT |
| 50 | sIL15ra polynucleotide | ATCACGTGCCCTCCCCCCATGTCCGTGGAACACGCAGACATCTGGGTCAAGAGCTACAGCTTGTACTCCAGGGAGCGGTACATTTGTAACTCTGGTTTCAAGCGTAAAGCCGGCACGTCCAGCCTGACGGAGTGCGTGTTGAACAAGGCCACGAATGTCGCCCACTGGACAACCCCCAGTCTCAAATGCATTAGAGACCCTGCCCTGGTTCACCAAAGGCCAGCGCCACCCTCCACAGTAACGACGGCAGGGGTGACCCCACAGCCAGAGAGCCTCTCCCCTTCTGGAAAAGAGCCCGCAGCTTCATCTCCCAGCTCAAACAACACAGCGGCCACAACAGCAGCTATTGTCCCGGGCTCCCAGCTGATGCCTTCAAAATCACCTTCCACAGGAACCACAGAGATAAGCAGTCATGAGTCCTCCCACGGCACCCCCTCTCAGACAACAGCCAAGAACTGGGAACTCACAGCATCCGCCTCCCACCAGCCGCCAGGTGTGTATCCACAGGGCCACAGCGACACCACT |
| 51 | soluble GP130 polynucleotide | ATGCTGACACTGCAGACTTGGCTGGTGCAGGCACTGTTTATTTTTCTGACTACTGAATCAACTGGCGAACTGCTGGACCCTTGTGGCTACATCAGCCCTGAGTCCCCAGTGGTGCAGCTGCACAGCAACTTCACCGCCGTGTGCGTGCTGAAGGAGAAGTGTATGGACTACTTTCACGTGAACGCCAATTATATCGTGTGGAAAACCAACCACTTCACAATCCCCAAGGAGCAGTACACCATCATCAATAGGACAGCCAGCTCCGTGACCTTTACAGACATCGCCTCCCTGAACATCCAGCTGACCTGCAATATCCTGACATTCGGCCAGCTGGAGCAGAACGTATATGGCATCACCATCATCTCTGGCCTGCCCCCTGAGAAGCCTAAGAACCTGAGCTGCATCGTGAATGAGGGCAAGAAGATGCGGTGTGAGTGGGACGGCGGCAGAGAGACACACCTGGAGACAAACTTCACCCTGAAGTCCGAGTGGGCCACACACAAGTTTGCCGACTGCAAGGCCAAGCGCGATACCCCAACATCCTGTACCGTGGATTACTCTACAGTGTATTTTGTGAACATCGAAGTGTGGGTGGAGGCCGAGAATGCCCTGGGCAAGGTGACCTCCGACCACATCAACTTCGATCCCGTGTACAAGGTGAAGCCTAACCCACCCCACAATCTGAGCGTGATCAATTCCGAGGAGCTGTCTAGCATCCTGAAGCTGACCTGGACAAACCCATCTATCAAGAGCGTGATCATCCTGAAGTACAATATCCAGTATCGGACCAAGGACGCCTCCACATGGAGCCAGATCCCTCCAGAGGATACCGCCAGCACAAGATCC |

TABLE 5-continued

Sequences referred to in example 2.

|  |  |  |
|---|---|---|
|  |  | TCTTTCACCGTGCAGGACCTGAAGCCCTTCACAGAGTACGTGTTTCGGATCAGATGT<br>ATGAAGGAGGACGGCAAGGGCTACTGGAGCGATTGGTCCGAGGAGGCCAGCGGCA<br>TCACCTATGAGGACAGGCCTTCTAAGGCCCCCAGCTTCTGGTACAAGATCGATCCAT<br>CCCACACCCAGGGCTATCGCACAGTGCAGCTGGTGTGGAAAACCCTGCCCCCTTTC<br>GAGGCCAACGGCAAGATCCTGGACTACGAGGTGACCCTGACACGGTGGAAGTCCC<br>ACCTGCAGAACTATACCGTGAATGCCACCAAGCTGACAGTGAACCTGACAAATGATC<br>GGTACCTGGCCACCCTGACAGTGAGAAACCTGGTGGGCAAGTCTGACGCCGCCGT<br>GCTGACCATCCCTGCCTGCGATTTCCAGGCCACACACCCAGTGATGGACCTGAAGG<br>CCTTTCCCAAGGATAATATGCTGTGGGTGGAGTGGACCACACCTAGAGAGTCCGTG<br>AAGAAGTACATCCTGGAGTGGTGCGTGCTGTCTGACAAGGCCCCCATGTATCACCGA<br>CTGGCAGCAGGAGGATGGCACCGTGCACAGGACATATCTGCGCGGCAACCTGGCC<br>GAGTCTAAGTGTTACCTGATCACCGTGACACCCGTATGCAGACGGACCAGGCTC<br>TCCTGAGAGCATCAAGGCCTACCTGAAGCAGGCACCACCAAGCAAGGGACCAACCG<br>TGCGGACAAAGAAGGTCGGCAAGAATGAGGCCGTGCTGGAGTGGGACCAGCTGCC<br>TGTGGATGTGCAGAACGGCTTCATCAGGAATTACACCATCTTTTATCGCACAATCATC<br>GGCAACGAGACAGCCGTGAATGTGGACAGCTCCCACACCGAGTATACACTGTCTAG<br>CCTGACCTCCGATACACTGTACATGGTGAGGATGGCCGCCTATACAGACGAGGGCG<br>GCAAGGATGGCCCCGAGTTT |
| 52 | IgE signal<br>sequence | GGTACCGGGTCCGCCACCATGGACTGGACCTGGATTCTGTTCCTCGTGGCTGCTGC<br>TACAAGAGTGCACAGC |
| 53 | F2A | GGTTCTGGCGTGAAACAGACTTTGAATTTTGACCTTCTCAAGTTGGCGGGAGACGTG<br>GAGTCCAACCCAGGGCCC |
| 54 | P2A | GGAAGCGGAGCTACTAACTTCAGCCTGCTGAAGCAGGCTGGAGACGTGGAGGAGA<br>ACCCTGGACCT |
| 55 | T2A | GAGGGCAGAGGCAGCCTGCTGACCTGCGGCGACGTCGAGGAGAACCCCGGGCCC |
| 56 | LNGFR | ATGGGGGCAGGTGCCACCGGCCGCGCCATGGACGGGCCGCGCCTGCTGCTGTTG<br>CTGCTTCTGGGGGTGTCCCTTGGAGGTGCCAAGGAGGCATGCCCCACAGGCCTGT<br>ACACACACAGCGGTGAGTGCTGCAAAGCCTGCAACCTGGGCGAGGGTGTGGCCCA<br>GCCTTGTGGAGCCAACCAGACCGTGTGTGAGCCCTGCCTGGACAGCGTGACGTTCT<br>CCGACGTGGTGAGCGCGACCGAGCCGTGCAAGCCGTGCACCGAGTGCGTGGGGC<br>TCCAGAGCATGTCGGCGCCGTGCGTGGAGGCCGATGACGCCGTGTGCCGCTGCGC<br>CTACGGCTACTACCAGGATGAGACGACTGGGCGCTGCGAGGCGTGCCGCGTGTGC<br>GAGGCGGGCTCGGGCCTCGTGTTCTCCTGCCAGGACAAGCAGAACACCGTGTGCG<br>AGGAGTGCCCCGACGGCACGTATTCCGACGAGGCCAACCACGTGGACCCGTGCCT<br>GCCCTGCACCGTGTGCGAGGACACCGAGCGCCAGCTCCGCGAGTGCACACGCTGG<br>GCCGACGCCGAGTGCGAGGAGATCCCTGGCCGTTGGATTACACGGTCCACACCCC<br>CAGAGGGCTCGGACAGCACAGCCCCCAGCACCCAGGAGCCTGAGGCACCTCCAGA<br>ACAAGACCTCATAGCCAGCACGGTGGCAGGTGTGGTGACCACAGTGATGGGCAGCT<br>CCCAGCCCGTGGTGACCCGAGGCACCACCGACAACCTCATCCCTGTCTATTGCTCC<br>ATCCTGGCTGCTGTGGTTGTGGGTCTTGTGGCCTACATAGCCTTCAAGAGGTGA |

| SEQ<br>ID<br>NO# | Sequence<br>Name | Polypeptide sequence |
|---|---|---|
| 57 | IL-12a<br>polypeptide | MWPPGSASQPPPSPAAATGLHPAARPVSLQCRLSMCPARSLLLVATLVLLDHLSLARNL<br>PVATPDPGMFPCLHHSQNLLRAVSNMLQKARQTLEFYPCTSEEIDHEDITKDKTSVEA<br>CLPLELTKNESCLNSRETSFITNGSCLASRKTSFMMALCLSSIYEDLKMYQVEFKTMNAK<br>LLMDPKRQIFLDQNMLAVIDELMQALNFNSETVPQKSSLEEPDFYKTKIKLCILLHAFRIRA<br>VTIDRVMSYLNAS |
| 58 | IL12b<br>polypeptide | MCHQQLVISWFSLVFLASPLVAIWELKKDVYVVELDWYPDAPGEMVVLTCDTPEEDGIT<br>WTLDQSSEVLGSGKTLTIQVKEFGDAGQYTCHKGGEVLSHSLLLLHKKEDGIWSTDILKD<br>QKEPKNKTFLRCEAKNYSGRFTCWWLTTISTDLTFSVKSSRGSSDPQGVTCGAATLSAE<br>RVRGDNKEYEYSVECQEDSACPAAEESLPIEVMVDAVHKLKYENYTSSFFIRDIIKPDPP<br>KNLQLKPLKNSRQVEVSWEYPDTWSTPHSYFSLTFCVQVQGKSKREKKDRVFTDKTSA<br>TVICRKNASISVRAQDRYYSSSWSEWASVPCS |
| 59 | IL15<br>polypeptide | GIHVFILGCFSAGLPKTEANWVNVISDLKKIEDLIQSMHIDATLYTESDVHPSCKVTAMKC<br>FLLELQVISLESGDASIHDTVENLIILANNSLSSNGNVTESGCKECEELEEKNIKEFLQSFV<br>HIVQMFINTS |
| 60 | sIL15ra<br>polypeptide | ITCPPPMSVEHADIWVKSYSLYSRERYICNSGFKRKAGTSSLTECVLNKATNVAHWTTPS<br>LKCIRDPALVHQRPAPPSTVTAGVTPQPESLSPSGKEPAASSPSSNNTAATTAAIVPGS<br>QLMPSKSPSTGTTEISSHESSHGTPSQTTAKNWELTASASHQPPGVYPQGHSDTT |
| 61 | soluble gp130 | MLTLQTWLVQALFIFLTTESTGELLDPCGYISPESPVVQLHSNFTAVCVLKEKCMDYFHV<br>NANYIVWKTNHFTIPKEQYTIINRTASSVTFTDIASLNIQLTCNILTFGQLEQNVYGITIISGL<br>PPEKPKNLSCIVNEGKKMRCEWDGGRETHLETNFTLKSEWATHKFADCKAKRDTPTSC<br>TVDYSTVYFVNIEVWVEAENALGKVTSDHINFDPVYKVPNPPHNLSVINSEELSSILKLT<br>WTNPSIKSVIILKYNIQYRTKDASTWSQIPPEDTASTRSSFTVQDLKPFTEYVFRIRCMKE<br>DGKGYWSDWSEEASGITYEDRPSKAPSFWYKIDPSHTQGYRTVQLVWKTLPPFEANGK<br>ILDYEVTLTRWKSHLQNYTVNATKLTVNLTNDRYLATLTVRNLVGKSDAAVLTIPACDFQA |

TABLE 5-continued

Sequences referred to in example 2.

| | | |
|---|---|---|
| | | THPVMDLKAFPKDNMLWVEWTTPRESVKKYILEWCVLSDKAPCITDWQQEDGTVHRTY<br>LRGNLAESKCYLITVTPVYADGPGSPESIKAYLKQAPPSKGPTVRTKKVGKNEAVLEWD<br>QLPVDVQNGFIRNYTIFYRTIIGNETAVNVDSSHTEYTLSSLTSDTLYMVRMAAYTDEGG<br>KDGPEF |
| 62 | soluble gp130<br>fused to a Fc | MLTLQTWLVQALFIFLTTESTGELLDPCGYISPESPVVQLHSNFTAVCVLKEKCMDYFHV<br>NANYIVWKTNHFTIPKEQYTIINRTASSVTFTDIASLNIQLTCNILTFGQLEQNVYGITIISGL<br>PPEKPKNLSCIVNEGKKMRCEWDGGRETHLETNFTLKSEWATHKFADCKAKRDTPTSC<br>TVDYSTVYFVNIEVWVEAENALGKVTSDHINFDPVYKVKPNPPHNLSVINSEELSSILKLT<br>WTNPSIKSVIILKYNIQYRTKDASTWSQIPPEDTASTRSSFTVQDLKPFTEYVFRIRCMKE<br>DGKGYWSDWSEEASGITYEDRPSKAPSFWYKIDPSHTQGYRTVQLVWKTLPPFEANGK<br>ILDYEVTLTRWKSHLQNYTVNATKLTVNLTNDRYLATLTVRNLVGKSDAAVLTIPACDFQA<br>THPVMDLKAFPKDNMLWVEWTTPRESVKKYILEWCVLSDKAPCITDWQQEDGTVHRTY<br>LRGNLAESKCYLITVTPVYADGPGSPESIKAYLKQAPPSKGPTVRTKKVGKNEAVLEWD<br>QLPVDVQNGFIRNYTIFYRTIIGNETAVNVDSSHTEYTLSSLTSDTLYMVRMAAYTDEGG<br>KDGPEFRSCDKTHTCPPCPAPEAEGGPSVFLFPPKPKDTLMISRTPEVTCVVVDVSHED<br>PEVKFNWYVDGVEVHNAKTKPREEQYNSTYRVVSVLTVLHQDWLNGKEYKCKVSNKAL<br>PAPIEKTISKAKGQPREPQVYTLPPSREEMTKNQVSLTCLVKGFYPSDIAVEWESNGQP<br>ENNYKTTPPVLDSGSFFLYSKLTVDKSRWQQGNVFSCSVMHEALHNHYTQKSLSLSP<br>GK |

| SEQ<br>ID<br>NO# | Sequence<br>Name | Polynucleotide sequence |
|---|---|---|
| 63 | Matrice TRAC<br>locus_CubiCAR<br>CD22<br>pCLS30056<br>full sequence | GTGGCACTTTTCGGGGAAATGTGCGCGGAACCCCTATTTGTTTATTTTTCTAAATACA<br>TTCAAATATGTATCCGCTCATGAGACAATAACCCTGATAAATGCTTCAATAATATTGAA<br>AAAGGAAGAGTATGAGTATTCAACATTTCCGTGTCGCCCTTATTCCCTTTTTTGCGGC<br>ATTTTGCCTTCCTGTTTTTGCTCACCCAGAAACGCTGGTGAAAGTAAAAGATGCTGAA<br>GATCAGTTGGGTGCACGAGTGGGTTACATCGAACTGGATCTCAACAGCGGTAAGAT<br>CCTTGAGAGTTTTCGCCCCGAAGAACGTTTTCCAATGATGAGCACTTTTAAAGTTCTG<br>CTATGTGGCGCGGTATTATCCCGTATTGACGCCGGGCAAGAGCAACTCGGTCGCCG<br>CATACACTATTCTCAGAATGACTTGGTTGAGTACTCACCAGTCACAGAAAAGCATCTT<br>ACGGATGGCATGACAGTAAGAGAATTATGCAGTGCTGCCATAACCATGAGTGATAAC<br>ACTGCGGCCAACTTACTTCTGACAACGATCGGAGGACCGAAGGAGCTAACCGCTTT<br>TTTGCACAACATGGGGGATCATGTAACTCGCCTTGATCGTTGGGAACCGGAGCTGA<br>ATGAAGCCATACCAAACGACGAGCGTGACACCACGATGCCTGTAGCAATGGCAACA<br>ACGTTGCGCAAACTATTAACTGGCGAACTACTTACTCTAGCTTCCCGGCAACAATTAA<br>TAGACTGGATGGAGGCGGATAAAGTTGCAGGACCACTTCTGCGCTCGGCCCTTCCG<br>GCTGGCTGGTTTATTGCTGATAAATCTGGAGCCGGTGAGCGTGGTTCTCGCGGTAT<br>CATTGCAGCACTGGGGCCAGATGGTAAGCCCTCCCGTATCGTAGTTATCTACACGA<br>CGGGGAGTCAGGCAACTATGGATGAACGAAATAGACAGATCGCTGAGATAGGTGCC<br>TCACTGATTAAGCATTGGTAACTGTCAGACCAAGTTTACTCATATATACTTTAGATTGA<br>TTTAAAACTTCATTTTTAATTTAAAAGGATCTAGGTGAAGATCCTTTTTTGATAATCTCAT<br>GACCAAAATCCCTTAACGTGAGTTTTCGTTCCACTGAGCGTCAGACCCCGTAGAAAA<br>GATCAAAGGATCTTCTTGAGATCCTTTTTTTCTGCGCGTAATCTGCTGCTTGCAAACA<br>AAAAAACCACCGCTACCAGCGGTGGTTTGTTTGCCGGATCAAGAGCTACCAACTCTT<br>TTTCCGAAGGTAACTGGCTTCAGCAGAGCGCAGATACCAAATACTGTTCTTCTAGTG<br>TAGCCGTAGTTAGGCCACCACTTCAAGAACTCTGTAGCACCGCCTACATACCTCGCT<br>CTGCTAATCCTGTTACCAGTGGCTGCTGCCAGTGGCGATAAGTCGTGTCTTACCGG<br>GTTGGACTCAAGACGATAGTTACCGGATAAGGCGCAGCGGTCGGGCTGAACGGGG<br>GGTTCGTGCACACAGCCCAGCTTGGAGCGAACGACCTACACCGAACTGAGATACCT<br>ACAGCGTGAGCTATGAGAAAGCGCCACGCTTCCCGAAGGGAGAAAGGCGGACAGG<br>TATCCGGTAAGCGGCAGGGTCGGAACAGGAGAGCGCACGAGGGAGCTTCCAGGGG<br>GAAACGCCTGGTATCTTTATAGTCCTGTCGGGTTTCGCCACCTCTGACTTGAGCGTC<br>GATTTTTGTGATGCTCGTCAGGGGGCGGAGCCTATGGAAAAACGCCAGCAACGCG<br>GCCTTTTTACGGTTCCTGGCCTTTTGCTGGCCTTTTGCTCACATGGTCTTTCCTGCGT<br>TATCCCCTGATTCTGTGGATAACCGTATTACCGCCTTTGAGTGAGCTGATACCGCTC<br>GCCGCAGCCGAACGACCGAGCGCAGCGAGTCAGTGAGCGAGGAAGCGGAGAGCG<br>CCCAATACGCAAACCGCCTCTCCCCGCGCGTTGGCCGATTCATTAATGCAGCTGGC<br>ACGACAGGTTTCCCGACTGGAAAGCGGGCAGTGAGCGCAACGCAATTAATGTGAGT<br>TAGCTCACTCATTAGGCACCCCAGGCTTTACACTTTATGCTTCCGGCTCGTATGTTGT<br>GTGGAATTGTGAGCGGATAACAATTTCACACAGGAAACAGCTATGACCATGATTACG<br>CCAAGCGCGTCAATTAACCCTCACTAAAGGGAACAAAAGCTGTTAATTAATTGCTGG<br>GCCTTTTTCCCATGCCTGCCTTTACTCTGCCAGAGTTATATTGCTGGGGTTTTGAAGA<br>AGATCCTATTAAATAAAAGAATAAGCAGTATTATTAAGTAGCCCTGCATTTCAGGTTT<br>CCTTGAGTGGCAGGCCAGGCCTGGCCGTGAACGTTCACTGAAATCATGGCCTCTTG<br>GCCAAGATTGATAGCTTGTGCCTGTCCCTGAGTCCCAGTCCATCACGAGCAGCTGG<br>TTTCTAAGATGCTATTTCCCGTATAAAGCATGAGACCGTGACTTGCCAGCCCCACAG<br>AGCCCCGCCCTTGTCCATCACTGGCATCTGGACTCCAGCCTGGGTTGGGGCAAAGA<br>GGGAAATGAGATCATGTCCTAACCCTGATCCTCTTGTCCCACAGATATCCAGTACCC<br>CTACGACGTGCCCGACTACGCCTCCGGTGAGGGCAGAGGAAGTCTTCTAACATGCG<br>GTGACGTGGAGGAGAATCGGGCCCCGGATCCGCTCTGCCCGTCACCGCTCTGCT<br>GCTGCCACTGGCACTGCTGCTGCACGCTGCTAGGCCCGAGGGGAGGCAGCTGC<br>CCCTACAGCAACCCCAGCCTGTGCAGCGAGGCGGCGGCAGCGGCGGAGGGGT<br>AGCCAGGTGCAGCTGCAGCAGAGCGGCCCTGGCCTGGTGAAGCCAAGCCAGACAC<br>TGTCCCTGACCTGCGCCATCAGCGGCGATTCCGTGAGCTCCAACTCCGCCGCCTGG<br>AATTGGATCAGGCAGTCCCCTTCTCGGGGCCTGGAGTGGCTGGGAAGGACATACTA TABLE 5-continued Sequences referred to in example 2.

```
TCGGTCTAAGTGGTACAACGATTATGCCGTGTCTGTGAAGAGCAGAATCACAATCAA
CCCTGACACCTCCAAGAATCAGTTCTCTCTGCAGCTGAATAGCGTGACACCAGAGGA
CACCGCCGTGTACTATTGCGCCAGGGAGGTGACCGGCGACCTGGAGGATGCCTTT
GACATCTGGGGCCAGGGCACAATGGTGACCGTGAGCTCCGGAGGCGGCGGATCTG
GCGGAGGAGGAAGTGGGGGCGGCGGGAGTGATATCCAGATGACACAGTCCCCATC
CTCTCTGAGCGCCTCCGTGGGCGACAGAGTGACAATCACCTGTAGGGCCTCCCAGA
CCATCTGGTCTTACCTGAACTGGTATCAGCAGAGGCCCGGCAAGGCCCCTAATCTG
CTGATCTACGCAGCAAGCTCCCTGCAGAGCGGAGTGCCATCCAGATTCTCTGGCAG
GGGCTCCGGCACAGACTTCACCCTGACCATCTCTAGCCTGCAGGCCGAGGACTTCG
CCACCTACTATTGCCAGCAGTCTTATAGCATCCCCCAGACATTTGGCCAGGGCACCA
AGCTGGAGATCAAGTCGGATCCCGGAAGCGGAGGGGGAGGCAGCTGCCCCTACAG
CAACCCCAGCCTGTGCAGCGGAGGCGGCGGCAGCGAGCTGCCCACCCAGGGCAC
CTTCTCCAACGTGTCCACCAACGTGAGCCCAGCCAAGCCCACCACCACCGCCTGTC
CTTATTCCAATCCTTCCCTGTGTGCTCCCACCACAACCCCCGCTCCAAGGCCCCCTA
CCCCCGCACCAACTATTGCCTCCCAGCCACTCTCACTGCGGCCTGAGGCCTGTCGG
CCCGCTGCTGGAGGCGCAGTGCATACAAGGGGCCTCGATTTCGCCTGCGATATTTA
CATCTGGGCACCCCTCGCCGGCACCTGCGGGGTGCTTCTCCTCTCCCTGGTGATTA
CCCTGTATTGCAGACGGGGCCGGAAGAAGCTCCTCTACATTTTTAAGCAGCCTTTCA
TGCGGCCAGTGCAGACAACCCAAGAGGAGGATGGGTGTTCCTGCAGATTCCCTGAG
GAAGAGGAAGGCGGGTGCGAGCTGAGAGTGAAGTTCTCCAGGAGCGCAGATGCCC
CCGCCTATCAACAGGGCCAGAACCAGCTCTACAACGAGCTTAACCTCGGGAGGCGC
GAAGAATACGACGTGTTGGATAAGAGAAGGGGGCGGGACCCCGAGATGGGAGGAA
AGCCCCGGAGGAAGAACCCTCAGGAGGGCCTGTACAACGAGCTGCAGAAGGATAA
GATGGCCGAGGCCTACTCAGAGATCGGGATGAAGGGGGAGCGGCGCCGCGGGAA
GGGGCACGATGGGCTCTACCAGGGGCTGAGCACAGCCACAAAGGACACATACGAC
GCCTTGCACATGCAGGCCCTTCCACCCCGGGAATAGTCTAGAGGGCCCGTTTAAAC
CCGCTGATCAGCCTCGACTGTGCCTTCTAGTTGCCAGCCATCTGTTGTTTGCCCCTC
CCCCGTGCCTTCCTTGACCCTGGAAGGTGCCACTCCCACTGTCCTTTCCTAATAAAA
TGAGGAAATTGCATCGCATTGTCTGAGTAGGTGTCATTCTATTCTGGGGGGTGGGGT
GGGGCAGGACAGCAAGGGGGAGGATTGGGAAGACAATAGCAGGCATGCTGGGGAT
GCGGTGGGCTCTATGACTAGTGGCGAATTCCCGTGTACCAGCTGAGAGACTCTAAA
TCCAGTGACAAGTCTGTCTGCCTATTCACCGATTTTGATTCTCAAACAAATGTGTCAC
AAAGTAAGGATTCTGATGTGTATATCACAGACAAAACTGTGCTAGACATGAGGTCTAT
GGACTTCAAGAGCAACAGTGCTGTGGCCTGGAGCAACAAATCTGACTTTGCATGTG
CAAACGCCTTCAACAACAGCATTATTCCAGAAGACACCTTCTTCCCCAGCCCAGGTA
AGGGCAGCTTTGGTGCCTTCGCAGGCTGTTTCCTTGCTTCAGGAATGGCCAGGTTC
TGCCCAGAGCTCTGGTCAATGATGTCTAAAACTCCTCTGATTGGTGGTCTCGGCCTT
ATCCATTGCCACCAAAACCCTCTTTTTACTAAGCGATCGCTCCGGTGCCCGTCAGTG
GGCAGAGCGCACATCGCCCACAGTCCCCGAGAAGTTGGGGGGAGGGGTCGGCAAT
TGAACGGGTGCCTAGAGAAGGTGGCGCGGGGTAAACTGGGAAAGTGATGTCGTGT
ACTGGCTCCGCCTTTTTCCCGAGGGTGGGGGAGAACCGTATATAAGTGCAGTAGTC
GCCGTGAACGTTCTTTTTCGCAACGGGTTTGCCGCCAGAACACAGCTGAAGCTTCG
AGGGGGCTCGCATCTCTCCTTCACGCGCCCGCCGCCCTACCTGAGGCCGCCATCCA
CGCCGGTTGAGTCGCGTTCTGCCGCCTCCCGCCTGTGGTGCCTCCTGAACTGCGTC
CGCCGTCTAGGTAAGTTTAAAGCTCAGGTCGAGACCGGGCCTTTGTCCGGCGCTCC
CTTGGAGCCTACCTAGACTCAGCCGGCTCTCCACGCTTTGCCTGACCCTGCTTGCT
CAACTCTACGTCTTTGTTTCGTTTTCTGTTCTGCGCCGTTACAGATCCAAGCTGTGAC
CGGCGCCTACCTGAGATCACCGGCGCCACCATGGCTTCTTACCCTGGACACCAGCA
TGCTTCTGCCTTTGACCAGGCTGCCAGATCCAGGGGCCACTCCAACAGGAGAACTG
CCCTAAGACCCAGAAGACAGCAGGAAGCCACTGAGGTGAGGCCTGAGCAGAAGAT
GCCAACCCTGCTGAGGGTGTACATTGATGGACCTCATGGCATGGGCAAGACCACCA
CCACTCAACTGCTGGTGGCACTGGGCTCCAGGGATGACATTGTGTATGTGCCTGAG
CCAATGACCTACTGGAGAGTGCTAGGAGCCTCTGAGACCATTGCCAACATCTACACC
ACCCAGCACAGGCTGGACCAGGGAGAAATCTCTGCTGGAGATGCTGCTGTGGTGAT
GACCTCTGCCCAGATCACAATGGGAATGCCCTATGCTGTGACTGATGCTGTTCGGC
TCCTCACATTGGAGGAGAGGCTGGCTCTTCTCATGCCCCTCCACCTGCCCTGACCC
TGATCTTTGACAGACACCCCATTGCAGCCCTGCTGTGCTACCCAGCAGCAAGGTAC
CTCATGGGCTCCATGACCCCACAGGCTGTGCTGGCTTTTGTGGCCCTGATCCCTCC
AACCCTCCCTGGCACCAACATTGTTCTGGGAGCACTGCCTGAAGACAGACACATTGA
CAGGCTGGCAAAGAGGCAGAGACCTGGAGAGAGACTGGACCTGGCCATGCTGGCT
GCAATCAGAAGGGTGTATGGACTGCTGGCAAACACTGTGAGATACCTCCAGTGTGG
AGGCTCTTGGAGAGAGGACTGGGGACAGCTCTCTGGAACAGCAGTGCCCCCTCAA
GGAGCTGAGCCCCAGTCCAATGCTGGTCAAGACCCCACATTGGGGACACCCTGTT
CACCCTGTTCAGAGCCCCTGAGCTGCTGGCTCCCAATGGAGACCTGTACAATGTGT
TTGCCTGGGCTCTGGATGTTCTAGCCAAGAGGCTGAGGTCCATCGCATGTGTTCATCC
TGGACTATGACCAGTCCCCTGCTGGATGCAGAGATGCTCTGCTGCAACTAACCTCTG
GCATGGTGCAGACCCATGTGACCACCCCTGGCAGCATCCCCACCATCTGTGACCTA
GCCAGAACCTTTGCCAGGGAGATGGGAGAGGCCAACTAAGGCGCGCCACTCGAGC
GCTAGCTGGCCAGACATGATAAGATACATTGATGAGTTTGGACAAACCACAACTAGA
ATGCAGTGAAAAAAATGCTTTATTTGTGAAATTTGTGATGCTATTGCTTTATTTGTAAC
CATTATAAGCTGCAATAAACAAGTTAACAACAACAATTGCATTCATTTTATGTTTCAGG
TTCAGGGGGAGGTGTGGGAGGTTTTTTAAAGCAAGTAAAACCTCTACAAATGTGGTA
TGGAAGGCGCGCCAATTCGCCCTATAGTGAGTCGTATTACGTCGCGCTCACTGGC
CGTCGTTTTACAACGTCGTGACTGGGAAAACCCTGGCGTTACCCAACTTAATCGCCT
TGCAGCACATCCCCCTTTCGCCAGCTGGCGTAATAGCGAAGAGGCCCGCACCGAAA
CGCCCTTCCCAACAGTTGCGCAGCCTGAATGGCGAATGGGAGCGCCCTGTAGCGG
CGCATTAAGCGCGGCGGGTGTGGTGGTTACGCGCAGCGTGACCGCTACACTTGCC
AGCGCCCTAGCGCCCGCTCCTTTCGCTTTCTTCCCTTCCTTTCTCGCCACGTTCGCC
```

TABLE 5-continued

Sequences referred to in example 2.

| | | |
|---|---|---|
| | | GGCTTTCCCCGTCAAGCTCTAAATCGGGGGCTCCCTTTAGGGTTCCGATTTAGTGCT<br>TTACGGCACCTCGACCCCAAAAAACTTGATTAGGGTGATGGTTGGCCTGTAGTGGG<br>CCATAGCCCTGATAGACGGTTTTTCGCCCTTTGACGTTGGAGTCCACGTTCTTTAATA<br>GTGGACTCTTGTTCCAAACTGGAACAACACTCAACCCTATCTCGGTCTATTCTTTTGA<br>TTTATAAGGGATTTTGCCGATTTCGGCCTATTGGTTAAAAAATGAGCTGATTTAACAA<br>AAATTTAACGCGAATTTTAACAAAATATTAACGCTTACAATTTAG |
| 64 | Matrice CD25<br>locus_IL15_<br>2A_sIL15Ra<br>pCLS30519<br>full sequence | GTTTATTATTCCTGTTCCACAGCTATTGTCTGCCATATAAAAACTTAGGCCAGGCACA<br>GTGGCTCACACCTGTAATCCCAGCACTTTGGAAGGCCGAGGCAGGCAGATCACAAG<br>GTCAGGAGTTCGAGACCAGCCTGGCCAACATAGCAAAACCCCATCTCTACTAAAAAT<br>ACAAAAATTAGCCAGGCATGGTGGCGTGTGCACTGGTTTAGAGTGAGGACCACATTT<br>TTTTGGTGCCGTGTTACACATATGACCGTGACTTTGTTACACCACTACAGGAGGAAG<br>AGTAGAAGAACAATCGGTTCTGGCGTGAAACAGACTTTGAATTTTGACCTTCTCAAGT<br>TGGCGGGAGACGTGGAGTCCAACCCAGGGCCCGGTACCGGGTCCGCCACCATGGA<br>CTGGACCTGGATTCTGTTCCTCGTGGCTGCTGCTACAAGAGTGCACAGCGGCATTC<br>ATGTCTTCATTTTGGGCTGTTTCAGTGCAGGGCTTCCTAAAACAGAAGCCAACTGGG<br>TGAATGTAATAAGTGATTTGAAAAAAATTGAAGATCTTATTCAATCTATGCATATTGAT<br>GCTACTTTATATACGGAAAGTGATGTTCACCCCAGTTGCAAAGTAACAGCAATGAAG<br>TGCTTTCTCTTGGAGTTACAAGTTATTTCACTTGAGTCCGGAGATGCAAGTATTCATG<br>ATACAGTAGAAAATCTGATCATCCTAGCAAACAACAGTTTGTCTTCTAATGGGAATGT<br>AACAGAATCTGGATGCAAAGAATGTGAGGAACTGGAGGAAAAAAATATTAAAGAATT<br>TTTGCAGAGTTTTGTACATATTGTCCAAATGTTCATCAACACTTCTGGAAGCGGAGCT<br>ACTAACTTCAGCCTGCTGAAGCAGGCTGGAGACGTGGAGGAGAACCCTGGACCTGG<br>GACCGGCTCTGCAACCATGGATTGGACGTGGATCCTGTTTCTCGTGGCAGCTGCCA<br>CAAGAGTTCACAGTATCACGTGCCCTCCCCCCATGTCCGTGGAACACGCAGACATC<br>TGGGTCAAGAGCTACAGCTTGTACTCCAGGGAGCGGTACATTTGTAACTCTGGTTTC<br>AAGCGTAAAGCCGGCACGTCCAGCCTGACGGAGTGCGTGTTGAACAAGGCCACGA<br>ATGTCGCCCACTGGACAACCCCCAGTCTCAAATGCATTAGAGACCCTGCCCTGGTTC<br>ACCAAAGGCCAGCGCCACCCTCCACAGTAACGACGGCAGGGGTGACCCCACAGCC<br>AGAGAGCCTCTCCCCTTCTGGAAAAGAGCCCGCAGCTTCATCTCCCAGCTCAAACAA<br>CACAGCGGCCACAACAGCAGCTATTGTCCCGGGCTCCCAGCTGATGCCTTCAAAAT<br>CACCTTCCACAGGAACCACAGAGATAAGCAGTCATGAGTCCTCCCACGGCACCCCC<br>TCTCAGACAACAGCCAAGAACTGGGAACTCACAGCATCCGCCTCCCACCAGCCGCC<br>AGGTGTGTATCCACAGGGCCACAGCGACACCACTGAGGGCAGAGGCAGCCTGCTG<br>ACCTGCGGCGACGTCGAGGAGAACCCCGGGCCCATGGGGGCAGGTGCCACCGGC<br>CGCGCCATGGACGGGCCGCGCCTGCTGCTGTTGCTGCTTCTGGGGGTGTCCCTTG<br>GAGGTGCCAAGGAGGCATGCCCCACAGGCCTGTACACACACAGCGGTGAGTGCTG<br>CAAAGCCTGCAACCTGGGCGAGGGTGTGGCCCAGCCTTGTGGAGCCAACCAGACC<br>GTGTGTGAGCCCTGCCTGGACAGCGTGACGTTCTCCGACGTGGTGAGCGCGACCG<br>AGCCGTGCAAGCCGTGCACCGAGTGCGTGGGGCTCCAGAGCATGTCGGCGCCGTG<br>CGTGGAGGCCGATGACGCCGTGTGCCGCTGCGCCTACGGCTACTACCAGGATGAG<br>ACGACTGGGCGCTGCGAGGCGTGCCGCGTGTGCGAGGCGGGCTCGGGCCTCGTG<br>TTCTCCTGCCAGGACAAGCAGAACACCGTGTGCGAGGAGTGCCCCGACGGCACGT<br>ATTCCGACGAGGCCAACCACGTGGACCCGTGCCTGCCCTGCACCGTGTGCGAGGA<br>CACCGAGCGCCAGCTCCGCGAGTGCACACGCTGGGCCGACGCCGAGTGCGAGGA<br>GATCCCTGGCCGTTGGATTACACGGTCCACACCCCCAGAGGGCTCGGACAGCACA<br>GCCCCCAGCACCCAGGAGCCTGAGGCACCTCCAGAACAAGACCTCATAGCCAGCA<br>CGGTGGCAGGTGTGGTGACCACAGTGATGGGCAGCTCCCAGCCCGTGGTGACCCG<br>AGGCACCACCGACAACCTCATCCCTGTCTATTGCTCCATCCTGGCTGCTGTGGTTGT<br>GGGTCTTGTGGCCTACATAGCCTTCAAGAGGTGAAAAACCAAAAGAACAAGAATTTC<br>TTGGTAAGAAGCCGGGAACAGACAACAGAAGTCATGAAGCCCAAGTGAAATCAAAG<br>GTGCTAAATGGTCGCCCAGGAGACATCCGTTGTGCTTGCCTGCGTTTTGGAAGCTCT<br>GAAGTCACATCACAGGACACGGGCAGTGGCAACCTTGTCTCTATGCCAGCTCAGT<br>CCCATCAGAGAGCGAGCGCTACCCACTTCTAAATAGCAATTTCGCCGTTGAAGAGGA<br>AGGGCAAAACCACTAGAACTCTCCATCTTATTTTCATGTATATGTGTTCATGCGATCG<br>CTCCGGTGCCCGTCAGTGGGCAGAGCGCACATCGCCCACAGTCCCCGAGAAGTTG<br>GGGGGAGGGGTCGGCAATTGAACGGGTGCCTAGAGAAGGTGGCGCGGGGTAAACT<br>GGGAAAGTGATGTCGTGTACTGGCTCCGCCTTTTTCCCGAGGGTGGGGGAGAACCG<br>TATATAAGTGCAGTAGTCGCCGTGAACGTTCTTTTTCGCAACGGGTTTGCCGCCAGA<br>ACACAGCTGAAGCTTCGAGGGGCTCGCATCTCTCCTTCACGCGCCCGCCGCCCTAC<br>CTGAGGCCGCCATCCACGCCGGTTGAGTCGCGTTCTGCCGCCTCCCGCCTGTGGT<br>GCCTCCTGAACTGCGTCCGCCGTCTAGGTAAGTTTAAAGCTCAGGTCGAGACCGGG<br>CCTTTGTCCGGCGCTCCCTTGGAGCCTACCTAGACTCAGCCGGCTCTCCACGCTTT<br>GCCTGACCCTGCTTGCTCAACTCTACGTCTTTGTTTCGTTTTCTGTTCTGCGCCGTTA<br>CAGATCCAAGCTGTGACCGGCGCCTACCTGAGATCACCGGCGCCACCATGGCTTCT<br>TACCCTGGACACCAGCATGCTTCTGCCTTTGACCAGGCTGCCAGATCCAGGGGCCA<br>CTCCAACAGGAGAACTGCCCTAAGACCCAGAAGCAGCAGGAAGCCACTGAGGTGA<br>GGCCTGAGCAGAAGATGCCAACCCTGCTGAGGGTGTACATTGATGGACCTCATGGC<br>ATGGGCAAGACCACCACCACTCAACTGCTGGTGGCACTGGGCTCCAGGGATGACAT<br>TGTGTATGTGCCTGAGCCAATGACCTACTGGAGAGTGCTAGGAGCCTCTGAGACCA<br>TTGCCAACATCTACACCACCCAGCACAGGCTGGACCAGGGAGAAATCTCTGCTGGA<br>GATGCTGCTGTGGTGATGACCTCTGCCCAGATCACAATGGGAATGCCCTATGCTGT<br>GACTGATGCTGTTCTGGCTCCTCACATTGGAGGAGAGGCTGGCTCTTCTCATGCCC<br>CTCCACCTGCCCTGACCCTGATCTTTGACAGACACCCCATTGCAGCCCTGCTGTGCT<br>ACCCAGCAGCAAGGTACCTCATGGGCTCCATGACCCCACAGGCTGTGCTGGCTTTT<br>GTGGCCCTGATCCCTCCAACCCTCCCTGGCACCAACATTGTTCTGGGAGCACTGCC<br>TGAAGACAGACACATTGACAGGCTGGCAAAGAGGCAGAGACCTGGAGAGAGACTG<br>GACCTGGCCATGCTGGCTGCAATCAGAAGGGTGTATGGACTGCTGGCAAACACTGT |

TABLE 5-continued

Sequences referred to in example 2.

|  |  |
|---|---|
|  | GAGATACCTCCAGTGTGGAGGCTCTTGGAGAGAGGACTGGGGACAGCTCTCTGGAA<br>CAGCAGTGCCCCCTCAAGGAGCTGAGCCCCAGTCCAATGCTGGTCCAAGACCCCAC<br>ATTGGGGACACCCTGTTCACCCTGTTCAGAGCCCCTGAGCTGCTGGCTCCCAATGG<br>AGACCTGTACAATGTGTTTGCCTGGGCTCTGGATGTTCTAGCCAAGAGGCTGAGGT<br>CCATGCATGTGTTCATCCTGGACTATGACCAGTCCCCTGCTGGATGCAGAGATGCTC<br>TGCTGCAACTAACCTCTGGCATGGTGCAGACCCATGTGACCACCCCTGGCAGCATC<br>CCCACCATCTGTGACCTAGCCAGAACCTTTGCCAGGGAGATGGGAGAGGCCAACTA<br>AGGCGCGCCACTCGAGCGCTAGCTGGCCAGACATGATAAGATACATTGATGAGTTT<br>GGACAAACCACAACTAGAATGCAGTGAAAAAAATGCTTTATTTGTGAAATTTGTGATG<br>CTATTGCTTTATTTGTAACCATTATAAGCTGCAATAAACAAGTTAACAACAACAATTGC<br>ATTCATTTTATGTTTCAGGTTCAGGGGGAGGTGTGGGAGGTTTTTTAAAGCAAGTAAA<br>ACCTCTACAAATGTGGTATGGAAGGCGCGCCCAATTCGCCCTATAGTGAGTCGTATT<br>ACGTCGCGCTCACTGGCCGTCGTTTTACAACGTCGTGACTGGGAAAACCCTGGCGT<br>TACCCAACTTAATCGCCTTGCAGCACATCCCCCTTTCGCCAGCTGGCGTAATAGCGA<br>AGAGGCCCGCACCGAAACGCCCTTCCCAACAGTTGCGCAGCCTGAATGGCGAATG<br>GGAGCGCCCTGTAGCGGCGCATTAAGCGCGGCGGGTGTGGTGGTTACGCGCAGCG<br>TGACCGCTACACTTGCCAGCGCCCTAGCGCCCGCTCCTTTCGCTTTCTTCCCTTCCT<br>TTCTCGCCACGTTCGCCGGCTTTCCCCGTCAAGCTCTAAATCGGGGGCTCCCTTTAG<br>GGTTCCGATTTAGTGCTTTACGGCACCTCGACCCCAAAAAACTTGATTAGGGTGATG<br>GTTGGCCTGTAGTGGGCCATAGCCCTGATAGACGGTTTTTCGCCCTTTGACGTTGGA<br>GTCCACGTTCTTTAATAGTGGACTCTTGTTCCAAACTGGAACAACACTCAACCCTATC<br>TCGGTCTATTCTTTTGATTTATAAGGGATTTTGCCGATTTCGGCCTATTGGTTAAAAAA<br>TGAGCTGATTTAACAAAAATTTAACGCGAATTTTAACAAAATATTAACGCTTACAATTT<br>AGGTGGCACTTTTCGGGGAAATGTGCGCGGAACCCCTATTTGTTTATTTTTCTAAATA<br>CATTCAAATATGTATCCGCTCATGAGACAATAACCCTGATAAATGCTTCAATAATATT<br>GAAAAAGGAAGAGTATGAGTATTCAACATTTCCGTGTCGCCCTTATTCCCTTTTTTGC<br>GGCATTTTGCCTTCCTGTTTTTGCTCACCCAGAAACGCTGGTGAAAGTAAAAGATGC<br>TGAAGATCAGTTGGGTGCACGAGTGGGTTACATCGAACTGGATCTCAACAGCGGTA<br>AGATCCTTGAGAGTTTTCGCCCCGAAGAACGTTTTCCAATGATGAGCACTTTTAAAGT<br>TCTGCTATGTGGCGCGGTATTATCCCGTATTGACGCCGGGCAAGAGCAACTCGGTC<br>GCCGCATACACTATTCTCAGAATGACTTGGTTGAGTACTCACCAGTCACAGAAAAGC<br>ATCTTACGGATGGCATGACAGTAAGAGAATTATGCAGTGCTGCCATAACCATGAGTG<br>ATAACACTGCGGCCAACTTACTTCTGACAACGATCGGAGGACCGAAGGAGCTAACC<br>GCTTTTTTGCACAACATGGGGGATCATGTAACTCGCCTTGATCGTTGGGAACCGGAG<br>CTGAATGAAGCCATACCAAACGACGAGCGTGACACCACGATGCCTGTAGCAATGGC<br>AACAACGTTGCGCAAACTATTAACTGGCGAACTACTTACTCTAGCTTCCCGGCAACA<br>ATTAATAGACTGGATGGAGGCGGATAAAGTTGCAGGACCACTTCTGCGCTCGGCCC<br>TTCCGGCTGGCTGGTTTATTGCTGATAAATCTGGAGCCGGTGAGCGTGGTTCTCGC<br>GGTATCATTGCAGCACTGGGGCCAGATGGTAAGCCCTCCCGTATCGTAGTTATCTAC<br>ACGACGGGGAGTCAGGCAACTATGGATGAACGAAATAGACAGATCGCTGAGATAGG<br>TGCCTCACTGATTAAGCATTGGTAACTGTCAGACCAAGTTTACTCATATATACTTTAG<br>ATTGATTTAAAACTTCATTTTTAATTTAAAAGGATCTAGGTGAAGATCCTTTTTGATAAT<br>CTCATGACCAAAATCCCTTAACGTGAGTTTTCGTTCCACTGAGCGTCAGACCCCGTA<br>GAAAAGATCAAAGGATCTTCTTGAGATCCTTTTTTTCTGCGCGTAATCTGCTGCTTGC<br>AAACAAAAAAACCACCGCTACCAGCGGTGGTTTGTTTGCCGGATCAAGAGCTACCAA<br>CTCTTTTTCCGAAGGTAACTGGCTTCAGCAGAGCGCAGATACCAAATACTGTTCTTCT<br>AGTGTAGCCGTAGTTAGGCCACCACTTCAAGAACTCTGTAGCACCGCCTACATACCT<br>CGCTCTGCTAATCCTGTTACCAGTGGCTGCTGCCAGTGGCGATAAGTCGTGTCTTAC<br>CGGGTTGGACTCAAGACGATAGTTACCGGATAAGGCGCAGCGGTCGGGCTGAACG<br>GGGGGTTCGTGCACACAGCCCAGCTTGGAGCGAACGACCTACACCGAACTGAGATA<br>CCTACAGCGTGAGCTATGAGAAAGCGCCACGCTTCCCGAAGGGAGAAAGGCGGAC<br>AGGTATCCGGTAAGCGGCAGGGTCGGAACAGGAGAGCGCACGAGGGAGCTTCCAG<br>GGGGAAACGCCTGGTATCTTTATAGTCCTGTCGGGTTTCGCCACCTCTGACTTGAGC<br>GTCGATTTTTGTGATGCTCGTCAGGGGGCGGAGCCTATGGAAAAACGCCAGCAAC<br>GCGGCCTTTTTACGGTTCCTGGCCTTTTGCTGGCCTTTTGCTCACATGGTCTTTCCT<br>GCGTTATCCCCTGATTCTGTGGATAACCGTATTACCGCCTTTGAGTGAGCTGATACC<br>GCTCGCCGCAGCCGAACGACCGAGCGCAGCGAGTCAGTGAGCGAGGAAGCGGAG<br>AGCGCCCAATACGCAAACCGCCTCTCCCCGCGCGTTGGCCGATTCATTAATGCAGC<br>TGGCACGACAGGTTTCCCGACTGGAAAGCGGGCAGTGAGCGCAACGCAATTAATGT<br>GAGTTAGCTCACTCATTAGGCACCCCAGGCTTTACACTTTATGCTTCCGGCTCGTAT<br>GTTGTGTGGAATTGTGAGCGGATAACAATTTCACACAGGAAACAGCTATGACCATGA<br>TTACGCCAAGCGCGTCAATTAACCCTCACTAAAGGGAACAAAAGCTGTTAATTAA |
| 65 | Matrice PD1 locus_IL15_2A_sIL15Ra pCLS30513 full sequence | GACTCCCCAGACAGGCCCTGGAACCCCCCCACCTTCTCCCCAGCCCTGCTCGTGGT<br>GACCGAAGGGGACAACGCCACCTTCACCTGCAGCTTCTCCAACACATCGGAGAGT<br>TCGTGCTAAACTGGTACCGCATGAGCCCCAGCAACCAGACGGACAAGCTGGCCGCC<br>TTCCCCGAGGACCGCAGCCAGCCCGGCCAGGACTGCCGCTTCCGTGTCACACAAC<br>TGCCCAACGGGCGTGACTTCCACATGAGCGTGGTCAGGGCCCGGCGCAATGACAG<br>CGGCACCTACCTCTGTGGGGCCGGTTCTGGCGTGAAACAGACTTTGAATTTGACCT<br>TCTCAAGTTGGCGGGAGACGTGGAGTCCAACCCAGGGCCCGGTACCGGGTCCGCC<br>ACCATGGACTGGACCTGGATTCTGTTCCTCGTGGCTGCTGCTACAAGAGTGCACAG<br>CGGCATTCATGTCTTCATTTTGGGCTGTTTCAGTGCAGGGCTTCCTAAAACAGAAGC<br>CAACTGGGTGAATGTAATAAGTGATTTGAAAAAAATTGAAGATCTTATTCAATCTATG<br>CATATTGATGCTACTTTATATACGGAAAGTGATGTTCACCCCAGTTGCAAAGTAACAG<br>CAATGAAGTGCTTTCTCTTGGAGTTACAAGTTATTTCACTTGAGTCCGAGATGCAAG<br>TATTCATGATACAGTAGAAAATCTGATCATCCTAGCAAACAACAGTTTGTCTTCTAAT<br>GGGAATGTAACAGAATCTGGATGCAAAGAATGTGAGGAACTGGAGGAAAAAATATT<br>AAAGAATTTTTGCAGAGTTTTGTACATATTGTCCAAATGTTCATCAACACTTCTGGAA |

TABLE 5-continued

Sequences referred to in example 2.

```
GCGGAGCTACTAACTTCAGCCTGCTGAAGCAGGCTGGAGACGTGGAGGAGAACCCT
GGACCTGGGACCGGCTCTGCAACCATGGATTGGACGTGGATCCTGTTTCTCGTGGC
AGCTGCCACAAGAGTTCACAGTATCACGTGCCCTCCCCCCATGTCCGTGGAACACG
CAGACATCTGGGTCAAGAGCTACAGCTTGTACTCCAGGGAGCGGTACATTTGTAACT
CTGGTTTCAAGCGTAAAGCCGGCACGTCCAGCCTGACGGAGTGCGTGTTGAACAAG
GCCACGAATGTCGCCCACTGGACAACCCCCAGTCTCAAATGCATTAGAGACCCTGC
CCTGGTTCACCAAAGGCCAGCGCCACCCTCCACAGTAACGACGGCAGGGGTGACC
CCACAGCCAGAGAGCCTCTCCCCTTCTGGAAAAGAGCCCGCAGCTTCATCTCCCAG
CTCAAACAACACAGCGGCCACAACAGCAGCTATTGTCCCGGGCTCCCAGCTGATGC
CTTCAAAATCACCTTCCACAGGAACCACAGAGATAAGCAGTCATGAGTCCTCCCACG
GCACCCCCTCTCAGACAACAGCCAAGAACTGGGAACTCACAGCATCCGCCTCCCAC
CAGCCGCCAGGTGTGTATCCACAGGGCCACAGCGACACCACTGAGGGCAGAGGCA
GCCTGCTGACCTGCGGCGACGTCGAGGAGAACCCCGGGCCCATGGGGGCAGGTG
CCACCGGCCGCGCCATGGACGGGCCGCGCCTGCTGCTGTTGCTGCTTCTGGGGGT
GTCCCTTGGAGGTGCCAAGGAGGCATGCCCCACAGGCCTGTACACACACAGCGGT
GAGTGCTGCAAAGCCTGCAACCTGGGCGAGGGTGTGGCCCAGCCTTGTGGAGCCA
ACCAGACCGTGTGTGAGCCCTGCCTGGACAGCGTGACGTTCTCCGACGTGGTGAG
CGCGACCGAGCCGTGCAAGCCGTGCACCGAGTGCGTGGGGCTCCAGAGCATGTCG
GCGCCGTCGTGGAGGCCGATGACGCCGTGTGCCGCTGCGCCTACGGCTACTACC
AGGATGAGACGACTGGGCGCTGCGAGGCGTGCCGCGTGTGCGAGGCGGGCTCGG
GCCTCGTGTTCTCCTGCCAGGACAAGCAGAACACCGTGTGCGAGGAGTGCCCCGA
CGGCACGTATTCCGACGAGGCCAACCACGTGGACCCGTGCCTGCCCTGCACCGTG
TGCGAGGACACCGAGCGCCAGCTCCGCGAGTGCACACGCTGGGCGACGCCGAGT
GCGAGGAGATCCCTGGCCGTTGGATTACACGGTCCACACCCCCAGAGGGCTCGGA
CAGCACAGCCCCCAGCACCCAGGAGCCTGAGGCACCTCCAGAACAAGACCTCATAG
CCAGCACGGTGGCAGGTGTGGTGACCACAGTGATGGGCAGCTCCCAGCCCGTGGT
GACCCGAGGCACCACCGACAACCTCATCCCTGTCTATTGCTCCATCCTGGCTGCTG
TGGTTGTGGGTCTTGTGGCCTACATAGCCTTCAAGAGGTGATCTAGAGGGCCCGTTT
AAACCCGCTGATCAGCCTCGACTGTGCCTTCTAGTTGCCAGCCATCTGTTGTTTGCC
CCTCCCCCGTGCCTTCCTTGACCCTGGAAGGTGCCACTCCCACTGTCCTTTCCTAAT
AAAATGAGGAAATTGCATCGCATTGTCTGAGTAGGTGTCATTCTATTCTGGGGGGTG
GGGTGGGGCAGGACAGCAAGGGGGAGGATTGGGAAGACAATAGCAGGCATGCTGG
GGATGCGGTGGGCTCTATGACTAGTGGCGAATTCGGCGCAGATCAAAGAGAGCCTG
CGGGCAGAGCTCAGGGTGACAGGTGCGGCCTCGGAGGCCCCGGGGCAGGGGTGA
GCTGAGCCGGTCCTGGGGTGGGTGTCCCCTCCTGCACAGGATCAGGAGCTCCAGG
GTCGTAGGGCAGGGACCCCCCAGCTCCAGTCCAGGGCTCTGTCCTGCACCTGGGG
AATGGTGACCGGCATCTCTGTCCTCTAGCTCTGGAAGCACCCCAGCCCCTCTAGTCT
GCCCTCACCCCTGACCCTGACCCTCCACCCTGACCCCGTCCTAACCCCTGACCTTT
GGCGATCGCTCCGGTGCCCGTCAGTGGGCAGAGCGCACATCGCCCACAGTCCCCG
AGAAGTTGGGGGGAGGGGTCGGCAATTGAACGGGTGCCTAGAGAAGGTGGCGCGG
GGTAAACTGGGAAAGTGATGTCGTGTACTGGCTCCGCCTTTTTCCCGAGGGTGGGG
GAGAACCGTATATAAGTGCAGTAGTCGCCGTGAACGTTCTTTTTCGCAACGGGTTTG
CCGCCAGAACACAGCTGAAGCTTCGAGGGGCTCGCATCTCTCCTTCACGCGCCCGC
CGCCCTACCTGAGGCCGCCATCCACGCCGGTTGAGTCGCGTTCTGCCGCCTCCCG
CCTGTGGTGCCTCCTGAACTGCGTCCGCCGTCTAGGTAAGTTTAAAGCTCAGGTCG
AGACCGGGCCTTTGTCCGGCGCTCCCTTGGAGCCTACCTAGACTCAGCCGGCTCTC
CACGCTTTGCCTGACCCTGCTTGCTCAACTCTACGTCTTTGTTTCGTTTTCTGTTCTG
CGCCGTTACAGATCCAAGCTGTGACCGGCGCCTACCTGAGATCACCGGCGCCACCA
TGGCTTCTTACCCTGGACACCAGCATGCTTCTGCCTTTGACCAGGCTGCCAGATCCA
GGGGCCACTCCAACAGGAGAACTGCCCTAAGACCCAGAAGACAGCAGGAAGCCAC
TGAGGTGAGGCCTGAGCAGAAGATGCCAACCCTGCTGAGGGTGTACATTGATGGAC
CTCATGGCATGGGCAAGACCACCACCACTGCAACTGCTGGTGGCACTGGGCTCCAGG
GATGACATTGTGTATGTGCCTGAGCCAATGACCTACTGGAGAGTGCTAGGAGCCTCT
GAGACCATTGCCAACATCTACACCACCCAGCACAGGCTGGACCAGGGAGAAATCTC
TGCTGGAGATGCTGCTGTGGTGATGACCTCTGCCCAGATCACAATGGGAATGCCCT
ATGCTGTGACTGATGCTGTTCTGGCTCCTCACATTGGAGGAGAGGCTGGCTCTTCTC
ATGCCCCTCCACCTGCCCTGACCCTGATCTTTGACAGACACCCCATTGCAGCCCTG
CTGTGCTACCCAGCAGCAAGGTACCTCATGGGCTCCATGACCCCACAGGCTGTGCT
GGCTTTTGTGGCCCTGATCCCTCCAACCCTCCCTGGCACCAACATTGTTCTGGGAG
CACTGCCTGAAGACAGACACATTGACAGGCTGGCAAAGAGGCAGAGACCTGGAGAG
AGACTGGACCTGGCCATGCTGGCTGCAATCAGAAGGGTGTATGGACTGCTGGCAAA
CACTGTGAGATACCTCCAGTGTGGAGGCTCTTGGAGAGAGGACTGGGGACAGCTCT
CTGGAACAGCAGTGCCCCTCAAGGAGCTGAGCCCCAGTCCAATGCTGGTCCAAGA
CCCCACATTGGGGACACCCTGTTCACCCTGTTCAGAGCCCCTGAGCTGCTGGCTCC
CAATGGAGACCTGTACAATGTGTTTGCCTGGGCTCTGGATGTTCTAGCCAAGAGGCT
GAGGTCCATGCATGTGTTCATCCTGGACTATGACCAGTCCCCTGCTGGATGCAGAG
ATGCTCTGCTGCAACTAACCTCTGGCATGGTGCAGACCCATGTGACCACCCCTGGC
AGCATCCCCACCATCTGTGACCTAGCCAGAACCTTTGCCAGGGAGATGGGAGAGGC
CAACTAAGGCGCGCCACTCGAGCGCTAGCTGGCCAGACATGATAAGATACATTGAT
GAGTTTGGACAAACCACAACTAGAATGCAGTGAAAAAAATGCTTTATTTGTGAAATTT
GTGATGCTATTGCTTTATTTGTAACCATTATAAGCTGCAATAAACAAGTTAACAACAAC
AATTGCATTCATTTTATGTTTCAGGTTCAGGGGGAGGTGTGGGAGGTTTTTTAAAGCA
AGTAAAACCTCTACAAATGTGGTATGGAAGGCGCGCCCAATTCGCCCTATAGTGAGT
CGTATTACGTCGCGCTCACTGGCCGTCGTTTTACAACGTCGTGACTGGGAAAACCCT
GGCGTTACCCAACTTAATCGCCTTGCAGCACATCCCCCTTTCGCCAGCTGGCGTAAT
AGCGAAGAGGCCCGCACCGAAACGCCCTTCCCAACAGTTGCGCAGCCTGAATGGC
GAATGGGAGCGCCCTGTAGCGGCGCATTAAGCGCGGCGGGTGTGGTGGTTACGCG
CAGCGTGACCGCTACACTTGCCAGCGCCCTAGCGCCCGCTCCTTTCGCTTTCTTCC
```

TABLE 5-continued

Sequences referred to in example 2.

```
CTTCCTTTCTCGCCACGTTCGCCGGCTTTCCCCGTCAAGCTCTAAATCGGGGCTCC
CTTTAGGGTTCCGATTTAGTGCTTTACGGCACCTCGACCCCAAAAAACTTGATTAGG
GTGATGGTTGGCCTGTAGTGGGCCATAGCCCTGATAGACGGTTTTTCGCCCTTTGAC
GTTGGAGTCCACGTTCTTTAATAGTGGACTCTTGTTCCAAACTGGAACAACACTCAAC
CCTATCTCGGTCTATTCTTTTGATTTATAAGGGATTTTGCCGATTTCGGCCTATTGGT
TAAAAAATGAGCTGATTTAACAAAAATTTAACGCGAATTTTAACAAAATATTAACGCTT
ACAATTTAGGTGGCACTTTTCGGGGAAATGTGCGCGGAACCCCTATTTGTTTATTTTT
CTAAATACATTCAAATATGTATCCGCTCATGAGACAATAACCCTGATAAATGCTTCAA
TAATATTGAAAAAGGAAGAGTATGAGTATTCAACATTTCCGTGTCGCCCTTATTCCCT
TTTTTGCGGCATTTTGCCTTCCTGTTTTTGCTCACCCAGAAACGCTGGTGAAAGTAAA
AGATGCTGAAGATCAGTTGGGTGCACGAGTGGGTTACATCGAACTGGATCTCAACA
GCGGTAAGATCCTTGAGAGTTTTCGCCCCGAAGAACGTTTTCCAATGATGAGCACTT
TTAAAGTTCTGCTATGTGGCGCGGTATTATCCCGTATTGACGCCGGGCAAGAGCAAC
TCGGTCGCCGCATACACTATTCTCAGAATGACTTGGTTGAGTACTCACCAGTCACAG
AAAAGCATCTTACGGATGGCATGACAGTAAGAGAATTATGCAGTGCTGCCATAACCA
TGAGTGATAACACTGCGGCCAACTTACTTCTGACAACGATCGGAGGACCGAAGGAG
CTAACCGCTTTTTTGCACAACATGGGGGATCATGTAACTCGCCTTGATCGTTGGGAA
CCGGAGCTGAATGAAGCCATACCAAACGACGAGCGTGACACCACGATGCCTGTAGC
AATGGCAACAACGTTGCGCAAACTATTAACTGGCGAACTACTTACTCTAGCTTCCCG
GCAACAATTAATAGACTGGATGGAGGCGGATAAAGTTGCAGGACCACTTCTGCGCT
CGGCCCTTCCGGCTGGCTGGTTTATTGCTGATAAATCTGGAGCCGGTGAGCGTGGT
TCTCGCGGTATCATTGCAGCACTGGGGCCAGATGGTAAGCCCTCCCGTATCGTAGT
TATCTACACGACGGGGAGTCAGGCAACTATGGATGAACGAAATAGACAGATCGCTG
AGATAGGTGCCTCACTGATTAAGCATTGGTAACTGTCAGACCAAGTTTACTCATATAT
ACTTTAGATTGATTTAAAACTTCATTTTTAATTTAAAAGGATCTAGGTGAAGATCCTTT
TTGATAATCTCATGACCAAAATCCCTTAACGTGAGTTTTCGTTCCACTGAGCGTCAGA
CCCCGTAGAAAAGATCAAAGGATCTTCTTGAGATCCTTTTTTTCTGCGCGTAATCTGC
TGCTTGCAAACAAAAAAACCACCGCTACCAGCGGTGGTTTGTTTGCCGGATCAAGAG
CTACCAACTCTTTTTCCGAAGGTAACTGGCTTCAGCAGAGCGCAGATACCAAATACT
GTTCTTCTAGTGTAGCCGTAGTTAGGCCACCACTTCAAGAACTCTGTAGCACCGCCT
ACATACCTCGCTCTGCTAATCCTGTTACCAGTGGCTGCTGCCAGTGGCGATAAGTCG
TGTCTTACCGGGTTGGACTCAAGACGATAGTTACCGGATAAGGCGCAGCGGTCGGG
CTGAACGGGGGGTTCGTGCACACAGCCCAGCTTGGAGCGAACGACCTACACCGAA
CTGAGATACCTACAGCGTGAGCTATGAGAAAGCGCCACGCTTCCCGAAGGGAGAAA
GGCGGACAGGTATCCGGTAAGCGGCAGGGTCGGAACAGGAGAGCGCACGAGGGA
GCTTCCAGGGGGAAACGCCTGGTATCTTTATAGTCCTGTCGGGTTTCGCCACCTCTG
ACTTGAGCGTCGATTTTTGTGATGCTCGTCAGGGGGCGGAGCCTATGGAAAAACG
CCAGCAACGCGGCCTTTTTACGGTTCCTGGCCTTTTGCTGGCCTTTTGCTCACATGG
TCTTTCCTGCGTTATCCCCTGATTCTGTGGATAACCGTATTACCGCCTTTGAGTGAGC
TGATACCGCTCGCCGCAGCCGAACGACCGAGCGCAGCGAGTCAGTGAGCGAGGAA
GCGGAGAGCGCCCAATACGCAAACCGCCTCTCCCCGCGCGTTGGCCGATTCATTAA
TGCAGCTGGCACGACAGGTTTCCCGACTGGAAAGCGGGCAGTGAGCGCAACGCAA
TTAATGTGAGTTAGCTCACTCATTAGGCACCCCAGGCTTTACACTTTATGCTTCCGGC
TCGTATGTTGTGTGGAATTGTGAGCGGATAACAATTTCACACAGGAAACAGCTATGA
CCATGATTACGCCAAGCGCGTCAATTAACCCTCACTAAAGGGAACAAAAGCTGTTAA
TTAA
```

| 66 | Matrice CD25 locus_IL12a_2A_IL12b pCLS30520 full sequence | ```
GTTTATTATTCCTGTTCCACAGCTATTGTCTGCCATATAAAAACTTAGGCCAGGCACA
GTGGCTCACACCTGTAATCCCAGCACTTTGGAAGGCCGAGGCAGGCAGATCACAAG
GTCAGGAGTTCGAGACCAGCCTGGCCAACATAGCAAAACCCCATCTCTACTAAAAAT
ACAAAAATTAGCCAGGCATGGTGGCGTGTGCACTGGTTTAGAGTGAGGACCACATTT
TTTTGGTGCCGTGTTACACATATGACCGTGACTTTGTTACACCACTACAGGAGGAAG
AGTAGAAGAACAATCGGTTCTGGCGTGAAACAGACTTTGAATTTTGACCTTCTCAAGT
TGGCGGGAGACGTGGAGTCCAACCCAGGGCCCATGTGGCCCCCTGGGTCAGCCTC
CCAGCCACCGCCCTCACCTGCCGCGGCCACAGGTCTGCATCCAGCGGCTCGCCCT
GTGTCCCTGCAGTGCCGGCTCAGCATGTGTCCAGCGCGCAGCCTCCTCCTTGTGGC
TACCCTGGTCCTCCTGGACCACCTCAGTTTGGCCAGAAACCTCCCCGTGGCCACTC
CAGACCCAGGAATGTTCCCATGCCTTCACCACTCCCAAAACCTGCTGAGGGCCGTC
AGCAACATGCTCCAGAAGGCCAGACAAACTCTAGAATTTTACCCTTGCACTTCTGAA
GAGATTGATCATGAAGATATCACAAAAGATAAAACCAGCACAGTGGAGGCCTGTTTA
CCATTGGAATTAACCAAGAATGAGAGTTGCCTAAATTCCAGAGAGACCTCTTTCATAA
CTAATGGGAGTTGCCTGGCCTCCAGAAAGACCTCTTTTATGATGGCCCTGTGCCTTA
GTAGTATTTATGAAGACTTGAAGATGTACCAGGTGGAGTTCAAGACCATGAATGCAA
AGCTTCTGATGGATCCTAAGAGGCAGATCTTTCTAGATCAAAACATGCTGGCAGTTA
TTGATGAGCTGATGCAGGCCCTGAATTTCAACAGTGAGACTGTGCCACAAAAATCCT
CCCTTGAAGAACCGGATTTTTATAAAACTAAAATCAAGCTCTGCATACTTCTTCATGC
TTTCAGAATTCGGGCAGTGACTATTGATAGAGTGATGAGCTATCTGAATGCTTCCGG
AAGCGGAGCTACTAACTTCAGCCTGCTGAAGCAGGCTGGAGACGTGGAGGAGAACC
CTGGACCTATGTGTCACCAGCAGTTGGTCATCTCTTGGTTTTCCCTGGTTTTTCTGG
CATCTCCCCTCGTGGCCATATGGAACTGAAGAAAGATGTTTATGTCGTAGAATTGG
ATTGGTATCCGGATGCCCCTGGAGAAATGGTGGTCCTCACCTGTGACACCCCTGAA
GAAGATGGTATCACCTGGACCTTGGACCAGAGCAGTGAGGTCTTAGGCTCTGGCAA
AACCCTGACCATCCAAGTCAAAGAGTTTGGAGATGCTGGCCAGTACACCTGTCACAA
AGGAGGCGAGGTTCTAAGCCATTCGCTCCTGCTGCTTCACAAAAAGGAAGATGGAA
TTTGGTCCACTGATATTTAAAGGACCAGAAGAACCCAAAAATAAGACCTTTCTAAG
ATGCGAGGCCAAGAATTATTCTGGACGTTTCACCTGCTGGTGGCTGACGACAATCAG
TACTGATTTGACATTCAGTGTCAAAAGCAGCAGAGGCTCTTCTGACCCCCAAGGGGT
GACGTGCGGAGCTGCTACACTCTCTGCAGAGAGAGTCAGAGGGGACAACAAGGAG
``` |

TABLE 5-continued

Sequences referred to in example 2.

```
TATGAGTACTCAGTGGAGTGCCAGGAGGACAGTGCCTGCCCAGCTGCTGAGGAGA
GTCTGCCCATTGAGGTCATGGTGGATGCCGTTCACAAGCTCAAGTATGAAAACTACA
CCAGCAGCTTCTTCATCAGGGACATCATCAAACCTGACCCACCCAAGAACTTGCAGC
TGAAGCCATTAAAGAATTCTCGGCAGGTGGAGGTCAGCTGGGAGTACCCTGACACC
TGGAGTACTCCACATTCCTACTTCTCCCTGACATTCTGCGTTCAGGTCCAGGGCAAG
AGCAAGAGAGAAAAGAAAGATAGAGTCTTCACGGACAAGACCTCAGCCACGGTCAT
CTGCCGCAAAAATGCCAGCATTAGCGTGCGGGCCCAGGACCGCTACTATAGCTCAT
CTTGGAGCGAATGGGCATCTGTGCCCTGCAGTGAGGGCAGAGGCAGCCTGCTGAC
CTGCGGCGACGTCGAGGAGAACCCCGGGCCCATGGGGGCAGGTGCCACCGGCCG
CGCCATGGACGGGCCGCGCCTGCTGCTGTTGCTGCTTCTGGGGGTGTCCCTTGGA
GGTGCCAAGGAGGCATGCCCCACAGGCCTGTACACACACAGCGGTGAGTGCTGCA
AAGCCTGCAACCTGGGCGAGGGTGTGGCCCAGCCTTGTGGAGCCAACCAGACCGT
GTGTGAGCCCTGCCTGGACAGCGTGACGTTCTCCGACGTGGTGAGCGCGACCGAG
CCGTGCAAGCCGTGCACCGAGTGCGTGGGGCTCCAGAGCATGTCGGCGCCGTGCG
TGGAGGCCGATGACGCCGTGTGCCGCTGCGCCTACGGCTACTACCAGGATGAGAC
GACTGGGCGCTGCGAGGCGTGCCGCGTGTGCGAGGCGGGCTCGGGCCTCGTGTT
CTCCTGCCAGGACAAGCAGAACACCGTGTGCGAGGAGTGCCCCGACGGCACGTAT
TCCGACGAGGCCAACCACGTGGACCCGTGCCTGCCCTGCACCGTGTGCGAGGACA
CCGAGCGCCAGCTCCGCGAGTGCACACGCTGGGCCGACGCCGAGTGCGAGGAGA
TCCCTGGCCGTTGGATTACACGGTCCACACCCCCAGAGGGCTCGGACAGCACAGC
CCCCAGCACCCAGGAGCCTGAGGCACCTCCAGAACAAGACCTCATAGCCAGCACG
GTGGCAGGTGTGGTGACCACAGTGATGGGCAGCTCCCAGCCCGTGGTGACCCGAG
GCACCACCGACAACCTCATCCCTGTCTATTGCTCCATCCTGGCTGCTGTGGTTGTGG
GTCTTGTGGCCTACATAGCCTTCAAGAGGTGAAAAACCAAAAGAACAAGAATTTCTT
GGTAAGAAGCCGGGAACAGACAACAGAAGTCATGAAGCCCAAGTGAAATCAAAGGT
GCTAAATGGTCGCCCAGGAGACATCCGTTGTGCTTGCCTGCGTTTTGGAAGCTCTG
AAGTCACATCACAGGACACGGGGCAGTGGCAACCTTGTCTCTATGCCAGCTCAGTC
CCATCAGAGAGCGAGCGCTACCCACTTCTAAATAGCAATTTCGCCGTTGAAGAGGAA
GGGCAAAACCACTAGAACTCTCCATCTTATTTTCATGTATATGTGTTCATGCGATCGC
TCCGGTGCCCGTCAGTGGGCAGAGCGCACATCGCCCACAGTCCCCGAGAAGTTGG
GGGGAGGGGTCGGCAATTGAACGGGTGCCTAGAGAAGGTGGCGCGGGGTAAACTG
GGAAAGTGATGTCGTGTACTGGCTCCGCCTTTTTCCCGAGGGTGGGGGAGAACCGT
ATATAAGTGCAGTAGTCGCCGTGAACGTTCTTTTTCGCAACGGGTTTGCCGCCAGAA
CACAGCTGAAGCTTCGAGGGGCTCGCATCTCTCCTTCACGCGCCCGCCGCCCTACC
TGAGGCCGCCATCCACGCCGGTTGAGTCGCGTTCTGCCGCCTCCCGCCTGTGGTG
CCTCCTGAACTGCGTCCGCCGTCTAGGTAAGTTTAAAGCTCAGGTCGAGACCGGGC
CTTTGTCCGGCGCTCCCTTGGAGCCTACCTAGACTCAGCCGGCTCTCCACGCTTTG
CCTGACCCTGCTTGCTCAACTCTACGTCTTTGTTTCGTTTTCTGTTCTGCGCCGTTAC
AGATCCAAGCTGTGACCGGCGCCTACCTGAGATCACCGGCGCCACCATGGCTTCTT
ACCCTGGACACCAGCATGCTTCTGCCTTTGACCAGGCTGCCAGATCCAGGGGCCAC
TCCAACAGGAGAACTGCCCTAAGACCCAGAAGACAGCAGGAAGCCACTGAGGTGAG
GCCTGAGCAGAAGATGCCAACCCTGCTGAGGGTGTACATTGATGGACCTCATGGCA
TGGGCAAGACCACCACCACTCAACTGCTGGTGGCACTGGGCTCCAGGGATGACATT
GTGTATGTGCCTGAGCCAATGACCTACTGGAGAGTGCTAGGAGCCTCTGAGACCAT
TGCCAACATCTACACCACCCAGCACAGGCTGGACCAGGGAGAAATCTCTGCTGGAG
ATGCTGCTGTGGTGATGACCTCTGCCCAGATCACAATGGGAATGCCCTATGCTGTGA
CTGATGCTGTTCTGGCTCCTCACATTGGAGGAGAGGCTGGCTCTTCTCATGCCCCTC
CACCTGCCCTGACCCTGATCTTTGACAGACACCCCATTGCAGCCCTGCTGTGCTACC
CAGCAGCAAGGTACCTCATGGGCTCCATGACCCCACAGGCTGTGCTGGCTTTTGTG
GCCCTGATCCCTCCAACCCTCCCTGGCACCAACATTGTTCTGGGAGCACTGCCTGA
AGACAGACACATTGACAGGCTGGCAAAGAGGCAGAGACCTGGAGAGAGACTGGAC
CTGGCCATGCTGGCTGCAATCAGAAGGGTGTATGGACTGCTGGCAAACACTGTGAG
ATACCTCCAGTGTGGAGGCTCTTGGAGAGAGGACTGGGGACAGCTCTCTGGAACAG
CAGTGCCCCCTCAAGGAGCTGAGCCCCAGTCCAATGCTGGTCCAAGACCCCACATT
GGGGACACCCTGTTCACCCTGTTCAGAGCCCCTGAGCTGCTGGCTCCAATGGAGA
CCTGTACAATGTGTTTGCCTGGGCTCTGGATGTTCTAGCCAAGAGGCTGAGGTCCAT
GCATGTGTTCATCCTGGACTATGACCAGTCCCCTGCTGGATGCAGAGATGCTCTGCT
GCAACTAACCTCTGGCATGGTGCAGACCCATGTGACCACCCCTGGCAGCATCCCCA
CCATCTGTGACCTAGCCAGAACCTTTGCCAGGGAGATGGGAGAGGCCAACTAAGGC
GCGCCACTCGAGCGCTAGCTGGCCAGACATGATAAGATACATTGATGAGTTTGGAC
AAACCACAACTAGAATGCAGTGAAAAAAATGCTTTATTTGTGAAATTTGTGATGCTAT
TGCTTTATTTGTAACCATTATAAGCTGCAATAAACAAGTTAACAACAACAATTGCATTC
ATTTTATGTTTCAGGTTCAGGGGAGGTGTGGGAGGTTTTTTAAAGCAAGTAAAACC
TCTACAAATGTGGTATGGAAGGCGCGCCCAATTCGCCCTATAGTGAGTCGTATTACG
TCGCGCTCACTGGCCGTCGTTTTACAACGTCGTGACTGGGAAAACCCTGGCGTTAC
CCAACTTAATCGCCTTGCAGCACATCCCCCTTTCGCCAGCTGGCGTAATAGCGAAGA
GGCCCGCACCGAAACGCCCTTCCCAACAGTTGCGCAGCCTGAATGGCGAATGGGA
GCGCCCGTAGCGGCGCATTAAGCGCGGCGGGTGTGGTGGTTACGCGCAGCGTGA
CCGCTACACTTGCCAGCGCCCTAGCGCCCGCTCCTTTCGCTTTCTTCCCTTCCTTTC
TCGCCACGTTCGCCGGCTTTCCCCGTCAAGCTCTAAATCGGGGGCTCCCTTTAGGG
TTCCGATTTAGTGCTTTACGGCACCTCGACCCCAAAAAACTTGATTAGGGTGATGGT
TGGCCTGTAGTGGGCCATAGCCCTGATAGACGGTTTTTCGCCCTTTGACGTTGGAGT
CCACGTTCTTTAATAGTGGACTCTTGTTCCAAACTGGAACAACACTCAACCCTATCTC
GGTCTATTCTTTTGATTTATAAGGGATTTTGCCGATTTCGGCCTATTGGTTAAAAAAT
GAGCTGATTTAACAAAAATTTAACGCGAATTTTAACAAAATATTAACGCTTACAATTTA
GGTGGCACTTTTCGGGGAAATGTGCGCGGAACCCCTATTTGTTTATTTTTCTAAATAC
ATTCAAATATGTATCCGCTCATGAGACAATAACCCTGATAAATGCTTCAATAATATTGA
AAAAGGAAGAGTATGAGTATTCAACATTTCCGTGTCGCCCTTATTCCCTTTTTTGCGG
```

TABLE 5-continued

Sequences referred to in example 2.

| | | |
|---|---|---|
| | | CATTTTGCCTTCCTGTTTTTGCTCACCCAGAAACGCTGGTGAAAGTAAAAGATGCTGA |
| | | AGATCAGTTGGGTGCACGAGTGGGTTACATCGAACTGGATCTCAACAGCGGTAAGA |
| | | TCCTTGAGAGTTTTCGCCCCGAAGAACGTTTTCCAATGATGAGCACTTTTAAAGTTCT |
| | | GCTATGTGGCGCGGTATTATCCCGTATTGACGCCGGGCAAGAGCAACTCGGTCGCC |
| | | GCATACACTATTCTCAGAATGACTTGGTTGAGTACTCACCAGTCACAGAAAAGCATCT |
| | | TACGGATGGCATGACAGTAAGAGAATTATGCAGTGCTGCCATAACCATGAGTGATAA |
| | | CACTGCGGCCAACTTACTTCTGACAACGATCGGAGGACCGAAGGAGCTAACCGCTT |
| | | TTTTGCACAACATGGGGGATCATGTAACTCGCCTTGATCGTTGGGAACCGGAGCTGA |
| | | ATGAAGCCATACCAAACGACGAGCGTGACACCACGATGCCTGTAGCAATGGCAACA |
| | | ACGTTGCGCAAACTATTAACTGGCGAACTACTTACTCTAGCTTCCCGGCAACAATTAA |
| | | TAGACTGGATGGAGGCGGATAAAGTTGCAGGACCACTTCTGCGCTCGGCCCTTCCG |
| | | GCTGGCTGGTTTATTGCTGATAAATCTGGAGCCGGTGAGCGTGGTTCTCGCGGTAT |
| | | CATTGCAGCACTGGGGCCAGATGGTAAGCCCTCCCGTATCGTAGTTATCTACACGA |
| | | CGGGGAGTCAGGCAACTATGGATGAACGAAATAGACAGATCGCTGAGATAGGTGCC |
| | | TCACTGATTAAGCATTGGTAACTGTCAGACCAAGTTTACTCATATATACTTTAGATTGA |
| | | TTTAAAACTTCATTTTTAATTTAAAAGGATCTAGGTGAAGATCCTTTTTGATAATCTCAT |
| | | GACCAAAATCCCTTAACGTGAGTTTTCGTTCCACTGAGCGTCAGACCCCGTAGAAAA |
| | | GATCAAAGGATCTTCTTGAGATCCTTTTTTTCTGCGCGTAATCTGCTGCTTGCAAACA |
| | | AAAAAACCACCGCTACCAGCGGTGGTTTGTTTGCCGGATCAAGAGCTACCAACTCTT |
| | | TTTCCGAAGGTAACTGGCTTCAGCAGAGCGCAGATACCAAATACTGTTCTTCTAGTG |
| | | TAGCCGTAGTTAGGCCACCACTTCAAGAACTCTGTAGCACCGCCTACATACCTCGCT |
| | | CTGCTAATCCTGTTACCAGTGGCTGCTGCCAGTGGCGATAAGTCGTGTCTTACCGG |
| | | GTTGGACTCAAGACGATAGTTACCGGATAAGGCGCAGCGGTCGGGCTGAACGGGG |
| | | GGTTCGTGCACACAGCCCAGCTTGGAGCGAACGACCTACACCGAACTGAGATACCT |
| | | ACAGCGTGAGCTATGAGAAAGCGCCACGCTTCCCGAAGGGAGAAAGGCGGACAGG |
| | | TATCCGGTAAGCGGCAGGGTCGGAACAGGAGAGCGCACGAGGGAGCTTCCAGGGG |
| | | GAAACGCCTGGTATCTTTATAGTCCTGTCGGGTTTCGCCACCTCTGACTTGAGCGTC |
| | | GATTTTTGTGATGCTCGTCAGGGGGGCGGAGCCTATGGAAAAACGCCAGCAACGCG |
| | | GCCTTTTTACGGTTCCTGGCCTTTTGCTGGCCTTTTGCTCACATGGTCTTTCCTGCGT |
| | | TATCCCCTGATTCTGTGGATAACCGTATTACCGCCTTTGAGTGAGCTGATACCGCTC |
| | | GCCGCAGCCGAACGACCGAGCGCAGCGAGTCAGTGAGCGAGGAAGCGGAGAGCG |
| | | CCCAATACGCAAACCGCCTCTCCCCGCGCGTTGGCCGATTCATTAATGCAGCTGGC |
| | | ACGACAGGTTTCCCGACTGGAAAGCGGGCAGTGAGCGCAACGCAATTAATGTGAGT |
| | | TAGCTCACTCATTAGGCACCCCAGGCTTTACACTTTATGCTTCCGGCTCGTATGTTGT |
| | | GTGGAATTGTGAGCGGATAACAATTTCACACAGGAAACAGCTATGACCATGATTACG |
| | | CCAAGCGCGTCAATTAACCCTCACTAAAGGGAACAAAAGCTGTTAATTAA |
| 67 | Matrice PD1 locus_IL12a_ 2A_IL12b pCLS30511 full sequence | TCGCGCGTTTCGGTGATGACGGTGAAAACCTCTGACACATGCAGCTCCCGGAGACG |
| | | GTCACAGCTTGTCTGTAAGCGGATGCCGGGAGCAGACAAGCCCGTCAGGGCGCGT |
| | | CAGCGGGTGTTGGCGGGTGTCGGGGCTGGCTTAACTATGCGGCATCAGAGCAGAT |
| | | TGTACTGAGAGTGCACCATATGCGGTGTGAAATACCGCACAGATGCGTAAGGAGAA |
| | | AATACCGCATCAGGCGCCATTCGCCATTCAGGCTGCGCAACTGTTGGGAAGGGCGA |
| | | TCGGTGCGGGCCTCTTCGCTATTACGCCAGCTGGCGAAAGGGGGATGTGCTGCAA |
| | | GGCGATTAAGTTGGGTAACGCCAGGGTTTTCCCAGTCACGACGTTGTAAAACGACG |
| | | GCCAGTGAATTCGAGCTCGGTACCTCGCGAATGCATCTAGATGACTCCCCAGACAG |
| | | GCCCTGGAACCCCCCACCTTCTCCCCAGCCCTGCTCGTGGTGACCGAAGGGGAC |
| | | AACGCCACCTTCACCTGCAGCTTCTCCAACACATCGGAGAGCTTCGTGCTAAACTGG |
| | | TACCGCATGAGCCCCAGCAACCAGACGGACAAGCTGGCCGCCTTCCCCGAGGACC |
| | | GCAGCCAGCCCGGCCAGGACTGCCGCTTCCGTGTCACACAACTGCCCAACGGGCG |
| | | TGACTTCCACATGAGCGTGGTCAGGGCCCGGCGCAATGACAGCGGCACCTACCTCT |
| | | GTGGGGCCGGTTCTGGCGTGAAACAGACTTTGAATTTTGACCTTCTCAAGTTGGCG |
| | | GGAGACGTGGAGTCCAACCCAGGGCCCATGTGCCCCTGGGTCAGCCTCCCAGC |
| | | CACCGCCCTCACCTGCCGCGGCCACAGGTCTGCATCCAGCGGCTCGCCCTGTGTC |
| | | CCTGCAGTGCCGGCTCAGCATGTGTCCAGCGCGCAGCCTCCTCTTGTGGCTACCC |
| | | TGGTCCTCCTGGACCACCTCAGTTTGGCCAGAAACCTCCCCGTGGCCACTCCAGAC |
| | | CCAGGAATGTTCCCATGCCTTCACCACTCCCAAAACCTGCTGAGGGCCGTCAGCAA |
| | | CATGCTCCAGAAGGCCAGACAAACTCTAGAATTTTACCCTTGCACTTCTGAAGAGAT |
| | | TGATCATGAAGATATCACAAAAGATAAAACCAGCACAGTGGAGGCCTGTTTACCATT |
| | | GGAATTAACCAAGAATGAGAGTTGCCTAAATTCCAGAGAGACCTCTTTCATAACTAAT |
| | | GGGAGTTGCCTGGCCTCCAGAAAAGACCTCTTTTATGATGGCCCTGTGCCTTAGTAGT |
| | | ATTTATGAAGACTTGAAGATGTACCAGGTGGAGTTCAAGACCATGAATGCAAAGCTT |
| | | CTGATGGATCCTAAGAGGCAGATCTTTCTAGATCAAAACATGCTGGCAGTTATTGAT |
| | | GAGCTGATGCAGGCCCTGAATTTCAACAGTGAGACTGTGCCACAAAAATCCTCCCTT |
| | | GAAGAACCGGATTTTTATAAAACTAAAATCAAGCTCTGCATACTTCTTCATGCTTTCA |
| | | GAATTCGGGCAGTGACTATTGATAGAGTGATGAGCTATCTGAATGCTTCCGGAAGCC |
| | | GAGCTACTAACTTCAGCCTGCTGAAGCAGGCTGGAGACGTGGAGGAGAACCCTGGA |
| | | CCTATGTGTCACCAGCAGTTGGTCATCTCTTGGTTTTCCCTGGTTTTTCTGGCATCTC |
| | | CCCTCGTGGCCATATGGGAACTGAAGAAAGATGTTTATGTCGTAGAATTGGATTGGT |
| | | ATCCGGATGCCCCTGGAGAAATGGTGGTCCTCACCTGTGACACCCCTGAAGAAGAT |
| | | GGTATCACCTGGACCTTGGACCAGAGCAGTGAGGTCTTAGGCTCTGGCAAAACCCT |
| | | GACCATCCAAGTCAAAGAGTTTGGAGATGCTGGCCAGTACACCTGTCACAAAGGAG |
| | | GCGAGGTTCTAAGCCATTCGCTCCTGCTGCTTCACAAAAAGGAAGATGGAATTTGGT |
| | | CCACTGATATTTTAAAGGACCAGAAAGAACCCAAAAATAAGACCTTTCTAAGATGCGA |
| | | GGCCAAGAATTATTCTGGACGTTTCACCTGCTGGTGGCTGACGACAATCAGTACTGA |
| | | TTTGACATTCAGTGTCAAAAGCAGCAGAGGCTCTTCTGACCCCCAAGGGGTGACGT |
| | | GCGGAGCTGCTACACTCTCTGCAGAGAGAGTCAGAGGGGACAACAAGGAGTATGAG |
| | | TACTCAGTGGAGTGCCAGGAGGACAGTGCCTGCCCAGCTGCTGAGGAGAGTCTGC |
| | | CCATTGAGGTCATGGTGGATGCCGTTCACAAGCTCAAGTATGAAAACTACACCAGCA |

TABLE 5-continued

Sequences referred to in example 2.

```
GCTTCTTCATCAGGGACATCATCAAACCTGACCCACCCAAGAACTTGCAGCTGAAGC
CATTAAAGAATTCTCGGCAGGTGGAGGTCAGCTGGGAGTACCCTGACACCTGGAGT
ACTCCACATTCCTACTTCTCCCTGACATTCTGCGTTCAGGTCCAGGGCAAGAGCAAG
AGAGAAAAGAAAGATAGAGTCTTCACGGACAAGACCTCAGCCACGGTCATCTGCCG
CAAAAATGCCAGCATTAGCGTGCGGGCCCAGGACCGCTACTATAGCTCATCTTGGA
GCGAATGGGCATCTGTGCCCTGCAGTGAGGGCAGAGGCAGCCTGCTGACCTGCGG
CGACGTCGAGGAGAACCCCGGGCCCATGGGGGCAGGTGCCACCGGCCGCGCCAT
GGACGGGCCGCGCCTGCTGCTGTTGCTGCTTCTGGGGGTGTCCCTTGGAGGTGCC
AAGGAGGCATGCCCCACAGGCCTGTACACACACAGCGGTGAGTGCTGCAAAGCCT
GCAACCTGGGCGAGGGTGTGGCCCAGCCTTGTGGAGCCAACCAGACCGTGTGTGA
GCCCTGCCTGGACAGCGTGACGTTCTCCGACGTGGTGAGCGCGACCGAGCCGTGC
AAGCCGTGCACCGAGTGCGTGGGGCTCCAGAGCATGTCGGCGCCGTGCGTGGAGG
CCGATGACGCCGTGTGCCGCTGCGCCTACGGCTACTACCAGGATGAGACGACTGG
GCGCTGCGAGGCGTGCCGCGTGTGCGAGGCGGGCTCGGGCCTCGTGTTCTCCTGC
CAGGACAAGCAGAACACCGTGTGCGAGGAGTGCCCCGACGGCACGTATTCCGACG
AGGCCAACCACGTGGACCCGTGCCTGCCCTGCACCGTGTGCGAGGACACCGAGCG
CCAGCTCCGCGAGTGCACACGCTGGGCCGACGCCGAGTGCGAGGAGATCCCTGGC
CGTTGGATTACACGGTCCACACCCCCAGAGGGCTCGGACAGCACAGCCCCCAGCA
CCCAGGAGCCTGAGGCACCTCCAGAACAAGACCTCATAGCCAGCACGGTGGCAGG
TGTGGTGACCACAGTGATGGGCAGCTCCCAGCCCGTGGTGACCCGAGGCACCACC
GACAACCTCATCCCTGTCTATTGCTCCATCCTGGCTGCTGTGGTTGTGGGTCTTGTG
GCCTACATAGCCTTCAAGAGGTGATCTAGAGGGCCCGTTTAAACCCGCTGATCAGC
CTCGACTGTGCCTTCTAGTTGCCAGCCATCTGTTGTTTGCCCCTCCCCCGTGCCTTC
CTTGACCCTGGAAGGTGCCACTCCCACTGTCCTTTCCTAATAAAATGAGGAAATTGC
ATCGCATTGTCTGAGTAGGTGTCATTCTATTCTGGGGGGTGGGGTGGGGCAGGACA
GCAAGGGGGAGGATTGGGAAGACAATAGCAGGCATGCTGGGGATGCGGTGGGCTC
TATGACTAGTGGCGAATTCGGCGCAGATCAAAGAGAGCCTGCGGGCAGAGCTCAGG
GTGACAGGTGCGGCCTCGGAGGCCCCGGGGCAGGGGTGAGCTGAGCCGGTCCTG
GGGTGGGTGTCCCCTCCTGCACAGGATCAGGAGCTCCAGGGTCGTAGGGCAGGGA
CCCCCCAGCTCCAGTCCAGGGCTCTGTCCTGCACCTGGGGAATGGTGACCGGCAT
CTCTGTCCTCTAGCTCTGGAAGCACCCCAGCCCCTCTAGTCTGCCCTCACCCCTGA
CCCTGACCCTCCACCCTGACCCCGTCCTAACCCTGACCTTTGATCGGATCCCGGG
CCCGTCGACTGCAGAGGCCTGCATGCAAGCTTGGCGTAATCATGGTCATAGCTGTT
TCCTGTGTGAAATTGTTATCCGCTCACAATTCCACACAACATACGAGCCGGAAGCAT
AAAGTGTAAAGCCTGGGGTGCCTAATGAGTGAGCTAACTCACATTAATTGCGTTGCG
CTCACTGCCCGCTTTCCAGTCGGGAAACCTGTCGTGCCAGCTGCATTAATGAATCG
GCCAACGCGCGGGAGAGGCGGTTTGCGTATTGGGCGCTCTTCCGCTTCCTCGCT
CACTGACTCGCTGCGCTCGGTCGTTCGGCTGCGGCGAGCGGTATCAGCTCACTCAA
AGGCGGTAATACGGTTATCCACAGAATCAGGGGATAACGCAGGAAAGAACATGTGA
GCAAAAGGCCAGCAAAAGGCCAGGAACCGTAAAAAGGCCGCGTTGCTGGCGTTTTT
CCATAGGCTCCGCCCCCCTGACGAGCATCACAAAAATCGACGCTCAAGTCAGAGGT
GGCGAAACCCGACAGGACTATAAAGATACCAGGCGTTTCCCCCTGGAAGCTCCCTC
GTGCGCTCTCCTGTTCCGACCCTGCCGCTTACCGGATACCTGTCCGCCTTTCTCCCT
TCGGGAAGCGTGGCGCTTTCTCATAGCTCACGCTGTAGGTATCTCAGTTCGGTGTA
GGTCGTTCGCTCCAAGCTGGGCTGTGTGCACGAACCCCCCGTTCAGCCCGACCGCT
GCGCCTTATCCGGTAACTATCGTCTTGAGTCCAACCCGGTAAGACACGACTTATCGC
CACTGGCAGCAGCCACTGGTAACAGGATTAGCAGAGCGAGGTATGTAGGCGGTGCT
ACAGAGTTCTTGAAGTGGTGGCCTAACTACGGCTACACTAGAAGAACAGTATTTGGT
ATCTGCGCTCTGCTGAAGCCAGTTACCTTCGGAAAAAGAGTTGGTAGCTCTTGATCC
GGCAAACAAACCACCGCTGGTAGCGGTGGTTTTTTTGTTTGCAAGCAGCAGATTACG
CGCAGAAAAAAAGGATCTCAAGAAGATCCTTTGATCTTTTCTACGGGGTCTGACGCT
CAGTGGAACGAAAACTCACGTTAAGGGATTTTGGTCATGAGATTATCAAAAAGGATC
TTCACCTAGATCCTTTTAAATTAAAAATGAAGTTTTAAATCAATCTAAAGTATATATGA
GTAAACTTGGTCTGACAGTTACCAATGCTTAATCAGTGAGGCACCTATCTCAGCGAT
CTGTCTATTTCGTTCATCCATAGTTGCCTGACTCCCCGTCGTGTAGATAACTACGATA
CGGGAGGGCTTACCATCTGGCCCCAGTGCTGCAATGATACCGCGAGACCCACGCTC
ACCGGCTCCAGATTTATCAGCAATAAACCAGCCAGCCGGAAGGGCCGAGCGCAGAA
GTGGTCCTGCAACTTTATCCGCCTCCATCCAGTCTATTAATTGTTGCCGGGAAGCTA
GAGTAAGTAGTTCGCCAGTTAATAGTTTGCGCAACGTTGTTGCCATTGCTACAGGCA
TCGTGGTGTCACGCTCGTCGTTTGGTATGGCTTCATTCAGCTCCGGTTCCCAACGAT
CAAGGCGAGTTACATGATCCCCCATGTTGTGCAAAAAAGCGGTTAGCTCCTTCGGTC
CTCCGATCGTTGTCAGAAGTAAGTTGGCCGCAGTGTTATCACTCATGGTTATGGCAG
CACTGCATAATTCTCTTACTGTCATGCCATCCGTAAGATGCTTTTCTGTGACTGGTGA
GTACTCAACCAAGTCATTCTGAGAATAGTGTATGCGGCGACCGAGTTGCTCTTGCCC
GGCGTCAATACGGGATAATACCGCGCCACATAGCAGAACTTTAAAAGTGCTCATCAT
TGGAAAACGTTCTTCGGGGCGAAAACTCTCAAGGATCTTACCGCTGTTGAGATCCAG
TTCGATGTAACCCACTCGTGCACCCAACTGATCTTCAGCATCTTTTACTTTCACCAGC
GTTTCTGGGTGAGCAAAAACAGGAAGGCAAAATGCCGCAAAAAAGGGAATAAGGGC
GACACGGAAATGTTGAATACTCATACTCTTCCTTTTTCAATATTATTGAAGCATTTATC
AGGGTTATTGTCTCATGAGCGGATACATATTTGAATGTATTTAGAAAAATAAACAAAT
AGGGGTTCCGCGCACATTTCCCCGAAAAGTGCCACCTGACGTCTAAGAAACCATTAT
TATCATGACATTAACCTATAAAAATAGGCGTATCACGAGGCCCTTTCGTC
```

TABLE 6

Preferred human endogenous gene loci responsive to T-cell activation

| symbol | description | inductionRatio12 hr | T.8Nve.Sp.OT1 | T.8Eff.Sp.OT1. 12 hr.LisOva | T.8Eff.Sp.OT1. 48 hr.LisOva | T.8Eff.Sp.OT1. d6.LisOva |
|---|---|---|---|---|---|---|
| Il3 | interleukin 21 | 16.4 | 12.8 | 208.9 | 18.4 | 13.6 |
| Il2 | interleukin 3 | 97.0 | 16.0 | 1554.4 | 17.7 | 18.1 |
| Ccl4 | isopentenyl-diphosphate delta isomerase 2 | 2.1 | 16.8 | 35.6 | 17.6 | 19.7 |
| Il21 | granzyme C | 9.2 | 17.4 | 160.5 | 20.4 | 24.9 |
| Gp49a | chemokine (C-C motif) receptor 8 | 5.9 | 18.5 | 108.4 | 31.5 | 20.9 |
| Cxcl10 | interleukin 2 | 58.4 | 21.1 | 1229.6 | 32.7 | 17.9 |
| Nr4a3 | interleukin 1 receptor, type I | 2.6 | 21.2 | 54.6 | 35.5 | 21.7 |
| Lilrb4 | tumor necrosis factor (ligand) superfamily, member 4 | 4.1 | 21.8 | 88.8 | 29.3 | 20.0 |
| Cd200 | neuronal calcium sensor 1 | 4.5 | 24.1 | 109.6 | 46.3 | 23.2 |
| Cdkn1a | CDK5 and Abl enzyme substrate 1 | 3.1 | 26.2 | 80.9 | 49.1 | 32.8 |
| Gzmc | transmembrane and tetratricopeptide repeat containing 2 | 2.0 | 26.8 | 53.9 | 26.2 | 29.4 |
| Nr4a2 | LON peptidase N-terminal domain and ring finger 1 | 3.2 | 28.4 | 90.4 | 50.4 | 28.3 |
| Cish | glycoprotein 49 A | 15.0 | 31.6 | 472.4 | 30.6 | 212.5 |
| Nr4a1 | polo-like kinase 2 | 3.6 | 31.7 | 114.3 | 39.0 | 32.5 |
| Tnf | lipase, endothelial | 2.1 | 32.4 | 66.7 | 35.9 | 33.3 |
| Ccr8 | cyclin-dependent kinase inhibitor 1A (P21) | 9.7 | 34.6 | 335.4 | 54.4 | 71.0 |
| Lad1 | grainyhead-like 1 (*Drosophila*) | 2.1 | 35.1 | 73.4 | 52.0 | 44.1 |
| Slamf1 | cellular retinoic acid binding protein II | 5.3 | 35.4 | 187.2 | 43.3 | 36.3 |
| Crabp2 | adenylate kinase 4 | 2.2 | 35.9 | 80.4 | 58.5 | 39.8 |
| Furin | microtubule-associated protein 1B | 2.1 | 36.2 | 77.7 | 36.4 | 38.4 |
| Gadd45g | acyl-CoA synthetase long-chain family member 6 | 2.0 | 37.2 | 76.0 | 45.2 | 41.3 |
| Bcl2l1 | zinc finger E-box binding homeobox 2 | 2.1 | 38.6 | 80.7 | 44.9 | 455.4 |
| Ncs1 | CD200 antigen | 9.8 | 41.2 | 404.3 | 70.4 | 36.8 |
| Ciart | carboxypeptidase D | 3.1 | 41.6 | 127.7 | 71.4 | 71.6 |
| Ahr | thioredoxin reductase 3 | 3.6 | 43.4 | 157.8 | 61.7 | 28.8 |
| Spry1 | myosin IE | 2.3 | 43.6 | 100.2 | 61.3 | 77.0 |
| Tnfsf4 | RNA binding protein with multiple splicing 2 | 2.1 | 43.6 | 91.5 | 49.8 | 36.5 |
| Myo10 | mitogen-activated protein kinase kinase 3, opposite strand | 2.9 | 44.8 | 127.9 | 66.4 | 43.1 |
| Dusp5 | PERP, TP53 apoptosis effector | 2.8 | 44.9 | 127.2 | 78.4 | 72.4 |
| Myc | myosin X | 4.1 | 45.5 | 184.9 | 81.6 | 57.5 |
| Psrc1 | immediate early response 3 | 2.7 | 45.6 | 121.6 | 63.9 | 66.2 |
| St6galnac4 | folliculin interacting protein 2 | 2.6 | 47.5 | 124.2 | 87.4 | 96.6 |
| Nfkbid | leukocyte immunoglobulin-like receptor, subfamily B, member 4 | 9.9 | 48.9 | 483.3 | 64.5 | 179.1 |
| Bst2 | circadian associated repressor of transcription | 4.5 | 50.6 | 225.5 | 100.3 | 33.8 |
| Txnrd3 | RAR-related orphan receptor gamma | 2.1 | 51.7 | 106.7 | 47.5 | 52.8 |
| Plk2 | proline/serine-rich coiled-coil 1 | 3.9 | 52.9 | 205.9 | 92.3 | 79.6 |
| Gfi1 | cysteine rich protein 2 | 2.4 | 54.2 | 127.7 | 90.3 | 182.9 |
| Pim1 | cAMP responsive element modulator | 2.0 | 55.7 | 112.6 | 54.4 | 57.3 |
| Pvt1 | chemokine (C-C motif) ligand 4 | 20.2 | 55.8 | 1125.8 | 103.1 | 89.0 |
| Nfkbib | nuclear receptor subfamily 4, group A, member 2 | 7.8 | 58.5 | 457.6 | 78.7 | 72.0 |
| Gnl2 | transglutaminase 2, C polypeptide | 2.3 | 58.7 | 132.1 | 69.8 | 64.7 |
| Cd69 | synapse defective 1, Rho GTPase, homolog 2 (*C. elegans*) | 2.1 | 62.5 | 132.7 | 111.3 | 31.0 |
| Dgat2 | sprouty homolog 1 (*Drosophila*) | 4.2 | 63.8 | 268.5 | 76.8 | 61.4 |
| Atf3 | activating transcription factor 3 | 3.2 | 65.8 | 210.3 | 88.3 | 75.8 |
| Tnfrsf21 | pogo transposable element with KRAB domain | 2.9 | 68.6 | 196.9 | 91.1 | 293.2 |
| Lonrf1 | tumor necrosis factor receptor superfamily, member 21 | 3.2 | 70.6 | 224.5 | 126.5 | 72.9 |
| Cables1 | cytokine inducible SH2-containing protein | 7.5 | 74.3 | 558.7 | 82.5 | 133.9 |
| Cpd | lymphotoxin A | 2.6 | 74.6 | 197.2 | 93.4 | 58.6 |
| Qtrtd1 | FBJ osteosarcoma oncogene | 3.0 | 74.9 | 224.1 | 89.0 | 61.1 |
| Polr3d | signaling lymphocytic activation molecule family member 1 | 5.4 | 75.6 | 412.0 | 108.4 | 190.4 |
| Kcnq5 | syndecan 3 | 2.4 | 76.0 | 180.0 | 77.2 | 85.3 |
| Fos | mitochondrial ribosomal protein L47 | 2.1 | 77.2 | 161.7 | 152.0 | 72.3 |
| Slc19a2 | ladinin | 5.5 | 77.3 | 423.2 | 152.5 | 70.4 |
| Hif1a | E2F transcription factor 5 | 2.5 | 77.7 | 198.0 | 92.0 | 65.2 |
| Il15ra | ISG15 ubiquitin-like modifier | 2.8 | 77.9 | 221.0 | 88.9 | 45.1 |
| Nfkb1 | aryl-hydrocarbon receptor | 4.2 | 78.7 | 333.2 | 145.7 | 91.4 |
| Phlda3 | diacylglycerol O-acyltransferase 2 | 3.2 | 81.0 | 259.2 | 150.0 | 84.4 |
| Mtrr | FBJ osteosarcoma oncogene B | 2.0 | 81.3 | 163.7 | 139.3 | 98.5 |
| Pogk | pleckstrin homology-like domain, family A, member 3 | 2.9 | 84.8 | 244.5 | 126.9 | 83.8 |
| Map2k3os | potassium voltage-gated channel, subfamily Q, member 5 | 3.0 | 86.3 | 261.0 | 118.1 | 63.4 |

TABLE 6-continued

Preferred human endogenous gene loci responsive to T-cell activation

| symbol | description | inductionRatio12 hr | T.8Nve.Sp.OT1 | T.8Eff.Sp.OT1. 12 hr.LisOva | T.8Eff.Sp.OT1. 48 hr.LisOva | T.8Eff.Sp.OT1. d6.LisOva |
|---|---|---|---|---|---|---|
| Egr2 | tumor necrosis factor receptor superfamily, member 10b | 2.5 | 88.6 | 219.0 | 106.1 | 51.0 |
| Isg15 | Mir17 host gene 1 (non-protein coding) | 2.1 | 90.4 | 190.1 | 120.0 | 51.2 |
| Perp | glucose-fructose oxidoreductase domain containing 1 | 2.2 | 92.9 | 208.5 | 168.7 | 237.4 |
| Ipo4 | plexin A1 | 2.1 | 94.8 | 200.7 | 118.0 | 90.3 |
| Mphosph10 | heat shock factor 2 | 2.4 | 96.8 | 233.2 | 191.0 | 104.8 |
| Plk3 | carbohydrate sulfotransferase 11 | 2.4 | 96.8 | 235.1 | 180.8 | 385.7 |
| Ifitm3 | growth arrest and DNA-damage-inducible 45 gamma | 4.8 | 104.6 | 504.8 | 109.3 | 95.0 |
| Polr1b | solute carrier family 5 (sodium-dependent vitamin transporter), member 6 | 2.1 | 107.0 | 227.3 | 192.8 | 75.8 |
| Usp18 | interferon induced transmembrane protein 3 | 2.8 | 109.2 | 302.6 | 43.9 | 106.4 |
| Top1mt | DENN/MADD domain containing 5A | 2.6 | 109.5 | 279.9 | 102.0 | 517.4 |
| Dkc1 | plasminogen activator, urokinase receptor | 2.1 | 112.4 | 234.8 | 55.7 | 57.3 |
| Polr1c | solute carrier family 19 (thiamine transporter), member 2 | 3.0 | 115.4 | 343.1 | 221.7 | 138.4 |
| Cdk6 | ubiquitin domain containing 2 | 2.2 | 117.4 | 255.7 | 198.9 | 122.2 |
| Ier3 | nuclear receptor subfamily 4, group A, member 3 | 11.8 | 118.0 | 1394.1 | 114.2 | 69.6 |
| Lta | zinc finger protein 52 | 2.5 | 118.8 | 295.6 | 160.9 | 167.4 |
| Ptprs | SH3 domain containing ring finger 1 | 2.4 | 119.3 | 280.9 | 116.5 | 156.5 |
| Fnip2 | dihydrouridine synthase 2 | 2.1 | 122.7 | 260.3 | 237.7 | 202.8 |
| Asna1 | cyclin-dependent kinase 5, regulatory subunit 1 (p35) | 2.1 | 122.7 | 259.3 | 168.4 | 124.0 |
| Mybbp1a | processing of precursor 7, ribonuclease P family, (*S. cerevisiae*) | 2.1 | 125.9 | 264.9 | 235.7 | 150.6 |
| Il1r1 | growth factor independent 1 | 3.5 | 126.8 | 437.7 | 212.0 | 156.6 |
| Dennd5a | interleukin 15 receptor, alpha chain | 2.9 | 130.9 | 380.1 | 144.3 | 167.8 |
| E2f5 | BCL2-like 1 | 4.7 | 133.7 | 627.4 | 257.4 | 231.2 |
| Rcl1 | protein tyrosine phosphatase, receptor type, S | 2.6 | 136.6 | 358.8 | 157.5 | 125.0 |
| Fosl2 | plasmacytoma variant translocation 1 | 3.4 | 136.7 | 465.5 | 179.8 | 140.7 |
| Atad3a | fos-like antigen 2 | 2.5 | 137.0 | 347.5 | 107.2 | 177.8 |
| Bax | BCL2-associated X protein | 2.5 | 138.0 | 347.3 | 260.1 | 150.2 |
| Phf6 | solute carrier family 4, sodium bicarbonate cotransporter, member 7 | 2.3 | 140.3 | 328.2 | 258.7 | 397.5 |
| Zfp52 | tumor necrosis factor receptor superfamily, member 4 | 2.2 | 141.7 | 311.1 | 161.7 | 111.6 |
| Crtam | chemokine (C—X—C motif) ligand 10 | 12.7 | 141.7 | 1798.3 | 242.1 | 59.4 |
| Nop14 | polo-like kinase 3 | 2.8 | 144.8 | 406.3 | 200.1 | 119.9 |
| Rel | CD3E antigen, epsilon polypeptide associated protein | 2.2 | 158.7 | 350.2 | 260.9 | 111.4 |
| Gramd1b | tumor necrosis factor (ligand) superfamily, member 11 | 2.1 | 162.4 | 342.1 | 242.1 | 169.7 |
| Ifi27l2a | polymerase (RNA) III (DNA directed) polypeptide D | 3.0 | 166.3 | 503.7 | 296.1 | 121.6 |
| Tnfrsf10b | early growth response 2 | 2.8 | 173.5 | 494.0 | 136.3 | 68.2 |
| Rpl7l1 | DnaJ (Hsp40) homolog, subfamily C, member 2 | 2.1 | 173.6 | 369.4 | 346.2 | 254.3 |
| Eif1a | DNA topoisomerase 1, mitochondrial | 2.7 | 182.2 | 498.2 | 338.6 | 114.4 |
| Nfkb2 | tripartite motif-containing 30D | 2.3 | 182.6 | 423.4 | 65.8 | 90.6 |
| Heatr1 | DnaJ (Hsp40) homolog, subfamily C, member 21 | 2.0 | 190.1 | 389.4 | 285.5 | 228.2 |
| Utp20 | SAM domain, SH3 domain and nuclear localization signals, 1 | 2.2 | 191.5 | 422.1 | 222.8 | 304.1 |
| Chst11 | solute carrier family 5 (inositol transporters), member 3 | 2.1 | 191.6 | 400.2 | 210.0 | 123.4 |
| Ddx21 | mitochondrial ribosomal protein L15 | 2.1 | 191.6 | 396.3 | 329.8 | 137.7 |
| Hsf2 | dual specificity phosphatase 5 | 4.0 | 203.5 | 818.1 | 307.5 | 560.7 |
| Bccip | apoptosis enhancing nuclease | 2.3 | 211.1 | 478.5 | 288.2 | 137.9 |
| Tagap | ets variant 6 | 2.3 | 218.3 | 508.1 | 220.5 | 297.3 |
| Sdc3 | DIM1 dimethyladenosine transferase 1-like (*S. cerevisiae*) | 2.2 | 218.4 | 486.0 | 356.0 | 129.7 |
| Sytl3 | 2'-5' oligoadenylate synthetase-like 1 | 2.1 | 229.0 | 473.3 | 130.7 | 124.3 |
| Gtpbp4 | UTP18, small subunit (SSU) processome component, homolog (yeast) | 2.1 | 232.0 | 494.3 | 384.9 | 189.5 |
| Crip2 | BRCA2 and CDKN1A interacting protein | 2.4 | 234.6 | 563.3 | 437.5 | 269.8 |
| Sh3rf1 | synaptotagmin-like 3 | 2.4 | 242.4 | 572.9 | 316.7 | 700.7 |
| Nsfl1c | 5-methyltetrahydrofolate-homocysteine methyltransferase reductase | 2.9 | 245.7 | 706.5 | 334.6 | 150.6 |
| Gtf2f1 | URB2 ribosome biogenesis 2 homolog (*S. cerevisiae*) | 2.0 | 245.7 | 500.2 | 489.8 | 184.6 |
| Slc4a7 | ubiquitin-conjugating enzyme E2C binding protein | 2.1 | 251.2 | 530.5 | 288.2 | 85.2 |

TABLE 6-continued

Preferred human endogenous gene loci responsive to T-cell activation

| symbol | description | inductionRatio12 hr | T.8Nve.Sp.OT1 | T.8Eff.Sp.OT1. 12 hr.LisOva | T.8Eff.Sp.OT1. 48 hr.LisOva | T.8Eff.Sp.OT1. d6.LisOva |
|---|---|---|---|---|---|---|
| Etv6 | lysine (K)-specific demethylase 2B | 2.2 | 251.8 | 547.1 | 332.7 | 262.1 |
| Trim30d | queuine tRNA-ribosyltransferase domain containing 1 | 3.0 | 260.3 | 788.7 | 358.0 | 75.5 |
| Ddx27 | ubiquitin specific peptidase 31 | 2.0 | 265.2 | 533.2 | 277.1 | 176.2 |
| Pwp2 | eukaryotic translation initiation factor 2-alpha kinase 2 | 2.0 | 267.7 | 540.5 | 260.8 | 244.8 |
| Chchd2 | ATPase family, AAA domain containing 3A | 2.5 | 268.8 | 679.7 | 523.1 | 147.1 |
| Myo1e | adhesion molecule, interacts with CXADR antigen 1 | 2.3 | 269.5 | 610.9 | 272.9 | 182.8 |
| Eif5b | SUMO/sentrin specific peptidase 3 | 2.0 | 272.5 | 548.7 | 544.5 | 298.4 |
| Stat5a | ESF1, nucleolar pre-rRNA processing protein, homolog (*S. cerevisiae*) | 2.2 | 276.3 | 610.4 | 482.2 | 266.5 |
| Cops6 | deoxynucleotidyltransferase, terminal, interacting protein 2 | 2.1 | 282.9 | 600.4 | 359.9 | 326.1 |
| D19Bwg1357e | TGFB-induced factor homeobox 1 | 2.1 | 300.5 | 618.9 | 217.5 | 210.6 |
| Aatf | eukaryotic translation initiation factor 1A | 2.5 | 300.8 | 738.7 | 597.7 | 262.8 |
| Aen | interferon-stimulated protein | 2.1 | 305.7 | 651.2 | 144.3 | 138.4 |
| Amica1 | pleiomorphic adenoma gene-like 2 | 2.1 | 311.5 | 651.9 | 376.2 | 405.9 |
| Wdr43 | PWP2 periodic tryptophan protein homolog (yeast) | 2.3 | 321.8 | 743.3 | 586.5 | 189.3 |
| Cct4 | furin (paired basic amino acid cleaving enzyme) | 5.2 | 329.7 | 1728.3 | 271.7 | 421.5 |
| Nifk | tumor necrosis factor | 6.6 | 330.7 | 2188.4 | 489.9 | 213.3 |
| Tgm2 | apoptosis antagonizing transcription factor | 2.3 | 331.4 | 754.8 | 523.1 | 221.5 |
| Ero1l | interferon, alpha-inducible protein 27 like 2A | 2.5 | 334.0 | 828.1 | 296.5 | 221.4 |
| Gfod1 | ST6 (alpha-N-acetyl-neuraminyl-2,3-beta-galactosyl-1,3)-N-acetylgalactosaminide alpha-2,6-sialyltransferase 4 | 3.9 | 338.4 | 1311.3 | 636.0 | 298.2 |
| Ak4 | methyltransferase like 1 | 2.2 | 339.4 | 744.7 | 662.8 | 94.5 |
| Sdad1 | notchless homolog 1 (*Drosophila*) | 2.0 | 339.4 | 690.3 | 610.3 | 158.1 |
| Dimt1 | mitochondrial ribosomal protein L3 | 2.1 | 340.0 | 725.5 | 651.4 | 359.8 |
| Esf1 | UBX domain protein 2A | 2.1 | 343.8 | 732.9 | 532.1 | 428.5 |
| Cd3eap | guanine nucleotide binding protein-like 2 (nucleolar) | 3.2 | 347.6 | 1124.7 | 647.4 | 227.5 |
| Samsn1 | programmed cell death 11 | 2.0 | 353.9 | 711.8 | 435.9 | 287.4 |
| Tnfrsf4 | cyclin-dependent kinase 8 | 2.0 | 364.0 | 731.1 | 702.5 | 346.2 |
| Mettl1 | eukaryotic translation initiation factor 5B | 2.3 | 365.1 | 838.2 | 544.5 | 355.5 |
| Cd274 | RNA terminal phosphate cyclase-like 1 | 2.5 | 373.3 | 948.8 | 746.4 | 155.6 |
| Ubtd2 | NSFL1 (p97) cofactor (p47) | 2.3 | 374.1 | 876.1 | 725.9 | 369.7 |
| Icos | nuclear factor of kappa light polypeptide gene enhancer in B cells inhibitor, delta | 3.9 | 378.5 | 1465.1 | 389.9 | 224.0 |
| Kdm2b | M-phase phosphoprotein 10 (U3 small nucleolar ribonucleoprotein) | 2.8 | 379.8 | 1069.3 | 738.4 | 290.8 |
| Larp4 | GRAM domain containing 1B | 2.5 | 382.7 | 949.6 | 363.4 | 659.2 |
| Eif3d | ERO1-like (*S. cerevisiae*) | 2.2 | 387.7 | 872.3 | 773.0 | 520.9 |
| Tnfaip3 | nuclear receptor subfamily 4, group A, member 1 | 6.8 | 387.8 | 2639.0 | 343.7 | 220.7 |
| Map1b | surfeit gene 2 | 2.1 | 399.8 | 852.2 | 696.3 | 204.0 |
| Cdv3 | N(alpha)-acetyltransferase 25, NatB auxiliary subunit | 2.1 | 405.7 | 847.3 | 669.5 | 194.1 |
| Plac8 | yrdC domain containing (*E, coli*) | 2.0 | 406.7 | 830.8 | 635.3 | 267.0 |
| Mrpl3 | La ribonucleoprotein domain family, member 4 | 2.2 | 408.8 | 887.9 | 586.6 | 358.3 |
| Surf2 | SDA1 domain containing 1 | 2.2 | 419.8 | 939.9 | 631.4 | 284.7 |
| Ubxn2a | importin 4 | 2.8 | 420.3 | 1183.6 | 777.8 | 173.5 |
| Utp18 | inducible T cell co-stimulator | 2.2 | 423.9 | 920.9 | 818.8 | 796.9 |
| Isg20 | solute carrier family 7 (cationic amino acid transporter, y+ system), member 1 | 2.1 | 439.4 | 934.4 | 842.6 | 344.6 |
| Dnajc2 | arsA arsenite transporter, ATP-binding, homolog 1 (bacterial) | 2.6 | 446.6 | 1165.0 | 717.9 | 963.9 |
| Jak2 | polymerase (RNA) I polypeptide C | 2.7 | 447.8 | 1208.4 | 854.0 | 295.9 |
| Slc7a1 | spermatogenesis associated 5 | 2.0 | 450.8 | 920.2 | 516.0 | 361.6 |
| Syde2 | ubiquitin specific peptidase 18 | 2.7 | 451.8 | 1240.5 | 296.0 | 250.7 |
| Slc5a6 | placenta-specific 8 | 2.1 | 452.4 | 967.3 | 888.6 | 590.8 |
| Dnttip2 | general transcription factor IIF, polypeptide 1 | 2.3 | 454.8 | 1063.9 | 890.0 | 680.8 |
| Idi2 | nuclear factor of kappa light polypeptide gene enhancer in B cells inhibitor, beta | 3.4 | 456.4 | 1535.5 | 679.1 | 502.7 |
| Dus2 | PHD finger protein 6 | 2.5 | 462.0 | 1159.5 | 775.8 | 510.4 |
| Pitrm1 | RRN3 RNA polymerase I transcription factor homolog (yeast) | 2.1 | 462.2 | 948.4 | 913.2 | 388.9 |
| Plxna1 | cytotoxic and regulatory T cell molecule | 2.5 | 473.7 | 1177.8 | 586.8 | 431.8 |
| Cdk5r1 | COP9 (constitutive photomorphogenic) homolog, subunit 6 (*Arabidopsis thaliana*) | 2.3 | 483.6 | 1101.9 | 947.8 | 560.3 |
| Ube2cbp | asparagine-linked glycosylation 3 (alpha-1,3-mannosyltransferase) | 2.1 | 485.9 | 1006.3 | 758.7 | 339.4 |

TABLE 6-continued

Preferred human endogenous gene loci responsive to T-cell activation

| symbol | description | inductionRatio12 hr | T.8Nve.Sp.OT1 | T.8Eff.Sp.OT1. 12 hr.LisOva | T.8Eff.Sp.OT1. 48 hr.LisOva | T.8Eff.Sp.OT1. d6.LisOva |
|---|---|---|---|---|---|---|
| Tnfsf11 | tryptophanyl-tRNA synthetase | 2.0 | 486.1 | 987.1 | 897.1 | 504.7 |
| Pop7 | hypoxia up-regulated 1 | 2.0 | 494.3 | 996.6 | 802.4 | 690.3 |
| Psme3 | family with sequence similarity 60, member A | 2.0 | 500.8 | 1002.1 | 834.7 | 417.6 |
| Mir17hg | bone marrow stromal cell antigen 2 | 3.8 | 502.5 | 1922.9 | 925.5 | 246.0 |
| Tsr1 | nuclear factor of kappa light polypeptide gene enhancer in B cells 2, p49/p100 | 2.4 | 503.2 | 1231.8 | 494.0 | 341.8 |
| Rbpms2 | UTP20, small subunit (SSU) processome component, homolog (yeast) | 2.4 | 510.5 | 1240.2 | 696.4 | 245.8 |
| Mrpl47 | CD274 antigen | 2.2 | 516.6 | 1128.7 | 246.9 | 220.2 |
| Rab8b | proviral integration site 1 | 3.4 | 518.4 | 1766.4 | 676.9 | 970.0 |
| Plagl2 | signal transducer and activator of transcription 5A | 2.3 | 530.0 | 1210.4 | 496.6 | 507.8 |
| GrhI1 | CD69 antigen | 3.2 | 535.7 | 1725.8 | 289.5 | 153.9 |
| Zeb2 | pitrilysin metallepetidase 1 | 2.1 | 544.9 | 1153.8 | 968.4 | 349.3 |
| sept-02 | cyclin-dependent kinase 6 | 2.7 | 550.3 | 1476.5 | 1064.0 | 642.1 |
| Slc5a3 | DEAD (Asp-Glu-Ala-Asp) box polypeptide 27 | 2.3 | 556.2 | 1286.9 | 987.2 | 480.4 |
| Naa25 | polymerase (RNA) I polypeptide B | 2.8 | 556.2 | 1536.0 | 1070.4 | 201.3 |
| Plaur | tumor necrosis factor, alpha-induced protein 3 | 2.2 | 560.6 | 1212.2 | 255.5 | 446.0 |
| Metap1 | nodal modulator 1 | 2.1 | 563.0 | 1161.0 | 988.9 | 439.8 |
| Alg3 | NOP14 nucleolar protein | 2.5 | 570.9 | 1418.9 | 925.3 | 398.0 |
| Mrpl15 | ribosomal protein L7-like 1 | 2.5 | 586.7 | 1448.7 | 1030.2 | 687.2 |
| Oasl1 | methionyl aminopeptidase 1 | 2.1 | 597.5 | 1244.1 | 1139.3 | 433.4 |
| Rorc | hypoxia inducible factor 1, alpha subunit | 3.0 | 624.2 | 1854.6 | 809.4 | 838.4 |
| Nomo1 | Janus kinase 2 | 2.1 | 624.5 | 1328.7 | 390.6 | 917.8 |
| Tgif1 | nuclear factor of kappa light polypeptide gene enhancer in B cells 1, p105 | 2.9 | 661.5 | 1913.3 | 713.9 | 720.5 |
| Lipg | reticuloendotheliosis oncogene | 2.5 | 678.9 | 1686.4 | 409.8 | 580.5 |
| Rrn3 | septin 2 | 2.1 | 687.3 | 1436.0 | 1354.1 | 1181.3 |
| Dnajc21 | nucleolar protein interacting with the FHA domain of MKI67 | 2.3 | 733.4 | 1658.2 | 1280.0 | 407.2 |
| Yrdc | elongation factor Tu GTP binding domain containing 2 | 2.0 | 739.3 | 1483.5 | 1439.0 | 904.3 |
| Acsl6 | myelocytomatosis oncogene | 4.0 | 761.0 | 3022.8 | 1064.0 | 211.5 |
| Spata5 | dyskeratosis congenita 1, dyskerin | 2.7 | 778.2 | 2112.0 | 1549.5 | 484.2 |
| Urb2 | carnitine deficiency-associated gene expressed in ventricle 3 | 2.1 | 801.6 | 1718.2 | 1274.7 | 1010.3 |
| Nle1 | GTP binding protein 4 | 2.4 | 824.2 | 1942.6 | 1578.7 | 567.3 |
| Wars | HEAT repeat containing 1 | 2.4 | 830.3 | 2020.6 | 1235.5 | 495.4 |
| Crem | proteaseome (prosome, macropain) activator subunit 3 (PA28 gamma, Ki) | 2.1 | 838.4 | 1763.5 | 1471.1 | 936.1 |
| Larp1 | La ribonucleoprotein domain family, member 1 | 2.0 | 861.7 | 1742.1 | 1250.9 | 854.3 |
| Eif2ak2 | DNA segment, Chr 19, Brigham & Women's Genetics 1357 expressed | 2.3 | 868.6 | 1978.4 | 1218.0 | 653.4 |
| Hyou1 | eukaryotic translation initiation factor 3, subunit D | 2.2 | 909.1 | 1971.6 | 1641.9 | 920.6 |
| Senp3 | TSR1 20S rRNA accumulation | 2.1 | 913.9 | 1915.9 | 1474.6 | 477.2 |
| Tmtc2 | MYB binding protein (P160) 1a | 2.6 | 1140.0 | 2962.9 | 2200.7 | 459.8 |
| Fosb | T cell activation Rho GTPase activating protein | 2.4 | 1176.7 | 2794.4 | 489.3 | 704.2 |
| Pdcd11 | RAB8B, member RAS oncogene family | 2.1 | 1189.5 | 2492.2 | 1671.3 | 2512.5 |
| Usp31 | DEAD (Asp-Glu-Ala-Asp) box polypeptide 21 | 2.4 | 1210.2 | 2928.0 | 2221.1 | 1098.2 |
| Cdk8 | chaperonin containing Tcp1, subunit 4 (delta) | 2.3 | 1321.4 | 2989.7 | 2462.5 | 1294.8 |
| Eftud2 | coiled-coil-helix-coiled-coil-helix domain containing 2 | 2.3 | 1374.2 | 3171.2 | 2636.9 | 1008.9 |
| Fam60a | WD repeat domain 43 | 2.3 | 1727.6 | 3912.6 | 2927.5 | 1014.9 |

TABLE 7

Selection of preferred endogenous genes that are constantly active during immune cell activation (dependent or independent from T-cell activation).

| Symbol | Gene description |
|---|---|
| CD3G | CD3 gamma |
| Rn28s1 | 28S ribosomal RNA |
| Rn18s | 18S ribosomal RNA |
| Rn7sk | RNA, 7SK, nuclear |
| Actg1 | actin, gamma, cytoplasmic 1 |
| B2m | beta-2 microglobulin |
| Rpl18a | ribosomal protein L18A |
| Pabpc1 | poly(A) binding protein, cytoplasmic 1 |
| Gapdh | glyceraldehyde-3-phosphate dehydrogenase |
| Rpl19 | ribosomal protein L19 |

TABLE 7-continued

Selection of preferred endogenous genes that are constantly active during immune cell activation (dependent or independent from T-cell activation).

| Symbol | Gene description |
| --- | --- |
| Rpl17 | ribosomal protein L17 |
| Rplp0 | ribosomal protein, large, P0 |
| Cfl1 | cofilin 1, non-muscle |
| Pfn1 | profilin 1 |

TABLE 8

Selection of genes that are transiently upregulated upon T-cell activation.

| Symbol | Gene description |
| --- | --- |
| Il3 | interleukin 3 |
| Il2 | interleukin 2 |
| Ccl4 | chemokine (C-C motif) ligand 4 |
| Il21 | interleukin 21 |
| Gp49a | glycoprotein 49 A |
| Nr4a3 | nuclear receptor subfamily 4, group A, member 3 |
| Lilrb4 | leukocyte immunoglobulin-like receptor, subfamily B, member 4 |
| Cd200 | CD200 antigen |
| Cdkn1a | cyclin-dependent kinase inhibitor 1A (P21) |
| Gzmc | granzyme C |
| Nr4a2 | nuclear receptor subfamily 4, group A, member 2 |
| Cish | cytokine inducible SH2-containing protein |
| Ccr8 | chemokine (C-C motif) receptor 8 |
| Lad1 | ladinin |
| Crabp2 | cellular retinoic acid binding protein II |

TABLE 9

Selection of genes that are upregulated over more than 24 hours upon T-cell activation.

| Symbol | Description |
| --- | --- |
| Gzmb | granzyme B |
| Tbx21 | T-box 21 |
| Pdcd1 | programmed cell death 1 |
| Plek | pleckstrin |
| Chek1 | checkpoint kinase 1 |
| Slamf7 | SLAM family member 7 |
| Zbtb32 | zinc finger and BTB domain containing 32 |
| Tigit | T cell immunoreceptor with Ig and ITIM domains |
| Lag3 | lymphocyte-activation gene 3 |
| Gzma | granzyme A |
| Wee1 | WEE 1 homolog 1 (S. pombe) |
| Il12rb2 | interleukin 12 receptor, beta 2 |
| Ccr5 | chemokine (C-C motif) receptor 5 |
| Eea1 | early endosome antigen 1 |
| Dtl | denticleless homolog (Drosophila) |

TABLE 10

Selection of genes that are down-regulated upon immune cell activation.

| Symbol | Gene description |
| --- | --- |
| Spata6 | spermatogenesis associated 6 |
| Itga6 | integrin alpha 6 |
| Rcbtb2 | regulator of chromosome condensation (RCC1) and BTB (POZ) domain containing protein 2 |
| Cd1d1 | CD1d1 antigen |
| St8sia4 | ST8 alpha-N-acetyl-neuraminide alpha-2,8-sialyltransferase 4 |
| Itgae | integrin alpha E, epithelial-associated |
| Fam214a | family with sequence similarity 214, member A |

TABLE 10-continued

Selection of genes that are down-regulated upon immune cell activation.

| Symbol | Gene description |
| --- | --- |
| Slc6a19 | solute carrier family 6 (neurotransmitter transporter), member 19 |
| Cd55 | CD55 antigen |
| Xkrx | X Kell blood group precursor related X linked |
| Mturn | maturin, neural progenitor differentiation regulator homolog (Xenopus) |
| H2-Ob | histocompatibility 2, O region beta locus |
| Cnr2 | cannabinoid receptor 2 (macrophage) |
| Itgae | integrin alpha E, epithelial-associated |
| Raver2 | ribonucleoprotein, PTB-binding 2 |
| Zbtb20 | zinc finger and BTB domain containing 20 |
| Arrb1 | arrestin, beta 1 |
| Abca1 | ATP-binding cassette, sub-family A (ABC1), member 1 |
| Tet1 | tet methylcytosine dioxygenase 1 |
| Slc16a5 | solute carrier family 16 (monocarboxylic acid transporters), member 5 |
| Trav14-1 | T cell receptor alpha variable 14-1 |
| Ampd3 | adenosine monophosphate deaminase 3 |

TABLE 11

Selection of human genes that are silent upon T-cell activation (safe harbor gene targeted integration loci).

| Symbol | Gene description |
| --- | --- |
| Zfp640 | zinc finger protein 640 |
| LOC100038422 | uncharacterized LOC100038422 |
| Zfp600 | zinc finger protein 600 |
| Serpinb3a | serine (or cysteine) peptidase inhibitor, clade B (ovalbumin), member 3A |
| Tas2r106 | taste receptor, type 2, member 106 |
| Magea3 | melanoma antigen, family A, 3 |
| Omt2a | oocyte maturation, alpha |
| Cpxcr1 | CPX chromosome region, candidate 1 |
| Hsf3 | heat shock transcription factor 3 |
| Pbsn | Probasin |
| Sbp | spermine binding protein |
| Wfdc6b | WAP four-disulfide core domain 6B |
| Meiob | meiosis specific with OB domains |
| Dnm3os | dynamin 3, opposite strand |
| Skint11 | selection and upkeep of intraepithelial T cells 11 |

TABLE 12

List of gene loci upregulated in tumor exhausted infiltrating lymphocytes (compiled from multiple tumors) useful for gene integration of exogenous coding sequences as per the present invention

| Gene names | Uniprot ID (human) |
| --- | --- |
| CXCL13 | O43927 |
| TNFRSF1B | P20333 |
| RGS2 | P41220 |
| TIGIT | Q495A1 |
| CD27 | P26842 |
| TNFRSF9 | Q12933 |
| SLA | Q13239 |
| INPP5F | Q01968 |
| XCL2 | Q9UBD3 |
| HLA-DMA | P28067 |
| FAM3C | Q92520 |
| WARS | P23381 |
| EIF3L | Q9Y262 |
| KCNK5 | O95279 |
| TMBIM6 | P55061 |
| CD200 | P41217 |
| C3H7A | O60880 |
| SH2D1A | O60880 |
| ATP1B3 | P54709 |

TABLE 12-continued

List of gene loci upregulated in tumor exhausted infiltrating lymphocytes (compiled from multiple tumors) useful for gene integration of exogenous coding sequences as per the present invention

| Gene names | Uniprot ID (human) |
| --- | --- |
| THADA | Q6YHU6 |
| PARK7 | Q99497 |
| EGR2 | P11161 |
| FDFT1 | P37268 |
| CRTAM | O95727 |
| IFI16 | Q16666 |

TABLE 13

List of gene loci upregulated in hypoxic tumor conditions useful for gene integration of exogenous coding sequences as per the present invention

| Gene names | Strategy | |
| --- | --- | --- |
| CTLA-4 | KO/KI | Target shown to be upregulated |
| LAG-3 (CD223) | KO/KI | in T-cells upon hypoxia exposure |
| PD1 | KO/KI | and T cell exhaustion |
| 4-1BB (CD137) | KI | |
| GITR | KI | |
| OX40 | KI | |
| IL10 | KO/KI | |
| ABCB1 | KI | HIF target |
| ABCG2 | KI | |
| ADM | KI | |
| ADRA1B | KI | |
| AK3 | KI | |
| ALDOA | KI | |
| BHLHB2 | KI | |
| BHLHB3 | KI | |
| BNIP3 | KI | |
| BNIP3L | KI | |
| CA9 | KI | |
| CCNG2 | KI | |
| CD99 | KI | |
| CDKN1A | KI | |
| CITED2 | KI | |
| COL5A1 | KI | |
| CP | KI | |
| CTGF | KI | |
| CTSD | KI | |
| CXCL12 | KI | |
| CXCR4 | KI | |
| CYP2S1 | KI | |
| DDIT4 | KI | |
| DEC1 | KI | |
| EDN1 | KI | |
| EGLN1 | KI | |
| EGLN3 | KI | |
| ENG | KI | |
| ENO1 | KI | |
| EPO | KI | |
| ETS1 | KI | |
| FECH | KI | |
| FN1 | KI | |
| FURIN | KI | |
| GAPDH | KI | |
| GPI | KI | |
| GPX3 | KI | |
| HK1 | KI | |
| HK2 | KI | |
| HMOX1 | KI | |
| HSP90B1 | KI | |
| ID2 | KI | |
| IGF2 | KI | |
| IGFBP1 | KI | |
| IGFBP2 | KI | |
| IGFBP3 | KI | |
| ITGB2 | KI | |
| KRT14 | KI | |
| KRT18 | KI | |
| KRT19 | KI | |

TABLE 13-continued

List of gene loci upregulated in hypoxic tumor conditions useful for gene integration of exogenous coding sequences as per the present invention

| Gene names | Strategy |
| --- | --- |
| LDHA | KI |
| LEP | KI |
| LOX | KI |
| LRP1 | KI |
| MCL1 | KI |
| MET | KI |
| MMP14 | KI |
| MMP2 | KI |
| MXI1 | KI |
| NOS2A | KI |
| NOS3 | KI |
| NPM1 | KI |
| NR4A1 | KI |
| NT5E | KI |
| PDGFA | KI |
| PDK1 | KI |
| PFKFB3 | KI |
| PFKL | KI |
| PGK1 | KI |
| PH-4 | KI |
| PKM2 | KI |
| PLAUR | KI |
| PMAIP1 | KI |
| PPP5C | KI |
| PROK1 | KI |
| SERPINE1 | KI |
| SLC2A1 | KI |
| TERT | KI |
| TF | KI |
| TFF3 | KI |
| TFRC | KI |
| TGFA | KI |
| TGFB3 | KI |
| TGM2 | KI |
| TPI1 | KI |
| VEGFA | KI |
| VIM | KI |
| TMEM45A | KI |
| AKAP12 | KI |
| SEC24A | KI |
| ANKRD37 | KI |
| RSBN1 | KI |
| GOPC | KI |
| SAMD12 | KI |
| CRKL | KI |
| EDEM3 | KI |
| TRIM9 | KI |
| GOSR2 | KI |
| MIF | KI |
| ASPH | KI |
| WDR33 | KI |
| DHX40 | KI |
| KLF10 | KI |
| R3HDM1 | KI |
| RARA | KI |
| LOC162073 | KI |
| PGRMC2 | KI |
| ZWILCH | KI |
| TPCN1 | KI |
| WSB1 | KI |
| SPAG4 | KI |
| GYS1 | KI |
| RRP9 | KI |
| SLC25A28 | KI |
| NTRK2 | KI |
| NARF | KI |
| ASCC1 | KI |
| UFM1 | KI |
| TXNIP | KI |
| MGAT2 | KI |
| VDAC1 | KI |
| SEC61G | KI |

TABLE 13-continued

List of gene loci upregulated in hypoxic tumor conditions useful for gene integration of exogenous coding sequences as per the present invention

| Gene names | Strategy |
|---|---|
| SRP19 | KI |
| JMJD2C | KI |
| SNRPD1 | KI |
| RASSF4 | KI |

SEQUENCE LISTING

```
Sequence total quantity: 80
SEQ ID NO: 1            moltype = DNA  length = 1000
FEATURE                 Location/Qualifiers
misc_feature            1..1000
                        note = PD1 left homology
source                  1..1000
                        mol_type = other DNA
                        organism = synthetic construct
SEQUENCE: 1
ccaagccctg accctggcag gcatatgttt caggaggtcc ttgtcttggg agcccaggt    60
cgggggcccc gtgtctgtcc acatccgagt caatggccca tctcgtctct gaagcatctt  120
tgctgtgagc tctagtcccc actgtcttgc tggaaaatgt ggaggcccca ctgcccactg  180
cccagggcag caatgcccat accacgtggt cccagctccg agcttgtcct gaaaaggggg  240
caaagactgg accctgagcc tgccaagggg ccacactcct cccagggctg gggtctccat  300
gggcagcccc ccacccaccc agaccagtta cactcccctg tgccagagca gtgcagacag  360
gaccaggcca ggatgcccaa gggtcagggg ctggggatgg gtagcccca aacagccctt   420
tctggggaa ctggcctcaa cggggaaggg ggtgaaggct cttagtagga aatcaggag    480
acccaagtca gagccaggtg ctgtgcagaa gctgcagcct cacgtagaag gaagaggctc  540
tgcagtggag gccagtgccc atccccgggt ggcagaggcc ccagcagaga cttctcaatg  600
acattccagc tggggtggcc cttccagagc ccttgctgcc cgagggatgt gagcaggtgg  660
ccggggaggc tttgtggggc cacccagccc cttcctcacc tctctccatc tctcagactc  720
cccagacagg ccctggaacc cccccacctt ctccccagcc ctgctcgtgg tgaccgaagg  780
ggacaacgcc accttcacct gcagcttctc caacacatcg agagcttcg tgctaaactg   840
gtaccgcatg agccccagca accagacgga caagctggcc gccttccccg aggaccgcag  900
ccagcccggc caggactgcc gcttccgtgt cacacaactg cccaacgggc gtgacttcca  960
catgagcgtg tcagggccc ggcgcaatga cagcggcacc                         1000

SEQ ID NO: 2            moltype = DNA  length = 1000
FEATURE                 Location/Qualifiers
misc_feature            1..1000
                        note = PD1 right homology
source                  1..1000
                        mol_type = other DNA
                        organism = synthetic construct
SEQUENCE: 2
gcctgcgggc agagctcagg gtgacaggtg cggcctcgga ggccccgggg caggggtgag   60
ctgagccggt cctggggtgg gtgtcccctc ctgcacagga tcaggagctc cagggtcgta  120
gggcagggac ccccagctc cagtccaggg ctctgtcctg cacctgggga atggtgaccg   180
gcatctctgt cctctagctc tggaagcacc ccagcccctc tagtctgccc tcacccctga  240
ccctgaccct ccaccctgac cccgtcctaa ccctgacct ttgtgccctt ccagagagaa   300
gggcagaagt gcccacagcc caccccagcc cctcacccag gccagccggc cagttccaaa  360
ccctggtggt tggtgtcgtg gcggcctgc tgggcagcct ggtgctgcta gtctgggtcc   420
tggccgtcat ctgctcccgg gccgcacgag gtaacgtcat cccagcccct cggcctgccc  480
tgccctaacc ctgctgcgg ccctcactcc cgcctcccct tcctccaccc ttccctcacc   540
ccacccacc tccccccatc tccccgccag gctaagtccc tgatgaaggc ccctggacta    600
agaccccca cctaggagca cggctcaggg tcggcctggt gacccaagt gtgtttctct    660
gcagggacaa taggagccag gcgcaccggc cagcccctgg tgagtctcac tctttttcctg 720
catgatccac tgtgccttcc ttcctgggtg ggcagaggtg gaaggacagg ctgggaccac  780
acggcctgca ggactcacat tctattatag ccaggacccc acctcccag cccccaggca    840
gcaacctcaa tccctaaagc catgatctgg ggccccagcc cacctgcggt ctccgggggt  900
gcccggccca tgtgtgtgcc tgcctgcggt tccaggggt gcctggccca cgcgtgtgcc  960
cgcctgcggt ctctggggt gcccggccca catatgtgcc                         1000

SEQ ID NO: 3            moltype = DNA  length = 2781
FEATURE                 Location/Qualifiers
misc_feature            1..2781
                        note = PD1_T3C-L2
source                  1..2781
                        mol_type = other DNA
                        organism = synthetic construct
SEQUENCE: 3
atgggcgatc ctaaaaagaa acgtaaggtc atcgatatcg ccgatctacg cacgctcggc    60
tacagccagc agcaacagga gaagatcaaa ccgaaggttc gttcgacagt ggcgcagcac  120
```

```
cacgaggcac tggtcggcca cgggtttaca cacgcgcaca tcgttgcgtt aagccaacac    180
ccggcagcgt tagggaccgt cgctgtcaag tatcaggaca tgatcgcagc gttgccagag    240
gcgacacacg aagcgatcgt tggcgtcggc aaacagtggt ccggcgcacg cgctctggag    300
gccttgctca cggtggcggg agagttgaga ggtccaccgt tacagttgga cacaggccaa    360
cttctcaaga ttgcaaaacg tggcggcgtg accgcagtgg aggcagtgca tgcatggcgc    420
aatgcactga cgggtgcccc gctcaacttg accccgagc  aagtggtggc tatcgcttcc    480
aagctggggg gaaagcaggc cctggagacc gtccaggccc ttctcccagt gctttgccag    540
gctcacggac tgacccctga acaggtggtg gcaattgcct cacacgacgg gggcaagcag    600
gcactggaga ctgtccagcg gctgctgcct gtcctctgcc aggcccacgg actcactcct    660
gagcaggtcg tggccattgc cagccacgat gggggcaaac aggctctgga gaccgtgcag    720
cgcctcctcc cagtgctgtg ccaggctcat gggctgaccc cacagcaggt cgtcgccatt    780
gccagtaacg gcgggggaa  gcaggccctc gaaacagtgc agaggctgct gcccgtcttg    840
tgccaagcac acggcctgac acccgagcag gtggtggcca tcgcctctca tgacggcggc    900
aagcaggccc ttgagacagt gcagaggactg ttgcccgtgt tgtgtcaggc ccacgggttg    960
acacccagc  aggtggtcgc catcgccagc aatggcgggg gaaagcaggc ccttgagacc   1020
gtgcagcggt tgcttccagt gttgtgccag gcacacggac tgacccctca acaggtggtc   1080
gcaatcgcca gctacaaggg cggaaagcag gctctggaga cagtgcagcg cctcctgccc   1140
gtgctgtgtc aggctcacgg actgacacca cagcaggtgg tcgccatcgc cagtaacggg   1200
ggcggcaagc aggctttgga gaccgtccag agactcctcc ccgtcctttg ccaggcccac   1260
gggttgacac tcagcaggt  cgtcgccatt gcctccaaca acgggggcaa gcaggccctc   1320
gaaactgtgc agaggctgct gcctgtgctg tgccaggctc atgggctgac ccccagcag   1380
gtggtggcca ttgcctctaa caacggcggg aaacaggcca tggagaccgt gcaaaggctg   1440
ctgcccgtcc tctgccaagc ccacgggctc actccacaga aggtcgtggc catcgcctca   1500
aacaatggcg ggaagcaggc cctggagact gtgcaaaggc tgctccctgt gctctgccaa   1560
gcacacggac tgacccctca gcaggtggtg gcaatcgctt ccaacaacgg gggaaagcag   1620
gccctcgaaa ccgtgcagcg cctcctccca gtgctgtgcc aggcacatgg cctcacaccc   1680
gagcaagtgg tggctatcgc cagccacgac ggagggaagc aggctctgga gaccgtgcag   1740
aggctgctgc ctgtcctgtg ccaggcccac gggcttactc cagagcaggt cgtcgccatc   1800
gccagtcatg atggggggaa gcaggccctt gagacagtcc agcggctgct gccagtcctt   1860
tgccaggctc acggcttgac tcccgagcag gtcgtggcca ttgcctcaaa cattggggag   1920
aaacaggccc tggagacagt gcaggccctg ctgccagtgt tgtgtcaggc ccacggcttg   1980
acacccagc  aggtggtcgc cattgcctct aatggcggcg ggagaccgc  cttggagagc   2040
attgttgccc agttatctcg ccctgatccg gcgttggccg cgttgaccaa cgaccacctc   2100
gtcgccttgg cctgcctcgg cgggcgtcct gcgctggatg cagtgaaaaa gggattgggg   2160
gatcctatca gccgttccca gctggtgaag tccgagctgg aggaagaaaa atccgagttg   2220
aggcacaagc tgaagtacgt gccccacgag tacatcgagc tgatcgagat cgcccggaac   2280
agcacccagg accgtatcct ggagatgaag gtgatggagt tcttcatgaa ggtgtacggc   2340
tacagggca  agcacctggg cggctccagg aagcccgacg gcgccatcta ccgtgtgggc   2400
tcccccatcg actacggcgt gatcgtggac accaaggcct actccggcgg ctacaacctg   2460
cccatcggcc aggccgacga aatgcagagg tacgtggagg agaaccagac caggaacaag   2520
cacatcaacc caacgagtg  gtggaaggtg taccctcca  gcgtgaccga gttcaagttc   2580
ctgttcgtgt ccggccactt caagggcaac tacaaggccc agctgaccag gctgaaccac   2640
atcaccaact gcaacggcgc cgtgctgtcc gtggaggagc tcctgatcgg cggcgagatg   2700
atcaaggccg gcacccgac  cctggaggag gtgaggagga gttcaacaa  cggcgagatc   2760
aacttcgcgg ccgactgata a                                             2781
SEQ ID NO: 4          moltype = DNA  length = 2778
FEATURE               Location/Qualifiers
misc_feature          1..2778
                      note = PD1T3R
source                1..2778
                      mol_type = other DNA
                      organism = synthetic construct
SEQUENCE: 4
atgggcgatc ctaaaaagaa acgtaaggtc atcgatatcg ccgatctacg cacgctcggc     60
tacagccagc agcaacagga gaagatcaaa ccgaaggttc gttcgacagt ggcgcagcac    120
cacgaggcac tggtcggcca cgggtttaca cacgcgcaca tcgttgcgtt aagccaacac    180
ccggcagcgt tagggaccgt cgctgtcaag tatcaggaca tgatcgcagc gttgccagag    240
gcgacacacg aagcgatcgt tggcgtcggc aaacagtggt ccggcgcacg cgctctggag    300
gccttgctca cggtggcggg agagttgaga ggtccaccgt tacagttgga cacaggccaa    360
cttctcaaga ttgcaaaacg tggcggcgtg accgcagtgg aggcagtgca tgcatggcgc    420
aatgcactga cgggtgcccc gctcaacttg acccccgagc aagtcgtcgc aatcgccagc    480
catgatgag  ggaagcaagc cctcgaaacc gtgcagcggt tgcttcctgt gctctgccag    540
gcccacgggc ttacccctca gcaggtggtg gccatcgca  gtaacggagg aggaaagcaa    600
gccttggaga cagtgcagcg cctgttgccc gtgctgtgcc aggcacacgg cctcacacca    660
gagcaggtcg tggccattgc ctcccatgac gggggcaaac aggctctgga gaccgtccag    720
aggctgctgc cgtcctctg  tcaagctcac ggcctgactc ccaacaagt  ggtcgccatc    780
gcctctaatg gcgcgggaa  gcaggcactg gaaacagtgc agaggactgc cctgtgtctt    840
tgccaagctc atggggttgac ccccaaacag gtcgtcgcta ttgcctcaaa cggggggaag    900
aagcaggccc ttgagactgt gcagaggctg ttgccagtgc tgtgtcaggc tcacgggctc    960
actccacaac aggtggtcgc aattgccagc aacggcggcg aaagcaagc  tcttgaaacc   1020
gtgcaacgcc tcctgcccgt gctctgtcag gctcatggcc tgacaccaca caagtcgtg    1080
gccatcgcca gtaataatgg cgggaaacag gctcttgaga ccgtcagag  gctgctccca   1140
gtgctctgcc aggcacacgg gctgaccccc gagcaggtgg tggctatcgc cagcaatatt   1200
gggggcaagc aggccctgga aacagtccag gccgctgtgc cagtgctttg ccaggctcac   1260
gggctcactc cccagcaggt cgtggcaatc gcctccaacg gcgagggaa  gcaggctctg   1320
gagaccgtgc agagactgct gccgtcttg tgccaggccc acggactcac acctgaacag   1380
gtcgtcgcca ttgcctctca cgatggggc  aaacaagccc tggagacagt gcagcggctg   1440
ttgcctgtgt tgtgccaagc ccacggcttg actcctcaac aagtggtcgc catcgcctca   1500
```

-continued

```
aatggcggcg gaaaacaagc tctggagaca gtgcagaggt tgctgcccgt cctctgccaa  1560
gcccacggcc tgactcccca acaggtcgtc gccattgcca gcaacaacgg aggaaagcag  1620
gctctcgaaa ctgtgcagcg gctgcttcct gtgctgtgtc aggctcatgg gctgaccccc  1680
gagcaagtgg tggctattgc ctctaatgga ggcaagcaag cccttgagac agtccagagg  1740
ctgttgccag tgctgtgcca ggcccacggg ctcacaccca agcaggtggt cgccatcgcc  1800
agtaacaacg ggggcaaaca ggcattggaa accgtccagc gcctgcttcc agtgctctgc  1860
caggcacacg gactgacacc cgaacaggtg gtggccattg catcccatga tgggggcaag  1920
caggccctgg agaccgtgca gagactcctg ccagtgttgt gccaagctca cggcctcacc  1980
cctcagcaag tcgtggccat cgcctcaaac ggggggggcc ggcctgcact ggagagcatt  2040
gttgccagt tatctcgccc tgatccggcg ttggccgcgt tgaccaacga ccacctcgtc  2100
gccttggcct gcctcggcgg gcgtcctgcg ctggatgcag tgaaaaaggg attggggat  2160
cctatcagcc gttcccagct ggtgaagtcc gagctggagg agaagaaatc cgagttgagg  2220
cacaagctga agtacgtgcc ccacgagtac atcgagctga tcgagatcgc ccggaacagc  2280
acccaggacc gtatcctgga gatgaaggtg atggagttct tcatgaaggt gtacggctac  2340
aggggcaagc acctgggcgg ctccaggaag cccgacggcc ccatctacac cgtgggctcc  2400
cccatcgact acggcgtgat cgtggacacc aaggcctact ccggcggcta caacctgccc  2460
atcggccagg ccgacgaaat gcagaggtac gtggaggaga accagaccag gaacaagcac  2520
atcaaccca acgagtggtg gaaggtgtac ccctccagcg tgaccgagtt caagttcctg  2580
ttcgtgtccg gccacttcaa gggcaactac aaggcccagc tgaccaggct gaaccacatc  2640
accaactgca acgcgccgt gctgtccgtg gaggagctcc tgatcggcgg cgagatgatc  2700
aaggccggca ccctgaccct ggaggaggtg aggaggaagt caacaacgg cgagatcaac  2760
ttcgcggccg actgataa                                                2778

SEQ ID NO: 5            moltype = DNA   length = 49
FEATURE                 Location/Qualifiers
misc_feature            1..49
                        note = PD1-T3
source                  1..49
                        mol_type = other DNA
                        organism = synthetic construct
SEQUENCE: 5
tacctctgtg gggccatctc cctggccccc aagcgcagca tcaaagaga              49

SEQ ID NO: 6            moltype = DNA   length = 60
FEATURE                 Location/Qualifiers
misc_feature            1..60
                        note = 2A-element
source                  1..60
                        mol_type = other DNA
                        organism = synthetic construct
SEQUENCE: 6
tccggtgagg gcagaggaag tcttctaaca tgcggtgacg tggaggagaa tccgggcccc  60

SEQ ID NO: 7            moltype = DNA   length = 1989
FEATURE                 Location/Qualifiers
misc_feature            1..1989
                        note = apoptosis CAR
source                  1..1989
                        mol_type = other DNA
                        organism = synthetic construct
SEQUENCE: 7
gctttgcctg tcactgcctt gctgcttcca cttgctctgt tgttgcacgc cgcaagaccc   60
gaggtcaagc tccaggaaag cggaccaggg ctggtggccc ctagtcagtc attgagcgtc  120
acttgcaccg tcagcggcgt gtctctgccc gattacggcg tgagctggat cagacagccc  180
ccaaggaagg gactggagtg gctgggcgtc atctggggga gcgagactac ctactacaac  240
agcgccctga agagcaggct gaccatcatt aaggacaact ccaagtccca ggtctttctg  300
aaaatgaaca gcctgcagac tgatgacact gccatctact actgcgccaa gcattactac  360
tacggggca gctacgctat ggactactgg ggcagggga cctctgtcac agtgtcaagt  420
ggcgaggag gcagtggcgg aggggaagt ggggcggcg gcagcgacat ccagatgcc  480
cagacaacat ccagcctctc cgcctctctg ggcgacagag tgacaatcag ctgccgggca  540
agtcaggaca tcagcaagta tctcaattga taccagcaga aaccagacgg gacagtgaaa  600
ttgctgatct accacacatc caggctgcac tcaggagtcc cagcaggtt ttccggctcc  660
ggctccggga cagattacag tctgaccatt ccaacctgg agcaggagga tattgccaca  720
tacttttgcc agcaaggcaa cactctgccc tatacctcg gcggggcac aaaactggaa  780
attactcggt cggatcccga gcccaaatct cctgacaaaa ctcacacatg cccaccgtgc  840
ccagcacctc ccgtggccgg cccgtcagtg ttcctcttcc ccccaaaacc caaggacacc  900
ctcatgatcg cccggacccc tgaggtcaca tgcgtggtgg tggacgtgag ccacgaggac  960
cctgaggtca agttcaactg gtacgtggac ggcgtggagg tgcataatgc caagacaaag 1020
ccgcggggag agcagtacaa cagcacgtac cgtgtggtca gcgtcctcac cgtcctgcac 1080
caggactggc tgaatggcaa ggagtacaag tgcaaggtgt ccaacaaagc cctcccagcc 1140
cccatcgaga aaaccatctc caaagccaaa gggcagcccc gagaaccaca ggtgtacacc 1200
ctgcccccat cccgggatga gctgaccaag aaccaggtca gcctgacctg cctggtcaaa 1260
ggcttctatc ccagcgacat cgccgtggag tgggagagca atgggcaacc ggagaacaac 1320
tacaagacca cgcctcccgt gctggactcc gacggctcct tcttcctcta cagcaagctc 1380
accgtggaca agagcaggtg gcagcagggg aacgtgttct catgctccgt gatgcatgag 1440
gccctgcaca atcactatac ccagaaatct ctgagtctga gccaggcaa gaaggatatt 1500
ttggggtggc tttgccttct tcttttgcca attccactaa ttgtttgggt gaagagaaag 1560
gaagtacaga aacatgcag aaagcacaga aggaaaacc aaggttctca tgaatctcca 1620
accttaaatc ctgaaacagt ggcaataaat ttatctgatg ttgacttgag taaatatatc 1680
```

```
accactattg ctggagtcat gacactaagt caagttaaag gctttgttcg aaagaatggt   1740
gtcaatgaag ccaaaataga tgagatcaag aatgacaatg tccaagacac agcagaacag   1800
aaagttcaac tgcttcgtaa ttggcatcaa cttcatggaa agaaagaagc gtatgacaca   1860
ttgattgcag atctcaaaaa agccaatctt tgtactcttg cagagaaaat tcagactatc   1920
atcctcaagg acattactag tgactcagaa aattcaaact tcagaaatga atccagagc    1980
ttggtcgaa                                                          1989

SEQ ID NO: 8            moltype = DNA   length = 276
FEATURE                 Location/Qualifiers
misc_feature            1..276
                        note = BGH polyA
source                  1..276
                        mol_type = other DNA
                        organism = synthetic construct
SEQUENCE: 8
tctagagggc cgtttaaac ccgctgatca gcctcgactg tgccttctag ttgccagcca    60
tctgttgttt gcccctcccc cgtgccttcc ttgaccctgg aaggtgccac tcccactgtc   120
ctttcctaat aaaatgagga aattgcatcg cattgtctga gtaggtgtca ttctattctg   180
gggggtgggg tggggcagga cagcaagggg gaggattggg aagacaatag caggcatgct   240
ggggatgcgg tgggctctat gactagtggc gaattc                             276

SEQ ID NO: 9            moltype = DNA   length = 1000
FEATURE                 Location/Qualifiers
misc_feature            1..1000
                        note = Lck left homology
source                  1..1000
                        mol_type = other DNA
                        organism = synthetic construct
SEQUENCE: 9
gggatagggg gtgcctctgt gtgtgtgtgt gagagtgtgt gtgtgtaggg tgtgtatatg    60
tatagggtgt gtgtgagtgt gtgtgtgtga gagagtgtgt gtgtggcaga atagactgcg   120
gaggtggatt tcatcttgat atgaaaggtc tggaatgcat ggtacattaa actttgagga   180
cagcgctttc caagcactct gaggagcagc cctagaagag gagagctgc agggactccg    240
ggggcttcaa agtgagggcc ccactctgct tcaggcaaaa cagcacaca tttatcactt    300
tatctatgga gttctgcttg atttcatcag acaaaaaatt tccactgcta aaacaggcaa   360
ataaacaaaa aaaagttat ggccaacaga gtcactggag ggtttctgc tggggagaag    420
caagcccgtg tttgaaggaa ccctgtgaga tgactgtggg ctgtgtgagg ggaacagcgg   480
gggcttgatg gtggacttcg ggagcagaag cctctttctc agcctcctca gctagacagg   540
ggaattataa taggaggtgt ggcgtgcaca cctctccagt agggagggt ctgataagtc     600
aggtctctcc caggcttggg aaagtgtgtg tcatctctag gaggtggtcc tcccaacaca   660
gggtactggc agagggagag ggaggggca gaggcaggaa gtgggtaact agactaacaa    720
aggtgcctgt ggcggttgtc ccatcccagg tgggaggtg gggctagggc tcaggggccg    780
tgtgtgaatt tacttgtagc ctgagggctc agagggagca ccggttttga gctgggaccc   840
cctatttag cttttctgtg gctggtgaat gggatccca ggatctcaca atctcaggta     900
cttttggaac tttccaggc aaggccccat tatatctgat gttgggggag cagatcttgg    960
gggagccct tcagccccct cttccattcc ctcagggacc                         1000

SEQ ID NO: 10           moltype = AA   length = 219
FEATURE                 Location/Qualifiers
REGION                  1..219
                        note = Interleukin-12 subunit alpha
source                  1..219
                        mol_type = protein
                        organism = synthetic construct
SEQUENCE: 10
MCPARSLLLV ATLVLLDHLS LARNLPVATP DPGMFPCLHH SQNLLRAVSN MLQKARQTLE    60
FYPCTSEEID HEDITKDKTS TVEACLPLEL TKNESCLNSR ETSFITNGSC LASRKTSFMM   120
ALCLSSIYED LKMYQVEFKT MNAKLLMDPK RQIFLDQNML AVIDELMQAL NFNSETVPQK   180
SSLEEPDFYK TKIKLCILLH AFRIRAVTID RVMSYLNAS                          219

SEQ ID NO: 11           moltype = AA   length = 328
FEATURE                 Location/Qualifiers
REGION                  1..328
                        note = Interleukin-12 subunit beta
source                  1..328
                        mol_type = protein
                        organism = synthetic construct
SEQUENCE: 11
MCHQQLVISW FSLVFLASPL VAIWELKKDV YVVELDWYPD APGEMVVLTC DTPEEDGITW    60
TLDQSSEVLG SGKTLTIQVK EFGDAGQYTC HKGGEVLSHS LLLLHKKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDPPKN   240
LQLKPLKNSR QVEVSWEYPD TWSTPHSYFS LTFCVQVQGK SKREKKDRVF TDKTSATVIC   300
RKNASISVRA QDRYYSSSWS EWASVPCS                                     328

SEQ ID NO: 12           moltype = DNA   length = 1000
FEATURE                 Location/Qualifiers
misc_feature            1..1000
                        note = lck right homology
```

```
source                  1..1000
                        mol_type = other DNA
                        organism = synthetic construct
SEQUENCE: 12
ggctgtggct gcagctcaca cccggaagat gactggatgg aaaacatcga tgtgtgtgag    60
aactgccatt atcccatagt cccactggat ggcaagggca cggtaagagg cgagacaggg   120
gccttggtga gggagttggg tagagaatgc aacccaggag aaagaaatga ccagcactac   180
aggcccttga aagaatagag tggccctctc ccctgaaata cagaaggaa aagaggccca   240
gagaggggaa gggaatctcc taagatcaca cagaaagtag ttggtaaact cagggataac   300
atctaaccag gctggagagg ctgagagcag agcaggggg aaggggggcca gggtctgacc   360
caatcttctg ctttctgacc ccaccctcat ccccactcc acagctgctc atccgaaatg   420
gctctgaggt gcgggaccca ctggttacct acgaaggctc caatccgccg gcttccccac   480
tgcaaggtga ccccaggcag cagggcctga aagacaaggc ctgcgatcc ctggctgttg   540
gcttccacct ctcccccacc tactttctcc ccggtcttgc cttccttgtc ccccacccctg   600
taactccagg cttcctgccg atcccagctc ggttctccct gatgcccctt gtctttacag   660
acaacctggt tatcgctctg cacagctatg agccctctca cgacggagat ctgggctttg   720
agaaggggga acagctccgc atcctggagc agtgagtccc tctccacctt gctctggcgg   780
agtccgtgag ggagcggcga tctccgagac ccgcagccct cctgcgccc ttgaccagct   840
cggggtggcc gccccttggga caaaattcga ggctcagtat tgctgagcca gggttggggg   900
aggctggctt aagggtgga ggggtctttg agggaggtc tcaggtcgac ggctgagcga   960
gccacactga cccacctccg tggcgcagga gcggcgagtg                         1000

SEQ ID NO: 13           moltype = DNA  length = 1992
FEATURE                 Location/Qualifiers
misc_feature            1..1992
                        note = apoptosis CAR
source                  1..1992
                        mol_type = other DNA
                        organism = synthetic construct
SEQUENCE: 13
atggctttgc ctgtcactgc cttgctgctt ccacttgctc tgttgttgca cgccgcaaga    60
cccgaggtca agctccagga aagcggacca gggctggtgg ccctagtca gtcattgagc   120
gtcacttgca ccgtcagcgg cgtgtctctg cccgattacg gcgtgagctg gatcagacag   180
ccccaagga agggactgga gtggctgggc gtcatctggg ggagcgagac tacctactac   240
aacagcgccc tgaagagcag gctgaccatc attaaggaca actccaagtc ccaggtcttt   300
ctgaaaatga cagcctgca gactgatgac actgccatct actactgcgc caagcattac   360
tactacgggg gcagctacgc tatggactac tggggcagg ggacctctgt cacagtgtca   420
agtggcggag gaggcagtgg cggagggga agtggggcg cggcagcga catccagatg   480
acccagacaa catccagcct ctccgcctct ctgggcgaca gagtgacaat cagctgccgg   540
gccagtcagg acatcagcaa gtatctcaat tggtaccagc agaaaccaga cgggacagtg   600
aaattgctga tctaccacac atccaggctg cactcaggag tcccagcag gttttccggc   660
tccggctccg ggacagatta cagtctgacc atttccaacc tggagcagga ggatattgcc   720
acatacttt gccagcaagg caacactctg ccctatacct tcggcggagg cacaaaactg   780
gagattactc ggtcggatcc cgagcccaaa tctcctgaca aaactcacac atgcccaccg   840
tgcccagcac ctcccgtggc cggccgtca gtgttcctct ccccccaaa acccaaggac   900
accctcatga tcgcccggac ccctgaggtc acatgcgtgg tggtggacgt gagccacgag   960
gaccctgagg tcaagttcaa ctggtacgtg gacggcgtgg aggtgcataa tgccaagaca  1020
aagccgcggg aggagcagta acagcacg taccgtgtgg tcagcgtcct caccgtcctg  1080
caccaggact ggctgaatgg caaggagtac aagtgcaagg tgtccaacaa agccctccca  1140
gcccccatcg agaaaaccat ctccaaagcc aaagggcagc cccgagaacc acaggtgtac  1200
accctgcccc catcccggga tgagctgacc aagaaccagg tcagcctgac ctgcctggtc  1260
aaaggcttct atcccagcga catcgccgtg gagtgggaga gcaatgggca accggagaac  1320
aactacaaga ccacgcctcc cgtgctggac tccgacggct ccttcttcct ctacagcaag  1380
ctcaccgtgg acaagagcag gtggcagcag gggaacgtgt tctcatgctc cgtgatgcat  1440
gaggccctgc acaatcacta cacccagaaa tctctgagtc tgagcccagg caagaaggat  1500
attttgggt ggctttgcct tcttcttttg ccaattccac taattgtttg ggtgaagaga  1560
aaggaagtac agaaaacatg cagaaagcac agaaaggaaa accaaggttc tcatgaatct  1620
ccaaccttaa atcctgaaac agtggcaata aatttatctg atgttgactt gagtaaatat  1680
atcaccacta ttgctggagt catgacatca agtcaagtta aagcttttgt tcgaaagaat  1740
ggtgtcaatg aagccaaaat agatgagatc aagaatgaca aagtccaaga cacagcagaa  1800
cagaaagttc aactgcttcg taattggcat caacttcatg gaaagaaaga agcgtatgac  1860
acattgatg cagatctcaa aaagccaat ctttgtactc ttgcagagaa aattcagact  1920
atcatcctca aggacattac tagtgactca gaaaattcaa acttcagaaa tgaaatccag  1980
agcttggtcg aa                                                    1992

SEQ ID NO: 14           moltype = DNA  length = 1000
FEATURE                 Location/Qualifiers
misc_feature            1..1000
                        note = Lck left homology
source                  1..1000
                        mol_type = other DNA
                        organism = synthetic construct
SEQUENCE: 14
ctcataacaa ttctatgagg taggaacagt tatttactct attttccaaa taaggaaact    60
gggctcgccc aaggttccac aactaacatg tgtgtattat tgagcattta atttacacca   120
gggaagcagg ttgtggtggt gtgcacctgt tgtccagcta tttaggaggc tgaggtgaaa   180
ggatcacttg aacggaggag ttcaattttg caatgtgcta tgattgtgcc tgtgaacagc   240
tgctgcactc cagcctgggc aacatagtga gatcccttat ctaaaacatt ttttttaagt   300
aaataatcag gtgggcacgg tggctcacgc ctgtaatcca gcactttggg aggctgaggc   360
```

```
gggcggatca    cctgaggtca    ggagttcaag    accagcctga    ccaacatgga    gaaacccgtc    420
tctactaaaa    atacaaaatt    agcttggcgt    ggtggtgcat    gcctgtaatc    ccagctactc    480
gagaagctga    ggcaggagaa    ttgtttgaac    ctgggaggtg    gaggttgcgg    tgagccgaga    540
tcgcaccatt    gcactccagc    ctgggcaaca    agagtgaaat    tgcatctcaa    aaaaaaagaa    600
aaggaaataa    tctataccag    gcactccaag    tggtgtgact    gatattcaac    aagtacctct    660
agtgtgacct    taccattgat    gaagaccaag    attctttttgg   attggtgctc    acactgtgcc    720
agttaaatat    tccgaacatt    acccttgcct    gtgggcttcc    agtgcctgac    cttgatgtcc    780
tttcacccat    caacccgtag    ggatgaccaa    cccggaggtg    attcagaacc    tggagcgagg    840
ctaccgcatg    gtgcgccctg    acaactgtcc    agaggagctg    taccaactca    tgaggctgtg    900
ctggaaggag    cgcccagagg    accggcccac    ctttgactac    ctgcgcagtg    tgctggagga    960
cttcttcacg    gccacagagg    gccagtacca    gcctcagcct                               1000

SEQ ID NO: 15          moltype = DNA  length = 1000
FEATURE                Location/Qualifiers
misc_feature           1..1000
                       note = lck right homology
source                 1..1000
                       mol_type = other DNA
                       organism = synthetic construct
SEQUENCE: 15
gaggccttga    gaggccctgg    ggttctcccc    ctttctctcc    agcctgactt    ggggagatgg    60
agttcttgtg    ccatagtcac    atggcctatg    cacatggaca    ctctgcacat    gaatcccatc    120
cacatgtgac    acatatgcac    cttgtgtctg    tacacgtgtc    ctgtagttgc    gtggactctg    180
cacatgtctt    gtacatgtgt    agcctgtgca    tgtatgtctt    ggacactgta    caaggtaccc    240
cttctctggct   ctcccatttc    ctgagaccac    agagagaggg    gagaagcctg    ggattgacag    300
aagcttctgc    ccacctactt    ttcttcctc    agatcatcca    gaagttcctc    aagggccagg    360
actttatcta    atacctctgt    gtgctcctcc    ttggtgcctg    gcctggcaca    catccaggagt   420
tcaataaatg    tctgttgatg    actgttgtac    atctctttgc    tgtccactct    ttgtgggtgg    480
gcagtggggg    ttaagaaaat    ggtaattagg    tcaccctgag    ttggggtgaa    agatgggatg    540
agtggatgtc    tggaggctct    gcagacccct    tcaaatggga    cagtgctcct    caccctccc    600
caaaggattc    agggtgactc    ctacctggaa    tcccttaggg    aatgggtgcg    tcaaaggacc    660
ttcctcccca    ttataaaagg    gcaacagcat    tttttactga    ttcaagggct    atatttgacc    720
tcagattttg    ttttttttaag   gctagtcaaa    tgaagcggcg    ggaatggagg    aggaacaaat    780
aaatctgtaa    ctatcctcag    attttttttt    tttttgaga    ctgggtctca    cttttttcatc   840
caggctggag    tgcagtcgca    tgatcacggc    tcactgtagc    ctcaacctct    ccagctcaaa    900
tgctcctcct    gtctcagcct    cccgagtacc    tgggactact    tcttgaggc    caggaattca    960
agaacagagt    aagatcctgg    tctccaaaaa    aagttttaaa                                1000

SEQ ID NO: 16          moltype = AA  length = 936
FEATURE                Location/Qualifiers
REGION                 1..936
                       note = TALEN TRAC
source                 1..936
                       mol_type = protein
                       organism = synthetic construct
SEQUENCE: 16
MGDPKKKRKV    IDYPYDVPDY    AIDIADLRTL    GYSQQQQEKI    KPKVRSTVAQ    HHEALVGHGF    60
THAHIVALSQ    HPAALGTVAV    KYQDMIAALP    EATHEAIVGV    GKQWSGARAL    EALLTVAGEL    120
RGPPLQLDTG    QLLKIAKRGG    VTAVEAVHAW    RNALTGAPLN    LTPQQVVAIA    SNGGGKQALE    180
TVQRLLPVLC    QAHGLTPQQV    VAIASNNGGK    QALETVQRLL    PVLCQAHGLT    PQQVVAIASN    240
GGGKQALETV    QRLLPVLCQA    HGLTPEQVVA    IASHDGGKQA    LETVQRLLPV    LCQAHGLTPE    300
QVVAIASHDG    GKQALETVQR    LLPVLCQAHG    LTPEQVVAIA    SHDGGKQALE    TVQRLLPVLC    360
QAHGLTPEQV    VAIASNIGGK    QALETVQALL    PVLCQAHGLT    PEQVVAIASH    DGGKQALETV    420
QRLLPVLCQA    HGLTPEQVVA    IASNIGGKQA    LETVQALLPV    LCQAHGLTPQ    QVVAIASNNG    480
GKQALETVQR    LLPVLCQAHG    LTPEQVVAIA    SNIGGKQALE    TVQRLLPVLC    QAHGLTPQQV    540
VAIASNGGGK    QALETVQRLL    PVLCQAHGLT    PEQVVAIASN    IGGKQALETV    QALLPVLCQA    600
HGLTPQQVVA    IASNGGGKQA    LETVQRLLPV    LCQAHGLTPE    QVVAIASHDG    GKQALETVQR    660
LLPVLCQAHG    LTPQQVVAIA    SNGGGRPALE    SIVAQLSRPD    PALAALTNDH    LVALACLGGR    720
PALDAVKKGL    GDPISRSQLV    KSELEEKKSE    LRHKLKYVPH    EYIELIEIAR    NSTQDRILEM    780
KVMEFFMKVY    GYRGKHLGGS    RKPDGAIYTV    GSPIDYGVIV    DTKAYSGGYN    LPIGQADEMQ    840
RYVEENQTRN    KHINPNEWWK    VYPSSVTEFK    FLFVSGHFKG    NYKAQLTRLN    HITNCNGAVL    900
SVEELLIGGE    MIKAGTLTLE    EVRRKFNNGE    INFAAD                                   936

SEQ ID NO: 17          moltype = AA  length = 942
FEATURE                Location/Qualifiers
REGION                 1..942
                       note = TALEN TRAC
source                 1..942
                       mol_type = protein
                       organism = synthetic construct
SEQUENCE: 17
MGDPKKKRKV    IDKETAAAKF    ERQHMDSIDI    ADLRTLGYSQ    QQQEKIKPKV    RSTVAQHHEA    60
LVGHGFTHAH    IVALSQHPAA    LGTVAVKYQD    MIAALPEATH    EAIVGVGKQW    SGARALEALL    120
TVAGELRGPP    LQLDTGQLLK    IAKRGGVTAV    EAVHAWRNAL    TGAPLNLTPQ    QVVAIASHDG    180
GKQALETVQR    LLPVLCQAHG    LTPQQVVAIA    SNGGGKQALE    TVQRLLPVLC    QAHGLTPEQV    240
VAIASHDGGK    QALETVQRLL    PVLCQAHGLT    PEQVVAIASN    IGGKQALETV    QALLPVLCQA    300
HGLTPQQVVA    IASNNGGKQA    LETVQRLLPV    LCQAHGLTPE    QVVAIASHDG    GKQALETVQR    360
LLPVLCQAHG    LTPQQVVAIA    SNGGGKQALE    TVQRLLPVLC    QAHGLTPQQV    VAIASNNGGK    420
QALETVQRLL    PVLCQAHGLT    PQQVVAIASN    NGGKQALETV    QRLLPVLCQA    HGLTPQQVVA    480
```

```
IASNGGGKQA  LETVQRLLPV  LCQAHGLTPE  QVVAIASNIG  GKQALETVQA  LLPVLCQAHG    540
LTPEQVVAIA  SHDGGKQALE  TVQRLLPVLC  QAHGLTPEQV  VAIASNIGGK  QALETVQALL    600
PVLCQAHGLT  PEQVVAIASH  DGGKQALETV  QRLLPVLCQA  HGLTPQQVVA  IASNNGGKQA    660
LETVQRLLPV  LCQAHGLTPQ  QVVAIASNGG  GRPALESIVA  QLSRPDPALA  ALTNDHLVAL    720
ACLGGRPALD  AVKKGLGDPI  SRSQLVKSEL  EEKKSELRHK  LKYVPHEYIE  LIEIARNSTQ    780
DRILEMKVME  FFMKVYGYRG  KHLGGSRKPD  GAIYTVGSPI  DYGVIVDTKA  YSGGYNLPIG    840
QADEMQRYVE  ENQTRNKHIN  PNEWWKVYPS  SVTEFKFLFV  SGHFKGNYKA  QLTRLNHITN    900
CNGAVLSVEE  LLIGGEMIKA  GTLTLEEVRR  KFNNGEINFA  AD                        942

SEQ ID NO: 18           moltype = AA  length = 913
FEATURE                 Location/Qualifiers
REGION                  1..913
                        note = TALEN CD25
source                  1..913
                        mol_type = protein
                        organism = synthetic construct
SEQUENCE: 18
MGDPKKKRKV  IDYPYDVPDY  AIDIADLRTL  GYSQQQQEKI  KPKVRSTVAQ  HHEALVGHGF     60
THAHIVALSQ  HPAALGTVAV  KYQDMIAALP  EATHEAIVGV  GKQWSGARAL  EALLTVAGEL    120
RGPPLQLDTG  QLLKIAKRGG  VTAVEAVHAW  RNALTGAPLN  LTQQVVAIA  SNNGGKQALE     180
TVQRLLPVLC  QAHGLTPQQV  VAIASNGGGK  QALETVQRLL  PVLCQAHGLT  PQQVVAIASN    240
GGGKQALETV  QRLLPVLCQA  HGLTPEQVVA  IASHDGGKQA  LETVQRLLPV  LCQAHGLTPQ    300
QVVAIASNGG  GKQALETVQR  LLPVLCQAHG  LTPQQVVAIA  SNGGGKQALE  TVQRLLPVLC    360
QAHGLTPQQV  VAIASNGGGK  QALETVQRLL  PVLCQAHGLT  PQQVVAIASN  GGGKQALETV    420
QRLLPVLCQA  HGLTPQQVVA  IASNNGGKQA  LETVQRLLPV  LCQAHGLTPQ  QVVAIASNNG    480
GKQALETVQR  LLPVLCQAHG  LTPQQVVAIA  SNGGGKQALE  TVQRLLPVLC  QAHGLTPQQV    540
VAIASNGGGK  QALETVQRLL  PVLCQAHGLT  PQQVVAIASN  GGGKQALETV  QRLLPVLCQA    600
HGLTPQQVVA  IASNGGGKQA  LETVQRLLPV  LCQAHGLTPE  QVVAIASHDG  KQALETVQR     660
LLPVLCQAHG  LTPQQVVAIA  SNGGGRPALE  SIVAQLSRPD  PSGSGSGGDP  ISRSQLVKSE    720
LEEKKSELRH  KLKYVPHEYI  ELIEIARNST  QDRILEMKVM  EFFMKVYGYR  GKHLGGSRKP    780
DGAIYTVGSP  IDYGVIVDTK  AYSGGYNLPI  GQADEMQRYV  EENQTRNKHI  NPNEWWKVYP    840
SSVTEFKFLF  VSGHFKGNYK  AQLTRLNHIT  NCNGAVLSVE  ELLIGGEMIK  AGTLTLEEVR    900
RKFNNGEINF  AAD                                                           913

SEQ ID NO: 19           moltype = AA  length = 913
FEATURE                 Location/Qualifiers
REGION                  1..913
                        note = TALEN CD25
source                  1..913
                        mol_type = protein
                        organism = synthetic construct
SEQUENCE: 19
MGDPKKKRKV  IDYPYDVPDY  AIDIADLRTL  GYSQQQQEKI  KPKVRSTVAQ  HHEALVGHGF     60
THAHIVALSQ  HPAALGTVAV  KYQDMIAALP  EATHEAIVGV  GKQWSGARAL  EALLTVAGEL    120
RGPPLQLDTG  QLLKIAKRGG  VTAVEAVHAW  RNALTGAPLN  LTPEQVVAIA  SNIGGKQALE    180
TVQALLPVLC  QAHGLTPEQV  VAIASHDGGK  QALETVQRLL  PVLCQAHGLT  PEQVVAIASN    240
IGGKQALETV  QALLPVLCQA  HGLTPQQVVA  IASNNGGKQA  LETVQRLLPV  LCQAHGLTPQ    300
QVVAIASNNG  GKQALETVQR  LLPVLCQAHG  LTPEQVVAIA  SNIGGKQALE  TVQALLPVLC    360
QAHGLTPQQV  VAIASNNGGK  QALETVQRLL  PVLCQAHGLT  PQQVVAIASN  NGGKQALETV    420
QRLLPVLCQA  HGLTPEQVVA  IASNIGGKQA  LETVQALLPV  LCQAHGLTPE  QVVAIASNIG    480
GKQALETVQA  LLPVLCQAHG  LTPQQVVAIA  SNNGGKQALE  TVQRLLPVLC  QAHGLTPEQV    540
VAIASNIGGK  QALETVQALL  PVLCQAHGLT  PQQVVAIASN  NGGKQALETV  QRLLPVLCQA    600
HGLTPQQVVA  IASNGGGKQA  LETVQRLLPV  LCQAHGLTPE  QVVAIASNIG  GKQALETVQA    660
LLPVLCQAHG  LTPQQVVAIA  SNGGGRPALE  SIVAQLSRPD  PSGSGSGGDP  ISRSQLVKSE    720
LEEKKSELRH  KLKYVPHEYI  ELIEIARNST  QDRILEMKVM  EFFMKVYGYR  GKHLGGSRKP    780
DGAIYTVGSP  IDYGVIVDTK  AYSGGYNLPI  GQADEMQRYV  EENQTRNKHI  NPNEWWKVYP    840
SSVTEFKFLF  VSGHFKGNYK  AQLTRLNHIT  NCNGAVLSVE  ELLIGGEMIK  AGTLTLEEVR    900
RKFNNGEINF  AAD                                                           913

SEQ ID NO: 20           moltype = AA  length = 936
FEATURE                 Location/Qualifiers
REGION                  1..936
                        note = TALEN PD1
source                  1..936
                        mol_type = protein
                        organism = synthetic construct
SEQUENCE: 20
MGDPKKKRKV  IDYPYDVPDY  AIDIADLRTL  GYSQQQQEKI  KPKVRSTVAQ  HHEALVGHGF     60
THAHIVALSQ  HPAALGTVAV  KYQDMIAALP  EATHEAIVGV  GKQWSGARAL  EALLTVAGEL    120
RGPPLQLDTG  QLLKIAKRGG  VTAVEAVHAW  RNALTGAPLN  LTPEQVVAIA  SKLGGKQALE    180
TVQALLPVLC  QAHGLTPEQV  VAIASHDGGK  QALETVQRLL  PVLCQAHGLT  PEQVVAIASH    240
DGGKQALETV  QRLLPVLCQA  HGLTPQQVVA  IASNGGGKQA  LETVQRLLPV  LCQAHGLTPE    300
QVVAIASHDG  KQALETVQR  LLPVLCQAHG  LTPQQVVAIA  SNGGGKQALE  TVQRLLPVLC     360
QAHGLTPQQV  VAIASYKGGK  QALETVQRLL  PVLCQAHGLT  PQQVVAIASN  GGGKQALETV    420
QRLLPVLCQA  HGLTPQQVVA  IASNNGGKQA  LETVQRLLPV  LCQAHGLTPQ  QVVAIASNNG    480
GKQALETVQR  LLPVLCQAHG  LTPQQVVAIA  SNNGGKQALE  TVQRLLPVLC  QAHGLTPQQV    540
VAIASNNGGK  QALETVQRLL  PVLCQAHGLT  PEQVVAIASH  DGGKQALETV  QRLLPVLCQA    600
HGLTPEQVVA  IASHDGGKQA  LETVQRLLPV  LCQAHGLTPE  QVVAIASNIG  GKQALETVQA    660
LLPVLCQAHG  LTPQQVVAIA  SNGGGRPALE  SIVAQLSRPD  PALAALTNDH  LVALACLGGR    720
```

```
PALDAVKKGL GDPISRSQLV KSELEEKKSE LRHKLKYVPH EYIELIEIAR NSTQDRILEM   780
KVMEFFMKVY GYRGKHLGGS RKPDGAIYTV GSPIDYGVIV DTKAYSGGYN LPIGQADEMQ   840
RYVEENQTRN KHINPNEWWK VYPSSVTEFK FLFVSGHFKG NYKAQLTRLN HITNCNGAVL   900
SVEELLIGGE MIKAGTLTLE EVRRKFNNGE INFAAD                            936

SEQ ID NO: 21            moltype = AA  length = 941
FEATURE                  Location/Qualifiers
REGION                   1..941
                         note = TALEN PD1
source                   1..941
                         mol_type = protein
                         organism = synthetic construct
SEQUENCE: 21
MGDPKKKRKV IDKETAAAKF ERQHMDSIDI ADLRTLGYSQ QQQEKIKPKV RSTVAQHHEA    60
LVGHGFTHAH IVALSQHPAA LGTVAVKYQD MIAALPEATH EAIVGVGKQW SGARALEALL   120
TVAGELRGPP LQLDTGQLLK IAKRGGVTAV EAVHAWRNAL TGAPLNLTPE QVVAIASHDG   180
GKQALETVQR LLPVLCQAHG LTPQQVVAIA SNGGGKQALE TVQRLLPVLC QAHGLTPEQV   240
VAIASHDGGK QALETVQRLL PVLCQAHGLT PQQVVAIASN GGGKQALETV QRLLPVLCQA   300
HGLTPQQVVA IASNGGGKQA LETVQRLLPV LCQAHGLTPQ QVVAIASNGG GKQALETVQR   360
LLPVLCQAHG LTPQQVVAIA SNNGGKQALE TVQRLLPVLC QAHGLTPEQV VAIASNIGGK   420
QALETVQALL PVLCQAHGLT PQQVVAIASN GGGKQALETV QRLLPVLCQA HGLTPEQVVA   480
IASHDGGKQA LETVQRLLPV LCQAHGLTPQ QVVAIASNGG GKQALETVQR LLPVLCQAHG   540
LTPQQVVAIA SNNGGKQALE TVQRLLPVLC QAHGLTPEQV VAIASNGGKQ ALETVQRLLP   600
VLCQAHGLTP QQVVAIASNN GGKQALETVQ RLLPVLCQAH GLTPEQVVAI ASHDGGKQAL   660
ETVQRLLPVL CQAHGLTPQQ VVAIASNGGG RPALESIVAQ LSRPDPALAA LTNDHLVALA   720
CLGGRPALDA VKKGLGDPIS RSQLVKSELE EKKSELRHKL KYVPHEYIEL IEIARNSTQD   780
RILEMKVMEF FMKVYGYRGK HLGGSRKPDG AIYTVGSPID YGVIVDTKAY SGGYNLPIGQ   840
ADEMQRYVEE NQTRNKHINP NEWWKVYPSS VTEFKFLFVS GHFKGNYKAQ LTRLNHITNC   900
NGAVLSVEEL LIGGEMIKAG TLTLEEVRRK FNNGEINFAA D                      941

SEQ ID NO: 22            moltype = DNA  length = 2814
FEATURE                  Location/Qualifiers
misc_feature             1..2814
                         note = TALEN TRAC pCLS11370
source                   1..2814
                         mol_type = other DNA
                         organism = synthetic construct
SEQUENCE: 22
atgggcgatc ctaaaaagaa acgtaaggtc atcgattacc catacgatgt tccagattac     60
gctatcgata tcgccgatct acgcacgctc ggctacagcc agcagcaaca ggagaagatc    120
aaaccgaagg ttcgttcgac agtggcgcag caccacgagg cactggtcgg ccacgggttt    180
acacacgcgc acatcgttgc gttaagccaa cacccggcag cgttagggac cgtcgctgtc    240
aagtatcagg acatgatcgc agcgttgcca gaggcgacca tcgaaggcgt cgttggcgtc    300
ggcaaacagt ggtccggcgc acgcgctctg gaggccttgc tcacggtggc gggagagttg    360
agaggtccac cgttacagtt ggacacaggc caacttctca agattgcaaa acgtggcggc    420
gtgaccgcag tggaggcagt gcatgcatgg cgcaatgcac tgacgggtgc cccgctcaac    480
ttgaccccc agcaggtggt ggccatcgcc agcaatgcgc gtgcaagca ggcgctggag     540
acggtccagc ggctgttgcc ggtgctgtgc caggcccacg gcttgacccc ccagcaggtg    600
gtggccatcg ccagcaataa tggtggcaag caggcgctgg agacggtcca gcggctgttg    660
ccggtgctgt gccaggccca cggcttgacc ccccagcagg tggtggccat cgccagcaat    720
ggcggtggca agcaggcgct ggagacggtc cagcggctgt tgccggtgct gtgccaggcc    780
cacggcttga ccccggagca ggtggtggcc atcgccagcc acgatggcgg caagcaggcg    840
ctggagacgg tccagcggct gttgccggtg ctgtgccagg cccacggctt gaccccggag    900
caggtggtgg ccatcgccag ccacgatggc ggcaagcagg cgctggagac ggtccagcgg    960
ctgttgccgg tgctgtgcca ggcccacggc ttgaccccc agcaggtggt ggccatcgcc    1020
agccacgatg gcggcaagca ggcgctggag acggtccagc ggctgttgcc ggtgctgtgc    1080
caggcccacg gcttgacccc ggagcaggtg gtggccatcg ccagcaatat tggtggcaag    1140
caggcgctgg agacggtgca ggcgctgttg ccggtgctgt gccaggccca cggcttgacc    1200
ccggagcagg tggtggccat cgccagccac gatggcggca agcaggcgct ggagacggtc    1260
cagcggctgt tgccggtgct gtgccaggcc cacggcttga ccccggagca ggtggtggcc    1320
atcgccagca atattggtgg caagcaggcg ctggagacgg tgcaggcgct gttgccggtg    1380
ctgtgccagg cccacggctt gaccccccag caggtggtgg ccatcgccag caataatggt    1440
ggcaagcagg cgctggagac ggtccagcgg ctgttgccgg tgctgtgcca ggcccacggc    1500
ttgaccccgg agcaggtggt ggccatcgcc agcaataatt ggtggcaagca gcgctggag    1560
acggtcagg cgctgttgcc ggtgctgtgc caggcccacg gcttgacccc ccagcaggtg    1620
gtggccatcg ccagcaatgg cggtggcaag caggcgctgg agacggtcca gcggctgttg    1680
ccggtgctgt gccaggccca cggcttgacc ccggagcagg tggtggccat cgccagcaat    1740
attggtggca agcaggcgct ggagacggtc agcggctgt tgccggtgct gtgccaggcc    1800
cacggcttga ccccccagca ggtgtggcc atcgccagcc acgatggcgg caagcaggcg    1860
ctggagacgg tccagcggct gttgccggtg ctgtgccagg cccacggctt gaccccggag    1920
caggtggtgg ccatcgccag ccacgatggc ggcaagcagg cgctggagac ggtccagcgg    1980
ctgttgccgg tgctgtgcca ggcccacggc ttgacccctc agcaggtggt ggccatcgcc    2040
agcaatggcg gcggcaggcc ggcgctggag agcattgttg cccagttatc tcgccctgat    2100
ccggcgcttg ccgcgcttga caacgaccac ctcgtcgcct tggcctgcct cggcgggcgt    2160
cctgcgctga tgcagtgaa aaagggattg ggggatccta tcagccgttc ccagctggtg    2220
aagtccgagc tggaggagaa gaaatccgag ttgaggcaca gctgaagta cgtcccccac    2280
gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acggcgccat ctacaccgtg ggctccccca tcgactacgg cgtgatcgtg    2460
```

```
gacaccaagg cctactccgg cggctacaac ctgcccatcg gccaggccga cgaaatgcag  2520
aggtacgtgg aggagaacca gaccaggaac aagcacatca accccaacga gtggtggaag  2580
gtgtacccct ccagcgtgac cgagttcaag ttcctgttcg tgtccggcca cttcaagggc  2640
aactacaagg cccagctgac caggctgaac cacatcacca actgcaacgg cgccgtgctg  2700
tccgtggagg agctcctgat cggcggcgag atgatcaagc ccggcaccct gaccctggag  2760
gaggtgagga ggaagttcaa caacggcgag atcaacttcg cggccgactg ataa         2814

SEQ ID NO: 23              moltype = DNA   length = 2832
FEATURE                    Location/Qualifiers
misc_feature               1..2832
                           note = TALEN TRAC pCLS11369
source                     1..2832
                           mol_type = other DNA
                           organism = synthetic construct
SEQUENCE: 23
atgggcgatc ctaaaaagaa acgtaaggtc atcgataagg agaccgccgc tgccaagttc   60
gagagacagc acatggacag catcgatatc gccgatctac gcacgctcgg ctacagccag  120
cagcaacagg agaagatcaa accgaaggtt cgttcgacag tggcgcagca ccacgaggca  180
ctggtcggcc acgggtttac acacgcgcac atcgttgcgt taagccaaca cccggcagca  240
ttagggaccg tcgctgtcaa gtatcaggac atgatcgcag cgttgccaga ggcgacacac  300
gaagcgatcg ttggcgtcgg caaacagtgg tccggcgcac gcgctctgga ggccttgctc  360
acggtggcgg gagagttgag aggtccaccg ttacagttga acacaggcca acttctcaag  420
attgcaaaac gtggcggcgt gaccgcagtg gaggcagtgc atgcatggcg caatgcactg  480
acgggtgccc cgctcaactt gaccccggag caggtggtgg ccatcgccag ccacgatggc  540
ggcaagcagg cgctggagac ggtccagcgg ctgttgccgg tgctgtgcca ggcccacggc  600
ttgaccccc agcaggtggt ggccatcgcc agcaatgatg gtggcaagca ggcgctggag  660
acggtccagc ggctgttgcc ggtgctgtgc caggcccacg gcttgacccc ggagcaggtg  720
gtggccatcg ccagcacga tggcggcaag caggcgctgg agacggtcca gcggctgttg  780
ccggtgctgt gccaggccca cggcttgacc ccggagcagg tggtggccat cgccagcaat  840
attgcaagca agcaggcgct ggagacggtg caggcgctgt tgccggtgct gtgccaggcc  900
cacggcttga ccccccagca ggtggtggca atcgccagca ataatggtgg caagcaggcg  960
ctggagacgg tccagcggct gttgccggtg ctgtgccagg cccacggctt gaccccggag 1020
caggtggtgg ccatcgccag ccacgatggc ggcaagcagg cgctggagac ggtccagcgg 1080
ctgttgccgg tgctgtgcca ggcccacggc ttgaccccc agcaggtggt ggccatcgcc 1140
agcaatggcg gtggcaagca ggcgctggag acggtccagc ggctgttgcc ggtgctgtgc 1200
caggcccacg gcttgacccc ccagcaggtg gtggccatcg ccagcaataa tggtggcaag 1260
caggcgctgg agacggtcca gcggctgttg ccggtgctgt gccaggccca cggcttgacc 1320
ccccagcagg tggtggccat cgccagcaat aatggtggca agcaggcgct ggagacggtc 1380
cagcggctgt tgccggtgct gtgccaggcc cacggcttga ccccccagca ggtggtggcc 1440
atcgccagca atggcggtgg caagcaggcg ctggagacgg tccagcggct gttgccggtg 1500
ctgtgccagg cccacggctt gaccccggag caggtggtgg ccatcgccag caatattggt 1560
ggcaagcagg cgctggagac ggtgcaggcg ctgttgccgg tgctgtgcca ggcccacggc 1620
ttgaccccgg agcaggtggt ggccatcgcc agccacgatg gcggcaagca ggcgctgtag 1680
acggtccagc ggctgttgcc ggtgctgtgc caggcccacg gcttgacccc ggagcaggtg 1740
gtggccatcg ccagcaatat tggtggcaag caggcgctgg agacggtgca ggcgctgttg 1800
ccggtgctgt gccaggccca cggcttgacc ccggagcagg tggtggccat cgccagccac 1860
gatggcggca agcaggcgct ggagacggtc cagcggctgt tgccggtgct gtgccaggcc 1920
cacggcttga ccccccagca ggtggtggcc atcgccagca ataatggtgg caagcaggcg 1980
ctggagacgg tccagcggct gttgccggtg ctgtgccagg cccacggctt gaccccctag 2040
caggtggtgg ccatcgccag caatggcggc ggcaggccgg cgctggagag cattgttgcc 2100
cagttatctc gccctgatcc ggcgttggcc gcgttgaaca agaccacct cgtcgccttg 2160
gcctgcctcg gcgggcgtcc tgcgctggat gcagtgaaaa agggattggg ggatcctatc 2220
agccgttccc agctggtgaa gtccgagctg gaggagaaga atccgagtt gaggcacaag 2280
ctgaagtacg tgcccacga gtacatcgag ctgatcgaga tcgcccggaa cagcacccag 2340
gaccgtatcc tggagatgaa ggtgatggag ttcttcatga aggtgtacgg ctacaggggc 2400
aagcacctgg gcggctccag gaagcccgac ggcgccatct acaccgtggg ctccccatc 2460
gactacggcc tgatcgtgga caccaaggcc tactccggcg gctacaacct gcccatcggc 2520
caggccgacg aaatgcagag gtacgtggag gagaaccaga ccaggaacaa gcacatcaac 2580
cccaacgagt ggtggaaggt gtacccctcc agcgtgacca gttcaagtt cctgttcgtg 2640
tccggccact tcaagggcaa ctacaaggcc cagctgacca tcaccaac              2700
tgcaacggcg ccgtgctgtc cgtggaggag ctcctgatcg gcggcgagat gatcaaggcc 2760
ggcaccctga ccctggagga ggtgaggagg aagttcaaca acggcgagat caacttcgcg 2820
gccgactgat aa                                                     2832

SEQ ID NO: 24              moltype = DNA   length = 2745
FEATURE                    Location/Qualifiers
misc_feature               1..2745
                           note = TALEN CD25 pCLS30480
source                     1..2745
                           mol_type = other DNA
                           organism = synthetic construct
SEQUENCE: 24
atgggcgatc ctaaaaagaa acgtaaggtc atcgattacc catacgatgt tccagattac   60
gctatcgata tcgccgatct acgcacgctc ggctacagcc agcagcaaca ggagaagatc  120
aaaccgaagg ttcgttcgac agtggcgcag caccacgagg cactggtcgg ccacgggttt  180
acacacgcgc acatcgttgc gttaagccaa cacccggcag cgttagggac cgtcgctgtc  240
aagtatcagg acatgatcgc agcgttgcca gaggcgacac acgaagcgat cgttggcgtc  300
ggcaaacagt ggtccggcgc acgcgctctg gaggccttgc tcacggtggc gggagagttg  360
agaggtccac cgttacagtt ggacacaggc caacttctca gattgcaaa acgtggcggc  420
```

```
gtgaccgcag tggaggcagt gcatgcatgg cgcaatgcac tgacgggtgc cccgctcaac   480
ttgacccccc agcaggtggt ggccatcgcc agcaataatg gtggcaagca ggcgctggag   540
acggtccagc ggctgttgcc ggtgctgtgc caggcccacg gcttgacccc ccagcaggtg   600
gtggccatcg ccagcaatgg cggtggcaag caggcgctgg agacggtcca gcggctgttg   660
ccggtgctgt gccaggccca cggcttgacc cccagcaggt ggtggccatc gccagcaat   720
ggcggtggca agcaggcgct ggagacggtc cagcggctgt gccggtgct gtgccaggcc   780
cacggcttga ccccgagca ggtggtggcc atcgccagcc acgatggcgg caagcaggcg   840
ctggagacgg tccagcggct gttgccggtg ctgtgccagg cccacggctt gaccccccag   900
caggtggtgg ccatcgccag caatggcggt ggcaagcagg cgctggagac ggtccagcgg   960
ctgttgccgg tgctgtgcca ggcccacggc ttgaccccc agcaggtggt ggccatcgcc  1020
agcaatggcg gtggcaagca ggcgctggag acggtccagc ggctgttgcc ggtgctgtgc  1080
caggcccacg gcttgacccc ccagcaggtg gtggccatcg ccagcaatgg cggtggcaag  1140
caggcgctgg agacggtcca gcggctgttg ccggtgctgt gccaggccca cggcttgacc  1200
cccagcagg tggtggccat cgccagcaat ggcggtggca agcaggcgct ggagacgtg  1260
cagcggctgt tgccggtgct gtgccaggcc cacggcttga ccccccagca ggtggtggcc  1320
atcgccagca ataatggtgg caagcaggcg ctggagacgg tccagcggct gttgccggtg  1380
ctgtgccagg cccacggctt gaccccccag caggtggtgg ccatcgccag caataatggt  1440
ggcaagcagg cgctggagac ggtccagcgg ctgttgccgg tgctgtgcca ggcccacggc  1500
ttgacccccc agcaggtggt ggccatcgcc agcaatggcg gtggcaagca ggcgctggag  1560
acggtccagc ggctgttgcc ggtgctgtgc caggcccacg gcttgacccc ccagcaggtg  1620
gtggccatcg ccagcaatgg cggtggcaag caggcgctgg agacggtcca gcggctgttg  1680
ccggtgctgt gccaggccca cggcttgacc cccagcagt ggtggccat cgccagcaat  1740
ggcggtggca agcaggcgct ggagacggtc cagcggctgt tgccggtgct gtgccaggcc  1800
cacggcttga ccccccagca ggtggtggcc atcgccagca atggcggtgg caagcaggcg  1860
ctggagacgg tccagcggct gttgccggtg ctgtgccagg cccacggctt gaccccgag  1920
caggtggtgg ccatcgccag ccacgatggc ggcaagcagg cgctggagac ggtccagcgg  1980
ctgttgccgg tgctgtgcca ggcccacggc ttgacccctc agcaggtggt ggccatcgcc  2040
agcaatggcg gcggcaggcc ggcgctggag agcattgttg cccagttatc tcgccctgat  2100
ccgagtggca gcggaagtgg cggggatcct atcagccgtt cccagctggt gaagtccgag  2160
ctgagggaga agaaatccga gttgaggcac aagctgaagt acgtgcccca cgagtacatc  2220
gagctgatcg agatcgcccg gaacagcacc caggaccgta tcctggagat gaaggtgatg  2280
gagttcttca tgaaggtgta cggctacagg ggcaagcacc tggcggctc caggaagccc  2340
gacggcgcca tctacaccgt gggctccccc atcgactacg gcgtgatcgt ggacaccaag  2400
gcctactccg gcggctacaa cctgcccatc ggccaggccg acgaaatgca gaggtacgtg  2460
gaggagaacc agaccaggaa caagcacatc aaccccaacg agtggtggaa ggtgtacccc  2520
tccagcgtga ccgagttcaa gttcctgttc gtgtccggcc acttcaaggg caactacaag  2580
gcccagctga ccaggctgaa ccacatcacc aactgcaacg gcgccgtgct gtccgtggag  2640
gagctcctga tcggcggcga gatgatcaag gccggcaccc tgaccctgga ggaggtgagg  2700
aggaagttca caacggcga gatcaacttc gcggccgact gataa             2745

SEQ ID NO: 25          moltype = DNA   length = 2745
FEATURE                Location/Qualifiers
misc_feature           1..2745
                       note = TALEN CD25 pCLS30479
source                 1..2745
                       mol_type = other DNA
                       organism = synthetic construct
SEQUENCE: 25
atgggcgatc ctaaaaagaa acgtaaggtc atcgattacc catacgatgt tccagattac    60
gctatcgata tcgccgatct acgcacgctc ggctacagcc agcagcaaca ggagaagatc   120
aaaccgaagg ttcgttcgac agtggcgcag caccacgaag cactggtcg ccacgggttt   180
acacacgcgc acatcgttgc gttaagccaa caccggcag cgttagggac cgtcgctgtc   240
aagtatcagg acatgatcgc agcgttgcca gaggcgacac acgaagcgat cgttggcgtc   300
ggcaaacagt ggtccggcgc acgcgctctg gaggccttgc tcacggtggc gggagagttg   360
agaggtccac cgttacagtt ggacacaggc caacttctca gagattgcaaa acgtggcggc   420
gtgaccgcag tggaggcagt gcatgcatgg cgcaatgcac tgacgggtgc cccgctcaac   480
ttgacccccg agcaggtggt ggccatcgcc agcaatattg gtggcaagca ggcgctggag   540
acggtgcagg cgctgttgcc ggtgctgtgc caggcccacg gcttgacccc ggagcaggtg   600
gtggccatcg ccagccacga tggcggcaag caggcgctgg agacggtcca gcggctgttg   660
ccggtgctgt gccaggccca cggcttgacc ccggagcagt ggtggccatc gccagcaat   720
attggtggca agcaggcgct ggagacggtc caggcgctgt tgccggtgct gtgccaggcc   780
cacggcttga ccccccagca ggtggtggcc atcgccagca ataatggtgg caagcaggcg   840
ctggagacgg tccagcggct gttgccggtg ctgtgccagg cccacggctt gaccccccag   900
caggtggtgg ccatcgccag caataatggt ggcaagcagg cgctggagac ggtccagcgg   960
ctgttgccgg tgctgtgcca ggcccacggc ttgaccccgg agcaggtggt ggccatcgcc  1020
agcaatattg gtggcaagca ggcgctggag acggtgcagg cgctgttgcc ggtgctgtgc  1080
caggcccacg gcttgacccc ccagcaggtg gtggccatcg ccagcaataa tggtggcaag  1140
caggcgctgg agacggtcca gcggctgttg ccggtgctgt gccaggccca cggcttgacc  1200
cccagcagg tggtggccat cgccagcaat aatggtggca agcaggcgct ggagacggtg  1260
cagcggctgt tgccggtgct gtgccaggcc cacggcttga ccccgagca ggtggtggcc  1320
atcgccagca atattggtgg caagcaggcg ctggagacgg tgcaggcgct gttgccggtg  1380
ctgtgccagg cccacggctt gaccccggag caggtggtgg ccatcgccag caatattggt  1440
ggcaagcagg cgctggagac ggtgcaggcg ctgttgccgg tgctgtgcca ggcccacggc  1500
ttgacccccc agcaggtggt ggccatcgcc agcaataatg gtggcaagca ggcgctggag  1560
acggtccagc ggctgttgcc ggtgctgtgc caggcccacg gcttgacccc ggagcaggtg  1620
gtggccatcg ccagcaatat tggtggcaag caggcgctgg agacggtgca ggcgctgttg  1680
ccggtgctgt gccaggccca cggcttgacc cccagcagg tggtggccat cgccagcaat  1740
aatggtggca agcaggcgct ggagacggtc cagcggctgt tgccggtgct gtgccaggcc  1800
cacggcttga ccccccagca ggtggtggcc atcgccagca atggcggtgg caagcaggcg  1860
```

```
ctggagacgg tccagcggct gttgccggtg ctgtgccagg cccacggctt gaccccggag   1920
caggtggtgg ccatcgccag caatattggt ggcaagcagg cgctggagac ggtgcaggcg   1980
ctgttgccgg tgctgtgcca ggcccacggc ttgacccctc agcaggtggt ggccatcgcc   2040
agcaatggcg gcggcaggcc ggcgctggag agcattgttg cccagttatc tcgccctgat   2100
ccgacggtgg cagcggaagt ggcggggatcct atcagccgtt cccagctgat gaagtccgag   2160
ctggaggaga agaaatccga gttgaggcac aagctgaagt acgtgcccca cgagtacatc   2220
gagctgatcg agatcgcccg gaacagcacc caggaccgta tcctggagat gaaggtgatg   2280
gagttcttca tgaaggtgta cggctacagg ggcaagcacc tgggcggctc caggaagccc   2340
gacgcgcca tctacaccgt gggctccccc atcgactacg gcgtgatcgt ggacaccaag   2400
gcctactccg gcggctacaa cctgcccatc ggccaggccg acgaaatgca gaggtacgtg   2460
gaggagaacc agaccaggaa caagcacatc aaccccaacg agtggtggaa ggtgtacccc   2520
tccagcgtga ccgagttcaa gttcctgttc gtgtccggcc acttcaaggg caactacaag   2580
gcccagctga ccaggctgaa ccacatcacc aactgcaacg gcgccgtgct gtccgtggag   2640
gagctcctga tcggcggcga gatgatcaag ccgcggcacc tgaccctgga ggaggtgagg   2700
aggaagttca acaacggcga gatcaacttc gcggccgact gataa               2745

SEQ ID NO: 26         moltype = DNA  length = 2814
FEATURE              Location/Qualifiers
misc_feature         1..2814
                     note = TALEN PD1 pCLS28959
source               1..2814
                     mol_type = other DNA
                     organism = synthetic construct
SEQUENCE: 26
atgggcgatc ctaaaaagaa acgtaaggtc atcgattacc catacgatgt tccagattac   60
gctatcgata tcgccgatct acgcacgctc ggctacagca gcagcaaca ggagaagatc   120
aaaccgaagg ttcgttcgac agtggcgcag caccacgagg cactggtcgg ccacgggttt   180
acacacgcgc acatcgttgc gttaagccaa caccggcag cgttagggac cgtcgctgtc   240
aagtatcagg acatgatcgc agcgttgcca gaggcgacac acgaagcgat cgttggcgtc   300
ggcaaacagt ggtccggcgc acgcgctctg gaggccttgc tcacggtggc gggagagttg   360
agaggtccac cgttacagtt ggacacaggc caacttctca agattgcaaa acgtggcggc   420
gtgaccgcag tggaggcagt gcatgcatgg cgcaatgcac tgacgggtgc cccgctcaac   480
ttgaccccg agcaagtggt ggctatcgct tccaagctgg ggggaaagca ggccctggag   540
accgtccagg cccttctccc agtgctttgc caggctcacg gactgacccc tgaacaggtg   600
gtggcaattg cctcacacga cggggcaag caggcactgg agactgtcca gcggctgctg   660
cctgtcctct gccaggccca cggactcact cctgagcagg tcgtggccat tgccagccac   720
gatggggca acaggctct ggagaccgtg cagcgcctcc tcccagtgct gtgccaggct   780
catgggctga ccccacagca ggtcgtcgcc attgccagta acggcggggg gaagcaggcc   840
ctcgaaacag tgcagaggct gctgcccgtc ttgtgccaaa cacaggcct gacacccgag   900
caggtggtgg ccatcgcctc tcatgacggc ggcaagcagg cccttgagac agtgcagaga   960
ctgttgcccg tgttgtgtca ggcccacggg ttgacacccc agcaggtggt cgccatcgcc   1020
agcaatggcg ggggaaagca ggcccttgag accgtgcagc ggttgcttcc agtgttgtgc   1080
caggcacacg gactgacccc tcaacaggtg gtcgcaatcg ccagctacaa ggcggaaag   1140
caggctctgg agacagtgca gcgcctcctg cccgtgctgt gtcaggctca cggactgaca   1200
ccacagcagg tggtcgccat cgccagtaac ggggggcggca agcaggcttt ggagaccgtc   1260
cagagactcc tcccgtcct tgccaggcc acgggttga cacctcagca ggtcgtcgcc   1320
attgcctcca acaacggggg caagcaggcc tcgaaactg tgcagaggct gctgcctgtg   1380
ctgtgccagg ctcatgggct gacacccag caggtggtgg ccattgcctc taacaacggc   1440
ggcaaacagg cactggagac cgtgcaaagg ctgctgcccg tcctctgcca gcccacgggg   1500
ctcactccac agcaggtcgt ggccatcgcc tcaaacaatg cgggaagca ggccctggag   1560
actgtgcaaa ggctgctccc tgtgctctgc caggcacacg gactgacccc tcagcaggtg   1620
gtggcaatcg cttccaacaa cggggggaag caggccctcg aaaccgtgca gcgcctcctc   1680
ccagtgctgt gccaggcaca tggcctcaca cccgagcaag tggtggctat cgccagccac   1740
gacgaggga agcaggctct ggagaccgtg cagaggctgc tgcctgtcct gtgccaggcc   1800
cacggcgtta ctccagagca ggtcgtcgcc atcgccagtc atgatggggg gaagcaggcc   1860
cttgagacag tccagcggct gctgccagtc ctttgccagg ctcacggctt gactccgag   1920
caggtcgtgg ccattgcctc aaacattggg gcaaacagg ccctggagac agtgcaggcc   1980
ctgctgcccg tgttgtgtca ggcccacggc ttgacacccc agcaggtggt cgccattgcc   2040
tctaatggcg gcgggagacc cgccttggag agcattgttg cccagttatc tcgccctgat   2100
ccggcgttgg ccgcgttgac caacgaccac ctcgtcgcct tggcctgcct cggcgggcgt   2160
cctcgcctgg atgcagtgaa aaagggattg gggatccta tcagccgttc ccagctggtg   2220
aagtccgagc tggaggagaa gaaatccgag ttgaggcaca agctgaagta cgtgccccac   2280
gagtacatcg agctgatcga gatcgcccgg aacagcaccc aggaccgtat cctggagatg   2340
aaggtgatgg agttcttcat gaaggtgtac ggctacaggg gcaagcacct gggcggctcc   2400
aggaagcccg acggcgccat ctacaccgtg ggctccccca tcgactacgg cgtgatcgtg   2460
gacaccaagg cctactccgg cggctacaac ctgcccatcg gccaggccga cgaaatgcag   2520
aggtacgtgg aggagaacca gaccaggaac aagcacatca accccaacga gtggtggaag   2580
gtgtaccccct ccagcgtgac cgagttcaag ttcctgttcg tgtccggcca cttcaagggc   2640
aactacaagg cccagctgac caggctgaac cacatcacta actgcaacgg cgccgtgctg   2700
tccgtggagg agctcctgat cggcggcgag atgatcaagg ccgcaccct gaccctggag   2760
gaggtgagga ggaagttcaa caacggcgag atcaacttcg cggccgactg ataa       2814

SEQ ID NO: 27         moltype = DNA  length = 2829
FEATURE              Location/Qualifiers
misc_feature         1..2829
                     note = TALEN PD1 pCLS18792
source               1..2829
                     mol_type = other DNA
                     organism = synthetic construct
```

-continued

```
SEQUENCE: 27
atgggcgatc ctaaaaagaa acgtaaggtc atcgataagg agaccgccgc tgccaagttc    60
gagagacagc acatggacag catcgatatc gccgatctac gcacgctcgg ctacagccag   120
cagcaacagg agaagatcaa accgaaggtt cgttcgacag tggcgcagca ccacgaggca   180
ctggtcggcc acgggtttac acacgcgcac atcgttcgt taagccaaca cccggcagcg   240
ttagggaccg tcgctgtcaa gtatcaggac atgatcgcac cgttgccaga ggcgacacac   300
gaagcgatcg ttggcgtcgg caaacagtgg tccggcgcac gcgctctgga ggccttgctc   360
acggtggcg gagagttgag aggtccaccg ttacagttgg acacaggcca acttctcaag    420
attgcaaaac gtggcggcgt gaccgcagtg gaggcagtga atgcatggcg caatgcactg   480
acgggtgccc cgctcaactt gacccccgag caagtcgtcg caatcgccag ccatgatgga   540
gggaagcaag ccctcgaaac cgtgcagcgg ttgcttcctg tgctctgcca ggcccacggc   600
cttaccccctc agcaggtggt ggccatcgca agtaacggag gaggaaagca agccttggag   660
acagtgcagc gcctgttgcc cgtgctgtgc caggcacacg gcctcacacc agagcaggtc   720
gtggccattg cctcccatga cggggggaaa caggctctgg agaccgtcca gaggctgctg   780
cccgtcctct gtcaagctca cggcctgact ccccaacaag tggtcgccat cgcctctaat   840
ggcggcggga agcaggcact ggaaacagtg cagagactgc tccctgtgct ttgccaagct   900
catgggttga ccccccaaca ggtcgtcgct attgcctcaa acgggggggg caagcaggcc   960
cttgagactg tgcagaggct gttgccagtg ctgtgtcagg ctcacgggct cactccacaa  1020
caggtggtcg caattgccag caacggcggc ggaaagcaag ctcttgaaac cgtgcaacgc  1080
ctcctgcccg tgctctgtca ggctcatggc ctgacaccac aacaagtcgt ggccatcgcc  1140
agtaataatg gcgggaaaca ggctcttgag accgtccaga ggctgctccc agtgctctgc  1200
caggcacacg ggctgacccc cgagcaggtg gtggctatcg ccagcaatat tggggggcaag  1260
caggccctgg aaacagtcca ggccctgctg ccagtgcttt gccaggctca cgggctcact  1320
ccccagcagg tcgtggcaat cgcctccaac ggcggaggga agcaggctct ggagaccgtg  1380
cagagactgc tgcccgtctt gtgccaggcc acggactca cacctgaaca ggtcgtcgcc  1440
attgcctctc acgatggggg caaacaagcc ctggagacag tgcagcggct gttgcctgtg  1500
ttgtgccaag cccacggctt gactcctcaa caagtggtcg ccatcgcctc aaatggcggc  1560
ggaaaacaag ctctggagac agtgcagagg ttgctgcccg tcctctgcca gcccacggc  1620
ctgactcccc aacaggtcgt cgccattgcc agcaacaacg gaggaaagca ggctctcgaa  1680
actgtgcagc ggctgcttcc tgtgctgtgt caggctcatg ggctgacccc cgagcaagtg  1740
gtggctattg cctctaatgg aagcaagcaa gcccttgaga cagtccagag gctgttgcca  1800
gtgctgtgcc aggcccacgg gctcacaccc agcaggtgg tcgccatcgc cagtaacaac  1860
gggggcaaac aggcattgga aaccgtccag cgcctgcttc cagtgctctg ccaggcacac  1920
ggactgacac ccgaacaggt ggtggccatt gcatcccatg gcgggggaa gcaggccctg  1980
gagaccgtgc agagactcct gccagtgttg tgccaagctc acggcctcac ccctcagcaa  2040
gtcgtggcca tcgcctcaaa cggggggggc cggcctgcac tggagagcat tgttgcccag  2100
ttatctcgcc ctgatccggc gttggccgcg ttgaccaacg accaccctcgt cgccttggcc  2160
tgcctcggcg ggcgtcctgc gctggatgca gtgaaaaagg gattggggga tcctatcagc  2220
cgttccgcac tggtgaaatc cgagctggag gagaagaaat ccgagttgag gcacaagctg  2280
aagtacgtgc cccacgagta catcgagctg atcgagatcg cccggaacag cacccaggac  2340
cgtatcctgg agatgaaggt gatggagttc ttcatgaagg tgtacggcta cagggggcaag  2400
cacctgggcg gctccaggaa gcccgacggc gccatctaca ccgtgggctc ccccatcgac  2460
tacggctga tcgtggacac caaggcctac tccggcggct acaacctgcc catcggccag  2520
gccgacgaaa tgcagaggta cgtggaggag aaccagacca ggaacaagca catcaacccc  2580
aacgagtggt ggaaggtgta ccctccagc gtgaccgagt caagttcct gttcgtgtcc  2640
ggccacttca agggcaacta caaggcccag ctgaccaggc tgaccacat caccaactgc  2700
aacggcgccg tgctgtccgt ggaggagctc ctgatcggcg gcgagatgat caaggccggc  2760
acccctgaccc tggaggaggt gaggaggaag ttcaacaacg gcgagatcaa cttcgcggcc  2820
gactgataa                                                           2829

SEQ ID NO: 28       moltype = DNA  length = 49
FEATURE             Location/Qualifiers
misc_feature        1..49
                    note = TALEN target TRAC
source              1..49
                    mol_type = other DNA
                    organism = synthetic construct
SEQUENCE: 28
ttgtcccaca gatatccaga accctgaccc tgccgtgtac cagctgaga                49

SEQ ID NO: 29       moltype = DNA  length = 45
FEATURE             Location/Qualifiers
misc_feature        1..45
                    note = TALEN target CD25
source              1..45
                    mol_type = other DNA
                    organism = synthetic construct
SEQUENCE: 29
tacaggagga agagtagaag aacaatctag aaaaccaaaa gaaca                    45

SEQ ID NO: 30       moltype = DNA  length = 49
FEATURE             Location/Qualifiers
misc_feature        1..49
                    note = TALEN target PD1
source              1..49
                    mol_type = other DNA
                    organism = synthetic construct
SEQUENCE: 30
tacctctgtg gggccatctc cctggccccc aaggcgcaga tcaaagaga               49
```

```
SEQ ID NO: 31            moltype = DNA  length = 2897
FEATURE                  Location/Qualifiers
misc_feature             1..2897
                         note = Matrice TRAC locus_CubiCAR CD22 pCLS30056
source                   1..2897
                         mol_type = other DNA
                         organism = synthetic construct
SEQUENCE: 31
ttgctgggcc ttttccccat gcctgccttt actctgccag agttatattg ctggggtttt    60
gaagaagatc ctattaaata aaagaataag cagtattatt aagtagccct gcatttcagg   120
tttccttgag tggcaggcca ggcctggccg tgaacgttca ctgaaatcat ggcctcttgg   180
ccaagattga tagcttgtgc ctgtccctga gtcccagtcc atcacgagca gctggtttct   240
aagatgctat ttcccgtata aagcatgaga ccgtgacttg ccagcccccac agagcccgag   300
ccttgtccat cactggcatc tggactccaa cctgggttgg ggcaaagagg gaaatgagat   360
catgtcctaa ccctgatcct cttgtccac agatatccag taccctacg acgtgcccga    420
ctacgcctcc ggtgagggca gaggaagtct tctaacatgc ggtgacgtgg aggagaatcc   480
gggcccccgga tccgctctgc ccgtcaccgc tctgctgctg ccactggcac tgctgctgca   540
cgctgctagg cccggagggg gaggcagctg cccctacagc aaccccagcc tgtgcagcgc   600
aggcggcggc agcggcggag ggggtagcca ggtgcagctg cagcagagcg gccctggcct   660
ggtgaagcca agccagacac tgtccctgac ctgcgccatc agcggcgatt ccgtgagctc   720
caactccgcc gcctggaatt ggatcaggca gtcccctcct cgggggcctgg agtggctgga   780
aaggacatac tatcggtcta agtggtacaa cgattatgcc gtgtctgtga agagcagaat   840
cacaatcaac cctgacacct ccaagaatca gttctctctg cagctgaata gcgtgacacc   900
agaggacacc gccgtgtact attgcgccag ggaggtgacc ggcgacctgg aggatgcctt   960
tgacatctgg ggccagggca aatggtgac cgtgagctcc ggaggcggcg gatctggcgg  1020
aggaggaagt gggggcggcg ggagtgatat ccagatgaca cagtccccat cctctctgag  1080
cgcctccgtg ggcgacagag tgacaatcac ctgtaggcc tcccagacca tctggtctta   1140
cctgaactgg tatcagcaga ggcccggcaa ggccctaat ctgctgatct acgcagcaag   1200
ctccctgcag agcggagtgc catccagatt tctggcaggg gtcccggca cagacttcac  1260
cctgaccatc tctagcctgc aggccgagga cttcgccacc tactattgcc agcagtctta   1320
tagcatcccc cagacatttg gccagggcac caagctggag atcaagtcgg atcccggaag  1380
cggaggggga ggcagctgcc cctacagcaa ccccagcctg tgcagcggag gcggcggcag  1440
cgagctgccc acccagggca cccttctcaa cgtgtccacc aacgtgagcc agcaagcc   1500
caccaccacc gcctgtcctt attccaatcc ttccctgtgt gctcccacca caacccccgc  1560
tccaaggcc cctaccccc caccaactat tgcctcccag ccactctcac tgcggcctga  1620
ggcctgtcgg cccgctgctg gaggcgcagt gcatacaagg ggcctcgatt cgcctgcga   1680
tatttacatc tgggcacccc tcgccggcac ctgcggggtc cttctcctct ccctggtgat  1740
tacccctgtat tgcagacggg gccggaagaa gctcctctat attttaagc agcctttcac  1800
gcggccagtg cagacaaccc aagaggagga tgggtgttcc tgcagattcc ctgaggaaga  1860
ggaaggcggg tgcgagctga gagtgaagtt ctccaggagc gcagatgccc ccgcctatca  1920
acagggccag aaccagctct acaacgagct taacctcggg aggcgcgaag aatacgacgt  1980
gttggataag agaagggggc gggacccccga gatgggagga aagcccgga ggaagaaccc  2040
tcaggagggc ctgtacaacg agctgcagaa ggataagatg gccgaggcct actcagagat  2100
cgggatgaag ggggagcggc gccgcgggaa ggggcacgat gggctctacc aggggctgag  2160
cacagccaca aaggacacat acgacgcctt gcacatgcag gcccttccac cccgggaata  2220
gtctagagg cccgtttaaa cccgctgatc agcctcgact tgccttcta gttgccagcc  2280
atctgttgtt tgcccctccc ccgtgccttc cttgaccctg gaaggtgcca ctcccactgt  2340
cctttcctaa taaaatgagg aaattgcatc gcattgtctg agtaggtgtc attctattct  2400
ggggggtggg gtggggcagg acagcaaggg ggaggattgg gaagacaata gcaggcatgc  2460
tggggatgcg gtgggctcta tgactagtgc cgaattcccg tgtaccagct gagagactcc  2520
aaatccagtg acaagtctgt ctgcctattc accgattttg attctcaaac aaatgtgtca  2580
caaagtaagg attctgatgt gtatatcaca gacaaaactg tgctagacat gaggtctatg  2640
gacttcaaga gcaacagtgc tgtggcctgg agcaacaaat ctgactttgc atgtgcaaac  2700
gccttcaaca acagcattat tccagaagac accttcttcc ccagcccagg taagggcagc  2760
tttggtgcct tcgcaggctg ttccttgct tcaggaatgg ccaggttctg cccagagctc  2820
tggtcaatga tgtctaaaac tcctctgatt ggtggtctcg gccttatcca ttgccaccaa  2880
aaccctcttt ttactaa                                                 2897

SEQ ID NO: 32            moltype = DNA  length = 2688
FEATURE                  Location/Qualifiers
misc_feature             1..2688
                         note = Matrice CD25 locus_IL15_2A_sIL15Ra pCLS30519
source                   1..2688
                         mol_type = other DNA
                         organism = synthetic construct
SEQUENCE: 32
gtttattatt cctgttccac agctattgtc tgccatataa aaacttaggc caggcacagt    60
ggctcacacc tgtaatccca gcactttgga aggccgaggc aggcagatca aaggtcagg   120
agttcgagac cagcctggcc aacatagcaa aaccccatct ctactaaaaa tacaaaaatt   180
agccaggcat ggtggcgtgt gcactggttt agagtgagga ccacatttt ttggtgccgt   240
gttacacata tgaccgtgac tttgttacac cactacagga ggaagagtag aagaacaatc   300
ggttctggcg tgaaacagac tttgaatttt gaccttctca gttggcggg agacgtggag   360
tccaacccag ggcccggtac cgggtccgcc accatggact ggacctggat tctgttcctc   420
gtggctgctg ctacaagagt gcacagcggc attcatgtct tcattttggg ctgtttcagt  480
gcagggcttc ctaaaacaga agccaactgg gtgaatgtaa taagtgattt gaaaaaaatt   540
gaagatctta ttcaatctat gcatattgat gctactttat atacggaaag tgatgttcac   600
cccagttgca aagtaacagc aatgaagtgc tttctcttgg agttacaagt tatttcactt   660
gagtccggag atgcaagtat tcatgataca gtagaaaatg tgatcatcct agcaaacaac   720
```

-continued

```
agtttgtctt ctaatgggaa tgtaacagaa tctggatgca aagaatgtga ggaactggag    780
gaaaaaaata ttaaagaatt tttgcagagt tttgtacata ttgtccaaat gttcatcaac    840
acttctggaa gcggagctac taacttcagc ctgctgaagc aggctggaga cgtggaggag    900
aaccctggac ctgggaccgg ctctgcaacc atggattgga cgtggatcct gtttctcgtg    960
gcagctgcca caagagttca cagtatcacg tgccctcccc ccatgtccgt ggaacacgca   1020
gacatctggg tcaagagcta cagcttgtac tccagggagc ggtacatttg taactctggt   1080
ttcaagcgta aagccggcac gtccagcctg acggagtgcg tgttgaacaa ggccacgaat   1140
gtcgcccact ggacaacccc cagtctcaaa tgcattagag accctgccct ggttcaccaa   1200
aggccagcgc caccctccac agtaacgacg gcaggggtga ccccacagcc agagagcctc   1260
tcccttctg gaaaagagcc cgcagcttca tctcccagct caaacaacac agcggccaca   1320
acagcagcta ttgtcccggg ctcccagctg atgccttcaa aatcaccttc cacaggaacc   1380
acagagataa gcagtcatga gtcctccac ggcacccct ctcagacaac agccaagaac   1440
tgggaactca cagcatccgc ctcccaccag ccgccaggtg tgtatccaca gggccacagc   1500
gacaccactg agggcagagg cagcctgctg acctgcggcg acgtcgagga aaccccggg   1560
cccatggggg caggtgccac cggccgcgcc atggacgggc cgcgcctgct gctgttgctg   1620
cttctggggg tgtcccttgg aggtgccaag gaggcatgcc ccacaggcct gtacacacac   1680
agcggtgagt gctgcaaagc ctgcaacctg gcgagggtg tgggcccagcc ttgtggagcc   1740
aaccagaccg tgtgtgagcc ctgcctggac agcgtgacgt tctccgacgt ggtgagcgcg   1800
accgagccgt gcaagccgtg caccgagtgc gtggggctcc agagcatgtc ggcgccgtgc   1860
gtggaggccg atgacgccgt gtgccgctgc gcctacggct actaccagga tgagacgact   1920
gggcgctgcg aggcgtgccg cgtgtgcgag gcgggctcgg gcctcgtgtt ctcctgccag   1980
gacaagcaga acaccgtgtg cgaggagtgc cccgacggca cgtattccga cgaggccaac   2040
cacgtggacc cgtgcctgcc ctgcaccgtg tgcgaggaca ccgagcgcca gctccgcgag   2100
tgcacacgct gggccgacgc cgagtgcgag gagatccctg gccgttggat tacacggtcc   2160
acccccag agggctcgga cagcacagcc cccagcaccc aggagcctga ggcacctcca   2220
gaacaagacc tcatagccag cacggtggca ggtgtggtca ccagtgat gggcagctcc   2280
cagcccgtgg tgacccgagg caccaccgac aacctcatcc ctgtctattg ctccatcctg   2340
gctgctgtgg ttgtgggtct tgtggcctac atagccttca gaggtgaaa accaaaaga   2400
acaagaattt cttggtaaga agccgggaac agacaacaga agtcatgaag cccaagtgaa   2460
atcaaaggtg ctaaatggtc gcccaaagga catccgttgt gcttgcctgc gttttggaag   2520
ctctgaagtc acatcacagg acacggggca gtggcaacct tgtctctatg ccagctcagt   2580
cccatcagag agcgagcgct acccacttct aaatagcaat ttcgccgttg aagaggaagg   2640
gcaaaaccac tagaactctc catcttattt tcatgtatat gtgttcat              2688
```

```
SEQ ID NO: 33         moltype = DNA   length = 2964
FEATURE               Location/Qualifiers
misc_feature          1..2964
                      note = Matrice PD1 locus_IL15_2A_sIL15Ra pCLS30513
source                1..2964
                      mol_type = other DNA
                      organism = synthetic construct
SEQUENCE: 33
gactcccag acaggccctg gaaccccccc acccttctccc cagccctgct cgtggtgacc     60
gaagggaca acgccacctt cacctgcagc ttctccaaca catcggagag cttcgtgcta    120
aactggtacc gcatgagccc cagcaaccag acggacaagc tggccgcctt ccccgaggac    180
cgcagccagc ccgccagga ctgccgcttc cgtgtcacac aactgcccaa cgggcgtgac    240
ttccacatga gcgtggtcag ggcccggcgc aatgacagcg gcacctacct ctgtggggcc    300
ggttctggcg tgaaacagac tttgaatttt gaccttctca agttggcggg agacgtggag    360
tccaaccag gcccggtac cggtgtccaa ccatggact ggacctggat tctgttcctc    420
gtggctgctg ctacaagagt gcacagcggc attcatgtct tcattttggg ctgtttcagt    480
gcagggcttc ctaaaacaga agccaactgg gtgaatgtaa taagtgattt gaaaaaaatt    540
gaagatctta ttcaatctat gcatattgat gctactttat atacggaaag tgatgttcac    600
cccagttgca aagtaacagc aatgaagtgc tttctcttgg agttacaagt tatttcactt    660
gagtccggag atgcaagtat tcatgataca gtagaaaatc tgatcatcct agcaaacaac    720
agtttgtctt ctaatgggaa tgtaacagaa tctggatgca aagaatgtga ggaactggag    780
gaaaaaaata ttaaagaatt tttgcagagt tttgtacata ttgtccaaat gttcatcaac    840
acttctggaa gcggagctac taacttcagc ctgctgaagc aggctggaga cgtggaggag    900
aaccctggac ctgggaccgg ctctgcaacc atggattgga cgtggatcct gtttctcgtg    960
gcagctgcca caagagttca cagtatcacg tgccctcccc ccatgtccgt ggaacacgca   1020
gacatctggg tcaagagcta cagcttgtac tccagggagc ggtacatttg taactctggt   1080
ttcaagcgta aagccggcac gtccagcctg acggagtgcg tgttgaacaa ggccacgaat   1140
gtcgcccact ggacaacccc cagtctcaaa tgcattagag accctgccct ggttcaccaa   1200
aggccagcgc caccctccac agtaacgacg gcaggggtga ccccacagcc agagagcctc   1260
tcccttctg gaaaagagcc cgcagcttca tctcccagct caaacaacac agcggccaca   1320
acagcagcta ttgtcccggg ctcccagctg atgccttcaa aatcaccttc cacaggaacc   1380
acagagataa gcagtcatga gtcctccac ggcacccct ctcagacaac agccaagaac   1440
tgggaactca cagcatccgc ctcccaccag ccgccaggtg tgtatccaca gggccacagc   1500
gacaccactg agggcagagg cagcctgctg acctgcggcg acgtcgagga aaccccggg   1560
cccatggggg caggtgccac cggccgcgcc atggacgggc cgcgcctgct gctgttgctg   1620
cttctggggg tgtcccttgg aggtgccaag gaggcatgcc ccacaggcct gtacacacac   1680
agcggtgagt gctgcaaagc ctgcaacctg gcgagggtg tgggcccagcc ttgtggagcc   1740
aaccagaccg tgtgtgagcc ctgcctggac agcgtgacgt tctccgacgt ggtgagcgcg   1800
accgagccgt gcaagccgtg caccgagtgc gtggggctcc agagcatgtc ggcgccgtgc   1860
gtggaggccg atgacgccgt gtgccgctgc gcctacggct actaccagga tgagacgact   1920
gggcgctgcg aggcgtgccg cgtgtgcgag gcgggctcgg gcctcgtgtt ctcctgccag   1980
gacaagcaga acaccgtgtg cgaggagtgc cccgacggca cgtattccga cgaggccaac   2040
cacgtggacc cgtgcctgcc ctgcaccgtg tgcgaggaca ccgagcgcca gctccgcgag   2100
tgcacacgct gggccgacgc cgagtgcgag gagatccctg gccgttggat tacacggtcc   2160
acccccag agggctcgga cagcacagcc cccagcaccc aggagcctga ggcacctcca   2220
```

```
gaacaagacc tcatagccag cacggtggca ggtgtggtga ccacagtgat gggcagctcc  2280
cagcccgtgg tgacccgagg caccaccgac aacctcatcc ctgtctattg ctccatcctg  2340
gctgctgtgt tgtgggtct tgtggcctac atagccttca agaggtgatc tagagggccc  2400
gtttaaaccc gctgatcagc ctcgactgtg ccttctagtt gccagccatc tgttgtttgc  2460
cctccccg tgccttcctt gaccctggaa ggtgccactc ccactgtcct ttcctaataa  2520
aatgaggaaa ttgcatcgca ttgtctgagt aggtgtcatt ctattctggg gggtggggtg  2580
gggcaggaca gcaaggggga ggattgggaa gacaatagca ggcatgctgg ggatgcggtg  2640
ggctctatga ctagtggcga attcggcgca gatcaaagag agcctgcggg cagagctcag  2700
ggtgacaggt gcggcctcgg aggcccggg gcaggggtga gctgagccgg tcctggggtg  2760
ggtgtcccct cctgcacagg atcaggagct ccagggtcgt agggcaggga cccccagct  2820
ccagtccagg gctctgtcct gcacctgggg aatggtgacc ggcatcctg tcctctagct  2880
ctggaagcac cccagcccct ctagtctgcc ctcaccctg accctgaccc tccaccctga  2940
ccccgtccta accctgacc tttg                                          2964

SEQ ID NO: 34        moltype = DNA  length = 3363
FEATURE              Location/Qualifiers
misc_feature         1..3363
                     note = Matrice CD25 locus_IL12a_2A_IL12b pCLS30520
source               1..3363
                     mol_type = other DNA
                     organism = synthetic construct
SEQUENCE: 34
gtttattatt cctgttccac agctattgtc tgccatataa aaacttaggc caggcacagt  60
ggctcacacc tgtaatccca gcactttgga aggccgaggc aggcagatca caaggtcagg  120
agttcgagac cagcctggcc aacatagcaa acccccatct ctactaaaaa tacaaaaatt  180
agccaggcat ggtggcgtgt gcactggttt agagtgagga ccacattttt ttggtgccgt  240
gttacacata tgaccgtgac tttgttacac cactacagga ggaagagtag aagaacaatc  300
ggttctggcg tgaaacagac tttgaatttt gaccttctca agttggcggg agacgtggag  360
tccaacccag ggcccatgtg gccccctggg tcagcctccc agccaccgcc ctcacctgcc  420
gcggccacag gtctgcatcc agcggctcgc cctgtgtccc tgcagtgcgg gctcagcatg  480
tgtccagcgc gcagcctcct ccttgtggct accctggtcc tcctggacca cctcagttg  540
gccagaaacc tccccgtggc cactccagac ccaggaatgt tccatgcct tcaccactcc  600
caaaacctgc tgagggccgt cagcaacatg ctccagaagg ccagacaaac tctagaattt  660
taccccttgca cttctgaaga gattgatcat gaagatatca caaaagataa aaccagcaca  720
gtggaggcct gtttaccatt ggaattaacc aagaatgaga gttgcctaaa ttccagagag  780
accctctttca taactaatgg gagttgcctg gcctccagaa agaccctctt tatgatggcc  840
ctgtgcctta gtagtatta tgaagacttg aagatgtacc aggtggagtt caagaccatg  900
aatgcaaagc ttctgatgga tcctaagagg cagatccttc tagatcaaaa catgctggca  960
gttattgatg agctgatgca ggccctgaat ttcaacagtg agactgtgcc acaaaaatcc  1020
tcccttgaag aaccggattt ttataaaact aaaatcaagc tctgcatact tcttcatgct  1080
ttcagaattc gggcagtgac tattgataga gtgatgagct atctgaatgc ttccggaagc  1140
ggagctacta acttcagcct gctgaagcag gctggagacg tggaggagaa ccctggacct  1200
atgtgtcacc agcagttggt catctcttgg tttccctgg ttttctgctc atctccctc  1260
gtggccatat gggaactgaa gaaagatgtt tatgtcgtag aattggattg gtatccggat  1320
gcccctggag aaatggtggt cctcacctgt gacacccctg aagaagatgg tatcacctgg  1380
accttggacc agagcagtga ggtcttaggc tctggcaaaa ccctgaccat ccaagtcaaa  1440
gagtttggag atgctggcca gtacacctgt cacaaaggag cgaggttct aagccattcg  1500
ctcctgctgc ttcacaaaaa ggaagatgga atttggtcca ctgatatttt aaaggaccag  1560
aaagaaccca aaaataagac cttttctaaga tgcgaggcca agaattattc tggacgtttc  1620
acctgctggt ggctgacgac aatcagtact gatttgacat tcagtgtcaa aagcagcaga  1680
ggctcttctg acccccaagg ggtgacgtgc ggagctgcta cactctctgc agagagagtc  1740
agagggggaca acaaggagta tgagtactca gtggagtgcc aggaggacag tgcctgccca  1800
gctgctgagg agagtctgcc cattgaggtc atggtggatg ccgttcacaa gctcaagtat  1860
gaaaactaca ccagcagctt cttcatcagg gacatcatca accctgaccc acccaagaac  1920
ttgcagctga agccattaaa gaattctcgg caggtgaggt tcagctggga gtaccctgac  1980
acctggagta ctccacattc ctacttctcc ctgacattct gcgttcaggt ccagggcaag  2040
agcaagagag aaaagaaaga tagagtcttc acggacaaga cctcagccac ggtcatctgc  2100
cgcaaaaatg ccagcattag cgtgcgggcc caggaccgct actatagctc atcttggagc  2160
gaatgggcat ctgtgcccctg cagtgagggc agaggcagcc tgctgacctg cggcgacgtc  2220
gaggagaacc ccgggcccat gggggagggt gccaccgagc gcgccatgga cggccgcgc  2280
ctgctgctgt tgctgcttct gggggtgtcc cttggaggtg ccaaggaggc atgcccaca  2340
ggcctgtaca cacacagcgg tgagtgctgc aaagcctgca acctgggcga gggtgtggcc  2400
cagccttgtg agccaaccca gaccgtgtgt gagccctgcc tggacagcgt gacgttctcc  2460
gacgtggtga gcgcgaccga gccgtgcaag ccgtgcaccg agtgcgtggg gctccgagagc  2520
atgtcgcgc cgtgcgtgga ggccgatgac gccgtgtgcc gctgcgccta cggctactac  2580
caggatgaga cgactgggcg ctgcgaggcg tgccgcgtgt gcgaggcggg ctcgggcctc  2640
gtgttctcct gccaggacaa gcagaacacc gtgtgcgagg agtgccccga cggcacgtat  2700
tccgacgagg ccaaccacgt ggaccctgtg ctgcctgca ccgtgtgcga ggacaccgag  2760
cgccagctcc gcgagtgcac acgctggccg acgccgagt gcgaggagat cctggccgt  2820
tggattacac ggtccacacc cccagagggc tcggacagca cagccccag cacccaggag  2880
cctgaggcac ctcagaaca agacctcata gccagcacgg tggcaggtgt ggtgaccaca  2940
gtgatgggca gctccagcc cgtggtgacc cgaggcacca ccgacaacct catccctgtc  3000
tattgctcca tcctggctgc tgtggttgtg gtcttgtgg cctacatagc cttcaagagg  3060
tgaaaaacca aaagaacaag aatttcttgg taagaagccg agacagaca acagaagtca  3120
tgaagcccaa gtgaaatcaa aggtgctaaa tggtcgccca ggagacatcc gttgtgcttg  3180
cctgcgtttt ggaagctctg aagtcacatc acaggcacg gggcagtggc aaccttgtct  3240
ctatgccagc tcagtcccat cagagagcga gcgctaccca cttctaaata gcaatttcgc  3300
cgttgaagag gaagggcaaa accactagaa ctctccatct tattttcatg tatatgtgtt  3360
cat                                                                3363
```

```
SEQ ID NO: 35           moltype = DNA  length = 3639
FEATURE                 Location/Qualifiers
misc_feature            1..3639
                        note = Matrice PD1 locus_IL12a_2A_IL12b pCLS30511
source                  1..3639
                        mol_type = other DNA
                        organism = synthetic construct
SEQUENCE: 35
gactccccag acaggccctg gaaccccccc accttctccc cagccctgct cgtggtgacc   60
gaagggggaca acgccacctt cacctgcagc ttctccaaca catcggagag cttcgtgcta  120
aactggtacc gcatgagccc cagcaaccag acggacaagc tggccgcctt ccccgaggac  180
cgcagccagc ccggccagga ctgccgcttc cgtgtcacac aactgcccaa cgggcgtgac  240
ttccacatga gcgtggtcag ggcccggcgc aatgacagcg gcacctacct ctgtggggcc  300
ggttctggcg tgaaacagac tttgaatttt gaccttctca agttggcggg agacgtggag  360
tccaacccag ggcccatgtg gcccctggg tcagcctccc agccaccgcc ctcacctgcc   420
gcggccacag gtctgcatcc agcggctcgc cctgtgtccc tgcagtgccg gctcagcatg  480
tgtccagcgc gcagcctcct cctt gtggct accctggtcc tcctgaccac cctcagtttg  540
gccagaaacc tccccgtggc cactccagac ccaggaatgt tcccatgcct tcaccactcc  600
caaaacctgc tgagggccgt cagcaacatg ctccagaagg ccagacaaac tctagaattt  660
tacccttgca cttctgaaga gattgatcat gaagatatca caaagataa aaccagcaca  720
gtggggcct gtttaccatt ggaattaacc aagaatgaca gttgcctaaa ttccagagag  780
acctctttca taactaatgg gagttgcctg gcctccagaa agacctcttt tatgatggcc  840
ctgtgcctta gtagtattta tgaagacttg aagatgtacc aggtggagtt caagaccatg  900
aatgcaaagc ttctgatgga tcctaagagg cagatctttc tagatcaaaa catgctggca  960
gttattgatg agctgatgca ggccctgaat ttcaacagtg agactgtgcc acaaaaatcc 1020
tcccttgaag aaccggattt ttataaaact aaaatcaagc tctgcatact tcttcatgct 1080
ttcagaattc gggcagtgac tattgataga gtgatgagct atctgaatgc ttccggaagc 1140
ggagctacta acttcagcct gctgaagcag gctggagacg tggaggagaa ccctggacct 1200
atgtgtcacc agcagttggt catctcttgg ttttcccttg ttttctggc atctcccctc 1260
gtggccatat gggaactgaa gaaagatgtt tatgtcgtag aattggattg gtatccggat 1320
gcccctggag aaatggtggt cctcacctgt gacacccctg aagaagatgg tatcacctgg 1380
accttggacc agagcagtga ggtcttagc tctggcaaaa ccctgaccat ccaagtcaaa 1440
gagtttggag atgctggcca gtacacctgt cacaaaggag gcgaggttct aagccattcg 1500
ctcctgctgc ttcacaaaaa ggaagatgga atttggtcca ctgatatttt aaaggaccag 1560
aaagaaccca aaaataagac ctttctaaga tgcgaggcca agaattattc tggacgtttc 1620
acctgctggt ggctgacgac aatcagtact gatttgacat tcagtgtcaa aagcagcaga 1680
ggctcttctg acccccaagg ggtgacgtgc ggagctgcta cactctctgc agagagagtc 1740
agaggggaca acaaggagta tgagtactca gtggagtgcc aggaggacag tgcctgccca 1800
gctgctgagg agagtctgcc cattgaggtc atggtggatg ccgttcacaa gctcaagtat 1860
gaaaactaca ccagcagctt cttcatcagg gacatcatca aacctgaccc acccaagaac 1920
ttgcagctga agcattaaa gaattctcgg caggtggagg tcagctggga gtaccctgac 1980
acctggagta ctccacattc ctacttctcc tgacattctg cgttcaggt ccagggcaag 2040
agcaagagag aaaagaaaga tagagtcttc acgacaaga cctcagccac ggtcatctgc 2100
cgcaaaaatg ccagcattag cgtgcgggcc caggaccgct actatagctc atcttggagc 2160
gaatgggcat ctgtgccctg cagtgagggc agaggcagcc tgctgacctg cggcgacgtc 2220
gaggaaaacc ccgggcccat gggggcaggt gccaccggcc gccatggca cgggccgcgc 2280
ctgctgctgt tgctgcttct gggggtgtcc cttggaggtg ccaaggaggc atgcccaca 2340
ggcctgtaca cacacagcgg tgagtgctgc aaagcctgca acctgggcga gggtgtggcc 2400
cagccttgtg gagccaacca gaccgtgtgt gagccctgcc tggacagcgt gacgttctcc 2460
gacgtggtga gcgcgaccga gccgtgcaag ccgtgcaccg agtgcgtggg gctccagagc 2520
atgtcggcgc cgtgcgtgga ggccgatgac gccgtgtgcc gctgcgccta cggctactac 2580
caggatgaga cgactgggcg ctgcgaggcg tgccgcgtgt gcgaggcggg ctcgggcctc 2640
gtgttctcct gccaggacaa gcagaacacc gtgtgcgagg agtgccccga cggcacgtat 2700
tccgacgagg ccaaccacgt ggaccgtgc ctgccctgcc agtcgtgcaa ggacaccgag 2760
cgccagctcc gcgagtgcac acgctgggcc gacgccgagt gcgaggagat ccctggccgt 2820
tggattacac ggtccacacc cccagagggc tcgacagca cagcccccag cacccaggag 2880
cctgaggcac ctcagaaca agacctcata gccagcacgg tggcaggtgt ggtgaccaca 2940
gtgatgggca gctcccagcc cgtggtgacc cgaggcacca ccgacaacct catccctgtc 3000
tattgctcca tcctggctgc tgtggttgtg ggtcttgtgg cctacatagc cttcaagagg 3060
tgatctagag ggcccgttta aacccgctga tcagcctcga ctgtgccttc tagttgccag 3120
ccatctgttg tttgcccctc cccgtgcctt ccttgaccc tggaaggtgc cactcccact 3180
gtcctttcct aataaaatga ggaaattgca tcgcattgtc tgagtaggtg tcattctatt 3240
ctggggggtg ggtggggca ggacagcaag ggggaggatt gggaagacaa tagcaggcat 3300
gctggggatg cggtgggctc tatgactagt ggcgaattcg gcgcagatca aagagagcct 3360
gcgggcagag ctcaggggtga caggtgcggg ctcggaggcc ccggggcagg ggtgagctga 3420
gccggtcctg gggtggggt ccctcctgc acaggatcag gagctccagg tcgtagggc 3480
agggaccccc cagctccagt ccagggtct gtcctgcacc tggggaatgg tgaccggcat 3540
ctctgtcctc tagctctgga agcacccag ccctctagt ctgccctcac ccctgaccct 3600
gaccctccac cctgacccg tcctaacccc tgacctttg                        3639

SEQ ID NO: 36           moltype = DNA  length = 3017
FEATURE                 Location/Qualifiers
misc_feature            1..3017
                        note = Inserted matrice TRAC locus_CubiCAR CD22 (60
                        nucleotides upstream and downstream)
source                  1..3017
                        mol_type = other DNA
                        organism = synthetic construct
```

```
SEQUENCE: 36
atgagatcat gtcctaaccc tgatcctctt gtcccacaga tatccagaac cctgaccctg    60
ttgctgggcc ttttttccat gcctgccttt actctgccag agttatattg ctggggtttt   120
gaagaagatc ctattaaata aaagaataag cagtattatt aagtagccct gcatttcagg   180
tttccttgag tggcaggcca ggcctggccg tgaacgttca ctgaaatcat ggcctcttgg   240
ccaagattga tagcttgtgc ctgtccctga gtcccagtcc atcacgagca gctggtttct   300
aagatgctat ttcccgtata aagcatgaga ccgtgacttg ccagcccac agagcccgc    360
ccttgtccat cactggcatc tggactccag cctgggttgg ggcaaagagg gaaatgagat   420
catgtcctaa ccctgatcct cttgtcccac agatatccag taccccctacg acgtgcccga   480
ctacgcctcc ggtgagggca gaggaagtct tctaacatgc ggtgacgtgg aggagaatcc   540
gggcccccgga tccgctctgc ccgtcaccgc tctgctgctg ccactggcac tgctgctgca   600
cgctgctagg cccggagggg gaggcagctg ccctacagc aaccccagcc tgtgcagcgg   660
aggcggcggc agcggcggag ggggtagcca ggtgcagctg cagcagagcg gcctggcct   720
ggtgaagcca agccagacac tgtccctgac ctgcgccatc accggcgatt ccgtgagctc   780
caactccgcc gcctggaatt ggatcaggca gtcccccttct cggggcctgg agtggctggg   840
aaggacatac tatcggtcta agtggtacaa cgattatgcc gtgtctgtga agagcagaat   900
cacaatcaac cctgacacct ccaagaatca gttctctctg cagctgaata gcgtgacacc   960
agaggacacc gccgtgtact attgcgccag ggaggtgacc ggcgacctgg aggatgcctt  1020
tgacatctgg ggccagggca atggtgac cgtgagctcc ggaggcggcg gatctggcgg  1080
aggaggaagt ggggcggcg ggagtgatat ccagatgaca cagtcccccat cctctctgag  1140
cgcctccgtg ggcgacagag tgacaatcac ctgtagggcc tcccagacca tctggtctta  1200
cctgaactgg tatcagcaga ggcccggcaa ggcccctaat ctgctgatct acgcagcaag  1260
ctccctgcag agcggagtgc catccagatt ctctggcagg ggctccggca cagacttcac  1320
cctgaccatc tctagcctgc aggccgagga cttcgccacc tactattgcc agcagtctta  1380
tagcatcccc cagacatttg gccagggcac caagctggag atcaagtcgg atcccggaag  1440
cggaggggga ggcagctgcc cctacagcaa ccccagcctg tcagcggag cgggcggcag  1500
cgagctgccc acccagggca ccttctccaa cgtgtccacc aacgtgagcc cagccaagcc  1560
caccaccacc gcctgtcctt attccaatcc ttccctgtgt gctcccacca caaccccgc  1620
tccaaggccc cctacccccg caccaactat tgcctcccag ccactctcac tgcggcctga  1680
ggcctgtcgg cccgctgctg gaggcgcagt gcatacaaagg cgctcgatt tcgcctgcga  1740
tatttacatc tgggcacccc tcgccggcac ctgcggggtg cttctcctct ccctggtgat  1800
taccctgtat tgcagacggg gccggaagaa gctcctctac attttaagc agcctttcat  1860
gcggccagtg cagacaaccc aagaggagga tgggtgttcc tgcagattcc ctgaggaaga  1920
ggaaggcggg tgcgagctga gagtgaagtt ctccaggagc gcagatgccc ccgcctatca  1980
acagggccag aaccagctct acaacgagct taacctcggg aggcgcgaag aatacgacgt  2040
gttggataag agaaggggc gggaccccga tgggagga aagccccgga ggaagaaccc  2100
tcaggaggggc ctgtacaacg agctgcagaa ggataagatg gccgaggcct actcagagat  2160
cgggatgaag ggggagcggc gccgcgggaa ggggcacgat gggctctacc aggggctgag  2220
cacagccaca aaggacacat acgacgcctt gcacatgcag gcccttccac cccgggaata  2280
gtctagaggg cccgtttaaa cccgctgatc agcctcgact gtgccttcta gttgccagcc  2340
atctgttgtt tgcccctccc ccgtgccttc cttgacccctg gaaggtgcca ctcccactgt  2400
cctttcctaa taaaatgagg aaattgcatc gcattgtctg agtaggtgtc attctattct  2460
ggggggtggg gtggggcagg acagcaaggg ggaggattgg gaagacaata gcaggcatgc  2520
tgggatgcg gtgggctcta tgactagtgg cgaattcccg tgtaccagct gagagactct  2580
aaatccagtg acaagtctgt ctgcctattc accgattttg attctcaaac aaatgtgtca  2640
caaagtaagg attctgatgt gtatatcaca gacaaaactg tgctagacat gaggtctatg  2700
gacttcaaga gcaacagtgc tgtggcctgg agcaacaaat ctgactttgc atgtgcaaac  2760
gccttcaaca acagcattat tccagaagac accttcttcc ccagcccagg taagggcagc  2820
tttggtgcct tcgcaggctg tttccttgct tcaggaatgg ccaggttctg cccagagctc  2880
tggtcaatga tgtctaaaac tcctctgatt ggtggtctcg gccttatcca ttgccaccaa  2940
aaccctcttt ttactaagaa acagtgagcc ttgttctggc agtccagaga atgacacggg  3000
aaaaaagcag atgaaga                                                 3017
```

SEQ ID NO: 37          moltype = DNA   length = 2808
FEATURE                Location/Qualifiers
misc_feature           1..2808
                       note = Inserted matrice CD25 locus_IL15_2A_sIL15Ra (60
                       nucleotides upstream and downstream)
source                 1..2808
                       mol_type = other DNA
                       organism = synthetic construct

```
SEQUENCE: 37
agtgctggct agaaaccaag tgctttactg catgcacatc atttagcaca gttagttgct    60
gtttattatt cctgttccac agctattgtc tgccatataa aaacttaggc caggcacagt   120
ggctcacacc tgtaatccca gcactttgga aggccgaggc aggcagatca caaggtcagg   180
agttcgagac cagcctggcc aacatagcaa aaccccatct ctactaaaaa tacaaaaatt   240
agccaggcat ggtggcgtgt gcactggttt agagtgagga ccacattttt ttggtgccgt   300
gttacacata tgaccgtgac tttgttacac cactacagga ggaagagtag aagaacaatc   360
ggttctggcg tgaaacagaa tttgaatttt gaccttctca agttggcggg agacgtggag   420
tccaacccag ggcccggtac cgggtccgcc accatggact ggaccctggat tctgttcctc   480
gtggctgctg ctacaagagt gcacagcggc attcatgtct tcattttggg ctgtttcagt   540
gcagggcttc ctaaaacaga agccaactgg gtgaatgtaa taagtgattt gaaaaaaatt   600
gaagatctta ttcaatctat gcatattgat gctactttat atacggaaag tgatgttcac   660
cccagttgca aagtaacagc aatgaagtgc tttctcttgg agttacaagt tatttcactt   720
gagtccggag atgcaagtat tcatgataca gtagaaaatc tgatcatcct agcaaacaac   780
agtttgtctt ctaatgggaa tgtaacagaa tctggatgca aagaatgtga ggaactggag   840
gaaaaaaata ttaagaaatt tttgcagagt tttgtacata ttgtccaaat gttcatcaac   900
acttctggaa gcgcagctac taactcagc ctgctgaagc aggctggaga cgtggaggag   960
aaccctggac ctgggaccgg ctctgcaacc atggattgga cgtggatcct gtttctcgtg  1020
```

-continued

```
gcagctgcca caagagttca cagtatcacg tgccctcccc ccatgtccgt ggaacacgca   1080
gacatctggg tcaagagcta cagcttgtac tccagggagc ggtacatttg taactctggt   1140
ttcaagcgta aagccggcac gtccagcctg acggagtgcg tgttgaacaa ggccacgaat   1200
gtcgcccact ggacaacccc cagtctcaaa tgcattagag accctgccct ggttcaccaa   1260
aggccagcgc caccctccac agtaacgacg cagggggtga cccacagcc agagagcctc   1320
tccccttctg gaaaagagcc cgcagcttca tctcccagct caaacaacac agcggccaca   1380
acagcagcta ttgtcccggg ctcccagctg atgccttcaa aatcaccttc cacaggaacc   1440
acagagataa gcagtcatga gtcctccac ggcaccccct ctcagacaac agccaagaac   1500
tgggaactca cagcatccgc ctcccaccag ccgccaggtg tgtatccaca gggccacagc   1560
gacaccactg agggcagagg cagcctgctg acctgcggcg acgtcgagga aaccccggg   1620
cccatggggg caggtgccac cggccgcgcc atggacgggc gcgcctgct gctgttgctg   1680
cttctggggg tgtcccttgg aggtgccaag gaggcatgcc ccacaggcct gtacacacac   1740
agcggtgagt gctgcaaagc ctgcaactg gcgcgagggtg tggcccagcc ttgtggagcc   1800
aaccagaccg tgtgtgagcc ctgcctggac agcgtgacgt tctccgacgt ggtgagcgcg   1860
accgagccgt gcaagccgtg caccgagtgc gtggggctcc agagcatgtc ggcgccgtgc   1920
gtggaggccg atgacgccgt gtgccgctgc gcctacggct actaccagga tgagacgact   1980
gggcgctgcg aggcgtgccg cgtgtgcgag gcgggctcgg gcctcgtgtt ctcctgccag   2040
gacaagcaga acaccgtgtg cgaggagtgc cccgacgcg cgtattccga cgaggccaac   2100
cacgtggacc cgtgcctgcc ctgcaccgtg tgcgaggaca ccgagcgcca gctccgcgag   2160
tgcacacgct gggccgacgc cgagtgcgag gagatccctg gccgttggat tacacggtcc   2220
acacccccag agggctcgga cagcacagcc cccagcaccc aggagcctga ggcacctcca   2280
gaacaagacc tcatagccag cacggtggca ggtgtggtga ccacagtgat gggcagctcc   2340
cagcccgtgg tgacccgagg caccaccgac aacctcatcc ctgtctattg ctccatcctg   2400
gctgctgtgg ttgtgggtct tgtgcctac atagccttca agaggtgaaa aaccaaaaga   2460
acaagaattt cttggtaaga agccgggaac agacaacaga agtcatgaag cccaagtgaa   2520
atcaaaggtg ctaaatggtc gcccaaggaa catccgttgt gcttgcctgc gttttggaag   2580
ctctgaagtc acatcacagg acacggggca gtggcaacct tgtctctatg ccagctcagt   2640
cccatcagag agcgagcgct acccacttct aaatagcaat ttcgccgttg aagaggaagg   2700
gcaaaaccac tagaactctc catcttattt tcatgtatat gtgttcatta aagcatgaat   2760
ggtatgggaac tctctccacc ctatatgtag tataaagaaa agtaggtt                2808
```

| SEQ ID NO: 38 | moltype = DNA length = 3084 |
|---|---|
| FEATURE | Location/Qualifiers |
| misc_feature | 1..3084 |
| | note = Inserted matrice PD1 locus_IL15_2A_sIL15Ra (60 nucleotides upstream and downstream) |
| source | 1..3084 |
| | mol_type = other DNA |
| | organism = synthetic construct |

SEQUENCE: 38

```
ggtggccggg gaggctttgt ggggccaccc agcccttcc tcacctctct ccatctctca   60
gactcccag acaggccctg gaaccccccc accttctccc cagccctgct cgtggtgacc   120
gaaggggaca acgccacctt cacctgcagc ttctccaaca tcgagagc cttcgtgcta   180
aactggtacc gcatgagccc cagcaaccag acggacaagc tggccgcctt ccccgaggac   240
cgcagccagc ccgccaggga ctgccgcttc cgtgtcacac aactgcccaa cgggcgtgac   300
ttccacatga gcgtggtcag ggcccggcgc aatgacagcg gcacctacct ctgtggggcc   360
ggttctggcg tgaaacagac tttgaatttt gaccttctca agttggcggg agacgttggag   420
tccaacccag ggcccggtac cgggtccgcc accatggact ggacctggat tctgttcctc   480
gtggctgctg ctacaagagt gcacagcggc attcatgtct tcattttggg ctgtttcagt   540
gcagggcttc ctaaaacaga agccaactgg gtgaatgtaa taagtgattt gaaaaaaatt   600
gaagatctta ttcaatctat gcatattgat gctactttat atacggaaag tgatgttcac   660
cccagttgca aagtaacagc aatgaagtgc tttctcttgg agttacaagt tatttcactt   720
gagtccggag atgcaagtat tcatgataca gtagaaatc tgatcatcct agcaaacaac   780
agtttgtctt ctaatgggaa tgtaacagaa tctggatgca aagaatgtga ggaactggag   840
gaaaaaaata ttaaagaatt tttgcagagt tttgtacata ttgtccaaat gttcatcaac   900
acttctggaa gcggagctac taacttcagc ctgctgaagc aggctggaga cgtggaggag   960
aaccctggac ctgggaccgg ctctgcaacc atggattgga cgtggatcct gtttctcgtg   1020
gcagctgcca caagagttca cagtatcacg tgccctcccc ccatgtccgt ggaacacgca   1080
gacatctggg tcaagagcta cagcttgtac tccagggagc ggtacatttg taactctggt   1140
ttcaagcgta aagccggcac gtccagcctg acggagtgcg tgttgaacaa ggccacgaat   1200
gtcgcccact ggacaacccc cagtctcaaa tgcattagag accctgccct ggttcaccaa   1260
aggccagcgc caccctccac agtaacgacg cagggggtga cccacagcc agagagcctc   1320
tccccttctg gaaaagagcc cgcagcttca tctcccagct caaacaacac agcggccaca   1380
acagcagcta ttgtcccggg ctcccagctg atgccttcaa aatcaccttc cacaggaacc   1440
acagagataa gcagtcatga gtcctccac ggcaccccct ctcagacaac agccaagaac   1500
tgggaactca cagcatccgc ctcccaccag ccgccaggtg tgtatccaca gggccacagc   1560
gacaccactg agggcagagg cagcctgctg acctgcggcg acgtcgagga gaaccccggg   1620
cccatggggg caggtgccac cggccgcgcc atggacgggc gcgcctgct gctgttgctg   1680
cttctggggg tgtcccttgg aggtgccaag gaggcatgcc ccacaggcct gtacacacac   1740
agcggtgagt gctgcaaagc ctgcaactg gcgcgagggtg tggcccagcc ttgtggagcc   1800
aaccagaccg tgtgtgagcc ctgcctggac agcgtgacgt tctccgacgt ggtgagcgcg   1860
accgagccgt gcaagccgtg caccgagtgc gtggggctcc agagcatgtc ggcgccgtgc   1920
gtggaggccg atgacgccgt gtgccgctgc gcctacggct actaccagga tgagacgact   1980
gggcgctgcg aggcgtgccg cgtgtgcgag gcgggctcgg gcctcgtgtt ctcctgccag   2040
gacaagcaga acaccgtgtg cgaggagtgc cccgacgcg cgtattccga cgaggccaac   2100
cacgtggacc cgtgcctgcc ctgcaccgtg tgcgaggaca ccgagcgcca gctccgcgag   2160
tgcacacgct gggccgacgc cgagtgcgag gagatccctg gccgttggat tacacggtcc   2220
acacccccag agggctcgga cagcacagcc cccagcaccc aggagcctga ggcacctcca   2280
gaacaagacc tcatagccag cacggtggca ggtgtggtga ccacagtgat gggcagctcc   2340
```

```
cagcccgtgg tgacccgagg caccaccgac aacctcatcc ctgtctattg ctccatcctg   2400
gctgctgtgg ttgtgggtct tgtggcctac atagccttca agaggtgatc tagagggccc   2460
gtttaaaccc gctgatcagc ctcgactgtg ccttctagtt gccagccatc tgttgtttgc   2520
ccctcccccg tgccttcctt gaccctggaa ggtgccactc ccactgtcct ttcctaataa   2580
aatgaggaaa ttgcatcgca ttgtctgagt aggtgtcatt ctattctggg gggtggggtg   2640
gggcaggaca gcaaggggga ggattgggaa gacaatagca ggcatgctgg ggatgcggtg   2700
ggctctatga ctagtggcga attcggcgca gatcaaagag agcctgcggg cagagctcag   2760
ggtgacaggt gcggcctcgg aggccccggg gcagggtga gctgagccgg tcctgggggtg    2820
ggtgtcccct cctgcacagg atcaggagct ccagggtcgt agggcaggga ccccccagct   2880
ccagtccagg gctctgtcct gcacctgggg aatggtgacc ggcatctctg tcctctagct   2940
ctggaagcac cccagcccct ctagtctgcc ctcaccctg accctgaccc tccacctga     3000
ccccgtccta accctgacc tttgtgccct tccagagaga agggcagaag tgcccacagc   3060
ccacccagc ccctcaccca ggcc                                             3084

SEQ ID NO: 39        moltype = DNA  length = 3475
FEATURE              Location/Qualifiers
misc_feature         1..3475
                     note = Inserted matrice CD25 locus_IL12a_2A_IL12b (60
                     nucleotides upstream and downstream)
source               1..3475
                     mol_type = other DNA
                     organism = synthetic construct
SEQUENCE: 39
agtgctggct agaaaccaag tgctttactg catgcacatc atttagcaca gttagttgct     60
gtttattatt cctgttccac agctattgtc tgccatataa aaacttaggc caggcacagt    120
ggctcacacc tgtaatccca gcactttgga aggccgaggc aggcagatca caaggtcagg    180
agttcgagac cagcctggcc aacatagcaa aaccccatct ctactaaaaa tacaaaaatt    240
agccaggcat ggtggcgtgt gcactggttt agagtgagga ccacatttt ttggtgccgt     300
gttacacata tgaccgtgac tttgttacac cactacagga ggaagagtag aagaacaatc    360
ggttctggcg tgaaacagac tttgaatttt gaccttctca agttggcgga agacgtggag    420
tccaacccag ggcccatgtg gcccctggg tcagcctccc agccaccgcc ctcacctgcc     480
gcggccacag gtctgcatcc agcggctcgc cctgtgtccc tgcagtgccg gctcagcatg    540
tgtccagcgc gcagcctcct ccttgtggct accctggtcc tcctgaccca cctcagtttg    600
gccagaaacc tccccgtggc cactccagac ccaggaatgt tcccatgcct tcaccactcc    660
caaaacctgc tgagggccgt cagcaacatg ctccagaagg ccagacaaac tctagaattt    720
tacccttgca cttctgaaga gattgatcat gaagatatca caaaagataa aaccagcaca    780
gtggaggcct gtttaccatt ggaattaacc aagaatgaga gttgcctaaa ttccagagag    840
acctctttca taactaatgg gagttgcctg gcctccagaa agacctcttt tatgatggcc    900
ctgtgcctta gtagtattta tgaagacttg aagatgtacc aggtggagtt caagaccatg    960
aatgcaaagc ttctgatgga tcctaagagg cagatctttc tagatcaaaa catgctggca   1020
gttattgatg agctgatgca ggccctgaat ttcaacagtg agactgtgcc acaaaaatcc   1080
tcccttgaag aaccggattt ttataaaact aaaatcaagc tctgcatact tcttcatgct   1140
ttcagaattc gggcagtgac tattgataga tgtggaagtc atccggaagc                1200
ggagctacta acttcagcct gctgaagcag gctggagacg tggaggagaa ccctggacct   1260
atgtgtcacc agcagttggt catctcttgg ttttccctgg tttttctggc atctcccctc   1320
gtggccatat gggaactgaa gaaagatgtt tatgtcgtag aattggattg gtatccggat   1380
gcccctggag aaatggttgt cctcacctgt gacacccctg aagaagatgg tatcacctgg   1440
accttggacc agagcagtga ggtcttaggc tctggcaaaa ccctgaccat ccaagtcaaa   1500
gagtttggag atgctggcca gtacacctgt cacaaaggag gcgaggttct aagccattcg   1560
ctcctgctgc ttcacaaaaa ggaagatgga atttggtcca ctgatatttt aaaggaccag   1620
aaagaaccca aaaataagac cttttctaaga tgcgaggcca agaattattc tggacgtttc   1680
acctgctggt ggctgacgac aatcagtact gatttgacat tcagtgtcaa aagcagcaga   1740
ggctcttctg accccaagg ggtgacgtgc ggagctgcta cactctctgc agagagagtc   1800
agagggggaca acaaggagta tgagtactca gtggagtgcc aggaggacag tgcctgccca   1860
gctgctgagg agagtctgcc cattgaggtc atggtggatg ccgttcacaa gctcaagtat   1920
gaaaactaca ccagcagctt cttcatcagg gacatcatca aacctgaccc acccaagaac   1980
ttgcagctga agccattaaa gaattctcgg caggtggagg tcagctggga gtaccctgac   2040
acctggagta ctccacattc ctacttctcc ctgacattct gcgttcaggt ccagggcaag   2100
agcaagagag aaaagaaaga tagagtcttc acggacaaga cctcagccac ggtcatctgc   2160
cgcaaaaatg ccagcattag cgtgcgggcc caggaccgct actatagctc atcttggagc   2220
gaatgggcat ctgtgccctg cagtgagggc agaggcagcc tgctgacctg cggcgacgtc   2280
gaggagaacc ccgggcccat gggggcaggt gccaccggcc gcgccatgga cgggcgcgc     2340
ctgctgctgt tgctgcttct gggggtgtcc cttggaggtg ccaaggaggc atgcccaca      2400
ggcctgtaca cacagcgg tgagtgctgc aaagcctgca agcccggggaa gggtgtggcc    2460
cagccttgtg gagccaacca gaccgtgtgt gagccctgcc tggacagcgt gacgttctcc   2520
gacgtggtga gcgcgaccga gccgtgcaag ccgtgcaccg agtgcgtggg gctccagagc   2580
atgtcggcgc cgtgcgtgga ggccgatgac gccgtgtgcc gctgcgccta cggctactac   2640
caggatgaga cgactgggcg ctgcgaggcg tgccgcgtgt gcgagcgggg ctcgggcctc   2700
gtgttctcct gccaggacaa gcagaacacc gtgtgcgagg agtgccccga cggcacgtat   2760
tccgacgagg ccaaccacgt ggacccgtgc ctgccctgca cggtgtgcga ggacaccgag   2820
cgccagctcc gcgagtgcac acgctgggcc gacgccgagt gcgaggagat ccctggccgt   2880
tggattacac ggtccacacc cccagagggc tcggacagca cagcccccag cacccaggag   2940
cctgaggcac ctcagaaca agacctcata gccagcacgg tggcaggtgt ggtgaccaca   3000
gtgatgggca gctcccagcc cgtggtgcaa gccgacaacct catccctgtc                3060
tattgctcca tcctggctgc tgtggttgtg gtcttgtgg cctacatagc cttcaagagg   3120
tgaaaaacca aaagaacaag aatttcttgg taagaagccg ggaacagaca acagaagtca   3180
tgaagcccaa gtgaaatcaa aggtgctaaa tggtcgccca ggagacatcc gttgtgcttg   3240
cctgcgtttt ggaagctctg aagtcacatc acaggacacg gggcagtggc aaccttgtct   3300
ctatgccagc tcagtcccat cagagagcga gcgctaccca cttctaaata gcaatttcgc   3360
```
cgttgaagag gaagggcaaa accactagaa ctctccatct tattttcatg tatatgtgtt 3420
catgaatggt atggaactct ctccacccta tatgtagtat aaagaaaagt aggtt 3475

```
SEQ ID NO: 40          moltype = DNA   length = 3759
FEATURE                Location/Qualifiers
misc_feature           1..3759
                       note = Inserted matrice PD1 locus_IL12a_2A_IL12b (60
                       nucleotides upstream and downstream)
source                 1..3759
                       mol_type = other DNA
                       organism = synthetic construct
SEQUENCE: 40
```
ggtggccggg gaggctttgt ggggccaccc agcccctttcc tcacctctct ccatctctca 60
gactcccccag acaggccctg gaaccccccc accttctccc cagccctgct cgtggtgacc 120
gaaggggaca acgccacctt cacctgcagc ttctccaaca catcggagag cttcgtgcta 180
aactggtacc gcatgagccc cagcaaccag acggacaagc tggccgcctt ccccgaggac 240
cgcagccagc ccggccagga ctgccgcttc cgtgtcacac aactgcccaa cgggcgtgac 300
ttccacatga gcgtggtcag ggcccggcgc aatgacagcg gcacctacct ctgtggggcc 360
ggttctggcg tgaaacagac tttgaatttt gaccttctca agttggcggg agacgtggag 420
tccaacccag ggcccatgtg gccccctggg tcagcctccc agccaccgcc ctcacctgcc 480
gcggccacag gtctgcatcc agcggctcgc cctgtgtccc tgcagtgccg gctcagcatg 540
tgtccagcgc gcagcctcct cctttgtggct accctggtcc tcctggacca cctcagttgg 600
gccagaaacc tccccgtggc cactccagac caggaatgt tcccatgcct tcaccactcc 660
caaaacctgc tgagggccgt cagcaacatg ctccagaagg ccagacaaac tctagaattt 720
tacccttgca cttctgaaga gattgatcat gaagatatca caaagataa aaccagcaca 780
gtgggaggcct gtttaccatt ggaattaacc aagaatgaga gttgcctaaa ttccagagag 840
accctctttca taactaatgg gagttgcctg gcctccagaa agacctcttt tatgatggcc 900
ctgtgcctta gtagtattta tgaagacttg aagatgtacc aggtggagtt caagaccatg 960
aatgcaaagc ttctgatgga tcctaagagg cagatctttc tagatcaaaa catgctggca 1020
gttattgatg agctgatgca ggccctgaat ttcaacagtg agactgtgcc acaaaaatcc 1080
tcccttgaag aaccggattt ttataaaact aaaatcaagc tctgcatact tcttcatgct 1140
ttcagaattc gggcagtgac tattgataga gtgatgagct atctgaatgc ttccggaagc 1200
ggagctacta acttcagcct gctgaagcag gctggacg tggaggagaa ccctggacct 1260
atgtgtcacc agcagttggt catctcttgg ttttcctgg ttttctggc atctcccctc 1320
gtggccatat gggaactgaa gaaagatgtt tatgtcgtag aattggattg gtatccggat 1380
gcccctggag aaatggtggt cctcacctgt gacacccctg aagaagatgg tatcacctgg 1440
accttggacc agagcagtga ggtcttaggc tctggcaaaa ccctgaccat ccaagtcaaa 1500
gagtttggag atgctggcca gtacacctgt cacaaaggag gcgaggttct aagccattcg 1560
ctcctgctgc ttcacaaaaa ggaagatgga atttggtcca ctgatatttt aaaggaccag 1620
aaagaaccca aaaataagac cttttctaaga tgcgaggcca agaattattc tggacgtttc 1680
acctgctggt ggctgacgac aatcagtact gatttgacat tcagtgtcaa aagcagaga 1740
ggctcttctg acccccaagg ggtgacgtgc ggagctgcta cactctctgc agagagagtc 1800
agagggagca acaaggagta tgagtactca gtggagtgcc aggaggacag tgcctgccca 1860
gctgctgagg agagtctgcc cattgaggtc atggtggatg ccgttcacaa gctcaagtat 1920
gaaaactaca ccagcagctt cttccatcagg gacatcatca acctgaccc acccaagaac 1980
ttgcagctga agccattaaa gaattctcgg caggtggagg tcagctggga gtaccctgac 2040
acctggagta ctccacattc ctacttctcc ctgacattct gcgttcaggt ccagggcaag 2100
agcaagagag aaaagaaaga tagagtcttc acgacaaga cctcagccac ggtcatctgt 2160
cgcaaaaatg ccagcattag cgtgcgggcc caggaccgct actatagctc atcttggagc 2220
gaatgggcat ctgtgccctg cagtgagggc agaggcagcc tgctgacctg cggcgacgtc 2280
gaggagaacc ccgggcccat gggggcaggt gccaccgagc gcgccatgga cgggccgcc 2340
ctgctgctgt tgctgcttct gggggtgtcc cttggaggtg ccaaggaggc atgcccaca 2400
ggcctgtaca cacacagcgg tgagtgctgc aaagcctgca acctgggcga gggtgtggcc 2460
cagccttgtg gagccaacca gaccgtgtgt gagccctgcc tggacagcgt gacgttctcc 2520
gacgtggtga gcgcgaccga gccgtgcaag ccgtgcacag agtgcgtgga gctccagagc 2580
atgtcggcgc cgtgcgtgga ggccgatgac gccgtgtgcc gctgcgccta cggctactac 2640
caggatgaga cgactgggcg ctgcgaggcg tgccgcgtgt gcgaggcggg ctcgggcctc 2700
gtgttctcct gccaggacaa gcagaacacc gtgtgcgagg agtgccccga cggcacgtat 2760
tccgacgagg ccaaccacgt ggaccgctgc ctgccctgca ccgtgtgcga ggacaccgag 2820
cgccagctcc gcgagtgcac acgctggcc gacgccgagt gcgaggagat ccctggccgt 2880
tggattacac ggtccacacc cccagagggc tcgacagca cagccccag cacccaggag 2940
cctgaggcac ctcagaaaca agacctcata gccagcacgg tggcaggtgt ggtgaccaca 3000
gtgatgggca gctcccagcc cgtggtgacc cgaggcacca ccgacaacct catccctgtc 3060
tattgctcca tcctggctgc tgtggtttgtg gtcttgttg ctacatagc cttcaagagg 3120
tgatctagag ggcccgttta aacccgctga tcagcctcga ctgtgccttc tagttgccaa 3180
ccatctgttg tttgccccctc cccgtgcctt tccttgaccc tggaaggtgc cactcccact 3240
gtcctttcct aataaaatga gaaattgca tcgcattgtc tgagtaggtg tcattctatt 3300
ctggggggtg ggtggggca ggacagcaag ggggaggatt gggaagacaa tagcaggcat 3360
gctggggata cggttgggctc tatgactagt ggcgaattcg gcgcagatca aagagagcct 3420
gcggcagag ctcagggtga caggtgcggc ctcggaggcc ccggggcagg ggtgagctga 3480
gccggtcctg gggtgggtgt cccctcctgc acaggatcag gagctccagg gtcgtagggc 3540
agggaccccc cagctccagt ccagggctct gtcctgcacc tggggaatgg tgaccggcat 3600
ctctgtcctc tagctctgga agcaccccag ccctctagt ctgccctcac ccctgaccct 3660
gaccctcac cctgaccccg tcctaaccc tgacctttgt gcccttccag agagaagggc 3720
agaagtgccc acagcccacc ccagcccctc acccaggcc 3759

```
SEQ ID NO: 41          moltype = DNA   length = 60
FEATURE                Location/Qualifiers
misc_feature           1..60
```

```
                    note = upstream TRAC locus polynucleotide sequence
source              1..60
                    mol_type = other DNA
                    organism = synthetic construct
SEQUENCE: 41
atgagatcat gtcctaaccc tgatcctctt gtcccacaga tatccagaac cctgaccctg    60

SEQ ID NO: 42           moltype = DNA  length = 60
FEATURE                 Location/Qualifiers
misc_feature            1..60
                    note = downstream TRAC locus polynucleotide sequence
source              1..60
                    mol_type = other DNA
                    organism = synthetic construct
SEQUENCE: 42
gaaacagtga gccttgttct ggcagtccag agaatgacac gggaaaaaag cagatgaaga    60

SEQ ID NO: 43           moltype = DNA  length = 60
FEATURE                 Location/Qualifiers
misc_feature            1..60
                    note = upstream CD25 locus polynucleotide sequence
source              1..60
                    mol_type = other DNA
                    organism = synthetic construct
SEQUENCE: 43
agtgctggct agaaaccaag tgctttactg catgcacatc atttagcaca gttagttgct    60

SEQ ID NO: 44           moltype = DNA  length = 52
FEATURE                 Location/Qualifiers
misc_feature            1..52
                    note = downstream CD25 locus polynucleotide sequence
source              1..52
                    mol_type = other DNA
                    organism = synthetic construct
SEQUENCE: 44
gaatggtatg gaactctctc caccctatat gtagtataaa gaaaagtagg tt            52

SEQ ID NO: 45           moltype = DNA  length = 60
FEATURE                 Location/Qualifiers
misc_feature            1..60
                    note = upstream PD1 locus polynucleotide sequence
source              1..60
                    mol_type = other DNA
                    organism = synthetic construct
SEQUENCE: 45
ggtggccggg gaggctttgt ggggccaccc agccccttcc tcacctctct ccatctctca    60

SEQ ID NO: 46           moltype = DNA  length = 60
FEATURE                 Location/Qualifiers
misc_feature            1..60
                    note = downstream PD1 locus polynucleotide sequence
source              1..60
                    mol_type = other DNA
                    organism = synthetic construct
SEQUENCE: 46
tgcccttcca gagagaaggg cagaagtgcc cacagcccac cccagcccct cacccaggcc    60

SEQ ID NO: 47           moltype = DNA  length = 759
FEATURE                 Location/Qualifiers
misc_feature            1..759
                    note = IL-12a polynucleotide
source              1..759
                    mol_type = other DNA
                    organism = synthetic construct
SEQUENCE: 47
atgtggcccc ctgggtcagc ctcccagcca ccgccctcac ctgccgcggc cacaggtctg    60
catccagcgg ctcgccctgt gtccctgcag tgccggctca gcatgtgtcc agcgcgcagc   120
ctcctccttg tggctaccct ggtcctcctg gaccacctca gtttggcag aaacctcccc    180
gtggccactc cagacccagg aatgttccca tgccttcacc actcccaaaa cctgctgagg   240
gccgtcagca acatgctcca gaaggccaga caaactctag aatttaccc ttgcacttct   300
gaagagattg atcatgaaga tatcacaaaa gataaaacca gcacagtgga ggcctgttta   360
ccattggaat taaccaagaa tgagagttgc ctaaattcca gagagacctc tttcataact   420
aatgggagtt gcctggcctc cagaaagacc tcttttatga tggccctgtg ccttagtagt   480
atttatgaag acttgaagat gtaccaggtg gagttcaaga ccatgaatgc aaagcttttg   540
atggatccta agaggcagat ctttctagat caaaacatgc tggcagttat tgatgagctg   600
atgcaggccc tgaatttcaa cagtgagact gtgccacaaa aatctcccct gaagaaccg   660
gatttttata aaactaaaat caagctctgc atacttcttc atgctttcag aattcgggca    720
gtgactattg atagagtgat gagctatctg aatgcttcc                           759
```

| SEQ ID NO: 48 | moltype = DNA length = 984 |
|---|---|
| FEATURE | Location/Qualifiers |
| misc_feature | 1..984 |
| | note = IL12b polynucleotide |
| source | 1..984 |
| | mol_type = other DNA |
| | organism = synthetic construct |

SEQUENCE: 48

```
atgtgtcacc agcagttggt catctcttgg ttttccctgg ttttttctggc atctcccctc    60
gtggccatat gggaactgaa gaaagatgtt tatgtcgtag aattggattg gtatccggat   120
gcccctggag aaatggtggt cctcacctgt gacacccctg aagaagatgg tatcacctgg   180
accttggacc agagcagtga ggtcttaggc tctggcaaaa ccctgaccat ccaagtcaaa   240
gagtttggag atgctggcca gtacacctgt cacaaaggag gcgaggttct aagccattcg   300
ctcctgctgc ttcacaaaaa ggaagatgga atttggtcca ctgatatttt aaaggaccag   360
aaagaaccca aaaataagac ctttctaaga tgcgaggcca agaattattc tggacgtttc   420
acctgctggt ggctgacgac aatcagtact gatttgacat tcagtgtcaa agcagcaga   480
ggctcttctg accccaagg ggtgacgtgc ggagctgcta cactctctgc agagagagtc   540
agaggggca acaaggagta tgagtactca gtggagtgcc aggaggacag tgcctgccca   600
gctgctgagg agagtctgcc cattgaggtc atggtggatg ccgttcacaa gctcaagtat   660
gaaaactaca ccagcagctt cttcatcagg gacatcatca aacctgaccc acccaagaac   720
ttgcagctga agccattaaa gaattctcgg caggtggagg tcagctggga gtaccctgac   780
acctggagta ctccacattc ctacttctcc ctgacattct gcgttcaggt ccagggcaag   840
agcaagagag aaaagaaaga tagagtcttc acggacaaga cctcagccac ggtcatctgc   900
cgcaaaaatg ccagcattag cgtgcgggcc caggaccgct actatagctc atcttggagc   960
gaatgggcat ctgtgccctg cagt                                           984
```

| SEQ ID NO: 49 | moltype = DNA length = 399 |
|---|---|
| FEATURE | Location/Qualifiers |
| misc_feature | 1..399 |
| | note = IL15 polynucleotide |
| source | 1..399 |
| | mol_type = other DNA |
| | organism = synthetic construct |

SEQUENCE: 49

```
ggcattcatg tcttcatttt gggctgtttc agtgcagggc ttcctaaaac agaagccaac    60
tgggtgaatg taataagtga tttgaaaaaa attgaagatc ttattcaatc tatgcatatt   120
gatgctactt tatatacgga aagtgatgtt caccccagtt gcaaagtaac agcaatgaag   180
tgctttctct tggagttaca agttatttca cttgagtccg gagatgcaag tattcatgat   240
acagtagaaa atctgatcat cctagcaaac aacagtttgt cttctaatgg gaatgtaaca   300
gaatctggat gcaaagaatg tgaggaactg gaggaaaaaa atattaaaga attttgcag   360
agttttgtac atattgtcca aatgttcatc aacacttct                          399
```

| SEQ ID NO: 50 | moltype = DNA length = 525 |
|---|---|
| FEATURE | Location/Qualifiers |
| misc_feature | 1..525 |
| | note = sIL15ra polynucleotide |
| source | 1..525 |
| | mol_type = other DNA |
| | organism = synthetic construct |

SEQUENCE: 50

```
atcacgtgcc ctcccccat gtccgtggaa cacgcagaca tctgggtcaa gagctcacagc    60
ttgtactcca gggagcggta catttgtaac tctggtttca gcgtaaagc cggcacgtcc   120
agcctgacgg agtgcgtgtt gaacaaggcc acgaatgtcg cccactggac aaccccagt   180
ctcaaatgca ttagagaccc tgccctggtt caccaaggc cagcgccacc ctccacagta   240
acgaggcag gggtgacccc acagccagag agcctctccc cttctgggaaa agagcccgca   300
gcttcatctc ccagctcaaa caacacagcg gccacaacag cagctattgt cccgggctca   360
cagctgatgc cttcaaaatc accttccaca ggaaccacag ataagcag tcatgagtcc   420
tcccacggca cccccctctca gacaacagcc aagaactggg aactcacagc atccgcctcc   480
caccagccgc caggtgtgta tccacagggc acagcgaca ccact                    525
```

| SEQ ID NO: 51 | moltype = DNA length = 1818 |
|---|---|
| FEATURE | Location/Qualifiers |
| misc_feature | 1..1818 |
| | note = soluble GP130 polynucleotide |
| source | 1..1818 |
| | mol_type = other DNA |
| | organism = synthetic construct |

SEQUENCE: 51

```
atgctgacac tgcagacttg gctggtgcag gcactgttta ttttctctgac tactgaatca    60
actggcgaac tgctggaccc ttgtggctac atcagccctg agtccccagt ggtgcagctg   120
cacagcaact tcaccgccgt gtgcgtgctg aaggagaagt gtatggacta ctttcacgtg   180
aacgccaatt atatcgtgtg gaaaaccaac cacttcacaa tccccaagga gcagtacacc   240
atcatcaata ggacagccag ctccgtgacc tttacagaca tcgcctccct gaacatccag   300
ctgacctgca atattctgac attccgccag ctggagcaga acgtgtatgg catcaccatc   360
atctctggcc tgccccctga aaagcctaag aacctgagct gcatcgtgaa tgagggcaag   420
aagatgcggt gtgagtggga cggcggcaga gagacacacc tggagacaaa cttcacccctg   480
aagtccgagt gggccacaca caagtttgcc gactgcaagg ccaagcgcga taccccaaca   540
tcctgtaccc tggattactc tacagtgtat tttgtgaaca tcgaagtgtg ggtggaggcc   600
gagaatgccc tgggcaaggt gacctccgac cacatcaact cgatcccgt gtacaaggtg   660
```

```
aagcctaacc cacccacaa tctgagcgtg atcaattccg aggagctgtc tagcatcctg    720
aagctgacct ggacaaaccc atctatcaag agcgtgatca tcctgaagta caatatccag   780
tatcggacca aggacgcctc cacatggagc cagatccctc cagaggatac cgccagcaca   840
agatcctctt tcaccgtgca ggacctgaag cccttcacag agtacgtgtt tcggatcaga   900
tgtatgaagg aggacggcaa gggctactgg agcgattggt ccgaggaggc cagcggcatc   960
acctatgagg acaggccttc taaggccccc agcttctggt acaagatcga tccatcccac  1020
acccagggct atcgcacagt gcagctggtg tggaaaaccc tgccccttt cgaggccaac   1080
ggcaagatcc tggactacga ggtgaccctg acacggtgga agtccaccct gcagaactat  1140
accgtgaatg ccaccaagct gacagtgaac ctgacaaatg atcggtacct ggccaccctg  1200
acagtgagaa acctggtggg caagtctgac gccgccgtgc tgaccatccc tgcctgcgat  1260
ttccaggcca cacccagt gatggacctg aaggcctttc caaggataa tatgctgtgg    1320
gtggagtgga ccacctag agagtccgtg aagaagtaca tcctggagtg gtgcgtgctg   1380
tctgacaagg ccccatgtat caccgactgg cagcaggagg atggcaccgt gcacaggaca  1440
tatctgcgcg gcaacctggc cgagtctaag tgttacctga tcaccgtgat accgtgtat   1500
gcagacggac caggctctcc tgagagcatc aaggcctacc tgaagcaggc accaccaagc  1560
aagggaccaa ccgtgcggac aaagaaggtc ggcaagaatg aggccgtgct ggagtgggac  1620
cagctgcctg tggatgtgca aacggcttc atcaggaatt acaccatctt ttatcgcaca  1680
atcatcggca acgagacagc cgtaatgtg gacagctccc acaccgagta tacactgtct  1740
agcctgacct ccgatacact gtacatggtg aggatggccg cctatacaga cgagggcggc  1800
aaggatggcc ccgagttt                                                1818

SEQ ID NO: 52           moltype = DNA  length = 72
FEATURE                 Location/Qualifiers
misc_feature            1..72
                        note = IgE signal sequence
source                  1..72
                        mol_type = other DNA
                        organism = synthetic construct
SEQUENCE: 52
ggtacccggt ccgccaccat ggactggacc tggattctgt tcctcgtggc tgctgctaca    60
agagtgcaca gc                                                       72

SEQ ID NO: 53           moltype = DNA  length = 75
FEATURE                 Location/Qualifiers
misc_feature            1..75
                        note = F2A
source                  1..75
                        mol_type = other DNA
                        organism = synthetic construct
SEQUENCE: 53
ggttctggcg tgaaacagac tttgaatttt gaccttctca gttggcggg agacgtggag    60
tccaacccag ggccc                                                    75

SEQ ID NO: 54           moltype = DNA  length = 66
FEATURE                 Location/Qualifiers
misc_feature            1..66
                        note = P2A
source                  1..66
                        mol_type = other DNA
                        organism = synthetic construct
SEQUENCE: 54
ggaagcggag ctactaactt cagcctgctg aagcaggctg agacgtgga ggagaaccct    60
ggacct                                                              66

SEQ ID NO: 55           moltype = DNA  length = 54
FEATURE                 Location/Qualifiers
misc_feature            1..54
                        note = T2A
source                  1..54
                        mol_type = other DNA
                        organism = synthetic construct
SEQUENCE: 55
gagggcagag gcagcctgct gacctgcggc gacgtcgagg agaaccccgg gccc          54

SEQ ID NO: 56           moltype = DNA  length = 825
FEATURE                 Location/Qualifiers
misc_feature            1..825
                        note = LNGFR
source                  1..825
                        mol_type = other DNA
                        organism = synthetic construct
SEQUENCE: 56
atgggggcag gtgccaccgg ccgcgccatg gacgggccgc gcctgctgct gttgctgctt    60
ctgggggtgt cccttggagg tgccaaggag gcatgccca caggcctgta cacacacagc   120
ggtgagtgct gcaaagcctg caacctgggc gaggtgtgg cccagccttg tggagccaac   180
cagaccgtgt gtgagccctg cctggacagc gtgacgttct ccgacgtggt gagcgcgacc   240
gagccgtgca agccgtgcac cgagtgcgtg gggctccaga gcatgtcggc gccgtgcgtg   300
gaggccgatg acgccgtgtg ccgctgcgcc tacggctact accaggatga gacgactggg   360
cgctgcgagg cgtgccgcgt gtgcgaggcg ggctcgggcc tcgtgttctc ctgccaggac   420
```

```
aagcagaaca ccgtgtgcga ggagtgcccc gacggcacgt attccgacga ggccaaccac    480
gtggacccgt gcctgccctg caccgtgtgc gaggacaccg agcgccagct ccgcgagtgc    540
acacgctggg ccgacgccga gtgcgaggag atccctggcc gttggattac acggtccaca    600
cccccagagg gctcggacag cacagccccc agcacccagg agcctgaggc acctccagaa    660
caagacctca tagccagcac ggtggcaggt gtggtgacca cagtgatggg cagctcccag    720
cccgtggtga cccgaggcac caccgacaac ctcatccctg tctattgctc catcctggct    780
gctgtggttg tgggtcttgt ggcctacata gccttcaaga ggtga                    825
```

```
SEQ ID NO: 57               moltype = AA   length = 253
FEATURE                     Location/Qualifiers
REGION                      1..253
                            note = IL-12a polypeptide
source                      1..253
                            mol_type = protein
                            organism = synthetic construct
SEQUENCE: 57
MWPPGSASQP PPSPAAATGL HPAARPVSLQ CRLSMCPARS LLLVATLVLL DHLSLARNLP     60
VATPDPGMFP CLHHSQNLLR AVSNMLQKAR QTLEFYPCTS EEIDHEDITK DKTSTVEACL    120
PLELTKNESC LNSRETSFIT NGSCLASRKT SFMMALCLSS IYEDLKMYQV EFKTMNAKLL    180
MDPKRQIFLD QNMLAVIDEL MQALNFNSET VPQKSSLEEP DFYKTKIKLC ILLHAFRIRA    240
VTIDRVMSYL NAS                                                      253

SEQ ID NO: 58               moltype = AA   length = 328
FEATURE                     Location/Qualifiers
REGION                      1..328
                            note = IL12b polypeptide
source                      1..328
                            mol_type = protein
                            organism = synthetic construct
SEQUENCE: 58
MCHQQLVISW FSLVFLASPL VAIWELKKDV YVVELDWYPD APGEMVVLTC DTPEEDGITW     60
TLDQSSEVLG SGKTLTIQVK EFGDAGQYTC HKGGEVLSHS LLLLHKKEDG IWSTDILKDQ    120
KEPKNKTFLR CEAKNYSGRF TCWWLTTIST DLTFSVKSSR GSSDPQGVTC GAATLSAERV    180
RGDNKEYEYS VECQEDSACP AAEESLPIEV MVDAVHKLKY ENYTSSFFIR DIIKPDPPKN    240
LQLKPLKNSR QVEVSWEYPD TWSTPHSYFS LTFCVQVQGK SKREKKDRVF TDKTSATVIC    300
RKNASISVRA QDRYYSSSWS EWASVPCS                                      328

SEQ ID NO: 59               moltype = AA   length = 133
FEATURE                     Location/Qualifiers
REGION                      1..133
                            note = IL15 polypeptide
source                      1..133
                            mol_type = protein
                            organism = synthetic construct
SEQUENCE: 59
GIHVFILGCF SAGLPKTEAN WVNVISDLKK IEDLIQSMHI DATLYTESDV HPSCKVTAMK     60
CFLLELQVIS LESGDASIHD TVENLIILAN NSLSSNGNVT ESGCKECEEL EEKNIKEFLQ    120
SFVHIVQMFI NTS                                                      133

SEQ ID NO: 60               moltype = AA   length = 175
FEATURE                     Location/Qualifiers
REGION                      1..175
                            note = sIL15ra polypeptide
source                      1..175
                            mol_type = protein
                            organism = synthetic construct
SEQUENCE: 60
ITCPPPMSVE HADIWVKSYS LYSRERYICN SGFKRKAGTS SLTECVLNKA TNVAHWTTPS     60
LKCIRDPALV HQRPAPPSTV TTAGVTPQPE SLSPSGKEPA ASSPSSNNTA ATTAAIVPGS    120
QLMPSKSPST GTTEISSHES SHGTPSQTTA KNWELTASAS HQPPGVYPQG HSDTT         175

SEQ ID NO: 61               moltype = AA   length = 606
FEATURE                     Location/Qualifiers
REGION                      1..606
                            note = soluble gp130
source                      1..606
                            mol_type = protein
                            organism = synthetic construct
SEQUENCE: 61
MLTLQTWLVQ ALFIFLTTES TGELLDPCGY ISPESPVVQL HSNFTAVCVL KEKCMDYFHV     60
NANYIVWKTN HFTIPKEQYT IINRTASSVT FTDIASLNIQ LTCNILTFGQ LEQNVYGITI    120
ISGLPPEKPK NLSCIVNEGK KMRCEWDGGR ETHLETNFTL KSEWATHKFA DCKAKRDTPT    180
SCTVDYSTVY FVNIEVWVEA ENALGKVTSD HINFDPVYKV KPNPPHNLSV INSEELSSIL    240
KLTWTNPSIK SVIILKYNIQ YRTKDASTWS QIPPEDTAST RSSFTVQDLK PFTEYVFRIR    300
CMKEDGKGYW SDWSEEASGI TYEDRPSKAP SFWYKIDPSH TQGYRTVQLV WKTLPPFEAN    360
GKILDYEVTL TRWKSHLQNY TVNATKLTVN LTNDRYLATL TVRNLVGKSD AAVLTIPACD    420
FQATHPVMDL KAFPKDNMLW VEWTTPRESV KKYILEWCVL SDKAPCITDW QQEDGTVHRT    480
YLRGNLAESK CYLITVTPVY ADGPGSPESI KAYLKQAPPS KGPTVRTKKV GKNEAVLEWD    540
QLPVDVQNGF IRNYTIFYRT IIGNETAVNV DSSHTEYTLS SLTSDTLYMV RMAAYTDEGG    600
```

-continued

```
KDGPEF                                                                    606

SEQ ID NO: 62           moltype = AA  length = 836
FEATURE                 Location/Qualifiers
REGION                  1..836
                        note = soluble gp130 fused to a Fc
source                  1..836
                        mol_type = protein
                        organism = synthetic construct
SEQUENCE: 62
MLTLQTWLVQ ALFIFLTTES TGELLDPCGY ISPESPVVQL HSNFTAVCVL KEKCMDYFHV    60
NANYIVWKTN HFTIPKEQYT IINRTASSVT FTDIASLNIQ LTCNILTFGQ LEQNVYGITI   120
ISGLPPEKPK NLSCIVNEGK KMRCEWDGGR ETHLETNFTL KSEWATHKFA DCKAKRDTPT   180
SCTVDYSTVY FVNIEVWVEA ENALGKVTSD HINFDPVYKV KPNPPHNLSV INSEELSSIL   240
KLTWTNPSIK SVIILKYNIQ YRTKDASTWS QIPPEDTAST RSSFTVQDLK PFTEYVFRIR   300
CMKEDGKGYW SDWSEEASGI TYEDRPSKAP SFWYKIDPSH TQGYRTVQLV WKTLPPFEAN   360
GKILDYEVTL TRWKSHLQNY TVNATKLTVN LTNDRYLATL TVRNLVGKSD AAVLTIPACD   420
FQATHPVMDL KAFPKDNMLW VEWTTPRESV KKYILEWCVL SDKAPCITDW QQEDGTVHRT   480
YLRGNLAESK CYLITVTPVY ADGPGSPESI KAYLKQAPPS KGPTVRTKKV GKNEAVLEWD   540
QLPVDVQNGF IRNYTIFYRT IIGNETAVNV DSSHTEYTLS SLTSDTLYMV RMAAYTDEGG   600
KDGPEFRSCD KTHTCPPCPA PEAEGGPSVF LFPPKPKDTL MISRTPEVTC VVVDVSHEDP   660
EVKFNWYVDG VEVHNAKTKP REEQYNSTYR VVSVLTVLHQ DWLNGKEYKC KVSNKALPAP   720
IEKTISKAKG QPREPQVYTL PPSREEMTKN QVSLTCLVKG FYPSDIAVEW ESNGQPENNY   780
KTTPPVLDSD GSFFLYSKLT VDKSRWQQGN VFSCSVMHEA LHNHYTQKSL SLSPGK       836

SEQ ID NO: 63           moltype = DNA  length = 7711
FEATURE                 Location/Qualifiers
misc_feature            1..7711
                        note = Matrice TRAC locus_CubiCAR CD22 pCLS30056 full
                        sequence
source                  1..7711
                        mol_type = other DNA
                        organism = synthetic construct
SEQUENCE: 63
gtggcactttt tcggggaaat gtgcgcggaa cccctatttg tttattttc taaatacatt    60
caaatatgta tccgctcatg agacaataac cctgataaat gcttcaataa tattgaaaaa   120
ggaagagtat gagtattcaa catttccgtg tcgcccttat tcccttttt gcggcatttt   180
gccttcctgt ttttgctcac ccagaaacgc tggtgaaagt aaaagatgct gaagatcagt   240
tgggtgcacg agtgggttac atcgaactgg atctcaacag cggtaagatc cttgagagtt   300
ttcgccccga agaacgtttt ccaatgatga gcacttttaa agttctgcta tgtggcgcgg   360
tattatcccg tattgacgcc gggcaagagc aactcggtcg ccgcatacac tattctcaga   420
atgacttggt tgagtactca ccagtcacag aaaagcatct tacggatggc atgacagtaa   480
gagaatttatg cagtgctgcc ataaccatga gtgataacac tgcgccaac ttacttctga   540
caacgatcgg aggaccgaag gagctaaccg ctttttttgca caacatgggg gatcatgtaa   600
ctcgccttga tcgttgggaa ccggagctga atgaagccat accaaacgac gagcgtgaca   660
ccacgatgcc tgtagcaatg gcaacaacgt tgcgcaaact attaactggc gaactactta   720
ctctagcttc ccggcaacaa ttaatagact ggatggaggc ggataaagtt gcaggaccac   780
ttctgcgctc ggcccttccg gctggctggt ttattgctga taaatctgga gccggtgagc   840
gtggttctcg cggtatcatt gcagcactgg ggccagatgg taagccctcc cgtatcgtag   900
ttatctacac gacggggagt caggcaacta tggatgaacg aaatagacag atcgctgaga   960
taggtgcctc actgattaag cattggtaac tgtcagacca agtttactca tatatactt   1020
agattgattt aaaacttcat ttttaattta aaaggatcta ggtgaagatc ctttttgata  1080
atctcatgac caaaatccct taacgtgagt tttcgttcca ctgagcgtca gaccccgtag  1140
aaaagatcaa aggatcttct tgagatcctt tttttctgcg cgtaatctgc tgcttgcaaa  1200
caaaaaaacc accgctacca gcggtggttt gtttgccgga tcaagagcta ccaactcttt  1260
ttccgaaggt aactggcttc agcagagcgc agataccaaa tactgttctt ctagtgtagc  1320
cgtagttagg ccaccacttc aagaactctg tagcaccgcc tacatacctc gctctgctaa  1380
tcctgttacc agtggctgct gccagtggcg ataagtcgtg tcttaccggg ttggactcaa  1440
gacgatagtt accggataag gcgcagcggt cgggctgaac ggggggttcg tgcacacagc  1500
ccagcttgga gcgaacgacc tacaccgaac tgagataccct acagcgtgag ctatgagaaa  1560
gcgccacgct tcccgaaggg agaaaggcgg acaggtatcc ggtaagcggc agggtcggaa  1620
caggagagcg cacgagggag cttccagggg gaaacgcctg gtatctttat agtcctgtcg  1680
ggtttcgcca cctctgactt gagcgtcgat ttttgtgatg ctcgtcaggg ggcggagcc   1740
tatggaaaaa cgccagcaac gcggcctttt tacggttcct ggccttttgc tggccttttg  1800
ctcacatggt ctttcctgcg ttatcccctg attctgtgga taaccgtatt accgcctttg  1860
agtgagctga taccgctcgc cgcagccgaa cgaccgagcg cagcgagtca gtgagcgagg  1920
aagcggagag cgcccaatac gcaaaccgcc tctccccgcg cgttggccga ttcattaatg  1980
cagctggcac gacaggttc ccgactggaa agcgggcagt gagcgcaacg caattaatgt   2040
gagttagctc actcattagg caccccaggc tttacacttt atgcttccgg ctcgtatgtt  2100
gtgtggaatt gtgagcggat aacaatttca cacaggaaac agctatgacc atgattacgc  2160
caagcgcgtc aattaaccct cactaaaggg aacaaaagct gttaattaat tgctgggcct  2220
ttttcccatg cctgccttta ctctgccaga gttatattgc tggggttttg aagaagatcc  2280
tattaaataa aagaataagc agtattatta agtagccctg catttcaggt tccttgagt   2340
ggcagggcag gcctgccgt gaaagttcac tgaaatcatg gcctcttggc caagattgat   2400
agcttgtgc tgtccctgag tcccagtcca tcacgagcag ctggtttcta agatgctatt   2460
tcccgtataa agcatgagac cgtgacttgc cagccccaca gagccccgcc cttgccatc   2520
actggcatct ggactccagc ctgggttggg gcaaagaggg aaatgagatc atgtcctaac   2580
cctgatcctc ttgtcccaca gatatccagt accctacga cgtgcccgac tacgcctccg   2640
gtgagggcag aggaagtctt ctaacatgcg gtgacgtgga ggagaatccg ggccccggat   2700
```

```
ccgctctgcc cgtcaccgct ctgctgctgc cactggcact gctgctgcac gctgctaggc  2760
ccggagggg  aggcagctgc ccctacagca accccagcct gtgcagcgga ggcggcggca  2820
gcggcggagg gggtagccag gtgcagctgc agcagagcgg ccctggcctg gtgaagccaa  2880
gccagacact gtccctgacc tgcgccatca gcggcgattc cgtgagctcc aactccgccg  2940
cctggaattg gatcaggcag tcccttctc  ggggcctgga gtggctggga aggacatact  3000
atcggtctaa gtggtacaac gattatgccg tgtctgtgaa gagcagaatc acaatcaacc  3060
ctgacacctc caagaatcag ttctctctgc agctgaatag cgtgacacca gaggacaccg  3120
ccgtgtacta ttgcgccagg gaggtgaccg gcgacctgga ggatgccttt gacatctggg  3180
gccagggcac aatggtgacc gtgagctccg gaggcggcg  atctggcgga ggaggaagtg  3240
ggggcggcgg gagtgatatc cagatgacac agtccccatc ctctctgagc gcctccgtgg  3300
gcgacagagt gacaatcacc tgtagggcct cccagaccat ctggtcttac ctgaactggt  3360
atcagcagag gcccggcaag gcccctaatc tgctgatcta cgcagcaagc tccctgcaga  3420
gcggagtgcc atccagattc tctggcaggg gctccggcac agacttcacc ctgaccatct  3480
ctagcctgca ggccgaggac ttcgccacct actattgcca gcagtcttat agcatccccc  3540
agacatttgg ccagggcacc aagctggaga tcaagtcgga tcccggaagc ggagggggag  3600
gcagctgccc ctacagcaac cccagcctgt gcagcggagg cggcggcagc gagctgccca  3660
cccagggcac cttctccaac gtgtccacca acgtgagccc agccaagccc accaccaccg  3720
cctgtcctta ttccaatcct tccctgtgtg ctcccaccac aaccccgcct ccaaggcccc  3780
ctaccccgc  accaactatt gcctcccagc cactctcact gcggcctgag gcctgtcggc  3840
ccgctgctgg aggcgcagtg catacaaggg gcctcgattt cgcctgcgat atttacatct  3900
gggcacccct cgccggcacc tgcggggtgc ttctcctctc cctggtgatt accctgtatt  3960
gcagcagggg ccggaagaag ctcctctaca ttttaagca  gccttttcatg ggccagtgc   4020
agacaaccca agaggaggat gggtgttcct gcagattccc tgaggaagag gaaggcgggt  4080
gcgagctgag agtgaagttc tccaggagcc cagatgcccc cgcctatcaa cagggccaga  4140
accagctcta caacgagctt aacctcggga ggcgcgaaga atacgacgtg ttggataaga  4200
gaagggggcg ggaccccgag atgggaggaa agccccggga gaagaacct  caggagggcc  4260
tgtacaacga gctgcagaag gataagatgg ccgaggccta ctcagagatc gggatgaagg  4320
gggagcggcg ccgcgggaag gggcacgatg ggctctacca ggggctgagc acagccacaa  4380
aggacacata cgacgccttg cacatgcagg cccttccacc ccgggaatag tctagagggc  4440
ccgtttaaac ccgctgatca gcctcgactg tgccttctag ttgccagcca tctgttgttt  4500
gcccctcccc cgtgccttcc ttgaccctgg aaggtgccac tcccactgtc ctttcctaat  4560
aaaatgagga aattgcatcg cattgtctga gtaggtgtca ttctattctg ggggtgggg   4620
tggggcagga cagcaagggg gaggattggg aagacaatag caggcatgct ggggatgcgg  4680
tgggctctat gactagtggc gaattcccgt gtaccagctc agagactcta aatccagtga  4740
caagtctgtc tgcctattca ccgattttga ttctcaaaca aatgtgtcac aaagtaagga  4800
ttctgatgtg tatatcacag acaaaactgt gctagacatg aggtctatgg acttcaagag  4860
caacagtgct gtggcctgga gcaacaaatc tgactttgca tgtgcaaacg ccttcaacaa  4920
cagcattatt ccagaagaca ccttcttccc cagcccaggt aagggcagct ttggtgcctt  4980
cgcaggctgt ttccttgctt caggaatggc caggttctgc ccagagctct ggtcaatgat  5040
gtctaaaact cctctgattg gtggtctcgg ccttatccat tgccaccaaa acctctcttt  5100
tactaagcga tcgctccggt gcccgtcagt gggcagagcg cacatcgccc acagtccccg  5160
agaagttggg gggaggggtc ggcaattgaa cgggtgccta gagaaggtgg cgcggggtaa  5220
actgggaaag tgatgtcctg tactggctcc gcctttttcc gcctttttcc gcctttttcc  5280
atataagtgc agtagtcgcc gtgaacgttc ttttcgcaa cggggtttgcc gccagaacac  5340
agctgaagct tcgaggggct cgcatctctc cttcacgcgc ccgccgccct acctgaggcc  5400
gccatccacg ccggttgagt cgcgttctgc cgcctcccgc ctgtggtgcc tcctgaactg  5460
cgtccgccgt ctaggtaagt ttaaagctca ggtcgagacc ggccttttgg ccggcgcttc  5520
cttggagcct acctagactc agccggctct ccacgctttg cctgacctg  cttgctcaac  5580
tctacgtctt tgtttcgttt tctgttctgc gccgttacag atccaagctg tgaccggcgc  5640
ctacctgaga tcaccggcgc caccatggct tcttaccctg acaccagca  tgcttctgcc  5700
tttgaccagg ctgccagatc caggggccac tccaacagga gaactgccct aagacccaga  5760
agacagcagg aagccactga ggtgaggcct gagcagaaga tgccaaccct gctgagggtg  5820
tacattgatg gacctcatgg catgggcaag accaccacca ctcaactgct ggtggcactg  5880
ggctccaggg atgacattgt gtatgtgcct gagccaatga cctactggag agtgctagga  5940
gcctctgaga ccattgccaa catctacacc acccagcaca ggctggacca gggagaaatc  6000
tctgctggaa atgctgctgt ggtgatgacc tctgcccaga tcacaatggg aatgcccta   6060
gctgtgactg atgctgttct ggctcctcac attggaggag aggctggctc ttctcatgcc  6120
cctccacctg ccctgaccct gatctttgac agacacccca ttgcagccct gctgtgctac  6180
ccagcagcaa ggtacctcat gggctccagg accccacagg ctgtgctggc ttttgtgcca  6240
ctgatccctc caaccctccc tggcaccaac attgttctgg gagcactgcc tgaagacaga  6300
cacattgaca ggctggcaaa gaggcagaga cctgagaga  gactggacct ggccatgctg  6360
gctgcaatca gaagggtgta tggactgctg gcaaacactg tgagatacct ccagtgtgga  6420
ggctcttgga gagaggactg gggacagctc tctggaacag cagtgccccc tcaaggagct  6480
gagccccagt ccaatgctgg tccaagaccc cacattgggt acacccgtct caccctgttc  6540
agagccctg  agctgctggc tcccaatgga gacctgtaca atgtgtttgc ctgggctctg  6600
gatgttctag ccaagaggct gaggtccatg catgtgttca tcctggacta tgaccagtcc  6660
cctgctggat gcagagatgc tctgctgcaa ctaacctctg gcatggtgca gacccatgtg  6720
accaccccctg gcagcatccc caccatctgt gacctagcca gaacctttgc cagggagatg  6780
ggagaggcca actaaggcgc gccactcgag cgctagctgg ccagacatga taagatacat  6840
tgatgagttt ggacaaacca caactagaat gcagtgaaaa aaatgcttta tttgtgaaat  6900
ttgtgatgct attgctttat ttgtaaccat tataagctgc aataaacaag ttaacaacaa  6960
caattgcatt cattttatgt ttcaggttca ggggaggtg  tgggaggttt tttaaagcaa  7020
gtaaaacctc tacaaatgtg gtatggaagg cgcgcccaat tcgccctata gtgagtcgta  7080
ttacgcgcga ctcactggcc gtcgttttac aacgtcgtga ctgggaaaac cctggcgtta  7140
cccaacttaa tcgccttgca gcacatcccc ctttcgccag ctggcgtaat agcgaagagg  7200
cccgcaccga acgcccttc  caacagttg  cgcagcctga atggcgaatg ggagcgccct  7260
gtagcggcgc attaagcgcg gcgggtgtgg tggttacgcg cagcgtgacc gctacacttg  7320
ccagcgccct agcgcccgct cctttcgctt tcttcccttc ctttctcgcc acgttcgccg  7380
gctttccccg tcaagctcta aatcggggc  tcccttagg  gttccgattt agtgctttac  7440
```

```
ggcacctcga cccaaaaaaa cttgattagg gtgatggttg gcctgtagtg ggccatagcc 7500
ctgatagacg gttttttcgcc ctttgacgtt ggagtccacg ttctttaata gtggactctt 7560
gttccaaact ggaacaacac tcaaccctat ctcggtctat tcttttgatt tataagggat 7620
tttgccgatt tcggcctatt ggttaaaaaa tgagctgatt taacaaaaat ttaacgcgaa 7680
ttttaacaaa atattaacgc ttacaatttta g                              7711
```

| | |
|---|---|
| SEQ ID NO: 64 | moltype = DNA   length = 7502 |
| FEATURE | Location/Qualifiers |
| misc_feature | 1..7502 |
| | note = Matrice CD25 locus_IL15_2A_sIL15Ra pCLS30519 full sequence |
| source | 1..7502 |
| | mol_type = other DNA |
| | organism = synthetic construct |

SEQUENCE: 64

```
gtttattatt cctgttccac agctattgtc tgccatataa aaacttaggc caggcacagt 60
ggctcacacc tgtaatccca gcactttgga aggccgaggc aggcagatca caaggtcagg 120
agttcgagac cagcctggcc aacatagcaa aaccccatct ctactaaaaa tacaaaaatt 180
agccaggcat ggtggcgtgt gcactggttt agagtgagga ccacattttt ttggtgccgt 240
gttacacata tgaccgtgac tttgttacac cactacagga ggaagagtag aagaacaatc 300
ggttctggcg tgaaacagac tttgaatttt gaccttctca agttggcggg agacgtggag 360
tccaacccag ggcccggtac cgggtccgcc accatggact tctgttcctc 420
gtggctgctg ctacaagagt gcacagcggc attcatgctt tcattttggg ctgtttcagt 480
gcagggcttc ctaaaacaga agccaactgg gtgaatgtaa taagtgattt gaaaaaaatt 540
gaagatctta ttcaatctat gcatattgat gctactttat atacgaaaag tgatgttcac 600
cccagttgca aagtaacagc aatgaagtgc tttctcttgg agttacaagt tatttcactt 660
gagtccggag atgcaagtat tcatgataca gtagaaaatc tgatcatcct agcaaacaac 720
agtttgtctt ctaatgggaa tgtaacagaa tctggatgca aagaatgtga ggaactggag 780
gaaaaaaata ttaaagaatt tttgcagagt tttgtacata ttgtccaaat gttcatcaac 840
acttctggaa gcggagctac taacttcagc ctgctgaagc aagctggaga cgtggaggag 900
aaccctggac ctgggaccgg ctctgcaacc atggattgga cgtggatcct gtttctcgtg 960
gcagctgcca caagagttca cagtatcacg tgccctcccc ccatgtccgt ggaacacgca 1020
gacatctggg tcaagagcta cagcttgtac tccaggagc ggtacatttg taactctggt 1080
ttcaagcgta aagccggcac gtccaagcct gacggagtgc gttgttgaacaa ggccacgaat 1140
gtcgcccact ggacaacccc cagtctcaaa tgcattagaa accctgccct ggttcaccaa 1200
aggccagcgc caccctccac agtaacgacg gcaggggtga ccccacagcc agagagcctc 1260
tcccttctg gaaagagcc cgcagcttca tctcccagct caaacaacac agcggccaca 1320
acagcagcta ttgtcccggg ctcccagctg atgccttcaa aatcaccttc cacaggaacc 1380
acagagataa gcagtcatga gtcctcccac ggcaccccct ctcagacaac agccaagaac 1440
tgggaactca cagcatccgc ctcccaccag ccgccaggtg tgtatccaca gggccacagc 1500
gacaccactg agggcagagg cagcctgctg acctgcggcg acgtcgagga gaaccccggg 1560
cccatggggg caggtgccac cggccgcgcc atggacgggc gcgcctgctg ctgttgctgc 1620
cttctggggg tgtcccttgg aggtgccaag gaggcagcct ccacagcgt gtacacacac 1680
agcggtgagt gctgcaaagc ctgcaactg ggcgagggtg tggcccagcc ttgtggagcc 1740
aaccagaccg tgtgtgagcc ctgcctggac agcgtgacgt tctccgacgt ggtgagcgcg 1800
accgagccgt gcaagccgtg caccgagtgc gtggggctcc agagcatgtc ggcgccgtgc 1860
gtggaggccg atgacgccgt gtgccgctgc cctacggct actaccagga tgagacgact 1920
gggcgctgcg aggcgtgccg cgtgtgcgag gcgggctcgg gcctcgtgtt ctcctgccaa 1980
gacaagcaga acaccgtgtg cgaggagtgc cccgacggca gtattccgag cgaggccaac 2040
cacgtggacc cgtgcctgcc ctgcaccgtg tgcgaggaca ccgagcgcca gctccgcgag 2100
tgcacacgct gggccgacgc cgagtgcgag gagatccctg gccgttggat tacacggtcc 2160
acacccccag agggctcgga cagcacagcc cccagcaccc aggagcctga ggcacctcca 2220
gaacaagacc tcatagccag cacggtggca ggtgtggtga ccacagtgat gggcagctcc 2280
cagcccgtgt tgaccgaggg caccaccgac aacctcatcc ctgtctattg ctccatcctg 2340
gctgctgtgg ttgtgggtct tgtggcctac atagcctta agaggtgaaa aaccaaaaga 2400
acaagaattt cttggtaaga agcgggaac agacaacaga agtcatgaag cccaagtgaa 2460
atcaaaggtg ctaaatggtc gcccaggaga catccgttgt gcttgcctgc gttttggaag 2520
ctctgaagtc acatcacagg acacgggca gtggcaacct tgtctctatg ccagctcagt 2580
cccatcagag agcgagcgct acccacttct aaatagcaat ttcgccgttg aagaggaagg 2640
gcaaaaccac tagaactctc catcttattt tcatgtatat gtgttcatgc gatcgctccg 2700
gtgcccgtca gtgggcagag cgcacatcgc ccacagtccc cgagaagttg gggggagggg 2760
tcggcaattg aacgggtgcc tagagaaggt ggcgcgggt aaactggaa agtgatgtcg 2820
tgtactggct ccgcctttttt cccgagggtg ggggagaacc gtatataagt gcagtagtcg 2880
ccgtgaacgt tctttttcgc aacgggtttg ccgccagaac agctgaag cttcgagggg 2940
ctcgcatctc tccttcacgc gcccgccgcc ctacctgagg ccgccatcca cgccggttga 3000
gtcgcgttct gccgcctccc gctgtggtgt cctctgaaac tgcgtccgcc gtctaggtaa 3060
gtttaaagct caggtcgaga ccgggccttt gtccggcgct cccttggagc ctacctagac 3120
tcagccggct ctccacgctt tgcctgaccc tgcttgctca actctacgtc tttgtttcgt 3180
tttctgttct gcgccgttac agatccaagc tgtgaccggc gcctacctga gatcaccgag 3240
gccaccatgg cttcttaccc tggacaccag catgcttctg cctttgacca ggctgccaga 3300
tccagggcc actccaacag gagaactgcc ctaagcccca aagacagca ggaagccact 3360
gaggtgaggc ctgagcagaa gatgccaacc tgctgaggg tgtacattga tggacctcat 3420
ggcatgggca agaccaccac cactcaactg ctggtggcac tgggtccag gatgacatt 3480
gtgtatgtgc ctgagcaat gaccctactgg agatgctgaa gagcctcacc tgaccatgga 3540
aacatctaca ccacccagca caggctggac cagggagaaa tctctgctgg agatgctgct 3600
gtggtgatga cctctgccca gatcacaatg ggaatgccct atgctgtgac tgatgctgtt 3660
ctggctcctc acattggagg agaggctggc tcttctcatg cccctccacc tgccctgacc 3720
ctgatctttg acagacaccc cattgcagcc ctgctgtgct acccagcagc aaggtacctc 3780
atgggctcca tgacccacag gctgtgctgg gcttttgtgg ccctgatccc tccaacccctc 3840
```

```
cctggcacca acattgttct gggagcactg cctgaagaca gacacattga caggctggca   3900
aagaggcaga gacctggaga gagactggac ctggccatgc tggctgcaat cagaagggtg   3960
tatggactgc tggcaaacac tgtgagatac ctccagtgtg gaggctcttg gagagaggac   4020
tggggacagc tctctggaac agcagtgccc cctcaaggag ctgagcccca gtccaatgct   4080
ggtccaagac cccacattgg ggacaccctg ttcacccgtg tcagagcccc tgagctgctg   4140
gctcccaatg gagacctgta caatgtgttt gcctgggctc tggatgttct agccaagagg   4200
ctgaggtcca tgcatgtgtt catcctggac tatgaccagt ccctgctgg atgcagagat    4260
gctctgctgc aactaacctc tggcatggtg cagacccatg tgaccacccc tggcagcatc   4320
cccaccatct gtgacctagc cagaaccttt gccagggaga tgggagaggc caactaaggc   4380
gcgccactcg agcgctagct ggccagacat gataagatac attgatgagt ttggacaaac   4440
cacaactaga atgcagtgaa aaaaatgctt tatttgtgaa atttgtgatg ctattgcttt   4500
atttgtaacc attataagct gcaataaaca agttaacaac aacaattgca ttcattttat   4560
gtttcaggtt cagggggagg tgtgggaggt tttttaaagc aagtaaaacc tctacaaatg   4620
tggtatggaa ggcgcgccca attcgcccta tagtgagtcg tattacgtcg cgctcactgg   4680
ccgtcgtttt acaacgtcgt gactgggaaa accctggcgt tacccaactt aatcgccttg   4740
cagcacatcc cctttcgcc agctggcgta atagcgaaga ggcccgcacc gaaacgccct    4800
tcccaacagt tgcgcagcct gaatggcgaa tgggagcgcc ctgtagcggc gcattaagcg   4860
cggcgggtgt ggtggttacg cgcagcgtga ccgctacact tgccagcgcc ctagcgcccg   4920
ctccttcgc tttcttccct tcctttctcg ccacgttcgc cggctttccc cgtcaagctc    4980
taaatcgggg gctcccttta gggttccgat ttagtgcttt acggcacctc gaccccaaaa   5040
aacttgatta gggtgatggt tggcctgtag tgggccatag ccctgataga cggttttttcg   5100
cccttgacg ttggagtcca cgttctttaa tagtggactc ttgttccaaa ctggaacaac    5160
actcaaccct atctcggtct attctttga tttataaggg attttgccga tttcggccta    5220
ttggttaaaa aatgagctga tttaacaaaa atttaacgcg aattttaaca aatattaac    5280
gcttacaatt taggtggcac ttttcgggga aatgtgcgcg gaaccccctat ttgtttattt   5340
ttctaaatac attcaaatat gtatccgctc atgagacaat aaccctgata aatgcttcaa   5400
taatattgaa aaaggaagag tatgagtatt caacatttcc gtgtcgccct tattcccttt   5460
tttgcggcat tttgccttcc tgttttgct cacccagaaa cgctggtgaa agtaaaagat    5520
gctgaagatc agttgggtgc acgagtgggt tacatcgaac tggatctcaa cagcggtaag   5580
atccttgaga gttttcgccc cgaagaacgt tttccaatga tgagcacttt taaagttctg   5640
ctatgtggcg cggtattatc ccgtattgac gccgggcaag agcaactcgg tcgccgcata   5700
cactattctc agaatgactt ggttgagtac tcaccagtca cagaaaagca tcttacggat   5760
ggcatgacag taagagaatt atgcagtgct gccataacca tgagtgataa cactgcggcc   5820
aacttacttc tgacaacgat cggaggaccg aaggagctaa ccgcttttttt gcacaacatg   5880
ggggatcatg taactcgcct tgatcgttgg gaaccggagc tgaatgaagc cataccaaac   5940
gacgagcgtg acaccacgat gcctgtagca atggcaacaa cgttgcgcaa actattaact   6000
ggcgaactac ttactctagc ttcccggcaa caattaatag actggatgga ggcggataaa   6060
gttgcaggac cacttctgcg ctcggccctt ccggctggct ggtttattgc tgataaatct   6120
ggagccggtg agcgtggttc tcgcggtatc attgcagcac tggggccaga tggtaagccc   6180
tcccgtatcg tagttatcta cacgacgggg agtcaggcaa ctatggatga acgaaataga   6240
cagatcgctg agataggtgc ctcactgatt aagcattggt aactgtcaga ccaagtttac   6300
tcatatatac tttagattga tttaaaactt cattttttaat ttaaaaggat ctaggtgaag   6360
atcctttttg ataatctcat gaccaaaatc ccttaacgtg agttttcgtt ccactgagcg   6420
tcagaccccg tagaaaagat caaaggatct tcttgagatc ctttttttct gcgcgtaatc   6480
tgctgcttgc aaacaaaaaa accaccgcta ccagcggtgg tttgtttgcc ggatcaagag   6540
ctaccaactc ttttttccgaa ggtaactggc ttcagcagag cgcagatacc aaatactgtt   6600
cttctagtgt agccgtagtt aggccaccac ttcaagaact ctgtagcacc gcctacatac   6660
ctcgctctgc taatcctgtt accagtggct gctgccagtg gcgataagtc gtgtcttacc   6720
gggttggact caagacgata gttaccggat aaggcgcagc ggtcgggctg aacggggggt   6780
tcgtgcacac agcccagctt ggagcgaacg acctacaccg aactgagata cctacagcgt   6840
gagctatgag aaagcgccac gcttcccgaa gggagaaagg cggacaggta tccggtaagc   6900
ggcagggtcg aacaggaga gcgcacgagg gagcttccag ggggaaacgc ctggtatctt    6960
tatagtcctg tcgggtttcg ccacctctga cttgagcgtc gatttttgtg atgctcgtca   7020
gggggcgga gcctatggaa aaacgccagc aacgcggcct ttttacggtt cctggccttt    7080
tgctggcctt ttgctcacat ggtctttcct gcgttatccc ctgattctgt ggataacgt    7140
attaccgcct ttgagtgagc tgataccgct cgccgcagcc gaacgaccga gcgcagcgag   7200
tcagtgagcg aggaagcgga gagcgcccaa tacgcaaacc gcctctcccc gcgcgttggc   7260
cgattcatta atgcagctgg cacgacaggt ttcccgactg gaaagcgggc agtgagcgca   7320
acgcaattaa tgtgagttag ctcactcatt aggcacccca ggctttacac tttatgcttc   7380
cggctcgtat gttgtgtgga attgtgagcg gataacaatt tcacacagga aacagctatg   7440
accatgatta cgccaagcgc gtcaattaac cctcactaaa gggaacaaaa gctgttaatt   7500
aa                                                                  7502
```

SEQ ID NO: 65         moltype = DNA   length = 7778
FEATURE               Location/Qualifiers
misc_feature          1..7778
                      note = Matrice PD1 locus_IL15_2A_sIL15Ra pCLS30513 full
                      sequence
source                1..7778
                      mol_type = other DNA
                      organism = synthetic construct
SEQUENCE: 65
```
gactccccag acaggccctg gaaccccccc accttctccc cagccctgct cgtggtgacc   60
gaaggggaca acgccacctt cacctgcagc ttctccaaca catcggagag cttcgtgcta   120
aactggtacc gcatgagccc cagcaaccag acgacaagc tggccgcctt ccccgaggac    180
cgcagccagc ccgccagga ctgccgcttc cgtgtcacac aactgccaa cgggcgtgac    240
ttccacatga gcgtggtcag ggcccggcgc aatgacagcg gcacctacct ctgtgggcc    300
ggttctggcc tgaaacagac tttgaatttt gaccttctca gttggcggg agacgtggag   360
tccaacccag ggcccggtac cgggtccgcc accatggact ggacctggat tctgttcctc   420
```

```
gtggctgctg ctacaagagt gcacagcggc attcatgtct tcattttggg ctgtttcagt  480
gcagggcttc ctaaaacaga agccaactgg gtgaatgtaa taagtgattt gaaaaaaatt  540
gaagatctta ttcaatctat gcatattgat gctactttat atacggaaag tgatgttcac  600
cccagttgca aagtaacagc aatgaagtgc tttctcttgg agttacaagt tatttcactt  660
gagtccggag atgcaagtat tcatgataca gtagaaaatc tgatcatcct agcaaacaac  720
agtttgtctt ctaatgggaa tgtaacagaa tctggatgca aagaatgtga ggaactggag  780
gaaaaaaata ttaaagaatt tttgcagagt tttgtacata ttgtccaaat gttcatcaac  840
acttctggaa gcggagctac taacttcagc ctgctgaagc aggctggaga cgtggaggag  900
aaccctggac ctgggaccgg ctctgcaacc atggattgga cgtggatcct gtttctcgtg  960
gcagctgcca caagagttca cagtatcacg tgccctcccc ccatgtccgt ggaacacgca 1020
gacatctggg tcaagagcta cagccttgtac tccagggagc ggtacatttg taactctggt 1080
ttcaagcgta aagccggcac gtccagcctg acggagtgcg tgttgaacaa ggccacgaat 1140
gtcgccact  ggacaacccc cagtctcaaa tgcattagag accctgccct ggttcaccaa 1200
aggccagcgc caccctccac agtaacgacg gcagggggtga ccccacagcc agagagcctc 1260
tcccttctg  gaaaagagcc cgcagcttca tctcccagct caaacaacac agcggccaca 1320
acagcagcta ttgtcccggg ctcccagctg atgccttcaa aatcaccttc cacaggaacc 1380
acagagataa gcagtcatga gtcctccccac ggcaccccct ctcagacaac agccaagaac 1440
tgggaactca cagcatccgc ctcccaccag ccgccaggtg tgtatccaca gggccacagc 1500
gacaccactg agggcagagg cagcctgctg acctgcggca acgtcgagga aaccccggg  1560
cccatggggg caggtgccac cggccgcgcc atggacgggc cgcgcctgct gctgttgctg 1620
cttctggggg tgtcccttgg aggtgccaag gaggcatgcc ccacaggcct gtacacacac 1680
agcggtgagt gctgcaagctg gcgcagggtg tggccagcc ttgtggagcc 1740
aaccagaccg tgtgtgagcc ctgcctggac agcgtgacgt tctccgacgt ggtgagcgca 1800
accgagccgt gcaagccgtg caccgagtgc gtggggctcc agagcatgtc ggcgccgtgc 1860
gtggaggccg atgacgccgt gtgccgctgc gcctacggct actaccagga tgagacgact 1920
gggcgctgcg aggcgtgccg cgtgtgcgag gcgggctcgg gcctcgtgtt ctccgccag  1980
gacaagcaga acaccgtgtg cgaggagtgc cccgacggca cgtattccga cgaggccaac 2040
cacgtggacc cgtgcctgcc ctgcaccgtg tgcgaggaca ccgagcgcca gctccgcgag 2100
tgcacacgct gggccgacgc cgagtgcgag gagatccctg gccgttggat tacacggtcc 2160
acacccccag agggctcgga cagcacagcc cccagcctga aggcctga ggcacctcca 2220
gaacaagacc tcatagccag cacggtggca ggtgtggtga ccacagtgat gggcagctcc 2280
cagcccgtgg tgacccgagg caccaccgac aacctcatcc ctgtctattg ctccatcctg 2340
gctgctgtgg ttgtgggtct tgtggcctac atagccttca agaggtgatc tagagggccc 2400
gtttaaaccc gctgatcagc ctcgactgtg ccttctagtt gccagccatc tgttgtttgc 2460
ccctccccg  tgccttcctt gaccctggaa ggtgccactc ccactgtcct ttcctaataa 2520
aatgaggaaa ttgcatcgca ttgtctgagt aggtgtcatt ctattctggg gggtggggtg 2580
gggcaggaca gcaagggga ggattgggaa gacaatagca ggcatgctgg ggatgcggtg 2640
ggctctatga ctagtggcga attcggcgca gatcaaagag agcctgcggg cagagctcag 2700
ggtgacaggt gcggcctcgg aggcccgggg gcaggggtga gctgagcggg tcctgggggtg 2760
ggtgtccccct cctgcacagg atcaggagct ccagggtcgt agggcaggga ccccccagct 2820
ccagtccagg gctctgtcct gcacctgggg aatggtgacc ggcatcctg  tcctctagct 2880
ctggaagcac cccagcccct ctagtctgcc ctcacccctg accctgaccc tccaccctga 2940
ccccgtccta acccctgacc tttggcgatc gctccggtgc ccgtcagtgg gcagagcgca 3000
catcgcccac agtccccgag aagttggggg gaggggtcgg caattgaacg ggtgcctaga 3060
gaaggtggcg cggggtaaac tgggaaagtg atgtcgtgta ctggctccgc ctttttcccg 3120
agggtggggg agaaccgtat ataagtgcag tagtcgccgt gaacgttctt tttcgcaacg 3180
ggtttgccg  cagaacacag ctgaagcttc gaggggctcg catctctcct tcacgcgccc 3240
gccgccctac ctgaggccgc catccacgcc ggttgagtcg cgttctgccg cctcccgcct 3300
gtggtgcctc ctgaactgcg tccgccgtct aggtaagttt aaagctcagg tcgagaccgg 3360
gcctttgtcc ggcgctccct tggagcctac ctagactcag ccggctctcc acgctttgcc 3420
tgaccctgct tgctcaactc tacgtctttg tttcgttttc tgttctgcgc cgttacagat 3480
ccaagctgtg accggcgcct acctgagatc accggcgcca ccatggcttc ttaccctgga 3540
caccagcatg cttctgcctt tgaccaggct gccagatcca ggggccactc caacaggaga 3600
actgccctaa gacccagaag acagcaggaa gccactgagg tgaggcctga gcagaagatg 3660
ccaaccctgc tgagggtgta cattgatgga cctcatggca tgggcaagac caccaccact 3720
caactgctgg tggcactggg ctccagggat gacattgtgt atgtgcctga gccaatgacc 3780
tactggagag tgctaggagc ctctgagacc attgccaaca tctacaccac ccagcacagg 3840
ctgaccagg  gagaaatctc tgctggagat gctgctgtgg tgatgacctc tgcccagatc 3900
acaatggaa  tgcctatgc  tgtgcatgat gctgttctgg ctcctcacat tggaggagag 3960
gctggctctt ctcatgcccc tccacctgcc ctgaccctga tctttgacag acaccccatt 4020
gcagccctgc tgtgctaccc agcagcaagg tacctcatgg gctccatgac cccacaggct 4080
gtgctggctt ttgtggccct gatccctcca accctccctg gcaccaacat tgttctggga 4140
gcactgcctg aagacagaca cattgacagg ctggcaaaga ggcagagacc tggagagaga 4200
ctggaccctgg ccatgctggc tgcaatcaga agggtgtatg gactgctgac aaacactgtg 4260
agatacctcc agtgtggagg ctcttggaga gaggactggg gacagctctc tggaacagca 4320
gtgccccctc aaggagctga gcccagtcc  aatgctggtc caagacccca cattggggac 4380
accctgttca ccctgttcag agccctgag  ctgctggctc caatggaga cctgtacaat 4440
gtgtttgcct gggctctgga tgttctagcc aagaggctga ggtccatgca tgtgttcatc 4500
ctggactatg accagtcccc tgctggatgc agagatgctc tgcaact   aacctctgc  4560
atggtgcaga cccatgtgac cacccctggc agcatcccca ccatctgtga cctagccaga 4620
accttttgcca gggagatggg agaggccaac taaggcgcgc cactcgagcg ctagctggcc 4680
agacatgata agatacattg atgagtttgg acaaccacca actagaatgc agtgaaaaaa 4740
atgctttatt tgtgaaattt gtgatgctat tgctttattt gtaaccatta taagctgcaa 4800
taaacaagtt aacaacaaca attgcattca ttttatgttt caggttcagg gggaggtgtg 4860
ggaggttttt taaagcaagt aaaacctcta caaatgtggt atggaaggcg cgcccaattc 4920
gccctatagt gagtcgtatt acgtcgcgct cactggccgt cgttttacaa cgtcgtgact 4980
gggaaaaccc tggcgttacc caacttaatc gccttgcagc acatccccct ttcgccagct 5040
ggcgtaatag cgaagaggcc cgcaccgaaa cgccctccc  aacagttgcg cagcctgaat 5100
ggcgaatggg agcgccctgt agcggcgcat taagcgcggc gggtgtggtg gttacgcgca 5160
```

```
gcgtgaccgc tacacttgcc agcgccctag cgcccgctcc tttcgctttc ttcccttcct   5220
ttctcgccac gttcgccggc tttccccgtc aagctctaaa tcgggggctc cctttagggt   5280
tccgatttag tgctttacgg cacctcgacc ccaaaaaact tgattagggt gatggttggc   5340
ctgtagtggg ccatagccct gatagacggt ttttcgccct tgacgttgg agtccacgtt    5400
ctttaatagt ggactcttgt tccaaactgg aacaacactc aacccatct cggtctattc    5460
ttttgattta aagggatttt tgccgatttc ggcctattgg ttaaaaaatg agctgattta   5520
acaaaaattt aacgcgaatt ttaacaaaat attaacgctt acaatttagg tggcactttt   5580
cggggaaatg tgcgcggaac ccctatttgt ttatttttct aaatacattc aaatatgtat   5640
ccgctcatga gacaataacc ctgataaatg cttcaataat attgaaaaag gaagagtatg   5700
agtattcaac atttccgtgt cgcccttatt ccctttttg cggcattttg ccttcctgtt    5760
tttgctcacc cagaaacgct ggtgaaagta aaagatgctg aagatcagtt gggtgcacga   5820
gtgggttaca tcgaactgga tctcaacagc ggtaagatcc ttgagagttt cgccccgaa    5880
gaacgttttc caatgatgag cacttttaaa gttctgctat gtggcgcggt attatcccgt   5940
attgacgccg ggcaagagca actcggtcgc cgcatacact attctcagaa tgacttggtt   6000
gagtactcac cagtcacaga aaagcatctt acggatgcc tgacagtaag agaattatgc    6060
agtgctgcca taaccatgag tgataacact gcggccaact tacttctgac aacgatcgga   6120
ggaccgaagg agctaaccgc ttttttgcac aacatgggg atcatgtaac tcgccttgat    6180
cgttgggaac cggagctgaa tgaagccata ccaaacgacg agcgtgacac cacgatgcct   6240
gtagcaatgg caacaacgtt gcgcaaacta ttaactggcg aactacttac tctagcttcc   6300
cggcaacaat taatagactg gatggaggcg gataaagttg caggaccact tctgcgctcg   6360
gcccttccgg ctggctggtt tattgctgat aaatctggag ccggtgagcg tggttctcgc   6420
ggtatcattg cagcactggg gccagatggt aagccctccc gtatcgtagt tatctacacg   6480
acggggagtc aggcaactat ggatgaacga aatagacaga tcgctgagat aggtgcctca   6540
ctgattaagc attggtaact gtcagaccaa gtttactcat atatacttta gattgattta   6600
aaacttcatt tttaatttaa aaggatctag gtgaagatcc tttttgataa tctcatgacc   6660
aaaatcccct aacgtgagtt ttcgttccac tgagcgtcag accccgtaga aaagatcaaa   6720
ggatcttctt gagatccttt ttttctgcgc gtaatctgct gcttgcaaac aaaaaaacca   6780
ccgctaccag cggtggtttg tttgccggat caagagctac caactctttt tccgaaggta   6840
actggcttca gcagagcgca gataccaaat actgttcttc tagtgtagcc gtagttaggc   6900
caccacttca agaactctgt agcaccgcct acataccta ctctgctaat cctgttacca    6960
gtggctgctg ccagtggcga taagtcgtgt cttaccgggt tggactcaag acgatagtta   7020
ccggataagg cgcagcggtc gggctgaacg ggggggttcgt gcacacagcc cagcttggag   7080
cgaacgacct acaccgaact gagatacta cagcgtgagc tatgagaaag cgccacgctt     7140
cccgaaggga gaaaggcgga caggtatccg gtaagcggca gggtcggaac aggagagcgc   7200
acgagggagc ttccaggggg aaacgcctgg tatctttata gtcctgtcgg gtttcgccac   7260
ctctgacttg agcgtcgatt tttgtgatgc tcgtcagggg gcggagcct atggaaaaac     7320
gccagcaacg cggccttttt acggttcctg gccttttgct ggccttttgc tcacatggtc   7380
tttcctgcgt tatcccctga ttctgtggat aaccgtatta ccgcctttga gtgagctgat   7440
accgctcgcc gcagccgaac gaccgagcgc agcgagtcag tgagcgagga agcggagagc   7500
gcccaatacg caaaccgcct ctccccgcgc gttggccgat tcattaatgc agctggcacg   7560
acaggtttcc cgactggaaa gcgggcagtg agcgcaacgc aattaatgtg agttagctca   7620
ctcattaggc accccaggct ttacacttta tgcttccggc tcgtatgttg tgtggaattg   7680
tgagcggata acaatttcac acaggaaaca gctatgacca tgattacgcc aagcgcgtca   7740
attaaccctc actaaaggga acaaaagctg ttaattaa                          7778

SEQ ID NO: 66           moltype = DNA  length = 8177
FEATURE                 Location/Qualifiers
misc_feature            1..8177
                        note = Matrice CD25 locus_IL12a_2A_IL12b pCLS30520 full
                        sequence
source                  1..8177
                        mol_type = other DNA
                        organism = synthetic construct
SEQUENCE: 66
gtttattatt cctgttccac agctattgtc tgccatataa aaacttaggc caggcacagt     60
ggctcacacc tgtaatccca gcactttgga aggccgaggc aggcagatca aaggtcagg    120
agttcgagac cagcctggcc aacatagcaa aaccccatct ctactaaaaa tacaaaaatt   180
agccaggcat ggtggcgtgt gcactggttt agagtgagga ccacattttt ttggtgccgt   240
gttacacata tgaccgtgac tttgttacac cactacagga ggaagagtag aagaacaatc   300
ggttctggcg tgaaacagac tttgaatttt gaccttctca agttggcggg agacgtggag   360
tccaacccag ggcccatgtg gcccctggg tcagcctccc agccaccgcc ctcacctgcc    420
gcggccacag gtctgcatcc agcggctcgc cctgtgtccc tgcagtgccg gctcagcatg   480
tgtccagcgc gcagcctcct ccttgtggct accctggtcc tcctgaccca cctcagttgg   540
gccagaaacc tccccgtggc cactccagac ccaggaatgt tcccatgcct tcaccatccc   600
caaaacctgc tgagggccgt cagcaacatg ctccagaagg ccagacaaac tctagaattt   660
tacccttgca cttctgaaga gattgatcat gaagatatca caaagataa aaccagcaca    720
gtggaggcct gtttaccatt ggaattaacc aagaatgaga gttgcctaa ttccagagag    780
acctcttca taactaatgg gagttgcctg gcctccagaa agacctcttt tatgatggc    840
ctgtgcctta gtagtattta tgaagacttg aagatgtacc aggtggagtt caagaccatg   900
aatgcaaagc ttctgatgga tcctaagagg cagatctttc tagatcaaaa catgctggca   960
gttattgatg agctgatgca ggccctgaat ttcaacagtg agactgtgcc acaaaaatcc  1020
tcccttgaag aaccggattt ttataaaact aaaatcaagc tctgcatact tcttcatgct  1080
ttcagaattc gggcagtgac tattgataga gtgatgagct atctgaatgc ttccggaagc  1140
ggagctacta cttcagcct gctgaagcag tctggagaca tggagagaat cctgaccct    1200
atgtgtcacc agcagttggt catctcttgg ttttccctgg tttttctggc atctcccctc  1260
gtggccatat gggaactgaa aaagatgtt tatgtcgtag aattggattg gtatccggat    1320
gcccctggag aaatggtggt cctcacctgt gacacccctg aagaagatgg tatcacctgg  1380
accttggacc agagcagtga ggtcttaggc tctggcaaaa ccctgaccat ccaagtcaaa   1440
gagtttggag atgctggcca gtacacctgt cacaaaggag gcgaggttct aagccattcg  1500
```

```
ctcctgctgc ttcacaaaaa ggaagatgga atttggtcca ctgatatttt aaaggaccag   1560
aaagaaccca aaaataagac ctttctaaga tgccgaggcca agaattattc tggacgtttc   1620
acctgctggt ggctgacgac aatcagtact gatttgacat tcagtgtcaa aagcagcaga   1680
ggctcttctg accccaagg ggtgacgtgc ggagctgcta cactctctgc agagagagtc   1740
agagggagaca acaaggagta tgagtactca gtggagtgcc aggaggacag tgcctgccca   1800
gctgctgagg agagtctgcc cattgaggtc atggtggatg ccgttcacaa gctcaagtat   1860
gaaaactaca ccagcagctt cttcatcagg gacatcatca aacctgaccc acccaagaac   1920
ttgcagctga agccattaaa gaattctcgg caggtggagg tcagctggga gtaccctgac   1980
acctggagta ctccacattc ctacttctcc ctgacattct gcgttcaggt ccagggcaag   2040
agcaagagag aaaagaaaga tagagtcttc acggacaaga cctcagccac ggtcatctgc   2100
cgcaaaaatg ccagcattag cgtgcgggcc caggaccgct actatagctc atcttggagc   2160
gaatgggcat ctgtgccctg cagtgagggc agaggcagcc tgctgacctg cggcgacgtc   2220
gaggagaacc ccgggcccat ggggggcaggt gccaccggcc gcgccatgga cgggccgcgc   2280
ctgctgctgt tgctgcttct gggggtgtcc cttggaggtg ccaaggaggc atgccccaca   2340
ggcctgtaca cacacagcgg tgagtgctgc aaagcctgca acctgggcga gggtgtggcc   2400
cagccttgtg gagccaacca gaccgtgtgt gagccctgcc tggacagcgt gacgttctcc   2460
gacgtggtga gcgcgaccga gccgtgcaag ccgtgcaccg agtgcgtggg gctccagagc   2520
atgtcggcgc cgtgcgtgga ggccgatgac gccgtgtgcc gctgcgccta cggctactac   2580
caggatgaga cgactgggcg ctgcgaggcg tgccgcgtgt gcgaggcggg ctcgggcctc   2640
gtgttctcct gccaggacaa gcagaacacc gtgtgcgagg agtgccccga cggcacgtat   2700
tccgacgagg ccaaccacgt ggacccgtgc ctgcctgca ccgtgtgcga ggacaccgag   2760
cgccagctcc gcgagtgcac acgctgggcc gacgccgagt gcgaggagat ccctggccgt   2820
tggattacac ggtccacacc cccagagggc tcgacagca cagcccccag cacccaggag   2880
cctgaggcac ctccagaaca agacctcata gccagcacgg tggcaggtgt ggtgaccaca   2940
gtgatgggca gctcccagcc cgtggtgacc cgaggcacca ccgacaacct catccctgtc   3000
tattgctcca tcctggctgc tgtggttgtg gtcttgttgg cctacatagc cttcaagagg   3060
tgaaaaacca aaagaacaag aatttcttgg taagaagccg ggaacagaca acagaagtca   3120
tgaagcccaa gtgaaatcaa aggtgctaaa tggtcgccca ggagacatcc gttgtgcttg   3180
cctgcgtttt ggaagctctg aagtcacatc acaggacacg gggcagtggc aaccttgtct   3240
ctatgccagc tcagtcccat cagagagcga gcgctaccca cttctaaata gcaatttcgc   3300
cgttgaagag gaagggcaaa accactagaa ctctccatct tatttcatg tatatgtgt    3360
catgcgatcg ctccggtgcc cgtcagtggg cagagcgcac atcgcccaca gtccccgaga   3420
agttgggggg agggtcggc aattgaacgg gtgcctagag aaggtggcgc ggggtaaact   3480
gggaaagtga tgtcgtgtac tggctccgcc tttttcccga gggtggggga gaaccgtata   3540
taagtgcagt agtcgccgtg aacgttcttt ttcgcaacgg gtttgccgcc agaacacagc   3600
tgaagcttcg aggggctcgc atctctcctt cacgcgcccg ccgccctacc tgaggccgcc   3660
atccacgccg gttgagtcgc gttctgccgc ctcccgcctg tggtgcctcc tgaactgcgt   3720
ccgccgtcta ggtaagtta aagctcaggt cgagaccggg cctttgtccg gcgctccctt   3780
ggagcctacc tagactcagc cggctctcca cgctttgcct gaccctgctt gctcaactct   3840
acgtctttgt ttcgttttct gttctgcgcc gttacagatc caagctgtga ccggcgccta   3900
cctgagatca ccggcgccac catggcttct taccctggac accagcatgc ttctgccttt   3960
gaccaggctg ccagatccag gggccactcc aacaggagaa ctgccctaag acccagaaga   4020
cagcaggaag ccactgaggt gaggcctgag cagaagatgc caaccctgct gagggtgtac   4080
attgatggac ctcatggcat gggcaagacc accaccactc aactgctggt ggcactgggc   4140
tccagggatg acattgtgta tgtgcctgag ccaatgacct actggagagt gctaggagcc   4200
tctgagacca ttgccaacat ctacaccacc agcacaggc tggaccaggg agaaatctct   4260
gctggagaga ctgctgtggt gatgacctct gcccagatca caatgggaat gcctatgct   4320
gtgactgatg ctgttctggc tcctcacatt ggaggagagg ctggctcttc tcatgccct   4380
ccacctgccc tgaccctgat cttttgacaga cacccattg cagccctgct gtgctaccca   4440
gcagcaaggt acctcatggg ctccatgacc ccacaggctg tgctggcttt tgtggccctg   4500
atccctccaa ccctccctgg caccaacatt gttctgggag cactgcctga agacagacaa   4560
attgacaggc tggcaaagag gcagagacct ggagagagac tggacctggc catgctggct   4620
gcaatcagaa gggtgtatgg actgctggca aacactgtga gatacctcca gtgtggaggc   4680
tcttggagag aggactgggg acagctctct ggaacagcag tgcccctca aggagctgag   4740
cccagtcca atgctggtcc aagacccac atggggaca ccctgttcac cctgttcaga   4800
gcccctgagc tgctggctcc caatggagac ctgtacaatg tgtttgcctg ggctctggat   4860
gttctagcca agaggctgag gtccatgcat gtgttcatcc tggactatga ccagtcccct   4920
gctggatgca gagatgctct gctgcaacta acctctggca tggtgcagac ccatgtgacc   4980
accctggca gcatcccac catctgtgac ctagccagaa cctttgccag gggatggga   5040
gaggccaact aaggcgcgcc actcgagcgc tagctggcca gacatgataa gatacattga   5100
tgagtttgga caaaccacaa ctagaatgca gtgaaaaaa tgctttattt gtgaaattg   5160
tgatgctatt gctttatttg taaccattat aagctgcaat aaacaagtta acaacaacaa   5220
ttgcattcat tttatgtttc aggttcaggg ggaggtgtgg gaggttttt aaagcaagta   5280
aaacctctac aaatgtggta tggaaggcgc gcccaattcg cctatagtg agtcgtatta   5340
cgtcgcgctc actggccgtc gttttacaac gtcgtgactg ggaaaaccct ggcgttaccc   5400
aacttaatcg ccttgcagca catccccctt cgccagctg gcgtaatagc gaagaggccc   5460
gcaccgaaac gcccttccca acagttgcgc agcctgaatg gcgaatggga cgccctgta   5520
gcggcgcatt aagcgcggcg ggtgtggtgg ttacgcgcag cgtgaccgct acacttgcca   5580
gcgccctagc gcccgctcct ttcgctttct ttcctttct tctcgccacg ttcgccgct   5640
ttccccgtca agctctaaat cgggggctcc ctttagggtt ccgatttagt gctttacggc   5700
acctcgaccc caaaaaactt gattagggtg atggttggcc tgtagtgggc catagccctg   5760
atagacggtt tttcgccctt tgacgttgga gtccacgttc tttaatagtg gactcttgtt   5820
ccaaactgga acaacactca accctatctc ggtctattct tttgatttat aagggatttt   5880
gccgatttcg gcctattggt taaaaaatga gctgatttaa caaaaattta acgcgaattt   5940
taacaaaata ttaacgctta caatttaggt ggcacttttc ggggaaatgt gcgcggaacc   6000
cctatttgtt tatttttcta aatacattca aatatgtatc cgctcatgag acaataaccc   6060
tgataaatgc ttcaataata ttgaaaaagg aagagtatga gtattcaaca tttccgtgtc   6120
gcccttattc ccttttttgc ggcattttgc cttcctgttt ttgctcaccc agaaacgctg   6180
gtgaaagtaa aagatgctga agatcagttg ggtgcacgag tgggttacat cgaactggat   6240
```

```
ctcaacagcg gtaagatcct tgagagtttt cgccccgaag aacgttttcc aatgatgagc    6300
acttttaaag ttctgctatg tggcgcggta ttatcccgta ttgacgccgg gcaagagcaa    6360
ctcggtcgcc gcatacacta ttctcagaat gacttggttg agtactcacc agtcacagaa    6420
aagcatctta cggatggcat gacagtaaga gaattatgca gtgctgccat aaccatgagt    6480
gataacactg cggccaactt acttctgaca acgatcggag gaccgaagga gctaaccgct    6540
tttttgcaca acatggggga tcatgtaact cgccttgatc gttgggaacc ggagctgaat    6600
gaagccatac caaacgacga gcgtgacacc acgatgcctg tagcaatggc aacaacgttg    6660
cgcaaactat taactggcga actacttact ctagcttccc ggcaacaatt aatagactgg    6720
atggaggcgg ataaagttgc aggaccactt ctgcgctcgg cccttccggc tggctggttt    6780
attgctgata aatctggagc cggtgagcgt ggttctcgcg gtatcattgc agcactgggg    6840
ccagatggta agccctcccg tatcgtagtt atctacacga cggggagtca ggcaactatg    6900
gatgaacgaa atagacagat cgctgagata ggtgcctcac tgattaagca ttggtaactg    6960
tcagaccaag tttactcata tatactttag attgatttaa aacttcattt ttaatttaaa    7020
aggatctagg tgaagatcct tttgataat ctcatgacca aaatcccta acgtgagttt    7080
tcgttccact gagcgtcaga ccccgtagaa aagatcaaag gatcttcttg agatcctttt    7140
tttctgcgcg taatctgctg cttgcaaaca aaaaaaccac cgctaccagc ggtggtttgt    7200
ttgccggatc aagagctacc aactcttttt ccgaaggtaa ctggcttcag cagagcgcag    7260
ataccaaata ctgttcttct agtgtagccg tagttaggcc accacttcaa gaactctgta    7320
gcaccgccta catacctcgc tctgctaatc ctgttaccag tggctgctgc cagtggcgat    7380
aagtcgtgtc ttaccgggtt ggactcaaga cgatagttac cggataaggc gcagcggtcg    7440
ggctgaacgg ggggttcgtg cacacagccc agcttggagc gaacgaccta caccgaactg    7500
agatacctac agcgtgagct atgagaaagc gccacgcttc ccgaagggag aaaggcggac    7560
aggtatccgg taagcggcag ggtcggaaca ggagagcgca cgagggagct tccaggggga    7620
aacgcctggt atctttatag tcctgtcggg tttcgccacc tctgacttga gcgtcgattt    7680
ttgtgatgct cgtcaggggg gcggagccta tggaaaaacg ccagcaacgc ggccttttta    7740
cggttcctgg cctttgctg gccttttgct cacatggttt ttcctgcgtt atcccctgat    7800
tctgtggata accgtattac cgcctttgag tgagctgata ccgctcgccg cagccgaacg    7860
accgagcgca gcgagtcagt gagcgaggaa gcggagagcg cccaatacgc aaaccgcctc    7920
tccccgcgcg ttggccgatt cattaatgca gctggcacga caggtttccc gactggaaag    7980
cgggcagtga gcgcaacgca attaatgtga gttagctcac tcattaggca cccccaggctt   8040
tacactttat gcttccggct cgtatgttgt gtggaattgt gagcggataa caatttcaca    8100
caggaaacag ctatgaccat gattacgcca agcgcgtcaa ttaaccctca ctaaagggaa    8160
caaaagctgt taattaa                                                    8177
```

```
SEQ ID NO: 67          moltype = DNA  length = 6349
FEATURE                Location/Qualifiers
misc_feature           1..6349
                       note = Matrice PD1 locus_IL12a_2A_IL12b pCLS30511 full
                       sequence
source                 1..6349
                       mol_type = other DNA
                       organism = synthetic construct
SEQUENCE: 67
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acctcgcgaa     420
tgcatctaga tgactcccca gacaggcccct ggaacctccc caccttctcc ccagcccgtc    480
tcgtggtgac cgaaggggac aacgccacct tcacctgcag cttctccaac acatcggaga    540
gcttcgtgct aaactggtac cgcatgagcc cagcaaccca gacggacaag ctggccgcct    600
tccccgagga ccgcagccag cccggccagg actgccgctt ccgtgtcaca caactgccca    660
acgggcgtga cttccacatg agcgtggtca gggcccggcc caatgacagc ggcacctacc   720
tctgtgggc cggttctggc gtgaaacaga ctttgaattt tgaccttctc aagttggcgg    780
gagacgtgga gtcaacccca ggcccatgt ggcccctgg gtcagcctcc agccaccgc     840
cctcacctgc cgcggccaca ggtctgcatc agcggctcg ccctgtgtcc ctgcagtgcc    900
ggctcagcat gtgtccagcg cgcagcctcc tccttgtggc taccctggtc ctcctggaca    960
acctcagttt ggccagaaac ctccccgtgg ccactccaga cccaggaatg ttccccatgc   1020
ttcaccactc ccaaaacctg ctgagggcc tcagcaacat gctccagaag ccagacaaa    1080
ctctagaatt ttacccttgc acttctgaag agattgatca tgaagatatc acaaaagata   1140
aaaccagcac agtggaggcc tgtttaccat ggaattaac caagaatgag agttgcctaa    1200
attccagaga gacctctttc ataactaatg gagttgcctc cagaaagacctctt        1260
ttatgatgc cctgtgcctt agtagtattt atgaagactt gaagatgtac caggtggagt    1320
tcaagaccat gaatgcaaag cttgatggga tcctaagag gcagatcttt ctagatcaaa    1380
acatgctggc agttattgat gagctgatgc aggcccctgaa tttcaacagt gagactgtgc    1440
cacaaaaatc ctcccttgaa gaaccggatt tttataaaaa taaatcaag tctgcatac      1500
ttcttcatgc tttcagaatt cgggcagtga ctattgatag agtgatgagt tatctgaatg    1560
cttccggaag cggagctact aacttcagcc tgctgaagca ggctggagac gtggaggaga    1620
accctggacc tatgtgtcac cagcagttgg tcatctcttg gtttcctg gttttctgg     1680
catctcccct cgtggccata tgggactga agaaagatgt ttatgtcgta gaattggatt    1740
ggtatccgga tgccctgga gaatggtgg tcctcacctg tgacacccct gaagaagatg    1800
gtatcacctg gaccttgac cagagcagtg aggtcttagg ctctggaaaa accctgacca    1860
tccaagtcaa agagtttgga gatgctggcc agtacacctg tcacaaagga gcgaggttc     1920
taagccattc gctcctgctg cttcacaaaa aggaagatgg aatttggtcc actgatattt    1980
taaaggacca gaaagaaccc aaaaataaga ccttctaag atgcgaggcc aagaattatt    2040
ctggacgttt cacctgctgg tggctgacga caatcagtac tgatttgaca ttcagtgtca    2100
aaagcagcag aggctcttct gaccccaag gggtgacgtg cggagctgct acactctctg   2160
```

```
cagagagagt cagaggggac aacaaggagt atgagtactc agtggagtgc caggaggaca   2220
gtgcctgccc agctgctgag gagagtctgc ccattgaggt catggtggat gccgttcaca   2280
agctcaagta tgaaaactac accagcagct tcttcatcag ggacatcatc aaacctgacc   2340
cacccaagaa cttgcagctg aagccattaa agaattctcg gcaggtggag gtcagctggg   2400
agtacccctga cacctggagt actccacatt cctacttctc cctgacattc tgcgttcagg   2460
tccagggcaa gagcaagaga gaaaagaaag atagagtctt cacggacaag acctcagcca   2520
cggtcatctg ccgcaaaaat gccagcatta gcgtgcgggc ccaggaccgc tactatagct   2580
catcttggag cgaatgggca tctgtgccct gcagtgaggg cagaggcagc ctgctgacct   2640
gcggcgacgt cgaggagaac cccgggccca tgggggcagg tgccaccggc cgcgccatgg   2700
acgggccgcg cctgctgctg ttgctgcttc tgggggtgtc ccttggaggt gccaaggagg   2760
catgccccac aggcctgtac acacacagcg tgagtgctgc caaagcctgc aacctgggcg   2820
agggtgtggc ccagccttgt ggagccaacc agaccgtgtg tgagccctgc ctggacagcg   2880
tgacgttctc cgacgtggtg agcgcgaccg agccgtgcaa gccgtgcacc gagtgcgtgg   2940
ggctccagag catgtcggcg ccgtgcgtgg aggccgatga cgccgtgtgc cgctgcgcct   3000
acggctacta ccaggatgag acgactgggc gctgcgaggc gtgccgcgtg tgcgaggcgg   3060
gctcgggcct cgtgttctcc tgccaggaca gcagaacac cgtgtgcgag gagtgccccg   3120
acggcacgta ttccgacgag gccaaccacg tggaccgtg cctgccctgc accgtgtgcg   3180
aggacaccga gcgccagctc cgcagcgca cacgctggcg ccgaccgag tgcgaggaga   3240
tccctggccg ttggattaca cggtccacac ccccagaggg ctcggacagc acagccccca   3300
gcacccagga gcctgaggca cctccagaac aagacctcat agccagcacg gtggcaggtg   3360
tggtgaccac agtgatgggc agctcccagc ccgtggtgac ccgaggcacc accgacaacc   3420
tcatccctgt ctattgctcc atcctggctg ctgtggttgt gggtcttgtg gcctacatag   3480
ccttcaagag gtgatctaga gggcccgttt aaacccgctg atcagcctcg actgtgcctt   3540
ctagttgcca gccatctgtt gtttgcccct ccccgtgcc ttccttgacc ctggaagtg    3600
ccactcccac tgtcctttcc taataaaatg aggaaattgc atcgcattgt ctgagtaggt   3660
gtcattctat tctgggggt ggggtgggc aggacagaa tggggaggat tgggaagaca      3720
atagcaggca tgctggggat cggtgggct ctatgactag tggcgaattc ggcgcagatc    3780
aaaagagagcc tgcgggcaga gctcaggggt acaggtgcgg cctcggaggc cccggggcag  3840
gggtgagctg agccggtcct ggggtgggtg tcccctcctg cacaggatca ggagctccag   3900
ggtcgtaggg cagggacccc ccagctccag tccagggctc tgtcctgcac ctgggggaatg  3960
gtgaccggca tctctgtcct ctagctctgg aagcacccca gccctctag tctgccctca    4020
cccctgaccc tgaccctcca ccctgaccc gtcctaaccc ctgaccttg atcggatccc     4080
gggcccgtcg actgcagagg cctgcatgca agcttggcgt aatcatggtc atagctgttt   4140
cctgtgtgaa attgttatcc gctcacaatt ccacacaaca tacgagccgg aagcataaag   4200
tgtaaagcct ggggtgccta atgagtgagc taactcacat taattgcgtt gcgctcactg   4260
cccgctttcc agtcgggaaa cctgtcgtgc cagctgcatt aatgaatcgg ccaacgcgcg   4320
gggagaggcg gtttgcgtat tgggcgctct tccgcttcct cgctcactga ctcgctgcgc   4380
tcggtcgttc ggctgcggcg agcggtatca gctcactcaa aggcggtaat acggttatcc   4440
acagaatcag gggataacgc aggaaagaac atgtgagcaa aaggccagca aaaggccagg   4500
aaccgtaaaa aggccgcgtt gctggcgttt ttccataggc tccgcccccc tgacgagcat   4560
cacaaaaatc gacgctcaag tcagaggtgg cgaaacccga caggactata agataccagg   4620
gcgtttcccc ctggaagctc cctcgtgcgc tctcctgttc cgaccctgcc gcttaccgga   4680
tacctgtccg ccttttctcc cttcgggaagc gtggcgcttt ctcatagctc acgctgtagg   4740
tatctcagtt cggtgtaggt cgttcgctcc aagctgggct gtgtgcacga accccccgtt   4800
cagcccgacc gctgcgcctt atccggtaac tatcgtcttg agtccaaccc ggtaagacac   4860
gacttatcgc cactggcagc agccactggt aacaggatta gcagagcgag gtatgtaggc   4920
ggtgctacag agttcttgaa gtggtggcct aactacggct acactagaag aacagtattt   4980
ggtatctgcg ctctgctgaa gccagttacc ttcggaaaaa gagttggtag ctcttgatcc   5040
ggcaaacaaa ccaccgctgg tagcggtggt ttttttgttt gcaagcagca gattacgcgc   5100
agaaaaaaag gatctcaaga agatcctttg atcttttcta cggggtctga cgctcagtgg   5160
aacgaaaact cacgttaagg gattttggtc atgagattat caaaaaggat cttcacctag   5220
atccttttaa attaaaaatg aagttttaaa tcaatctaaa gtatatatga gtaaacttgg   5280
tctgacagtt accaatgctt aatcagtgag gcacctatct cagcgatctg tctatttcgt   5340
tcatccatag ttgcctgact ccccgtcgtg tagataacta cgatacggga gggcttacca   5400
tctggcccca gtgctgcaat gataccgcga gacccacgct caccggctcc agatttatca   5460
gcaataaacc agccagccgg aagggccgag cgcagaagtg gtcctgcaac tttatccgcc   5520
tccatccagt ctattaattg ttgccggaa gctagagtaa gtagttcgcc agttaatagt    5580
ttgcgcaacg ttgttgccat tgctacaggc atcgtggtgt cacgctcgtc gtttggtatg   5640
gcttcattca gctccggttc ccaacgatca aggcgagtta catgatcccc catgttgtgc   5700
aaaaaagcgg ttagctcctt cggtcctccg atcgttgtca gaagtaagtt ggccgcagtg   5760
ttatcactca tggttatggc agcactgcat aattctctta ctgtcatgcc atccgtaaga   5820
tgcttttctg tgactggtga gtactcaacc aagtcattct gagaatagtg tatgcggcga   5880
ccgagttgct cttgcccggc gtcaatacgg gataataccg cgccacatag cagaacttta   5940
aaagtgctca tcattggaaa acgttcttcg gggcgaaaac tctcaaggat cttaccgctg   6000
ttgagatcca gttcgatgta acccactcgt gcacccaact gatcttcagc atcttttact   6060
ttcaccagcg tttctgggtg agcaaaaaca ggaaggcaaa atgccgcaaa aaagggaata   6120
agggcgacac ggaaatgttg aatactcata ctcttccttt tcaatattat tgaagcatt    6180
tatcagggtt attgtctcat gagcggatac atatttgaat gtatttagaa aaataaacaa   6240
ataggggttc cgcgcacatt tccccgaaaa gtgccacctg acgtctaaga aaccattatt   6300
atcatgacat taacctataa aaataggcgt atcacgaggc cctttcgtc                6349

SEQ ID NO: 68        moltype = AA  length = 14
FEATURE              Location/Qualifiers
VARIANT              5
                     note = MISC_FEATURE - Xaa is Ile or Val
VARIANT              13
                     note = MISC_FEATURE - Xaa is Lys, Arg, or Gln
source               1..14
                     mol_type = protein
```

```
                        organism = Human immunodeficiency virus 1
SEQUENCE: 68
LQARXLAVER YLXD                                                         14

SEQ ID NO: 69           moltype = AA  length = 14
FEATURE                 Location/Qualifiers
VARIANT                 13
                        note = MISC_FEATURE - Xaa is Lys, Ala, or Gln
VARIANT                 14
                        note = MISC_FEATURE - Xaa is Asp or His
source                  1..14
                        mol_type = protein
                        organism = Human immunodeficiency virus 2
SEQUENCE: 69
LQARVTAIEK YLXX                                                         14

SEQ ID NO: 70           moltype = AA  length = 14
FEATURE                 Location/Qualifiers
source                  1..14
                        mol_type = protein
                        organism = Simian immunodeficiency virus
SEQUENCE: 70
LQARLLAVER YLKD                                                         14

SEQ ID NO: 71           moltype = AA  length = 14
FEATURE                 Location/Qualifiers
source                  1..14
                        mol_type = protein
                        organism = unidentified
                        note = Moloney murine leukemia virus
SEQUENCE: 71
LQNRRGLDLL FLKE                                                         14

SEQ ID NO: 72           moltype = AA  length = 14
FEATURE                 Location/Qualifiers
source                  1..14
                        mol_type = protein
                        organism = unidentified
                        note = Human T-cell lymphotropic virus
SEQUENCE: 72
AQNRRGLDLL FWEQ                                                         14

SEQ ID NO: 73           moltype = AA  length = 14
FEATURE                 Location/Qualifiers
source                  1..14
                        mol_type = protein
                        organism = Mason-Pfizer monkey virus
SEQUENCE: 73
LQNRRGLDLL TAEQ                                                         14

SEQ ID NO: 74           moltype = AA  length = 14
FEATURE                 Location/Qualifiers
source                  1..14
                        mol_type = protein
                        organism = Homo sapiens
SEQUENCE: 74
LQNRRALDLL TAER                                                         14

SEQ ID NO: 75           moltype = AA  length = 14
FEATURE                 Location/Qualifiers
source                  1..14
                        mol_type = protein
                        organism = Homo sapiens
SEQUENCE: 75
LQNRRGLDML TAAQ                                                         14

SEQ ID NO: 76           moltype = AA  length = 14
FEATURE                 Location/Qualifiers
source                  1..14
                        mol_type = protein
                        organism = unidentified
                        note = Human endogenous retrovirus K
SEQUENCE: 76
LANQINDLRQ TVIW                                                         14

SEQ ID NO: 77           moltype = AA  length = 14
FEATURE                 Location/Qualifiers
source                  1..14
                        mol_type = protein
```

```
                        organism = Feline leukemia virus
SEQUENCE: 77
LQNRRGLDIL FLQE                                                                      14

SEQ ID NO: 78           moltype = AA  length = 9
FEATURE                 Location/Qualifiers
source                  1..9
                        mol_type = protein
                        organism = Human immunodeficiency virus 1
SEQUENCE: 78
GALFLGFLG                                                                             9

SEQ ID NO: 79           moltype = AA  length = 9
FEATURE                 Location/Qualifiers
REGION                  1..9
                        note = Synthetic peptide
source                  1..9
                        mol_type = protein
                        organism = synthetic construct
SEQUENCE: 79
AGFGLLLGF                                                                             9

SEQ ID NO: 80           moltype = AA  length = 9
FEATURE                 Location/Qualifiers
REGION                  1..9
                        note = Synthetic peptide
source                  1..9
                        mol_type = protein
                        organism = synthetic construct
SEQUENCE: 80
AGLFLGFLG                                                                             9
```

The invention claimed is:

1. A method for preparing a population of engineered primary human NK or T cells for immunotherapy comprising:
   providing primary human NK or T cells;
   introducing an exogenous coding sequence encoding an interleukin selected from IL-15, IL-12, or IL-2 with a sequence-specific endonuclease targeting an endogenous gene into the primary human NK or T cells;
   cleaving the endogenous gene and inserting the exogenous coding sequence into the endogenous gene such that said interleukin is under transcriptional control of the promoter of the endogenous gene, while disrupting the coding sequence of the endogenous gene,
   wherein the endogenous gene encodes PD1; and
   introducing an exogenous coding sequence encoding a chimeric antigen receptor (CAR) or a recombinant TCR into the primary human NK or T cells;
   wherein said engineered primary human NK or T cells secrete a level of the interleukin sufficient to enhance the antitumor activity of the cells.

2. The method of claim 1, wherein said interleukin is IL-2.

3. The method of claim 1, wherein said interleukin is IL-12.

4. The method of claim 1, wherein said interleukin is IL-15.

5. The method of claim 1, wherein more than 50% of said engineered primary human NK or T cells are TCR negative T-cells and/or more than 50% of said engineered primary human NK or T cells are CAR positive cells.

6. The method of claim 1, wherein the CAR is an antiCD22 CAR.

7. The method of claim 2, wherein the CAR is an antiCD22 CAR.

8. The method of claim 3, wherein the CAR is an antiCD22 CAR.

9. The method of claim 4, wherein the CAR is an antiCD22 CAR.

10. The method of claim 5, wherein the CAR is an antiCD22 CAR.

11. The method of claim 1, wherein the exogenous coding sequence encoding an interleukin is inserted into the middle of the PD1 open reading frame using TALENS having the sequence of SEQ ID NO:20 and 21.

12. The method of claim 2, wherein the exogenous coding sequence encoding an interleukin is inserted into the middle of the PD1 open reading frame using TALENS having the sequence of SEQ ID NO:20 and 21.

13. The method of claim 3, wherein the exogenous coding sequence encoding an interleukin is inserted into the middle of the PD1 open reading frame using TALENS having the sequence of SEQ ID NO:20 and 21.

14. The method of claim 4, wherein the exogenous coding sequence encoding an interleukin is inserted into the middle of the PD1 open reading frame using TALENS having the sequence of SEQ ID NO:20 and 21.

15. The method of claim 5, wherein the exogenous coding sequence encoding an interleukin is inserted into the middle of the PD1 open reading frame using TALENS having the sequence of SEQ ID NO:20 and 21.

* * * * *